(12) United States Patent
Capon et al.

(10) Patent No.: US 7,279,279 B2
(45) Date of Patent: *Oct. 9, 2007

(54) COMPOSITIONS AND METHODS FOR DETERMINING ANTI-VIRAL DRUG SUSCEPTIBILITY AND RESISTANCE AND ANTI-VIRAL DRUG SCREENING

(75) Inventors: Daniel J. Capon, Hillsborough, CA (US); Christos J. Petropoulos, Half Moon Bay, CA (US)

(73) Assignee: Monogram Biosciences, Inc., South San Francisco, CA (US)

( * ) Notice: Subject to any disclaimer, the term of this patent is extended or adjusted under 35 U.S.C. 154(b) by 114 days.

This patent is subject to a terminal disclaimer.

(21) Appl. No.: 10/846,181

(22) Filed: May 14, 2004

(65) Prior Publication Data

US 2005/0214746 A1    Sep. 29, 2005

Related U.S. Application Data

(63) Continuation of application No. 09/875,082, filed on Jun. 5, 2001, now Pat. No. 6,942,969, which is a continuation of application No. 09/371,774, filed on Aug. 10, 1999, now Pat. No. 6,242,187, which is a continuation-in-part of application No. 08/903,507, filed on Jul. 30, 1997, now abandoned, which is a continuation-in-part of application No. 08/790,963, filed on Jan. 29, 1997, now Pat. No. 5,837,464.

(60) Provisional application No. 60/010,715, filed on Jan. 29, 1996.

(51) Int. Cl.
  *C12Q 1/68* (2006.01)
(52) U.S. Cl. .................................. 435/6; 435/235.1
(58) Field of Classification Search ................ None
  See application file for complete search history.

(56) References Cited

U.S. PATENT DOCUMENTS

| | | | |
|---|---|---|---|
| 4,952,496 A | 8/1990 | Studier et al. | |
| 5,126,251 A | 6/1992 | Moss et al. | |
| 5,135,855 A | 8/1992 | Moss et al. | |
| 5,354,674 A | 10/1994 | Hodgson | |
| 5,439,809 A | 8/1995 | Haynes et al. | |
| 5,462,873 A | 10/1995 | Garfinkel et al. | |
| 5,837,464 A | 11/1998 | Capon et al. | |
| 5,866,348 A * | 2/1999 | Scheirer | 435/8 |
| 5,874,565 A | 2/1999 | Rice et al. | |
| 5,985,926 A * | 11/1999 | Leung et al. | 514/558 |
| 6,033,902 A | 3/2000 | Haseltine et al. | |
| 6,127,116 A | 10/2000 | Rice et al. | |
| 6,242,187 B1 | 6/2001 | Capon et al. | |
| 2002/0034732 A1 | 3/2002 | Capon et al. | |

FOREIGN PATENT DOCUMENTS

| EP | 0 291 893 | 5/1987 |
|---|---|---|
| EP | 0 291 893 | 11/1988 |
| EP | 0 361 749 | 4/1990 |
| EP | 0 372 904 | 6/1990 |
| EP | 0 414 475 | 2/1991 |
| EP | 98940779.6 | 8/2004 |
| HU | P9900388 | 2/2005 |
| WO | WO91/19798 | 12/1991 |
| WO | WO92/07943 | 5/1992 |
| WO | WO94/08002 | 4/1994 |
| WO | WO94/19478 | 9/1994 |
| WO | WO94/29438 | 12/1994 |
| WO | WO95/05453 | 2/1995 |
| WO | WO95/22622 | 8/1995 |
| WO | WO95/29703 | 11/1995 |
| WO | WO95/30763 | 11/1995 |
| WO | PCT/US97/01609 | 4/1997 |
| WO | WO97/27319 | 7/1997 |
| WO | WO97/27480 | 7/1997 |
| WO | PCT/US98/15967 | 10/1998 |
| WO | WO99/06597 | 2/1999 |
| WO | PCT/US2003/013791 | 4/2003 |

OTHER PUBLICATIONS

Blight et al. 2000, "Efficient Initiation of HCV RNA Replication in Cell Culture," *Science* 290:1972-1974.

(Continued)

*Primary Examiner*—James Ketter
(74) *Attorney, Agent, or Firm*—Jones Day

(57) ABSTRACT

This invention provides a method for determining susceptibility for an anti-viral drug comprising: (a) introducing a resistance test vector Comprising a patient-derived segment and an indicator gene into a host cell; (b) culturing the host cell from (a); (c) measuring expression of the indicator gene in a target host cell; and (d) comparing the expression of the indicator gene from (c) with the expression of the indicator gene measured when steps (a)-(c) are carried out in the absence of the anti-viral drug, wherein a test concentration of the anti-viral drug is present at steps (a)-(c); at steps (b)-(c); or at step (c). This invention also provides a method for determining anti-viral drug resistance in a patient comprising: (a) determining anti-viral drug susceptibility in the patient at a first time using the susceptibility test described above, wherein the patient-derived segment is obtained from the patient at about said time; (b) determining anti-viral drug susceptibility of the same patient at a later time; and (c) comparing the anti-viral drug susceptibilities determined in step (a) and (b), wherein a decrease in anti-viral drug susceptibility at the later time compared to the first time indicates development or progression of anti-viral drug resistance in the patient.

23 Claims, 40 Drawing Sheets

OTHER PUBLICATIONS

Brown et al. 1994, "In Vitro Characterization of an Internal Ribosomal Entry Site (IRES) Present Within the 5' Nontranslated Region of Hepatitis A Virus RNA: Comparison with the IRES of Encephalomyocarditis Virus," *Journal of Virology* 68(2): 1066-74.

Chou et al. 1995, "Frequency of UL97 Phosphotransferase Mutations Related to Ganciclovir Resistance in Clinical Cytomegalovirus Isolates," *The Journal of Infectious Diseases* 172:239-242.

Chung et al. 2001, "Hepatitis C Virus Replication is Directly Inhibited By IFN-α in a Full Length Binary Expression System," *Proc. Natl. Acad Sci USA*, 98(17):9847-9852.

Enami et al. 1991, "High-Efficiency Formation of Influenza Virus Transfectants" *Journal of Virology* 65(5):2711-13.

Enomoto et al. 1995, "Hepatitis C Virus Quasispecies Populations During Chronic Hepatitis C Infection", *Trends in Microbiology* 3(11):445-447.

Fuerst et al. 1986, "Eukaryotic Transient-Expression System Based on Recombinant Vaccinia Virus That Synthesizes Bacteriophage T7 RNA Polymerase," *Proc. Natl. Acad Sci USA*, 83:8122-26.

Gerna et al. 1995, "Rapid Screening for Resistance to Ganciclovir and Foscarnet of Primary Isolates of Human Cytomegalovirus From Culture-Positive Blood Samples," *Journal of Microbiology*, 33(3):738-741.

Glass et al. 1993, "Identification of the Hepatitis A Virus Internal Ribosome Entry Site: In Vivo and In Vitro Analysis of Bicistronic RNAs Containing the HAV 5' Noncoding Region," *Virology*, 193:842-852.

Hahm et al. 1996, "Generation of a Novel Poliovirus with a Requirement of Hepatitis C Virus Protease NS3 Activity," *Virology*, 266:318-326.

Hirowatari et al. 1995, "A Novel Method for Analysis of Viral Proteinase Activity Encoded by Hepatitis C Virus in Cultured Cells," *Analytical Biochemistry*, 225:113-120.

Houghton et al. 1996, "Hepatitis C Viruses" Fields Virology, 3rd Edition, Chapter 32: 1035-1058.

Jang et al. 1989, "Initiation of Protein Synthesis by Internal Entry of Ribosomes into the 5' Nontranslated Region of Encephalomyocarditis Virus RNA In Vivo," *Journal of Virology*, 63(4):1651-1660.

Kellam et al. 1992 "Fifth Mutation in Human Immunodeficiency Virus Type I Reverse Transcriptase Contributes to the Development of High-Level Resistance to Zidovudine" *PNAS* 89:1934-1938.

Lawson et al. 1995, "Recombinant Vesicular Stomatitis Viruses From DNA," *Proc. Natl. Acad. Sci. USA*, 63: 4477-4481.

Lu et al. 1996, "Poliovirus Chimeras Replicating Under the Translational Control of Genetic Elements of Hepatitis C Virus Reveal Unusual Properties of the Internal Ribosomal Entry Site of Hepatitis C Virus," *Proc Natl. Acad. Sci. USA*, 93:1412-1417.

Mocarski, Edward S., 1996, "Cytomegaloviruses and Their Replication," Fields Virology, 3rd Edition, Chapter 76, 2447-22492.

Morgenstern et al. 1990 "Advanced Mammalian Gene Transfer: High Titre Retroviral Vectors with Multiple Drug Selection Markers and a Complementary Helper-Free Packaging Cell Line," *Nucleic Acid Research* 18(12):3587-3596.

Pelletier et al. 1988, "Internal Initiation of Translation of Eukaryotic mRNA Directed by a Sequence Derived From Poliovirus RNA," *Nature*, 334:320-325.

Rohll et al. 1994, "The 5'-Untranslated Regions of Picornavirus RNAs Contain Independent Functional Domains Essential for RNA Replication and Translation," *Journal of Virology*, 68(7):4384-91.

Saltarelli et al. 1993 "The CAEV tat Gene Trans-Activates the Viral LTR and is Necessary for Efficient Viral Replication", *Virology* 197:35-44.

Schnell et al. 1994, "Infectious Rabies Viruses From Cloned cDNA," *The EMBO Journal*, 13(18):4195-4203.

Steinkuhler et al. 1996, "Activity of Purified Hepatitis C Virus Protease NS3 on Peptide Substrates," *Journal of Virology*, 70(10): 6694-6700.

Strair et al. 1993, "Recombinant Retroviral Systems for the Analysis of Drug Resistant HIV", *Nucleic Acids Research* 21(20):4836-4842.

Tsukiyama-Kohara et al. 1992, "Internal Ribosome Entry Site Within Hepatitis C Virus RNA," *Journal of Virology*, 66(3): 1476-1483.

Wang et al. 1993, "Translation of Human Hepatitis C Virus RNA in Cultured Cells is Mediated by an Internal Ribosome-Binding Mechanism," *Journal of Virology*, 67(6):3338-3344.

Danos, Olivier and Mulligan, Richard C. 1988, "Safe and Efficient Generation of Recombinant Retroviruses with Amphotropic and Ecotropic Host Ranges," *Proc. Natl. Acad Sci. USA*, 85:6460-6464.

Fuerst, Thomas R., and Moss, Bernard 1989, "Structure and Stability of mRNA Synthesized by Vaccinia Virus-encoded Bacteriophage 17 RNA Polymerase in Mammalian Cells" *J. Mol. Biol.* 206:333-348.

Lieber Andre et al. 1989, "High Level Gene Expression in Mammalian Cells by a Nuclear 17-Phage RNAPolymerase," *Nucleic Acids Research* 17(21):8485-8493.

Larder, Brendan A., et al. 1989, "HIV with Reduced Sensitivity to Zidovudine (AZT) Isolated During Prolonged Therapy," *Science*, 243:1731-1734.

Andreasson K.I., et al. 1989, "Production of Pro-Opiomelanocortin (POMC) by a Vaccinia Virus Transient Expression System and In Vitro Processing of the Expressed Prohormone by POMC-converting Enzyme" *F.E.B.S Letters*, 248(1)1:43-47.

Elroy-Stein Orna et al. 1989, "Cap-Independent Translation of mRNA Conferred by Encephalomyocarditis Virus 5' Sequence Improves the Performance of the Vaccinia Virus/Bacteriophage T7 Hybrid Expression System" *Proc. Natl. Acad. Sci. USA*, 86:6126-6130.

Larder, Brendan A., and Sharon D.Kemp, 1989, "Multiple Mutations in HIV-1 Reverse Transcriptase confer High-Level Resistance of Zidovudine (AZT)" *Science*, 246: 1155-1158.

Page, Kathleen A., et al. 1990, "Construction and Use of a Human Immunodeficiency Virus Vector for Analysis of Virus Infectivity" *Journal of Virology*, 64(11):5270-5276.

Moss B et al. 1990 "New Mammalian Expression Vectors" *Nature*, 348:91-92.

Deng Hong et al. 1991, "High-Efficiency Protein Synthesis from T7 RNA Polymerase Transcripts in 3T3 Fibroblasts" *GENE*, pp. 193-201.

Goldman Mark E. et al. 1992, "L-696,229 Specifically Inhibits Human Immunodeficiency Virus Type 1 Reverse Transcriptase and Possesses Antiviral Activity In Vitro," 36(5):1019-1023.

Saari Walfred et al. 1991, "2-Pyridinone Derivatives: A New Class of Nonnucleoside, HIV-1 Spedivid Reverse Transcriptase Inhibitors," *Journal of Medicinal Chemistry*, 34(9):2922-2925.

Landau Nathaniel et al. 1991, "Pseudotyping with Human T-Cell Leukemia Virus Type 1 Broadens the Human Immunodeficiency Virus Host Range," *Journal of Medicinal Chemistry*, 34(9):2922-2925.

Nunberg Jack et al. 1991, "Viral Resistance to Human Immunodeficiency Virus Type-1 Specific Pyridinone Reverse Transcriptase Inhibitors," *Journal of Virology* 65(9):4887-4892.

St. Clair, M.H., et al. 1991, "Resistance to ddl and Sensitivity to AZT Induced by a Mutation in HIV-1 Reverse transcriptase" *Science*, 253:1557-1559.

Huang, Mingjun and Summers, Jesse 1991, "Infection Initiated by the RNA Pregenome of a DNA Virus" *Journal of Virology*, 65(10):5435-543.

Larder Brendan et al. 1991, "Zidovudine-Resistant Human Immunodeficiency Virus Selected by Passage in Cell Culture," *Journal of Virology*, 65(10):5232-5236.

Homberger F .R. et al. 1991, "Detection of Rodent Coronaviruses in Tissues and Cell Cultures by Using Polymerase Chain Reaction" *J. Clin. Microbiol.*, 29:2789-2793.

Yang Xian-Cbeng et al. 1991, "Cell-Specific Posttranslational Events Affect Functional Expression at the Plasma Membrane but not Tetrodotoxin Sensitivity of the Rat Brain VIA Sodium Channel a-Subunit Expressed in Mammalian Cells" *The Journal of Neuroscience* vol. 12(1):268-277.

Richman, Douglas D. 1992, "Antiretroviral Drug Resistance: Mechanisms, Pathogenesis, Clinical Significance," pp. 1-13.

Condra Jon et al. 1992, "Identification of the Human Immunodeficiency Virus Reverse Transcriptase Residues That Contribute to the Activity of Diverse Nonnucleoside Inhibitors," *Antimicrobial Agents and Chemotherapy* 36(7):1441-1446.

Trono, Didier, 1992, "Partial Reverse Transcripts in Virions from Human Immunodeficiency and Murine Leukemia Viruses" *Journal of Virology*, 66(8):4893-4900.

Franco et al. 1992, "viral DNA Carried by Human Immunodeficiency Virus Type 1 Virions" *Journal of Virology*, 66(8):5067-5074.

Larder, Brendan A., 1992, "3' Azido-3'-Deoxythymidine Resistance Suppressed by a Mutation Conferring Human Immunodeficiency Virus Type 1 Resistance to Nonnucleoside Reverse Transcriptase Inhibitors," *Antimicrobial Agents and Chemotherapy*,36(12):2664-2669.

Gu et al. 1992, "Novel Mutation in the Human Immunodeficiency Virus Type 1 Reverse Transcriptase Gene That Encodes Cross-Resistance to 2",3'-Dideoxyinosine and 2', 3'-Dideoxycytidine" *Journal of Virology*, 66(12): 7128-7135.

Baltimore, David, 1992, "The Treasure Under the Right Stone" *Reverse Transcriptase*, pp. 1-3.

Larder, Brendan A., 1992, "Inhibitors of HIV Reverse Transcriptase as Antiviral Agents and Drug Resistance," Chapter 11 Reverse Transcriptase pp. 205-222 Cold Spring Harbor Laboratory Press (1993).

Gao, Xiang, and Huang, Leaf, 1993, "Cytoplasmic Expression of a Reporter Gene by Co-Delivery of T7 RNA Polymerase and T7 Promoter Sequence with Cationic Liposomes" *Nucleic acids Research*, 21(12):267-2872.

Gottesman, Michael M., and Pastan, Ira, 1993, "Biochemistry of Multidrug Resistance Mediated by the Multidrug Transporter" *Annu. Rev. Biochem.*, 62:385-427.

Le Grice, Stuart FJ., 1993, "Human Immunodeficiency Virus Reverse Transcriptase" *Reverse Transcriptace* pp. 163-191.

Telesnitsky, Alice and Goff, Stephen P.,1993, "Strong-stop Strand transfer during Reverse Transcription" *Reverse Transcriptase*, pp. 49-83.

Wlodawer, Alexander and Erickson, John W., 1993, "StructureBased Inhibitors of HIV-1 1 Protease" *Annu. Rev. Biochem.*, 62:543-585.

Richman, Douglas D., 1993, "HIV Drug Resistance" *Annu. Rev. Pharmacol. Toxicol.*, 32:149-164.

Sandig et al. 1993, "A Phage T7 Class-III Promoter Functions as a Polymerase II Promoter in Mammalian Cells" *GENE*, pp. 255-259.

Lieber et al. 1993, "A Mutant T7 Phage Promoter is Specifically Transcribed by T7-RNA Polymerase in Mammalian Cells" *Eur. J. Biochem.*, 217:387-394.

Chattopadhyay et al. 1981, "Genomes of Murine Leukemia Viruses Isolated from Wild Mice" *Journal of Virology* vol. 39(3)3:777-791.

Richman, Douglas D., 1993, "Minireview, Resistance of Clinical Isolates of Human Immunodeficiency Virus to Antiretroviral Agents" *Antimicrobial Agents and Chemotherapy*, 37(6):1207-1213.

Richardson et al. 1993, "Packaging of Human Immunodeficiency Virus Type 1 RNA Requires cis-Acting Sequences Outside the 5' Leader Region" *Journal of Virology*, 67(7):3997-4005.

Byrnes, et al. 1993, "Comprehensive Mutant Enzyme and Viral Variant Assessment of Human Immunodeficiency Virus Type 1 Reverse Transcriptase Resistance to Nonnucleoside Inhibitors" *Antimicrobial Agents and Chemotherapy*, 37(8):1576-1579.

Emini et al. 1993, "HIV-1 Error Revealed" *Nature*, 364:679.

Balzarini et al. 1993, "Treatment of Human Immunodeficiency Virus Type 1 (HIV-1)-Infected Cells with Combinations of HIV-1-Specific Inhibitors Results in a Different Resistance Pattern Than Does Treatment with Single-Drug Therapy" *Journal of Virology*, 67(9):5353-5359.

Larder et al. 1993, "Convergent Combination Therapy can Select Viable Multidrug Multidrug-Resistant HIV-1 In Vitro" *Nature*, 365:451-453.

Sag et al. 1993, "A short Term Clinical Evaluation of L-697,661, A Non-Nucleoside Inhibitor of HIV-1 Reverse Transcriptase" *The New England Journal of Medicine*, 329(15):1065-1072.

Boyer et al. 1994, "Mutational Analysis of the Fingers and Palm Subdomains of Human Immunodeficiency Virus Type-1 (HIV-1) Reverse Transcriptase" *J. Mol. Biology*, 243:472-483.

Deng, Hong, and Wolff, Jon A., 1994, "Self-Amplifying Expression from the 17 Promoter in 3D Mouse Fibroblasts" *GENE*, pp. 245-249.

Richman, Douglas D., 1994, "Resistance, Drug Failure, and Disease Progression" *AIDS research and Human Retroviruses*, 10(8):901-905.

Ansari-Lari, M. Ali and Gibbs, Richard A., 1994, "Analysis of HIV Type 1 Reverse Transcriptase Expression in a Human Cell Line" *AIDS Research and Human Retroviruses*, 10(9): 1117-1124.

Katz, Richard A., and Skalka, Anna Marie 1994, "The Retroviral Enzymes" Annu. Rev. Biochem.63:133-173.

Chen et al. 1994, "A Self-Initiating Eukaryotic Transient Gene Expression System Based on Cotransfection of Bacteriophase T7 RNA Polymerase and DNA Vectors Containing a T7 Autogene" *NucleicAcids Research*, 22(11):2114-2120.

Kellam et al. 1994, "Zidovudine Treatment Results in the Selection of Human Immunodeficiency Virus Type 1 Variants Whose Genotypes Confer Increasing Levels of Drug Resistance" *Journal of General Virology*, 75:341-351.

Kellam, Paul, and Larder, Brendan A,. 1994, "Recombinant Virus Assay: a Rapid, Phenotypic Assay for Assissment of Drug Susceptibility of Human Immunodeficiency Virus Type 1 Isolates" *Antimicrobial Agents and Chemotherapy*, 38(1):23-30.

El-Farrash, et al. 1994, "Generation and Characterization of a Human Immunodeficiency Virus Type 1 (HIV-1) Mutant Resistant to an HIV-1 Protese Inhibitor" *Journal of Virology*, 68(1):233-239.

Chen et al. 1994, "Distant Modes of Human Immunodeficiency Virus Type 1 Proviral Latency Revealed by Superinfection of Nonproductively Infected Cell Lines with Recombinant Luciferase Encoded Viruses" *Journal of Virology*, 68(2):654-660.

Richman et al. 1994, "Nevirapine Resistance Mutations of Human Immunodeficiency Virus Type 1 Selected During Therapy" *Journal of Virology*, 68:1660-1666.

Ho et al.1994, "Characterization of Human Immunodeficiency Virus Type 1 Variants with Increased Resistance to a C2-Symmetric Protese Inhibitor" *Journal of Virology*, 68(3):2016-2020.

Brynes et al. 1994, "Susceptibilities of Human Immunodeficiency Virus Type 1 Enzyme and Viral Variants Expressing Multiple Resistance-Engendering Amino Acid Substitutions to Reverse Transcriptase Inhibitors" *Antimicrobial Agents and Chemotherapy*, 38(6):1404-1407.

Parolin et al. 1994, "Analysis in Human Immunodeficiency Virus Type 1 Vectors of cis-Acting Sequences That Affect Gene Transfer into Human Lymphocytes" *Journal of Virology*,68(6):3888-3895.

Carroll et al. 1994, "A Human Immunodeficiency Virus Type 1(HIV-1)-Based Retroviral Vectory System Utilizing Stable HIV-1 Packaging Cell Lines" *Journal of Virology*, 68(9):6047-6051.

Richman, Douglas D., 1994, "Drug Resistance in Viruses" Trends in Microbiology 2(10):401-408.

Zhang et al. 1994, "Intravirion Reverse Transcripts in the Peripheral Blood Plasma of luman Immunodeficiency Virus Type 1-Infected Individuals" *Journal of Virology*, 68(11):7591-7597.

Kalderon et al. 1984, "A Short Amino Acid Sequence Able to Specify Nuclear Location" *Cell*, 39:499-509.

Ho. David D. 1995, "Time to Hit HIV, Early and Hard" *The New England Journal of Medicine*, 333(7):450-451.

Wyatt et al. 1995, "Replication-Deficient Vaccinia Encoding Bacteriophage T7 RNA Polymerase for Transient Gene Expression in Mammalian Cells" *Virology*, 210:202-205.

Wei et al. 1995, "Viral Dynamics in Human Immunodeficiency Virus Type 1 Infection" *Nature*, 373:117-122.

Richman, Douglas D., 1995, "Drug Resistance in Relation to Pathogenesis" *AIDS*, 9(Suppl A):S49-S53.

Volberding, Paul, 1995, "The Need for Additional Options in the Treatment of Human Immunodeficiency Virus Infection" *The Journal of Infectious Diseases*, 17(Suppl 2):S150-S154.

Coffin, John M., 1996, "HIV Population Dynamics in Vivo: Implications for Genetic Variation, Pathogenesis, and Therapy" *Science*, 267:483-489.

Wain-Hobson, Simon, 1995, "Virological Mayhem" *Nature*, 373:102.

Ho et al. 1995, "Rapid Turnover of Plasma Virions and CD4 Lymphocytes in HIV-1 Infection" *Nature*, pp. 123-126.

D'Aquila et al. 1995, "Zidovudine Resistance and HIV-1 Disease Progression During Antiretroviral Therapy" *Annals of Internal Medicine*, 122(6):401-408.

Condra et al. 1995, "In Vivo Emergence of HIV-1 Variants Resistant to Multiple Protease Inhibitors" *Nature*, 374:569-571.

Boyer, Paul L., and Hughes, Stephen H., 1995, "Analysis of Mutations at Position 184 in Reverse Transcriptase of Human Immunodeficiency Virus Type 1" *Antimicrobial Agents and Chemotherapy*, 39(7):1624-1628.

Saunders, J., and Cameron, J.M., 1995, "Recent Development in the Design of Antiviral Agents" *Med Res. Rev.*, 15:497-531.

Young et al. 1995, "L-743,726 (DMP-266): a Novel, Highly Potent Nonnucleoside Inhibitor of the Human Immunodeficiency Virus Type 1 Reverse Transcriptase" *AntimicrobialAgents and Chemotherapy*, 39(12):2602-2605.

Goldman et al. 1993, "A Nonnucleoside Reverse Transcriptase Inhibitor Active on Human Immunodeficiency Virus Type 1 Isolates Resistant to Related Inhibitors" *Antimicrobial Agents and Chemotherapy*, 37(5):947-949.

Fang et al. 1996, "Molecular Cloning of Full-Length HIV-1 Genomes Directly from Plasma Viral RNA," *Journal of Acquired Immune Deficiency Syndromes and Human Retrovirology*, 12(4):352-357.

Heid et al. 1996, "Real Time Quantitative PCR" *Genome Research*, pp. 986-994.

Romeyn, Mary, 1996, "Report from the 3rd Conference of Retroviruses and Opportunistic Infections" *BETA* .

Schapiro, Jonathan, M., 1996, "Causes of Long Term Efficacy and/or Drug Failure in Protese (PR) Inhibitor Monotherapy" ICA Abstracts.

Mamtora et al. 1996, "HIV-1 Genechiptm and Dideoxynucleotide Sequence Analysis of HIV-1 Genomes Present in Plasma Samples from Patients of ACTG 143 Study" ICA Abstracts.

Garrett et al. 1996, "Sequencing HIV Isolates Using the Genechiptm HIV PRT Assay" ICA Abstracts.

Gingeras et al. "Detection of Rifampin Conferring Mutations and Mycobacteria Speciation Using Myco Genechiptm" ICA Abstracts.

Fischl, Margaret A., "Treatment of HIV Infection" Section II-Management of HIV Infections and Their Complications, Chapter 8, pp. 141-160.

Saag, Michael S. 1994, "AIDS Testing Now and in the Future" Section 1-The Virus: Its Transmission and Infection, Chapter 4, pp. 65-88.

Richman, Douglas, D., 1996, "Antiviral Drug Resistance: Issues and Challenges" Antiviral Drug Resistance, Introductory Chapter, pp. 1-19.

Japour, Anthony J., 1993, "Standardized Peripheral Blood Mononuclear Cell Culture Assay for Determination of Drug Susceptibilities of Clinical Human Immunodeficiency Virus Type 1 isolates" *Antimicrobial Agents and Chemotherapy*, 37:1095-1101.

Pauwels, Rudi, et al. 1988, "Rapid and Automated Tetrazoliumbased Colorimetric Assay for the Detection of anti-HIV Compounds" *Journal of Virological Methods*, 20:309-321.

Larder, B. A., 1994, "Interactions Between Drug Resistance Mutations In Human Immunodeficiency Virus Type 1 Reverse Transcriptase" *Journal of General Virology*, 75:951-957.

Piatak et al. 1993, "High Levels of HIV-1 In Plasma During All Stages of Infection Determined by Competitive PCR" *Science*, 259:1749-1754.

Popovic et al. 1984, "Detection, Isolation, and Continuous Production of Cytopathic Retroviruses (HTLV-III) From Patients With AIDS And Pre-AIDS" *Science*, 224:497-500.

Urdea, M. S., 1993, "Synthesis And Characterization of Branched DNA (bDNA) For The Direct And Quantitative Detection of CMV, HBV, HCV, and HIV" *Clin. Chem.*, 39:725-726.

Allain et al. 1987, "Long-Term Evaluation Of HIV Antigen And Antibodies To p24 And gp41 In Patients With Hemophilia" *N. EngL J. Med.*, 317:1114-1121.

Barre-Sinoussi et al. 1983, "Isolation Of A T-Lymphotrophic Retrovirus From A Patient At Risk For Acquired Immune Deficiency Syndrome (AIDS)" Science 220:868-871.

Geodert et al. 1987, "Effect Of T4 Count And Cofactors On The Incidence Of AIDS In Homosexual Men Infected With Human Immunodeficiency Virus", *JAMA*, 257:331-334.

Alam et al. 1990, "Reporter Genes: Application to the Study of Mammalian Gene Transcription," *Analytical Biochemistry*, 188:245-254.

Bernard, 1996, "Positive Selection of Recombinant DNA by CcdB," *Biotechniques*, 21:320-323.

Blight et al. 1990, "Efficient Initiation of HCV RNA Replication in Cell Culture," *Science*, 290:1972-1974.

Chalfie, 1995, "Green Fluorescent Protein," *Photochemistry and Photobiology*, 62:651-656.

Cheng et al.1999, "Specific Interaction Between the Hepatitis C Virus Ns5B RNA Polymerase and the 3' End of the Viral RNA," *J. Virol.*, 73:7044-7049.

Chowrira et al. 1994, "In Vitro and in Vivo Comparison of Hammerhead Hairpin, and Hepatitis Delta Virus Self Processing Ribozyme Cassettes," *J. Biol. Chem.*, 269: 25856-25864.

Chung et al.2001, "Hepatitis C Virus Replication Is Directly Inhibited By IFN-a in a Full Length Binary Expression System," 98:9847-9852.

Frese et al.I 2002, "Interferon-Inhbits Replication of Subgenomic and Genomic Hepatitis C Virus RNAs," *Hepatology*, 35:694-703.

Gould et al. 1998, "Firefly Luciferase as a Tool in Molecular and Cell Biology," *Analytical Biochemistry*, 175:5-13.

Grakoui et al. 1993, "Characterization of the Hepatitis C Virus-Encoded Serine Proteinase: Determination of Proteinase-Dependent Polyprotein Cleavage Sites," *J. Virol.,*, 67:2832-2843.

Guo et al. 2001, "Effect of Alpha Interferon on the Hepatitis C Virus Replicon," *J. Virol.,*, 75:8516-8523.

Hiramatsu et al. 1997, "HCV cDNA Transfection to HepG2 Cells," *J. Viral Hepatol.*, 4(suppl. 1):61-67.

Hoshida et al. 2001, "Improvement of Chemosensitivity Prediction by Transcriptional Profiling in Hepatorna Cells," *Genome Informatics*, 12:257-58.

Ikeda et al. 2002, "Selectable Subgenomic and Genome-Length Dicistronic RNAs Derived from an Infectious Molecular Clone of the HCV-N Strain of Hepatitis C Virus Replicate Efficiently in Cultured Huh7 Cells" *J. Virol.,*, 76:2997-3006.

Kawai et al.I 2001, "a-Fetoprotein-Producing Hepatoma Cell Lines Share Common Expression Profiles of Genes in Various Categories Demonstrated by cDNA Microarray Analysis" *Hepatology*, 33:676-691.

Krieger et al. 2001, "Enhancement of Hepatitis C Virus RNA Replication by Cell Culture-Adaptive Mutations," *J. Virol* 75:4614-24.

Lohmann et al. 1999, "Replication of SubgenorrOc Hepatitis C Virus RNAs in a Hepatoma Cell Line" *Science*, 285:110-113.

Lohmann et al. 2001, "Mutations in Hepatitis C Virus RNAs Conferring Cell Culture Adaptation," *J. Virol.,*, 75:1437-1449.

Mizutani et al. 1996, "Characterization of Hepatitis C Virus Replication in Cloned Cells Obtained from a Human T-Cell Leukemia Virus Type 1-Infected Cell Line, MT-2," *J. Virol.,*, 70:7219-7223.

Moore et al. 1997, "The Development of P-Lactamase as a Highly Versatile Genetic Reporter for Eukaryotic Cells," *Analytical Chemistry*, 247:203-209.

Mulligan et al. 1980, "Expression of a Bacterial Gene in Mammalian Cells," *Science*, 209: 1422-1427.

Olesen et al. 1990, Detection of P-Glactosidase and P-Glucuronidase Using Chemiluminescent Reporter Gene Assays, Methods in Molecular Biology, Recombinant Protein Protocols: Detection and Isolation, 63:61-70.

Perotta et al. "A Pseudoknot-Like Structure Required for Efficient Self-Cleavage of Hepatitis Delta Virus RNA," *Nature*, 350:434-436.

Pflugheber et al. 2002, "Regulation of PKR and IRF-1 During Hepatitis C Virus RNA Replication," *PNAS*, 99:4650-4655.

Pietsch, et al. 1996, "Characterization of the Continuous Cell Line HepTl Derived from a Human Hepatoblastoma," *Lab Invest* 74:809-818.

Pietschmann et al. 2002, "Persistent and Transient Replication of Full Length Hepatitis C Virus Gernomes in Cell Culture," *Virol.*, 76:4008-4021.

Schenborn et al. 1999, "Reporter Gene Vectors and Assays," *Molecular Biotechnology*, 13:29-44.

Shimizu et al. 1994, "Neutralizing Antibodies Against Hepatitis C Virus and the Emergence of Neutralization Escape Mutant Viruses," *J. Virol.*, 68:1494-1500.

Shimizu et al. 1994, "Multicycle Infection of Hepatitis C Virus in Cell Culture and Inhibition by Alpha and Beta Interferons," *J. Virol.*, 68:8406-8408.

Shimizu et al. 1993, "Correlation Between the Infectivity of Hepatitis C Virus In Vivo and its Infectivity In Vitro," (1993), *PNAS*, 90:6037-6041.

Shimizu et al. 1992, "Evidence for In Vitro Replication of Hepatitis C Virus Genome in a Human T-Cell Line," (1992), *PNAS*, 89:5477-5481.

Southern et al. 1982, "Transformation of Mammalian Cells to Antibiotic Resistance with a Baterial Gene Under Control of the SV40 Early Region Promoter," *J. Molec. Appl. Genet.*, 1:327-341.

Steinkühler et al. 1996, "Activity of Purified Hepatitis C Virus Protease NS3 on Peptide Substrates," *J. Virol.*, 70:6694-6700.

Sugden et al. 1985, "A Vector that Replicates as a Plasmid and can be Efficiently Selected in B-Lymphoblasts Transformed by Epstein-Barr Virus," *Mol, Cell. Biol.*, 5, 410-413.

Valli at al. 1997, "*Hepatitis C Virus* Infection *of a Vero* Cell Clone Displaying *Efficient* Virus-Cell Binidng," *Res. Virol.*, 148:181-186.

Vassilev et al. 1997, "Authentic and Chimeric Full-Length Genomic cDNA Clones of Bovine Viral Diarrhea Virus That Yield Infectious Transcripts," *J. Virol.*, 71:471-478.

Wadkins at al., 2002, "Ribozyme Activity in the Genomic and Antigenomic RNA Strands of Hepatitis Delta Virus," *Cell Mal. Life Sci.*, 59:112-25.

Witherell et al. 2001, "Statistical Analysis *of* Combined Sustitutions *in* Nonstructural 5 *A Region of* Hepatitis C Virus and Interferon Responses," *J. Med. Virol.*, 63:8-16.

Wright-Minogue et al. 2000, "Cross-Genotypic interaction Between Hepatitis C Virus NS3 Protease Domains and NS4A Cofactors," *J. Hepatology*, 32:497-504.

Yang et al. 1997, "*Quantification of Gene* Expression *with a* Secreted Alkaline Phosphatase Reporter System," *BioTechniques*, 23:1110-1114.

Yoo et al.1995, "Transfection of a Differentiated Human Hepatoma Cell Line (Huh7) with In Vitro-Transcribed Hepatitis C Virus (HCV) RNA and Establishment of a Long-Term Culture Persistently Infected With HCV," 69:32-38.

Zlokarnik, 2000, "Fusions to 13-Lactamase as a Reporter for Gene Expression in Live Mammalian Cells," *Methods in Enzymology*, 326:221-241.

Danos, Olivier and Mulligan, Richard C. 1988, "Safe and Efficient Generation of Recombinant Retroviruses with Amphotropic and Ecotropic Host Ranges" *Proc. Nat !. Acad Sci. USA*, 85:6460-6464.

Fuerst, Thomas R., and Moss, Bernard 1989, "Structure and Stability of mRNA Synthesized by Vaccinia Virus-encoded Bacteriophage 17 RNA Polymerase in Mammalian Cells" *J. Mol. Biol.*, 206:333-348.

Lieber et al. 1989, "High Level Gene Expression in Mammalian Cells by a Nuclear 17-Phage RNAPolymerase" *Nucleic Acids Research*, 17(21):8485-8493.

Larder et al. 1989, "HIV with Reduced Sensitivity to Zidovudine (AZT) Isolated During Prolonged Therapy," *Science*, vol. 243, pp. 1731-1734.

Andreasson et al. 1989, "Production of Pro-Opiomelanocortin (POMC) by a Vaccinia Virus Trasient Expression System and In Vitro Processing of the Expressed Prohormone by POMC-converting Enzyme" *FEBS Letters*, 248(12):43-47.

Elroy-Stein et al. 1989, "Cap-Independent Translation of mRNA Conferred by Encephalomyocarditis Virus 5' Sequence Improves the Performance of the Vaccinia Virus/ Bacteriophage T7 Hybrid Expression System" *Proc. Natl. Acad. Sci. USA*, 86:6126-6130.

Larder, Brendan A., and Sharon D.Kemp, 1989, "Multiple Mutations in HIV-1 Reverse Transcriptase confer High-Level Resistance of Zidovudine (AZT)" *Science*, 246:1155-1158.

Elroy-Stein, Orna and Bernard Moss, 1990, "Cytoplasmic Expression System Based on Constructive Synthesis of Bacteriophage T7 RNA Polymerase in Mammalian Cells" *Proc. Natl. Acad. Sci. USA*, 87:6743-6747.

Page et al.1990, "Construction and Use of a Human Immunodeficiency Virus Vector for Analysis of Virus Infectivity" *Journal of Virology*, 64(11):5270-5276.

Moss, B et al. 1990, "New Mammalian Expression Vectors," *Nature*, 348:91-92.

Deng, Hong, et al. 1991, "High-Efficiency Protein Synthesis from T7 RNA Polymerase Transcripts in 3T3 Fibroblasts," *GENE*, pp. 193-201.

Goldman, Mark E., et al. 1992, "L-696,229 Specifically Inhibits Human Immunodeficiency Virus Type 1 Reverse Transcriptase and Possesses Antiviral Activity In Vitro" *Antimicrobial Agents and Chemotherapy*, 36(5):1019-1023.

Saari et al. 1991, "2-Pyridinone Derivatives: A New Class of Nonnucleoside, HIV-1 Spedivid Reverse Transcriptase inhibitors" *Journal of Medicinal Chemistry*, 34(9):2922-2925.

Landau et al. 1991, "Pseudotyping with Human T-Cell Leukemia Virus Type I Broadens the Human immunodeficiency Virus Host Range" *Journal of Medicinal Chemistry*, 34(9):2922-2925.

\* cited by examiner

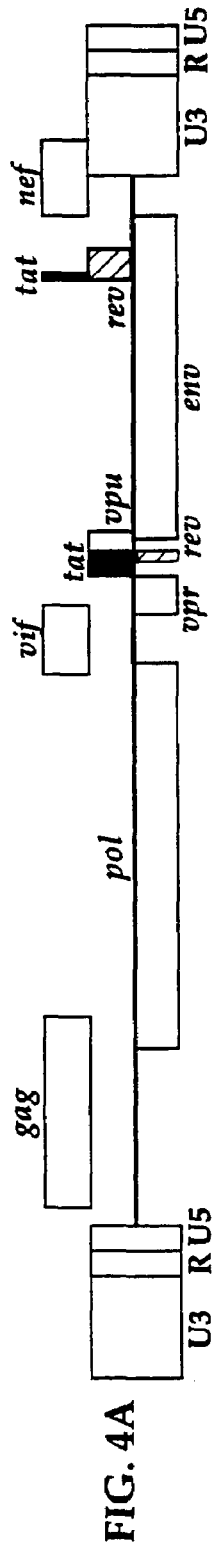
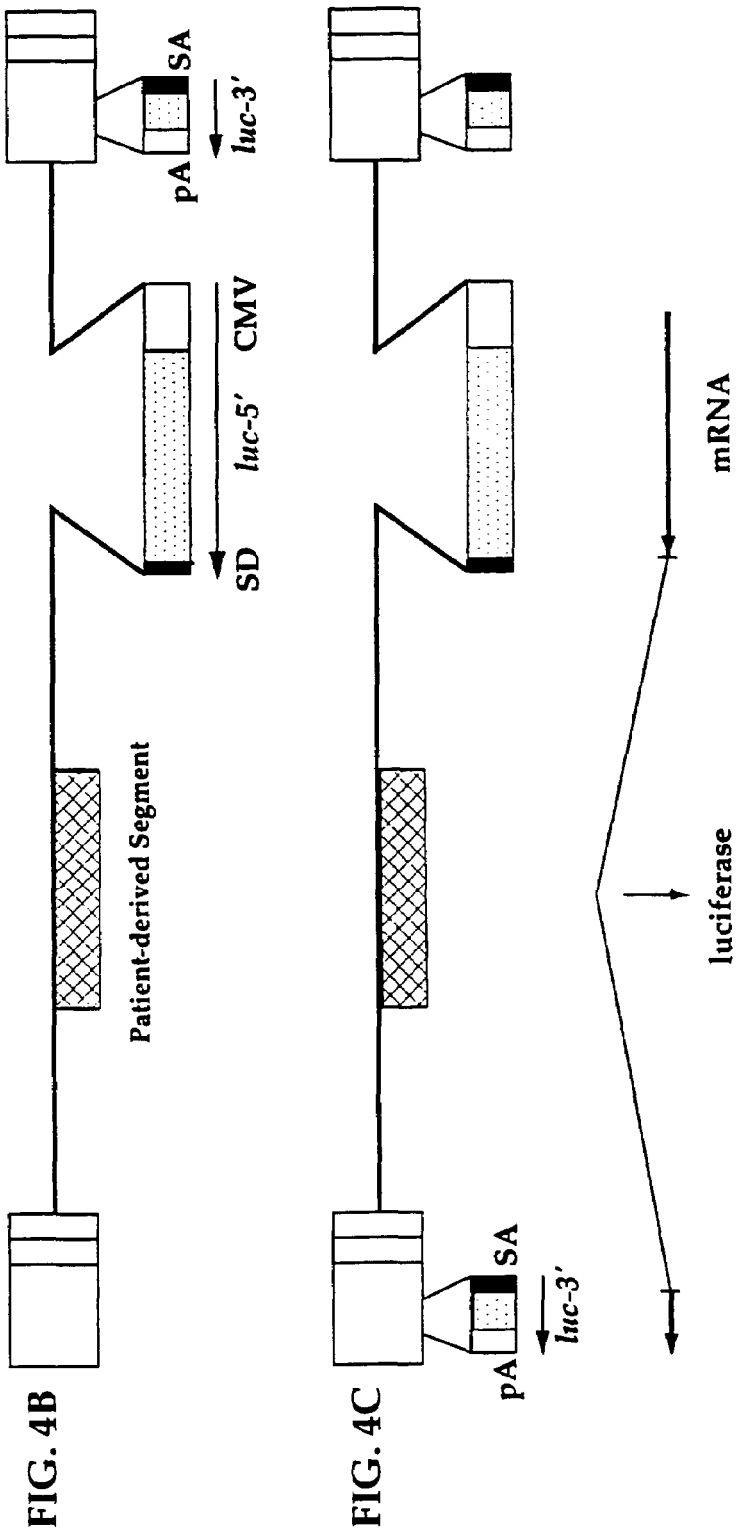
FIG. 4A
FIG. 4B
FIG. 4C

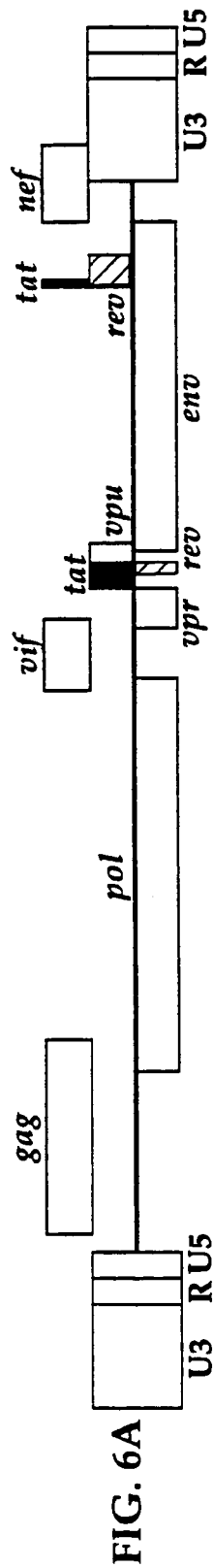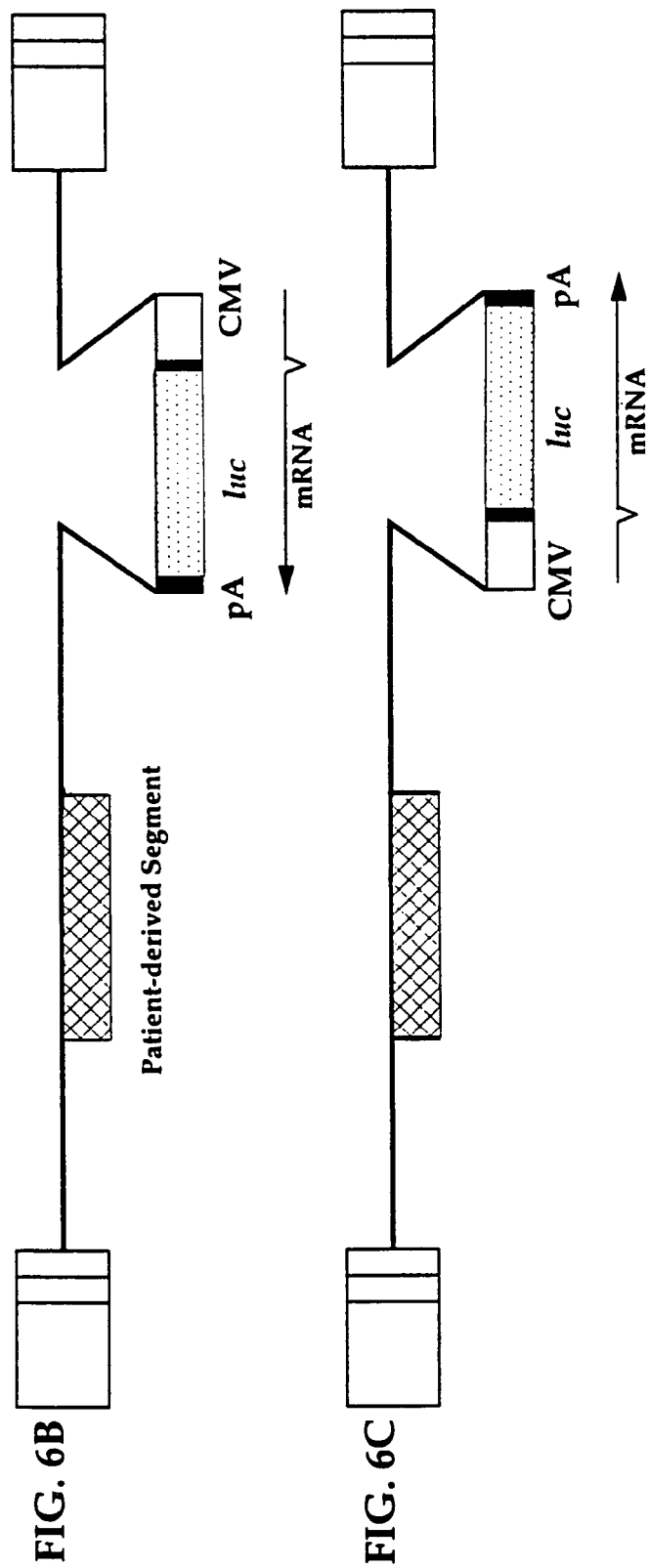
FIG. 6A  FIG. 6B  FIG. 6C

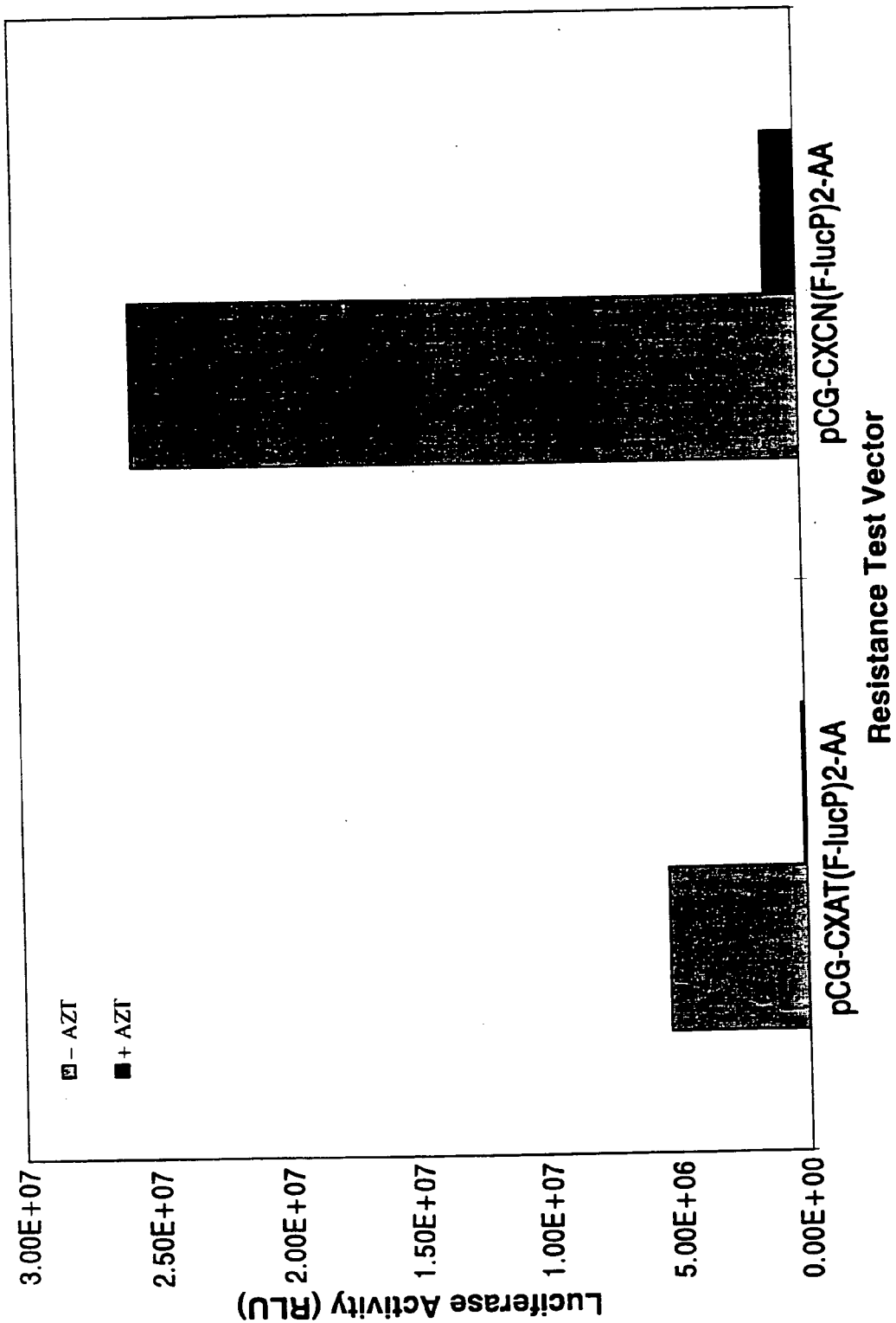

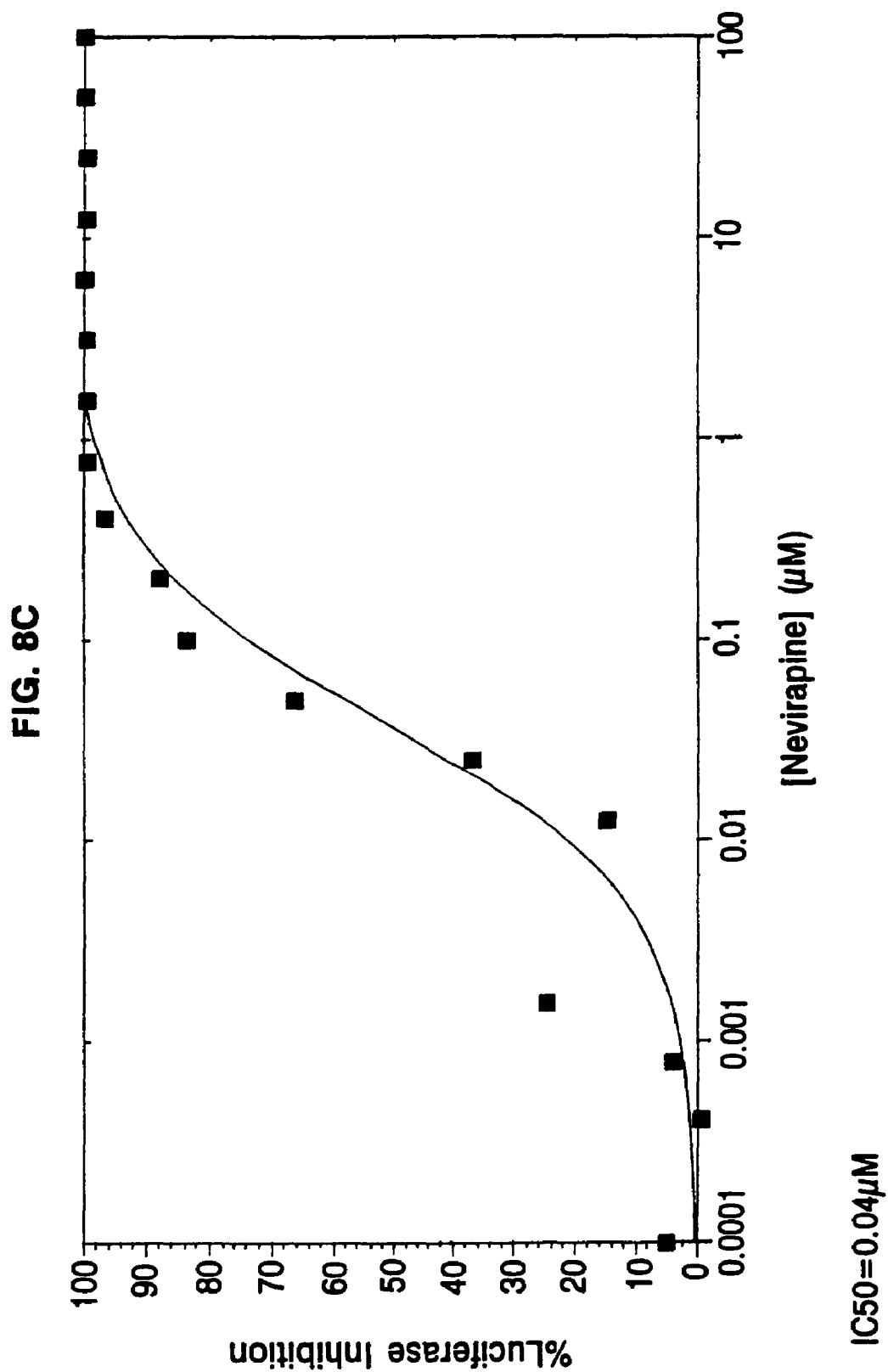

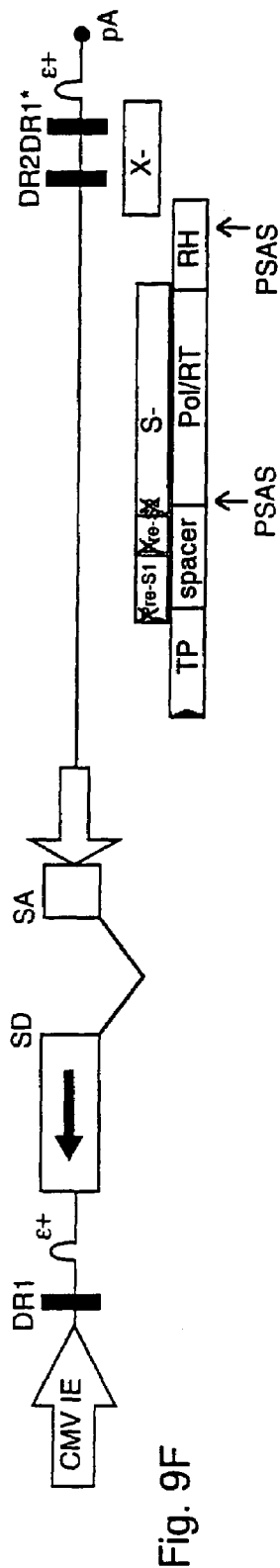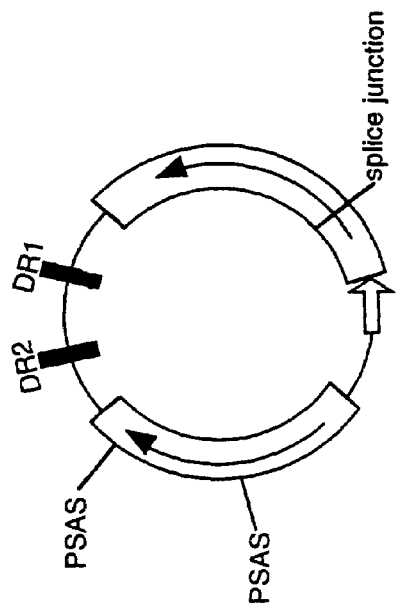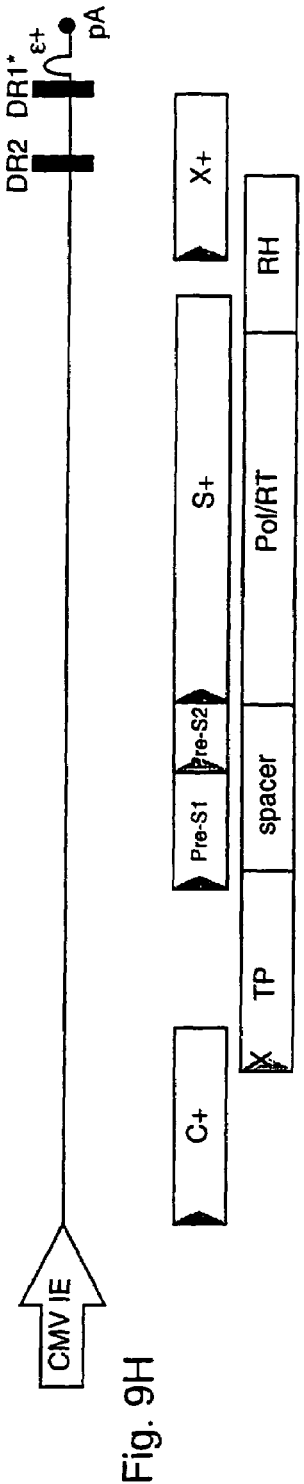
Fig. 9F
Fig. 9G
Fig. 9H

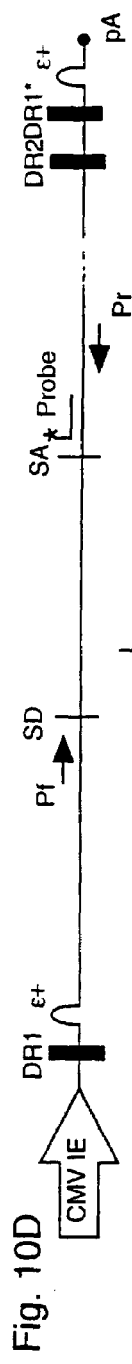
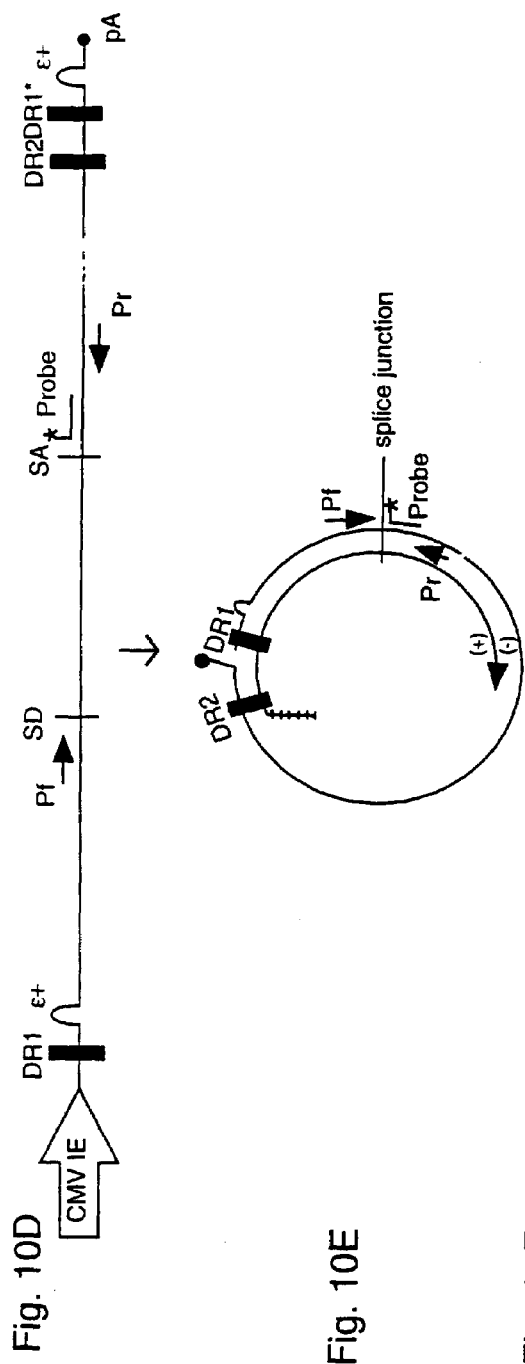
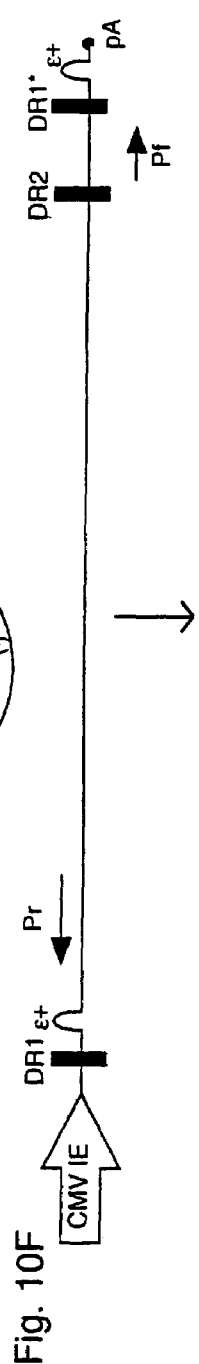
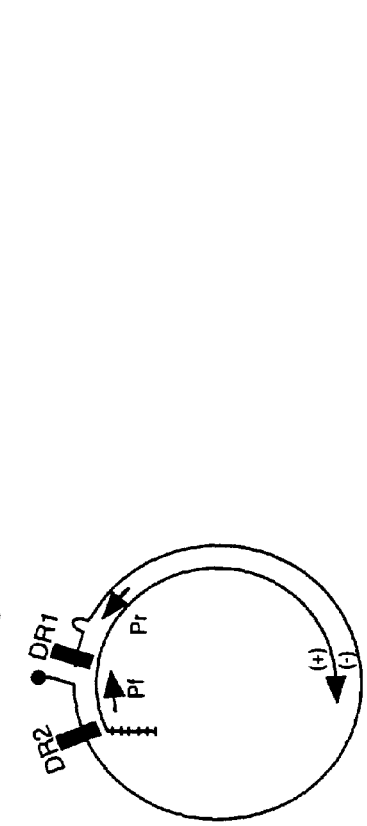
Fig. 10D
Fig. 10E
Fig. 10F
Fig. 10G

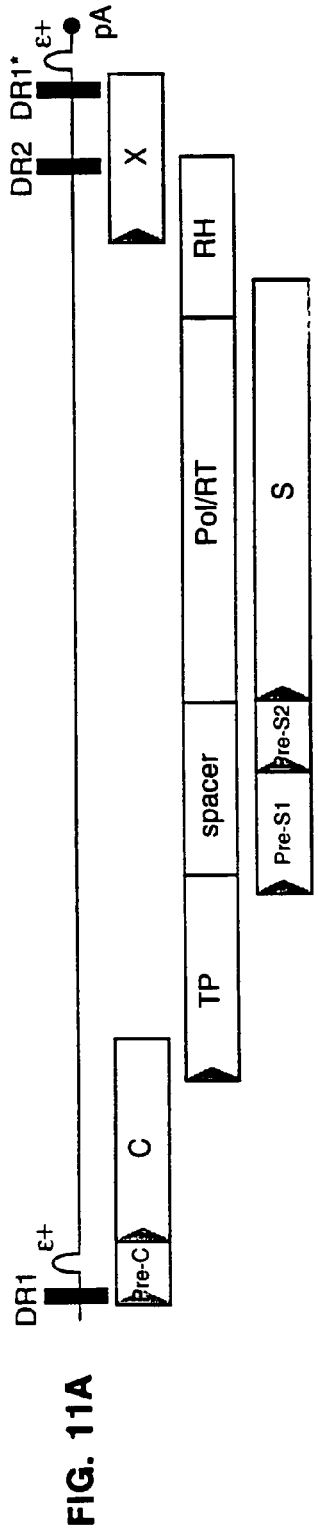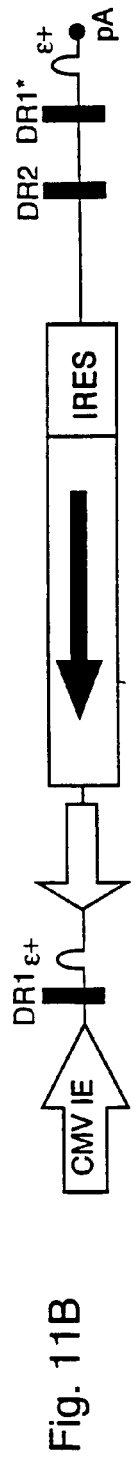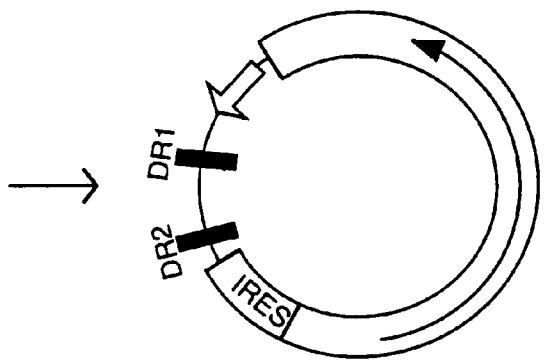
FIG. 11A
Fig. 11B
Fig. 11C

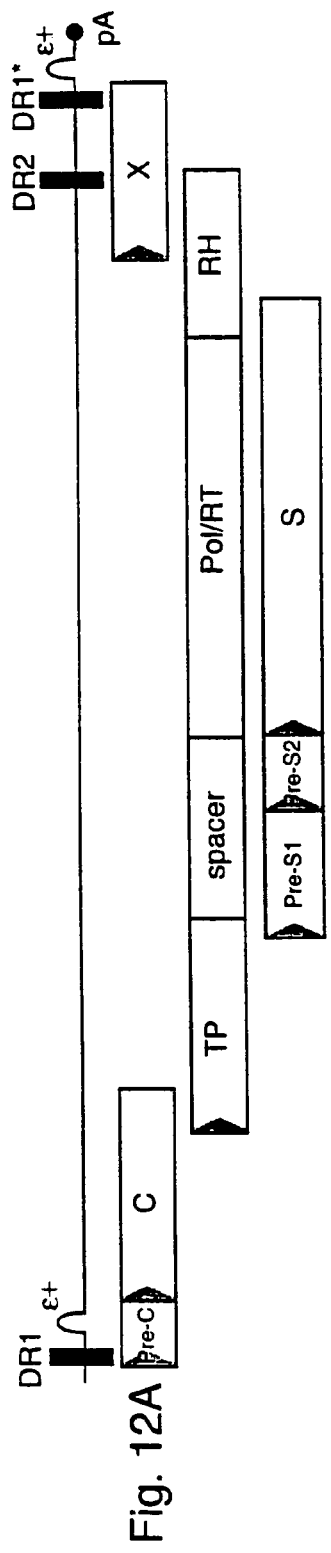
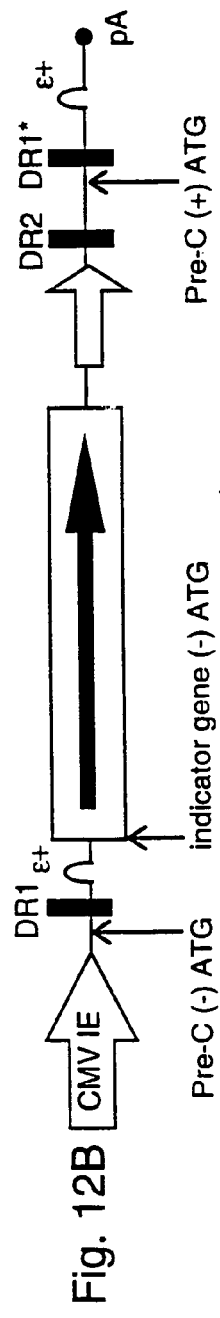
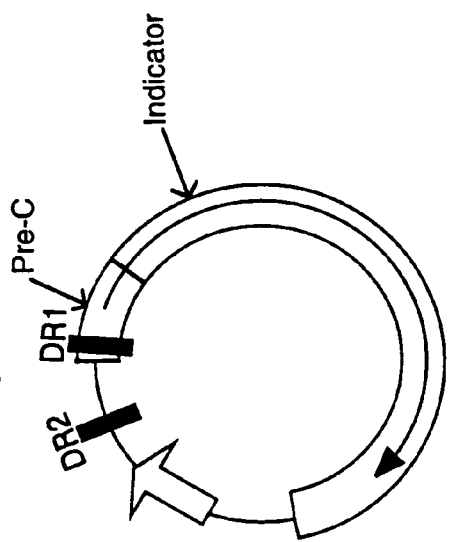
Fig. 12A
Fig. 12B
Fig. 12C

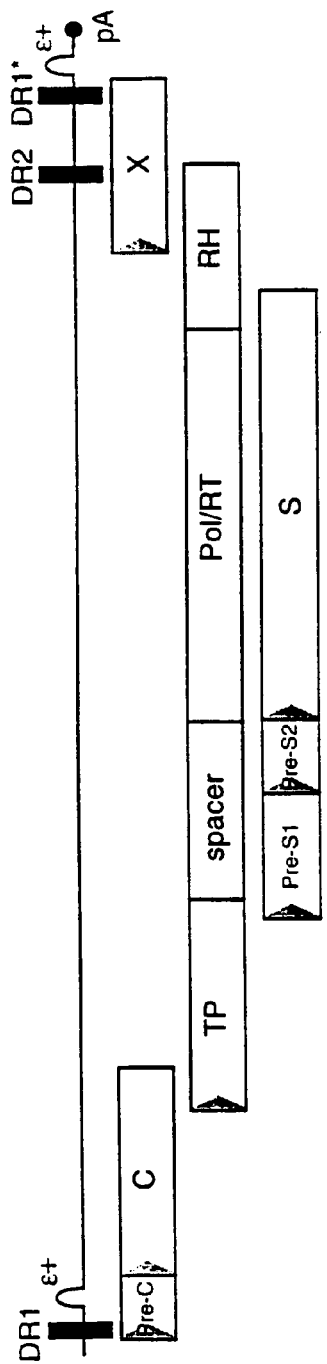
Fig. 14A
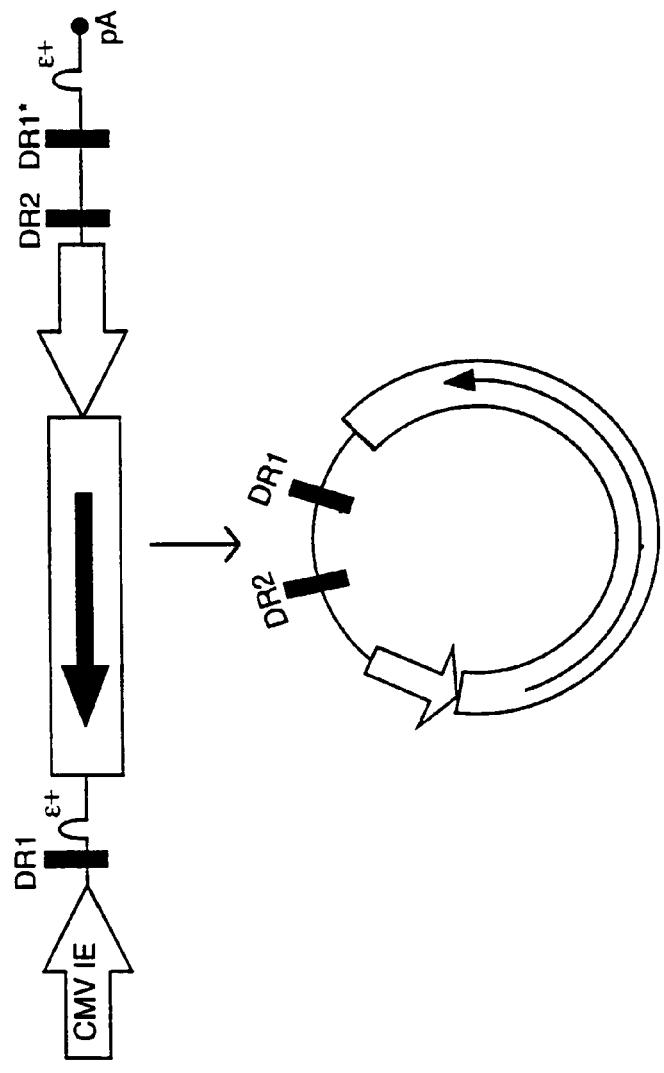
Fig. 14B
Fig. 14C

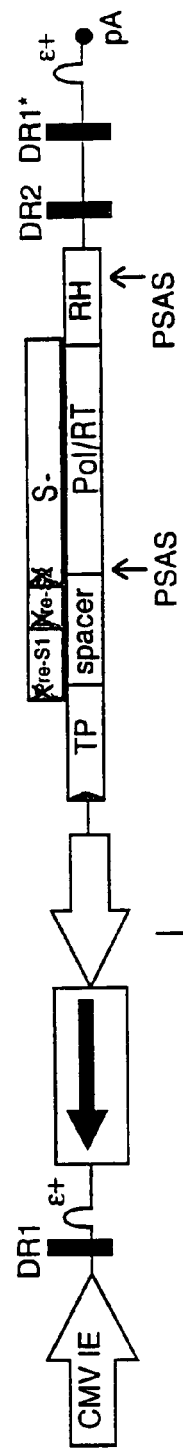
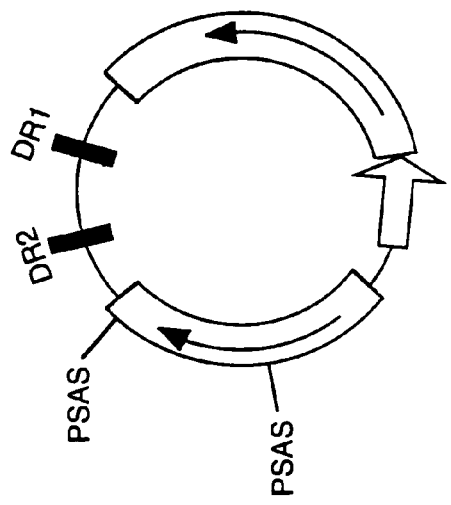
Fig. 14D
Fig. 14E

COMPOSITIONS AND METHODS FOR DETERMINING ANTI-VIRAL DRUG SUSCEPTIBILITY AND RESISTANCE AND ANTI-VIRAL DRUG SCREENING

This is a continuation of and claims priority under 37 C.F.R. § 1.53(b) to each of U.S. application Ser. No. 09/875,082, filed Jun. 5, 2001, now U.S. Pat. No. 6,942,969 which is a continuation of U.S. application Ser. No. 09/371,774, filed Aug. 10, 1999, and which issued as U.S. Pat. No. 6,242,187 on Jun. 5, 2001, which is a continuation in part of U.S. application Ser. No. 08/903,507, filed Jul. 30, 1997, now abandoned, which is a continuation-in-part of U.S. application Ser. No. 08/790,963, filed Jan. 29, 1997, and which issued as U.S. Pat. No. 5,837,464 on Nov. 17, 1998, which claims the benefit of U.S. Provisional Application No. 60/010,715, filed Jan. 29, 1996, the contents of which are each hereby incorporated by reference in their entirety.

TECHNICAL FIELD

This invention relates to anti-viral drug susceptibility and resistance tests to be used in identifying effective drug regimens for the treatment of viral infections. The invention further relates to novel vectors, host cells and compositions for carrying out these novel anti-viral drug susceptibility and resistance tests. This invention also relates to the screening of candidate drugs for their capacity to inhibit selected viral sequences and/or viral proteins. More particularly, the invention relates to the use of recombinant DNA technology to first construct a resistance test vector comprising a patient-derived segment and an indicator gene, then introducing the resistance test vector into a host cell, and determining the expression or inhibition of the indicator gene product in a target host cell in the presence of an anti-viral drug. This invention is also related to the means and methods of identifying anti-viral drugs which have distinct patterns of resistance when compared with existing anti-viral drugs. This invention also relates to methods and compositions for the identification and assessment of the biological effectiveness of potential therapeutic compounds. This invention is more particularly related to drug susceptibility and resistance tests useful in providing an optimal therapeutic regimen for the treatment of various viral diseases, including for example, HIV/AIDS and hepatitis.

BACKGROUND OF THE INVENTION

Viral Drug Resistance

The use of anti-viral compounds for chemotherapy and chemoprophylaxis of viral diseases is a relatively new development in the field of infectious diseases, particularly when compared with the more than 50 years of experience with antibacterial antibiotics. The design of anti-viral compounds is not straightforward because viruses present a number of unique problems. Viruses must replicate intracellularly and often employ host cell enzymes, macromolecules, and organelles for the synthesis of virus particles. Therefore, safe and effective anti-viral compounds must be able to discriminate with a high degree of efficiency between cellular and virus-specific functions. In addition, because of the nature of virus replication, evaluation of the in vitro sensitivity of virus isolates to anti-viral compounds must be carried out in a complex culture system consisting of living cells (e.g. tissue culture). The results from such assay systems vary widely according to the type of tissue culture cells which are employed and the conditions of assay. Despite these complexities nine drugs have been approved for AIDS therapy, five reverse transcriptase inhibitors AZT, ddI, ddC, d4T, 3TC, one non-nucleoside reverse transcriptase inhibitor, nevirapine and three protease inhibitors saquinavir, ritonavir and indinovir and several additional anti-viral drug candidates have been recently developed such as nelfinavir, delaviridine, VX-478 and 1592.

Viral drug resistance is a substantial problem given the high rate of viral replication and mutation frequencies. Drug resistant mutants were first recognized for poxviruses with thiosemicarbazone (Appleyard and Way (1966) *Brit. J. Exptl. Pathol.* 47, 144-51), for poliovirus with guanidine (Melnick et al. (1961) *Science* 134, 557), for influenza A virus with amantadine (Oxford et al. (1970) *Nature* 226, 82-83; Cochran et al. (1965) *Ann. NY Acad Sci* 130, 423-429) and for herpes simplex virus with iododeoxyuridine (Jawetz et al. (1970) *Ann. NY Acad Sci* 173, 282-291). Approximately 75 HIV drug resistance mutations to various anti-viral agents have been identified to date (Mellors et al. (1995) *Intnl. Antiviral News*, supplement and Condra, J. H. et al. (1996) *J. Virol.* 70, 8270-8276).

The small and efficient genomes of viruses have lent themselves to the intensive investigation of the molecular genetics, structure and replicative cycles of most important human viral pathogens. As a consequence, the sites and mechanisms have been characterized for both the activity of and resistance to anti-viral drugs more precisely than have those for any other class of drugs. (Richman (1994) *Trends Microbiol.* 2, 401-407). The likelihood that resistant mutants will emerge is a function of at least four factors: 1) the viral mutation frequency; 2) the intrinsic mutability of the viral target site with respect to a specific anti-viral; 3) the selective pressure of the anti-viral drug; and, 4) the magnitude and rate of virus replication. With regard to the first factor, for single stranded RNA viruses, whose genome replication lacks a proofreading mechanism, the mutation frequencies are approximately $3 \times 10^{-5}$ per base-pair per replicative cycle (Holland et al. (1992) *Curr. Topics Microbiol Immunol.* 176, 1-20; Mansky et al. (1995) *J. Virol.* 69, 5087-94; Coffin (1995) *Science* 267, 483-489). Thus, a single 10 kilobase genome, like that of human immunodeficiency virus (HIV), would be expected to contain on average one mutation for every three progeny viral genomes. As to the second factor, the intrinsic mutability of the viral target site in response to a specific anti-viral agent can significantly affect the likelihood of resistant mutants. For example, zidovudine (AZT) selects for mutations in the reverse transcriptase of HIV more readily in vitro and in vivo than does the other approved thymidine analog d4T (stavudine).

One, perhaps inevitable consequence of the action of an anti-viral drug is that it confers sufficient selective pressure on virus replication to select for drug-resistant mutants (Herrmann et al. (1977) *Ann NY Acad Sci* 284, 632-7). With respect to the third factor, with increasing drug exposure, the selective pressure on the replicating virus population increases to promote the more rapid emergence of drug resistant mutants. For example, higher doses of AZT tend to select for drug resistant virus more rapidly than do lower doses (Richman et al. (1990) *J. AIDS.* 3, 743-6). This selective pressure for resistant mutants increases the likelihood of such mutants arising as long as significant levels of virus replication are sustained.

The fourth factor, the magnitude and rate of replication of the virus population, has major consequences on the likelihood of emergence of resistant mutants. Many virus infections are characterized by high levels of virus replication with high rates of virus turnover. This is especially true of chronic infections with HIV as well as hepatitis B and C viruses. The likelihood of emergence of AZT resistance increases in HIV-infected patients with diminishing CD4 lymphocyte counts which are associated with increasing levels of HIV replication (Ibid).

Higher levels of virus increase the probability of preexisting mutants. It has been shown that the emergence of a resistant population results from the survival and selective proliferation of a previously existing subpopulation that randomly emerges in the absence of selective pressure. All viruses have a baseline mutation rate. With calculations of approximately $10^{10}$ new virions being generated daily during HIV infection (Ho et al. (1995) *Nature* 373, 123-126), a mutation rate of $10^{-4}$ to $10^{-5}$ per nucleotide guarantees the preexistence of almost any mutation at any time point during HIV infection. Evidence is accumulating that drug resistant mutants do in fact exist in subpopulations of HIV infected individuals (Najera et al. (1994) *AIDS Res Hum Retroviruses* 10, 1479-88; Najera et al. (1995) *J. Virol.* 69, 23-31). The preexistence of drug resistant picornavirus mutants at a rate of approximately $10^{-5}$ is also well documented (Ahmad et al. (1987) *Antiviral Res.* 8, 27-39).

Human Immunodeficiency Virus (HIV)

Acquired immune deficiency syndrome (AIDS) is a fatal human disease, generally considered to be one of the more serious diseases to ever affect humankind. Globally, the numbers of human immunodeficiency virus (HIV) infected individuals and of AIDS cases increase relentlessly and efforts to curb the course of the pandemic, some believe, are of limited effectiveness. Two types of HIV are now recognized: HIV-1 and HIV-2. By Dec. 31, 1994 a total of 1,025,073 AIDS cases had been reported to the World Health Organization. This is only a portion of the total cases, and WHO estimates that as of late 1994, allowing for underdiagnosis, underreporting and delays in reporting, and based on the estimated number of HIV infections, there have been over 4.5 million cumulative AIDS cases worldwide (Mertens et al. (1995) *AIDS* 9 (Suppl A), S259-S272). Since HIV began its spread in North America, Europe and sub-Saharan Africa, over 19.5 million men, women and children are estimated to have been infected (Ibid). One of the distinguishing features of the AIDS pandemic has been its global spread within the last 20 years, with about 190 countries reporting AIDS cases today. The projections of HIV infection worldwide by the WHO are staggering. The projected cumulative total of adult AIDS cases by the year 2000 is nearly 10 million. By the year 2000, the cumulative number of HIV-related deaths in adults is predicted to rise to more than 8 million from the current total of around 3 million.

HIV-1 and HIV-2 are enveloped retroviruses with a diploid genome having two identical RNA molecules. The molecular organization of HIV is (5') U3-R-U5-gag-pol-env-U3-R-U5 (3') as shown in FIG. 1a. The U3, R, and U5 sequences form the long terminal repeats (LTR) which are the regulatory elements that promote the expression of the viral genes and sometimes nearby cellular genes in infected hosts. The internal regions of the viral RNA code for the structural proteins: gag (p55, p17, p24 and p7 core proteins), pol (p10 protease, p66 and p51 reverse transcriptase and p32 integrase) and env (gp120 and gp41 envelope glycoproteins). Gag codes for a polyprotein precursor that is cleaved by a viral protease into three or four structural proteins; pol codes for reverse transcriptase (RT) and the viral protease and integrase; env codes for the transmembrane and outer glycoprotein of the virus. The gag and pol genes are expressed as a genomic RNA while the env gene is expressed as a spliced subgenomic RNA. In addition to the env gene there are other HIV genes produced by spliced subgenomic RNAs that contribute to the replication and biologic activities of the virus. These genes include: tat which encodes a protein that activates the expression of viral and some cellular genes; rev which encodes a protein that promotes the expression of unspliced or single-spliced viral mRNAs; nef which encodes a myristylated protein that appears to modulate viral production under certain conditions; vif which encodes a protein that affects the ability of virus particles to infect target cells but does not appear to affect viral expression or transmission by cell-to-cell contact; vpr which encodes a virion-associated protein; and vpu which encodes a protein that appears to promote the extracellular release of viral particles.

No disease better exemplifies the problem of viral drug resistance than AIDS. Drug resistant HIV isolates have been identified for nucleoside and non-nucleoside reverse transcriptase inhibitors and for protease inhibitors. The emergence of HIV isolates resistant to AZT is not surprising since AZT and other reverse transcriptase inhibitors only reduce virus replication by about 90%. High rates of virus replication in the presence of the selective pressure of drug treatment provide ideal conditions for the emergence of drug-resistant mutants. Patients at later stages of infection who have higher levels of virus replication develop resistant virus with AZT treatment more quickly than those at early stages of infection (Richman et al. (1990) *J AIDS* 3, 743-6). The initial description of the emergence of resistance to AZT identified progressive and stepwise reductions in drug susceptibility (Larder et al. (1989) *Science* 243, 1731-1734). This was explained by the recognition of multiple mutations in the gene for reverse transcriptase that contributed to reduced susceptibility (Larder et al. (1989) *Science* 246, 1155-1158). These mutations had an additive or even synergistic contribution to the phenotype of reduced susceptibility (Kellam et al. (1992) *Proc. Natl. Acad. Sci.* 89, 1934-1938). The cumulative acquisition of such mutations resulted in progressive decreases in susceptibility. Similar effects have been seen with non-nucleoside reverse transcriptase inhibitors (Nunberg et al. (1991) *J Virol* 65, 4887-4892; Sardanna et al. (1992) *J Biol Chem* 267, 17526-17530). Studies of protease inhibitors have found that the selection of HIV strains with reduced drug susceptibility occurs within weeks (Ho et al. (1994) *J Virol* 68, 2016-2020; Kaplan et al. (1994) *Proc. Natl. Acad. Sci.* 91, 5597-5601). While recent studies have shown protease inhibitors to be more powerful than reverse transcriptase inhibitors, nevertheless resistance has developed. (Condra et al., Id. and Report 3rd Conference on Retroviruses and Opportunistic Infections, March 1996). Subtherapeutic drug levels, whether caused by reduced dosing, drug interactions, malabsorption or reduced bioavailability due to other factors, or self-imposed drug holidays, all permit increased viral replication and increased opportunity for mutation and resistance. (Id.)

The selective pressure of drug treatment permits the outgrowth of preexisting mutants. With continuing viral replication in the absence of completely suppressive antiviral drug activity, the cumulative acquisition of multiple mutations can occur over time, as has been described for AZT and protease inhibitors of HIV. Indeed viral mutants multiply resistant to different drugs have been (observed (Larder et al. (1989) *Science* 243, 1731-1734; Larder et al. (1989) *Science* 246, 1155-1158; Condra et al. (1995) *Nature*

374, 569-71). With the inevitable emergence of resistance in many viral infections, as with HIV for example, strategies must be designed to optimize treatment in the face of resistant virus populations. Ascertaining the contribution of drug resistance to drug failure is a difficult problem because patients who are more likely to develop drug resistance are more likely to have other confounding factors that will predispose them to a poor prognosis (Richman (1994) *AIDS Res Hum Retroviruses* 10, 901-905). In addition patients contain mixtures of viruses with different susceptibilities.

Hepatitis B (HBV)

HBV is a causative agent for acute and chronic hepatitis, which strikes about 200 million patients worldwide. Zuckerman A. J. *Trans. R. Soc. Trop. Med. Hygiene* (1982) 76, 711-718. HBV infection acquired in adult life is often clinically inapparent, and most acutely infected adults recover completely from the disease and clear the virus. Rarely, however, the acute liver disease may be so severe that the patient dies of fulminant hepatitis. A small fraction, perhaps 5 to 10%, of acutely infected adults, becomes persistently infected by the virus and develops chronic liver disease of varying severity. Neonatally transmitted HBV infection, however, is rarely cleared, and more than 90% of such children become chronically infected. Because HBV is commonly spread from infected mother to newborn infant in highly populated areas of Africa and Asia, several hundred million people throughout the world are persistently infected by HBV for most of their lives and suffer varying degrees of chronic liver disease, which greatly increases their risk of developing cirrhosis and hepatocellular carcinoma (HCC). Indeed, the risk of HCC is increased 100-fold in patients with chronic hepatitis, and the lifetime risk of HCC in males infected at birth approaches 40%. Beasley R P et al., *Lancet* (1981) 2, 1129-1133. Accordingly, a large fraction of the world's population suffers from and dies of these late complications of HBV infection. The development of anti-HBV drugs has been long awaited, but has been hampered by the extremely narrow host range of HBV: HBV replicates mainly in human and chimpanzee livers and rot in experimental animals or in cultured cells. Tiollais, P et al. *Nature* (London) (1985) 317, 489-495.

Hepatitis B virus is a DNA virus with a compact genomic structure; despite its small, circular, 3200 base pairs, HBV DNA codes for four sets of viral products and has a complex, multiparticle structure. HBV achieves its genomic economy by relying on an efficient strategy of encoding proteins from four overlapping genes: S, C, P, and X. HBV is one of a family of animal viruses, hepadnaviruses, and is classified as hepadnavirus type 1. Similar viruses infect certain species of woodchucks, ground and tree squirrels, and Pekin ducks. All hepadnaviruses, including HBV, share the following characteristics: 1) three distinctive morphological forms exist, 2) all members have proteins that are functional and structural counterparts to the envelope and nucleocapsid antigens of HBV, 3) they replicate within the liver but can also exist in extrahepatic sites, 4) they contain an endogenous DNA polymerase with both RNA- and DNA-dependent DNA polymerase activities, 5) their genomes are partially double stranded circular DNA molecules, 6) they are associated with acute and chronic hepatitis and hepatocellular carcinoma and 7) replication of their genome goes through an RNA intermediate which is reverse transcribed into DNA using the virus's endogenous RNA-dependent DNA polymerase activity in a manner analogous to that seen in retroviruses. In the nucleus of infected liver cells, the partially double stranded DNA is converted to a covalently closed circular double stranded DNA (cccDNA) by the DNA-dependent DNA polymerase. Transcription of the viral DNA is accomplished by a host RNA polymerase and gives rise to several RNA transcripts that differ in their initiation sites but all terminate at a common polyadenylation signal. The longest of these RNAs acts as the pregenome for the virus as well as the message for the some of the viral proteins. Viral proteins are translated from the pregenomic RNAs, and the proteins and RNA pregenome are packaged into virions and secreted from the hepatocyte. Although HBV is difficult to cultivate in vitro, several cells have been successfully transfected with HBV DNA resulting in the in vitro production of HBV particles.

There are three particulate forms of HBV: non-infectious 22 nm particles, which appear as either spherical or long filamentous forms, and 42 nm double-shelled spherical particles which represent the intact infectious hepatitis B virion. The envelope protein, HBsAg, is the product of the S gene of HBV and is found on the outer surface of the virion and on the smaller spherical and tubular structures. Upstream of the S gene open reading frame are the pre-S gene open reading frames, pre-S1 and pre-S2, which code for the pre-S gene products, including receptors on the HBV surface for polymerized human serum albumin and the attachment sites for hepatocyte receptors. The intact 42 nm virion can be disrupted by mild detergents and the 27 nm nucleocapsid core particle isolated. The core is composed of two nucleocapsid proteins coded for by the C gene. The C gene has two initiation codons defining a core and a precore region. The major antigen expressed on the surface of the nucleocapsid core is coded for by the core region and is referred to as hepatitis B core antigen (HBcAg). Hepatitis B e antigen (HBeAg) is produced from the same C gene by initiation at the precore ATG.

Also packaged within the nucleocapsid core is a DNA polymerase, which directs replication and repair of HBV DNA. The DNA polymerase is coded for by the P gene, the third and largest of the HBV genes. The enzyme has both DNA-dependent DNA polymerase and RNA-dependent reverse transcriptase activities and is also required for efficient encapsidation of the pregenomic RNA. The fourth gene, X, codes for a small, non-particle-associated protein which has been shown to be capable of transactivating the transcription of both viral and cellular genes.

Although HBV replication is fairly well understood, early steps in HBV infection have not been well defined. Cellular receptors or attachment sites on the virions cannot be studied without appropriate tissue culture assays. In an effort to address this problem, certain cell lines have been developed, human hepatoblastoma cells Huh (HB 611) (Ueda, K. et al., *Virology* (1989) 169, 213-216) and HepG2 cells (Galle, P. R. and Theilmann, L. *Arzneim-Forsch. Drug Res.* (1990) 40, 1380-1382) for evaluation of anti-HBV drugs.

Recently, attention has focused on molecular variants of HBV. Variation occurs throughout the HBV genome, and clinical isolates of HBV that do not express viral proteins have been attributed to mutation in individual or even multiple gene locations. For example, variants have been described which lack nucleocapsid proteins, envelope proteins, or both. Two mutants have attracted attention. The first is found in certain patients with severe chronic HBV infection. These patients were found to be infected with an HBV mutant that contained an alteration in the precore region rendering the virus incapable of encoding HBeAg. The most commonly encountered mutation in such patients is a single base substitution, from G to A, which occurs in the second to last codon of the pre-C gene at nucleotide 1896. This substitution results in the replacement of the TGG tryptophan codon by a stop codon (TAG), which prevents the translation of HBeAg. Patients with such precore mutants that are unable to secrete HBeAg tend to have severe liver disease that progresses rapidly to cirrhosis and that does not respond readily to anti-viral therapy.

The second category of HBV mutants consists of escape mutants, in which a single amino acid substitution, from glycine to arginine, occurs at position 145 of the immunodominant a determinant common to all subtypes of HBsAg. This change in HBsAg leads to a critical conformational change that results in a loss of neutralizing activity by anti-HBs antibody.

Presently Available Viral Resistance Assays

The definition of viral drug susceptibility is generally understood to be the concentration of the anti-viral agent at which a given percentage of viral replication is inhibited (e.g. the $IC_{50}$ for an anti-viral agent is the concentration at which 50% of virus replication is inhibited). Thus, a decrease in viral drug susceptibility is the hallmark that an anti-viral has selected for mutant virus that is resistant to that anti-viral drug. Viral drug resistance is generally defined as a decrease in viral drug susceptibility in a given patient over time. In the clinical context, viral drug resistance is evidenced by the anti-viral drug being less effective or no longer being clinically effective in a patient.

At present the tools available to the researcher and clinician to assess anti-viral drug susceptibility and resistance are inadequate. The classical test for determining the resistance and sensitivity of HIV to an anti-viral agent is complex, time-consuming, expensive, and is hazardous in that it requires the culture of pathogenic virus from each and every patient (Barre-Sinoussi et al (1983) *Science* 220, 868-871; Popovic et al. (1984) *Science* 224, 497-500). In this procedure, the patient's peripheral blood mononuclear cells (PBMC) are first cultured to establish a viral stock of known multiplicity of infection (moi), and the viral stock thereby produced is used to infect a target indicator cell line. The resulting burst of viral replication is then typically measured in the presence and absence of an anti-viral agent by determining the production of viral antigens in the cell culture. Such tests can be performed reliably only in the hands of expert investigators, and may take two to three months to carry out at a cost of thousands of dollars per patient for each agent tested. Furthermore, as viral stocks of sufficient moi cannot be established from the PBMC of some HIV patients, the classical test for HIV resistance cannot be performed on all HIV-infected individuals. More significantly, in the course of generating the viral stock by passage of the virus in culture, the characteristics of the viruses themselves can change and may therefore obscure the true nature of the patient's virus. Thus, the application of the classical test has been limited to gathering information about trends in clinical trials and has not been available for a prospective analysis which could be used to custom tailor anti-viral therapy for a given patient. Notwithstanding these limitations, the classical test has two important qualities: it is specific for the agent under evaluation, and it provides information on the phenotype of the patient's own virus, that is, the concentration of the drug which inhibits 50% of viral replication ($IC_{50}$).

A number of attempts have been made to improve upon the classical test, but each of these has serious shortcomings. The first type of these tests can be described as nonspecific in that they do not determine the characteristics of a patient's own virus at all, but rather provide an independent measure of the course of the infection. Among these tests are those which measure the patient's $CD4^+$ T cell count, the hallmark of HIV disease progression (Goedert et al. (1987) *JAMA* 257, 331-334), those which measure viral antigen levels (e.g., p24 core antigen (Allain et al. (1987) *N. Engl. J. Med.* 317, 1114-1121)), and those which measure viral RNA and DNA levels (e.g., quantitative polymerase chain reaction and branched DNA assays (Piatak et al. (1993) *Science* 259, 1749-1754; Urdea (1993) *Clin. Chem.* 39, 725-726)). The primary disadvantage of such nonspecific tests is that they do not provide any information on viral drug resistance per se, but rather attempt to infer this information from the apparent course of the patient's disease. In addition, many factors other than viral drug resistance can affect the level of the parameter under consideration. In other words, $CD4^+$ T cell counts, p24 antigen levels and HIV viral RNA levels can vary for reasons other than drug resistance during the course of disease.

Another modified classical test amplifies the viral gene that is the target of the anti-viral agent. In this test the viral gene from a given patient is amplified and then recombined into a biologically active proviral clone of HIV. This proviral clone is transfected into human cells to generate a viral stock of known moi which can then be used to infect a target indicator cell line. In the manner of the classical test, one then determines the production of viral antigens in the presence or absence of the anti-viral agent. One such assay described by Kellam and Larder (1994) *Antimicrobial Agents and Chemo.* 38, 23-30, involves PCR amplification of reverse transcriptase coding sequences from a patient, which is then introduced into a proviral DNA clone by homologous recombination to reconstitute the complete viral genome including the reverse transcriptase gene which was deleted. The resulting recombinant virus produced from such clones is then cultured in T-cell lines, and the drug sensitivity is tested in the HeLa $CD4^+$ plaque reduction assay. However, this class of test still requires the culturing of virus to determine drug resistance, and is thus difficult, lengthy and costly and requires the laboratory investigator to handle hazardous viral cultures. Furthermore, given the attendant variation of the virus itself during the culture process, the results may be correspondingly inaccurate.

A second class of test attempts to provide specific information on the genotype of the patient's HIV, with the ultimate goal of correlating this genotypic information with the virus' drug resistant phenotype. Indeed, specific amino acid substitutions within viral genes such as reverse transcriptase and protease genes have been shown to correspond to specific levels of viral resistance to reverse transcriptase and protease inhibitors, respectively (Larder et al. (1994) *J. Gen Virol.* 75, 951-957). A major shortcoming associated with such an analysis is that it is indirect and can be obfuscated by secondary mutations which have been shown to add to or counter the effects of the first mutation. It is the complex interplay of all amino acid residues within a given viral polypeptide which ultimately determines the gene product's activity in the presence or absence of an inhibitor. Thus, a database of vast and impractical proportions would be necessary to interpret the status of drug resistance or sensitivity of a given genotype, given the number of potential amino acid changes in the HIV genome.

A third class of test, a recently developed bacterial-based assay makes use of a molecularly cloned viral gene (specifically, the reverse transcriptase gene) which has been inserted into a bacterial expression vector. Upon transformation of special strains of *E. coli* which are deficient in the bacterial DNA polymerase I, the cloned reverse transcriptase gene can rescue the growth of the bacteria under selected growth conditions. In making *E. coli* dependent upon reverse transcriptase for their growth, one can ascertain the effects of certain reverse transcriptase inhibitors on the activity of the viral gene (PCT Application No. WO 95/22622). A major shortcoming with this approach, however, is that the inhibitor may be transported across the cell membrane and metabolized differently by the bacteria than it is by a human cell, and as a result the concentration of the true metabolic inhibitor of the reverse transcriptase may be grossly different in the bacterium than it would be in a relevant human cell target of infection, or the true inhibitor may be absent altogether. Indeed, nucleoside metabolism is known to differ markedly between human and bacterial cells. Another significant shortcoming of this approach is that the assay measures DNA-dependent DNA polymerase activity of reverse transcriptase but not the RNA-dependent DNA polymerase, strand transfer or RNAse H activities of the reverse transcriptase. Thus, an anti-viral compound which acts, at least in part, on these other activities would not have its full inhibitory activity in this assay. Yet another difficulty with this approach is that it is a growth-based test; thus if an inhibitor (eg., a nucleoside analog) also blocks bacterial growth for reasons other than its effects on reverse transcriptase, it can not be adequately tested in this system.

Viral Vectors

Viral vectors and particularly retroviral vectors have been used for modifying mammalian cells because of the high efficiency with which retroviral vectors infect target cells and integrate into the target cell genome. Because of their ability to insert into the genome of mammalian cells much attention has focused on retroviral vectors for use in gene therapy. Details on retroviral vectors and their use can be found in patents and patent publications including European Patent Application EPA 0 178 220, U.S. Pat. No. 4,405,712, PCT Application WO 92/07943, U.S. Pat. No. 4,980,289, U.S. Pat. No. 5,439,809 and PCT Application WO 89/11539. The teachings of these patents and publications are incorporated herein by reference.

One consequence of the emphasis on retroviral vector technology has been the development of packaging cell lines. A major problem with the use of retroviruses is the possibility of the spread of replication-competent retrovirus. There is thus a need for producing helper vectors which could not be processed into virions. As a result packaging defective vectors and packaging cell lines were developed. Details on packaging-defective vectors and packaging cell lines can be found in patents and patent publications, including U.S. Pat. No. 5,124,263, European Patent Application Pub. No. 0386 882, PCT Application No. WO 91/19798, PCT Application No. WO 88/08454, PCT Application No. WO 93/03143, U.S. Pat. No. 4,650,764, U.S. Pat. No. 4,861,719 and U.S. Pat. No. 5,278,056, the disclosures of which are incorporated herein by reference.

It is an object of this invention to provide a drug susceptibility and resistance test capable of showing whether a viral population in a patient is resistant to a given prescribed drug. Another object of this invention is to provide a test that will enable the physician to substitute one or more drugs in a therapeutic regimen for a patient that has become resistant to a given drug or drugs after a previous course of therapy. Yet another object of this invention is to provide a test that will enable selection of an effective drug regimen for the treatment of virus infections. Yet another object of this invention is to provide a safe, standardized, affordable, rapid, precise and reliable assay of drug susceptibility and resistance for clinical and research application. Still another object of this invention is to provide a test and methods for evaluating the biological effectiveness of candidate drug compounds which act on specific viral genes and/or viral proteins particularly with respect to viral drug resistance and cross resistance. It is also an object of this invention to provide the means and compositions for evaluating viral drug resistance and susceptibility. This and other objects of this invention will be apparent from the specification as a whole.

Viral Drug Resistance

The use of anti-viral compounds for chemotherapy and chemoprophylaxis of viral diseases is a relatively new development in the field of infectious diseases, particularly when compared with the more than 50 years of experience with antibacterial antibiotics. The design of anti-viral compounds is not straightforward because viruses present a number of unique problems. Viruses must replicate intracellularly and often employ host cell enzymes, macromolecules, and organelles for the synthesis of virus particles. Therefore, safe and effective anti-viral compounds must be able to discriminate with a high degree of efficiency between cellular and virus-specific functions. In addition, because of the nature of virus replication, evaluation of the in vitro sensitivity of virus isolates to anti-viral compounds must be carried out in a complex culture system consisting of living cells (e.g. tissue culture). The results from such assay systems vary widely according to the type of tissue culture cells which are employed and the conditions of assay.

Viral drug resistance is a substantial problem given the high rate of viral replication and mutation frequencies. Drug resistant mutants were first recognized for poxviruses with thiosemicarbazone (Appleyard and Way (1966) *Brit. J. Exptl. Pathol.* 47, 144-51), for poliovirus with guanidine (Melnick et al. (1961) *Science* 134, 557), for influenza A virus with amantadine (Oxford et al. (1970) *Nature* 226, 82-83; Cochran et al. (1965) *Ann. NY Acad Sci* 130, 423-429) and for herpes simplex virus with iododeoxyuridine (Jawetz et al. (1970) *Ann. NY Acad Sci* 173, 282-291). Approximately 140 HIV drug resistance mutations to various anti-viral agents have been identified to date (Mellors et al. (1995) *Intnl. Antiviral News*, supplement and Condra, J. H. et al. (1996) *J. Virol.* 70, 8270-8276). Approximately 20 human cytomegalovirus (HCMV) drug resistance mutations to various anti-viral agents have been identified to date (Biron (1996) *Antiviral Chemotherapy*, 4, 135-143).

The small and efficient genomes of viruses have lent themselves to the intensive investigation of the molecular genetics, structure and replicative cycles of most important human viral pathogens. As a consequence, the sites and mechanisms have been characterized for both the activity of and resistance to anti-viral drugs more precisely than have those for any other class of drugs. (Richman (1994) *Trends Microbiol.* 2, 401-407). The likelihood that resistant mutants will emerge is a function of at least four factors: 1) the viral mutation frequency; 2) the intrinsic mutability of the viral target site with respect to a specific anti-viral; 3) the selective pressure of the anti-viral drug; and, 4) the magnitude and rate of virus replication. With regard to the first factor, for single stranded RNA viruses, whose genome replication lacks a proofreading mechanism, the mutation frequencies are approximately $3 \times 10^{-5}$ per base-pair per replicative cycle (Holland et al. (1992) *Curr. Topics Microbiol Immunol.* 176, 1-20; Mansky et al. (1995) *J Virol.* 69, 5087-94; Coffin (1995) *Science* 267, 483-489). Thus, a single 10 kilobase genome, like that of human immunodeficiency virus (HIV)

or hepatitis C virus (HCV), would be expected to contain on average one mutation for every three progeny viral genomes. As to the second factor, the intrinsic mutability of the viral target site in response to a specific anti-viral agent can significantly affect the likelihood of resistant mutants. For example, zidovudine (AZT) selects for mutations in the reverse transcriptase of HIV more readily in vitro and in vivo than does the other approved thymidine analog d4T (stavudine).

One, perhaps inevitable consequence of the action of an anti-viral drug is that it confers sufficient selective pressure on virus replication to select for drug-resistant mutants (Herrmann et al. (1977) *Ann NY Acad Sci* 284, 632-7). With respect to the third factor, with increasing drug exposure, the selective pressure on the replicating virus population increases to promote the more rapid emergence of drug resistant mutants. For example, higher doses of AZT tend to select for drug resistant virus more rapidly than do lower doses (Richman et al. (1990) *J. AIDS.* 3, 743-6). This selective pressure for resistant mutants increases the likelihood of such mutants arising as long as significant levels of virus replication are sustained.

The fourth factor, the magnitude and rate of replication of the virus population, has major consequences on the likelihood of emergence of resistant mutants. Many virus infections are characterized by high levels of virus replication with high rates of virus turnover. (Perelson et al. (1996) *Science,* 271, 1582-1586; Nowak et al. (1996), *PNAS* 93, 4398-4402). This is especially true of chronic infections with HIV as well as hepatitis B and C viruses. The likelihood of emergence of AZT resistance increases in HIV-infected patients with diminishing CD4 lymphocyte counts which are associated with increasing levels of HIV replication (Ibid).

Higher levels of virus increase the probability of preexisting mutants. It has been shown that the emergence of a resistant population results from the survival and selective proliferation of a previously existing subpopulation that randomly emerges in the absence of selective pressure. All viruses have a baseline mutation rate. With calculations of approximately $10^{10}$ new virions being generated daily during HIV infection (Ho et al. (1995) *Nature* 373, 123-126), a mutation rate of $10^{-4}$ to $10^{-5}$ per nucleotide guarantees the preexistence of almost any single point mutation at any time point during HIV infection. Evidence is accumulating that drug resistant mutants do in fact exist in subpopulations of HIV infected individuals (Najera et al. (1994) *AIDS Res Hum Retroviruses* 10, 1479-88; Najera et al. (1995) *J. Virol.* 69, 23-31; Havlir et al. (1996) *J. Virol.*, 70, 7894-7899). The preexistence of drug resistant picornavirus mutants at a rate of approximately $10^{-5}$ is also well documented (Ahmad et al. (1987) *Antiviral Res.* 8, 27-39).

Hepatitis C Virus (HCV)

Hepatitis C virus (HCV) infection occurs throughout the world and, prior to its identification, represented the major cause of transfusion-associated hepatitis. The seroprevalence of anti-HCV in blood donors from around the world has been shown to vary between 0.02% and 1.23%. HCV is also a common cause of hepatitis in individuals exposed to blood products. There have been an estimated 150,000 new cases of HCV infection each year in the United States alone during the past decade (Alter 1993, Infect. Agents Dis. 2, 155-166; Houghton 1996, in Fields Virology, 3rd Edition, pp. 1035-1058).

The hepatitis C virus (HCV) is a member of the flaviviridae family of viruses, which are positive stranded, non-segmented, RNA viruses with a lipid envelope. Other members of the family are the pestiviruses (e.g. bovine viral diarrheal virus, or BVDV, and classical swine fever virus, or CSFV), and flaviviruses (e.g. yellow fever virus and Dengue virus). See Rice, 1996 in Fields Virology, 3rd Edition, pp. 931-959. Molecular dissection of HCV replication and hence understanding the functions of its encoded proteins, while greatly advanced by the isolation of the virus and sequencing of the viral genome, has been hampered by the lack of an efficient cell culture system for production of native or recombinant HCV from molecular clones. However, low-level replication has been observed in several cell lines infected with virus from HCV-infected humans or chimpanzees, or transfected with RNA derived from cDNA clones of HCV.

HCV replicates in infected cells in the cytoplasm, in close association with the endoplasmic reticulum (see FIG. 1). Incoming positive sense RNA is released and translation is initiated via an internal initiation mechanism (Wang et al. 1993, J. Virol. 67, 3338-3344; Tsukiyama-Kohara et al. 1992, J. Virol. 66, 1476-1483). Internal initiation is directed by a cis-acting RNA element at the 5' end of the genome; some reports have suggested that full activity of this internal ribosome entry site, or IRES, is seen with the first 700 nucleotides, which spans the 5' untranslated region (UTR) and the first 123 amino acids of the open reading frame (ORF) (Lu and Wimmer, PNAS 93, 1412, 1996). All of the protein products of HCV are produced by proteolytic cleavage of a large (3010-3030 amino acids, depending on the isolate) polyprotein, carried out by one of three proteases: the host signal peptidase, the viral self-cleaving metalloproteinase, NS2, or the viral serine protease NS3/4A (see FIG. 2). The combined action of these enzymes produces the structural proteins (C, E1 and E2) and non-structural (NS2, NS3, NS4A, NS4B, NS5A, and NS5B) proteins which are required for replication and packaging of viral genomic RNA. NS5B is the viral RNA-dependent RNA polymerase (RDRP) that is responsible for the conversion of the input genomic RNA into a negative stranded copy (complimentary RNA, or cRNA); the cRNA then serves as a template for transcription by NS5B of more positive sense genomic/messenger RNA.

Several institutions and laboratories are attempting to identify and develop anti-HCV drugs. Currently the only effective therapy against HCV is alpha-interferon, which can control the amount of virus in the liver and blood (viral load) in only a small proportion of infected patients (Houghton 1996, in Fields Virology, 3rd Edition, pp. 1035-1058). However, given the availability of the molecular structure of the HCV serine protease, NS3/4A (Love et al., 1996, Cell 87, 331-342; Kim et al. 1996, Cell 87, 343-355), and success using protease inhibitors in the treatment of HIV-1 infection, there should soon be alternatives available. In addition to HCV protease inhibitors, other inhibitors which might specifically interfere with HCV replication could target virus specific activities such as internal initiation directed by the IRES, RDRP activity encoded by NS5B, or RNA helicase activity encoded by NS3.

As a result of a high error rate of their RDRPs, RNA viruses are particularly able to adapt to many new growth conditions. Most polymerases in this class have an estimated error rate of 1 in 10,000 nucleotides copied. With a genome size of approximately 9.5 kb, at least one nucleotide position in the genome of HCV is likely to sustain a mutation every time the genome is copied. It is therefore likely for drug resistance to develop during chronic exposure to an anti-viral agent. As in the case of HIV, a rapid and convenient assay for drug resistant HCV would greatly improve the likelihood of successful antiviral therapy, given a selection of drugs and non-overlapping patterns of drug resistant genotypes. Resistance-associated mutations can sometimes be identified rapidly by growing the virus in cell culture in the presence of the drug, an approach used with considerable success for HIV-1. To date, however, a convenient cell culture system for HCV is lacking. It is therefore not possible to determine the precise nature of genetic changes which confer drug resistance in vitro. Thus, in the absence of a list of known resistance-associated mutations, the preferred resistance assay is one that relies on a phenotypic readout rather than a genotypic one.

Presently Available Drug Resistance Assays

There are no well established drug resistance assays for HCV currently available. However, several investigators have devised chimeric virus systems containing the HCV NS3 protease such that replication of the chimera, or expression of a reporter gene, is dependent on NS3 activity. These systems were devised in order to study various aspects of NS3 function and its cofactor, NS4A, and to serve as prototypes for cell-based drug screening assays.

Hirowatari et al (Anal. Biochem. 225:113, 1995) constructed an expression vector to synthesize an endoplasmic reticulum-tethered NS2-NS3-tax1 fusion protein (tax1 is the transcriptional trans-activator from the HTLV-I retrovirus). Upon cleavage by NS3 (or NS2), the tax1 transactivator is released and migrates to the nucleus, where it acts to activate the expression of a reporter gene (CAT) controlled by the HTLV-1 LTR.

Hahm et al (Virology 226:318, 1996) constructed a chimeric poliovirus containing HCV NS3 upstream of the poliovirus polyprotein; replication of the chimera is dependent on NS3 protease activity, since liberation of the native N-terminus of the poliovirus polyprotein is essential for initiation of poliovirus replication. However, this chimera does not include the NS4A protein of HCV, which has been shown to modify the activity of NS3.

Filocamo et al (J. Virol. 71:1417, 1997) constructed a chimeric Sindbis virus containing HCV NS3/4A upstream of the Sindbis virus polyprotein; replication of the chimera is dependent on NS3 protease activity, since liberation of the native N-terminus of the Sindbis virus polyprotein is essential for initiation of Sindbis virus replication.

In Vitro Expression Systems

Resistance test vectors rely on a cell culture system for transfection, replication, and expression of the indicator gene. Others have described systems for transfection of intact HCV RNA synthesized in vitro from cDNA constructs into Huh7 cells, and have demonstrated that replication can occur (Yoo et al. (1995) J. Virol. 69, 32-38). In addition, several cell lines have been identified which support HCV replication following infection with virus present in HCV-infected human or chimpanzee serum or plasma (Valli et al. (1997) Res. Virol. 148, 181-186; Shimizu et al. (1992) PNAS 89, 5477-5481; Shimizu et al. (1993) PNAS 90, 6037-6041; Shimizu and Yoshikura (1994) J. Virol. 68, 8406-8408; Shimizu et al. (1994) J. Virol. 68, 1494-1500; Mizutani et al. (1996) J. Virol. 70, 7219-7223). Currently these systems are limited to those in which replication is detected by sensitive methods such as RT/PCR, and are unlikely to allow for efficient production of an indicator gene (IG). Improved methods may soon become available as new cell lines and transfection methods are discovered. One example of a potential improvement would be to transfect the RNA as RNP complexes, prepared by in vitro transcription in the presence of purified NS5B, so that transcription can commence immediately upon uptake into the cells; this strategy has been applied to the negative-stranded RNA viruses such as influenza virus (Enami and Palese (1991) J. Virol. 65, 2711-2713, rabies virus (Schnell et al. (1994) EMBO J. 13, 4195-4203), and vesicular stomatitis virus (Lawson et al. (1995) PNAS 92, 4477-4481).

Since the genome length RNA of flaviviruses is infectious, HCV vectors may be in the form of a cDNA construct containing a promoter for the T7 RNA polymerase at the 5 end, and a T7 polymerase terminator sequence at the 3 end. Thus RNA can be synthesized in large quantities in vitro and transfected into cells. An alternative approach is to transfect DNA constructs, which contain a strong eucaryotic promoter (such as the CMV IE promoter), directly into cells. Potential advantages of transfection of RNA, rather than DNA, include the following: transfection of RNA circumvents potential cell-type specific restrictions of promoter activity; translation of recombinant protein usually occurs within minutes to hours following transfection of biologically active RNA, whereas translation following DNA transfection must be preceded by transcription and RNA processing events, which incurs delays of hours to days before maximal expression levels are reached. Representation of viral quasispecies is more straightforward when transfecting RNA since sufficient quantities of RNA can be synthesized from uncloned PCR products by including the sequence of a bacteriophage RNA polymerase in the 5' PCR primer. This approach has been shown to preserve quasispecies diversity of poliovirus (Chumakov, J. Virol. 70:7331-7334, 1996). Generation of precise 5' and 3' termini on the RNA is more easily achieved by in vitro transcription, through the placement of the promoter sequence at the 5' end and a restriction endonuclease recognition site at the 3' end (used for DNA template linearization prior to transcription) relative to the viral sequences. However, the 3' terminus may also be generated precisely via the placement of a self-cleaving RNA ribozyme sequence, present in a cDNA construct (e.g. see Chowrira et al. (1994), J. Biol. Chem. 269, 25856-25864.).

A third transfection strategy, which possesses some of the advantages of RNA transfection, is DNA transfection of constructs containing a T7 RNA polymerase promoter at the 5' end, and a T7 RNA polymerase terminator at the 3' end, into cells which express the T7 RNA polymerase. Expression of the polymerase may be achieved by various means, perhaps the most efficient of these being the infection of the transfected cells with a recombinant T7 polymerase/vaccinia virus (Fuerst et al. (1986) PNAS 83, 8122-8126.)

Human Cytomegalovirus (HCMV)

Human Cytomegalovirus (HCMV) is endemic throughout the world and infection rates appear to be relatively constant throughout the year rather than seasonal. Humans are the only known reservoir for HCMV and natural transmission occurs by direct or indirect person-to-person contact. Between 0.2% and 2.2% of infants born in the United States are infected in utero. Another 8% to 60% become infected during the first six months of life as a result of infection acquired during birth or following breast feeding. Because of the high incidence of reactivation of HCMV infection in the breast, breast milk transmission could represent the most common mode of HCMV transmission worldwide. In most developed countries, 40% to 80% of children are infected before puberty. In other areas of the world, 90% to 100% of the population become infected during childhood.

Human cytomegalovirus (HCMV) is a member of the herpesvirus family. A typical herpes virion consists of a core containing a linear double-stranded DNA and icosadeltahedral capsid approx. 100-110 nm in diameter containing 162 capsomeres with a hole running down the long axis, an amorphous "tegument" that surrounds the core and an envelope containing viral glycoprotein spikes on its surface. Virion sizes range from 120-300 nm due to differences in the thickness of the tegument layer. There are three subgroups of herpesviruses:

1. Alphaherpesvirinae: HSV, VZV. variable host range, relatively short reproductive cycle, rapid spread in culture, efficient destruction of infected cells, capacity to establish latent infections in sensory ganglia.

2. Betaherpesvirinae: HCMV. Restricted host range, long reproductive cycle, slow progression of infection in culture. Infected cells become enlarged and carrier cells are readily established. Virus can be maintained in latent form in secretory glands, lymphoreticular cells, kidneys and other tissues.

3. Gammaherpesvirinae: EBV. experimental host range extremely narrow, replicate in lymphoblastoid cells and cause lytic infections in some types of epithelial and fibroblastoid cells.

There are 8 known human herpesviruses: Human herpesvirus 1 (Herpes simplex virus 1, HSV-1), Human herpesvirus 2 (Herpes simplex virus 2, HSV-2), Human herpesvirus 3 (Varicella-zoster virus, VZV), Human herpesvirus 4 (Epstein-Barr virus, EBV), Human herpesvirus 5 (Human cytomegalovirus), Human herpesvirus 6, Human herpesvirus 7, and Human herpesvirus 8. The genomes of herpes viruses consist of a linear double-stranded (ds) DNA in the virion which circularizes and concatamerizes upon release from the virus capsid in the nucleus of infected cells (See FIG. 10). The genomes of herpesviruses range in size from 120 to 230 kilobase pairs (kbp). The genomes are polymorphic in size (up to 10 kbp differences) within an individual population of virus. This variation is due to the presence of terminal and internal reiterated sequences. Herpes viruses can be classified into six groups, A through F, based on their overall genome organization. HSV and HCMV fall into group E, in which sequences from both termini are repeated in an inverted orientation and juxtaposed internally, dividing the genomes into two components, L (long) and S (short), each of which consists of unique sequences, $U_L$ and $U_S$, flanked by inverted repeats (FIG. 10). In these viruses both components can invert relative to each other and DNA extracted form virions consists of four equimolar populations differing in the relative orientation of the two components (See FIG. 11).

HCMV is a betaherpesvirus and is unique among the betaherpesvirinae in that it falls into the class E genome type. The genome of HCMV is approximately 230 kbp in length and has been completely sequenced (EMBL Seq database accession # X17403). In a naturally occurring population of virus the genome exists in 4 isomers (See FIG. 11). In HCMV, as in HSV, the L-S junction can be deleted, thereby freezing the genome in one of four isomers without dramatically affecting the ability of the virus to grow in cultured cells.

The HCMV genome contains terminal repeat sequences "a" and "a'" present in a variable number in direct orientation at both ends of the linear genome. A variable number of "a" repeats are also present in an inverted orientation at the L-S junction. The number of "a" sequences in these locations ranges from 1-10 with 1 predominating. The size of "a" in HCMV ranges from 700-900 bp. The "a" sequence carries the cleavage and packaging signal. The packaging signals are two highly conserved short sequence elements located within "a" designated pac-1 and pac-2. A 220-bp fragment that carries both the pac-1 and pac-2 elements is sufficient to convey sites for cleavage/packaging as well as inversion on a recombinant CMV construct. The termini of the linear genome are generated by a cleavage event that leaves a single 3' overhanging nucleotide at either end of the genome. The genome is further characterized by large inverted repeats called "b" and "b'" (or TRL and IRL) and "c" and "c'" (or IRS and TRS) that flank unique sequences $U_L$ and $U_S$ that make up the L and S components of the genome (See FIG. 10)

The HCMV replication cycle is relatively slow compared to other herpesviruses. Viral replication involves the ordered expression of consecutive sets of viral genes. These sets are expressed at different times after infection and include the α (immediate early), β1 and β2 (delayed early), and γ1 and γ2 (late) sets based on the time after infection that their transcripts accumulate. DNA replication, genome maturation and virion morphogenesis are coordinated through the temporal regulation of the appropriate gene products required for each step. Expression of a gene products is rapid. Late gene expression is delayed for 24-36 hours. Progeny virions begin to accumulate 48 hours post-infection and reach maximal levels at 72-96 hours. In permissive fibroblasts, DNA replication can be detected as early as 14-16 hours post-infection. HCMV stimulates host DNA, RNA and protein synthesis. HCMV replicates more rapidly in actively dividing cells and HCMV replication is inhibited by pre-treating cells with agents that reduce host cell metabolism. The HCMV genome circularizes soon after infection. Circles give rise to concatamers and genomic inversion occurs within concatameric forms of the DNA. The majority of replicating DNA is larger than unit length and lacks terminal fragments based on southern blot analysis.

Targets for Drug Resistance

The drugs currently used to treat HCMV (ganciclovir (GCV), foscarnet, cidofovir) are known to select for mutations in two viral genes, the UL97 phosphotransferase and the UL54 viral DNA polymerase.

UL97: phosphotransferase 707 amino acids (aa) (2121 bp). Mutations associated with GCV resistance include aa#: 460, 520, 590, 591, 592, 593, 594, 595, 596, 600, 603, 607, 659, 665. The phosphotransferase protein has two functional domains, 1) the amino terminal 300 aa code for a regulatory domain and 2) the carboxy terminal 400 aa define the catalytic domain. All known drug-resistance mutations are found in the catalytic domain (approx 1.2 kb of sequence). In HSV the thymidine kinase gene product (TK) is responsible for the phosphorylation of GCV in cells and resistance to GCV in HSV is associated with mutations in the thymidine kinase gene. HCMV has no homolog to the HSV thymidine kinase gene. The gene homologous to UL97 in HSV (UL13) is a protein kinase.

UL54: viral DNA polymerase, 1242 a.a. (3726 bp). Mutations in this gene can result in resistance to GCV and other nucleoside analogs (including cidofovir) as well as foscarnet. Mutations associated with foscarnet resistance include aa #: 700 and 715. Mutations associated with GCV resistance include aa#: 301, 412, 501, 503, and 987. The mature protein has four recognized domains: 1) a 5'-3' exoRNase H, a 3'-5' exonuclease, a proposed catalytic domain and an accessory protein binding domain.

New therapies in development include agents targeted to the CMV protease (UL80) and the DNA maturational enzyme ("terminase").

GCV-resistant HCMV has been recovered from the central nervous system (CNS) of patients with HCMV-associated neurologic disease who had received long-term GCV maintenance therapy. Resistant strains of HCMV may be selected and preferentially located in the CNS. It is frequently not possible to culture virus from the cerebral spinal fluid (CSF) but it is possible to amplify HCMV DNA using PCR.

Primary isolates of CMV may replicate slowly. In addition, there is a marked delay in the growth rate of some of the drug resistant clinical isolates. In a mixed virus population, a resistant virus population could be masked by a sensitive one. Thus assay results that depend on the growth of virus could be unreliable.

Most assays for viral culture use blood or urine, because they are easy to obtain. However, the virus from these compartments may not represent the virus in specific tissues where disease is occurring (especially vitreous fluid and Csf). Although there are a few amino acid residues that are modified relatively frequently among drug-resistant strains of herpesviruses recovered from patients, the broad distribution of mutations in the majority of strains makes rapid genetic screening methods impractical. Importantly, since the drug-susceptibility phenotypes resulting from individual genetic changes are complex and variable, a biological test for anti-viral susceptibility of HCMV would be more informative.

Presently Available Viral Resistance Assays

The definition of viral drug susceptibility is generally understood to be the concentration of the anti-viral agent at which a given percentage of viral replication is inhibited (e.g. the $IC_{50}$ for an anti-viral agent is the concentration at which 50% of virus replication is inhibited). Thus, a decrease in viral drug susceptibility is the hallmark that an anti-viral has selected for mutant virus that is resistant to that anti-viral drug. Viral drug resistance is generally defined as a decrease in viral drug susceptibility in a given patient over time. In the clinical context, viral drug resistance is evidenced by the anti-viral drug being less effective or no longer being clinically effective in a patient.

Several types of assays are available to detect and measure antiviral drug susceptibility of HCMV. The two most commonly used methods are a plaque reduction assay and a DNA hybridization assay. At present the plaque reduction assay is considered the standard. Both assays require HCMV isolation and passage in cell culture. Generally, it takes four to six weeks to obtain the results from the assays.

Plaque reduction assays with increased sensitivity can now be performed directly on clinical specimens, including blood, urine, bronchoalveolar lavage, and cerebrospinal fluid. Two assays which are modified from the standard plaque reduction assay detect either the CMV immediate-early antigen or late antigen. The procedure is essentially the same as the standard plaque reduction assay except that the virus is tested directly without prior passage and the incubation time is reduced to ninety-six hours (Gerna et al. (1995) *J. Clin. Microbiol.* 33, 738-741). The limitation of these assays is that they can only be performed in patients with high level of viremia. Virus culture remains an essential step in the detection of drug resistant isolates.

An alternative approach is the detection of specific viral DNA mutations related to drug resistance. In this assay, PCR primers are used to amplify viral DNA and restriction sites present in mutant viral DNA but not wildtype DNA are used to determine the genotype of the viral DNA. It is suggested that the analysis of two PCR products with a total of three or four restriction digests is adequate to detect 78-83% of UL97 (certain mutations of UL97 which codes for a phosphotransferase, result in resistance to ganciclovir) mutants resistant to ganciclovir (Chou et al. (1995) *J. Infect. Dis.* 172, 239-242.). The main limitation of this assay is that infrequent or new resistance mutations are not identified. Also, DNA polymerase mutations (UL54) which are indicative of high-level ganciclovir resistance and a high probability of multidrug resistance are not detected.

It is an object of this invention to provide a drug susceptibility and resistance test capable of showing whether a viral population in a patient is resistant to a given prescribed drug. Another object of this invention is to provide a test that will enable the physician to substitute one or more drugs in a therapeutic regimen for a patient that has become resistant to a given drug or drugs after a previous course of therapy. Yet another object of this invention is to provide a test that will enable selection of an effective drug regimen for the treatment of virus infections. Yet another object of this invention is to provide a safe, standardized, affordable, rapid, precise and reliable assay of drug susceptibility and resistance for clinical and research application. Still another object of this invention is to provide a test and methods for evaluating the biological effectiveness of candidate drug compounds which act on specific viral genes and/or viral proteins particularly with respect to viral drug resistance and cross resistance. It is also an object of this invention to provide the means and compositions for evaluating viral drug resistance and susceptibility. This and other objects of this invention will be apparent from the specification as a whole.

SUMMARY OF THE INVENTION

Objects of the present invention are accomplished by a novel test for determining susceptibility for an anti-viral drug comprising: (a) introducing a resistance test vector comprising a patient-derived segment and an indicator gene into a host cell; (b) culturing the host cell from step (a); (c) measuring expression of the indicator gene in a target host cell; and (d) comparing the expression of the indicator gene from step (c) with the expression of the indicator gene measured when steps (a)-(c) are carried out in the absence of the anti-viral drug, wherein a test concentration of the anti-viral drug is present at steps (a)-(c); at steps (b)-(c); or at step (c).

This invention also provides a method for determining anti-viral drug resistance in a patient comprising: (a) developing a standard curve of drug susceptibility for an anti-viral drug; (b) determining anti-viral drug susceptibility in the patient using the susceptibility test described above; and (c) comparing the anti-viral drug susceptibility in step (b) with the standard curve determined in step (a), wherein a decrease in anti-viral susceptibility indicates development of anti-viral drug resistance in the patient.

This invention further provides a method for determining anti-viral drug resistance in a patient comprising: (a) determining anti-viral drug susceptibility in the patient at a first time according to the above method, wherein the patient-derived segment is obtained from the patient at said time; (b) determining anti-viral drug susceptibility of the same patient at a later time; and (c) comparing the anti-viral drug susceptibilities determined in step (a) and (b), wherein a decrease in anti-viral drug susceptibility at the later time compared to the first time indicates the development or progression of anti-viral drug resistance in the patient.

The assay of this invention enables a physician to assess whether a viral gene encoding a viral protein or a functional viral sequence, each of which may be the target of an anti-viral agent, has mutated to render the drug less effective. More particularly, the novel assay of this invention enables one to determine whether a virus has become resistant to a particular anti-viral drug. Furthermore, this invention enables a physician to assess drug susceptibility and resistance of combination therapy. In addition the assay enables one to alter a therapeutic regimen prospectively by testing particular drug(s) or combinations of drugs and determining whether these drugs, alone or in combination, inhibit one or more viral gene(s) and/or viral protein(s). This invention provides significant advantages over presently available assays by providing a safer, more affordable, more reliable, more rapid and more effective drug susceptibility and resistance assay to assess the therapeutic efficacy of particular anti-viral drug(s) or combinations of drugs enabling a physician to optimize treatment. The assay of this invention has the significant advantage of enabling the evaluation of resistance and susceptibility at all stages of drug development: 1) during preclinical evaluation of candidate compounds; 2) during clinical evaluation of new drugs; 3) during patient therapy enabling design of an effective therapeutic regimen to overcome the problem of drug resistance; and 4) as part of epidemiologic surveillance, evaluating the prevalence of resistance during the use of approved and experimental drugs.

The present invention is directed to the methods and compositions of assessing drug susceptibility and resistance, including: a) the assay method of determining the susceptibility and resistance of a patient-derived segment to an anti-viral drug; b) compositions including resistance test vectors comprising a patient-derived segment and an indicator gene; and c) host cells containing the resistance test vectors. This invention is further directed to the compositions and methods of constructing the vectors and host cells which are used in the drug susceptibility and resistance assay of this invention.

In one aspect of the invention there is provided a method for determining susceptibility for an anti-HIV drug comprising: (a) introducing a resistance test vector comprising a patient-derived segment and an indicator gene into a host cell; (b) culturing the host cell from step (a); (c) measuring expression of the indicator gene in a target host cell; and (d) comparing the expression of the indicator gene from step (c) with the expression of the indicator gene measured when steps (a)-(c) are carried out in the absence of the anti-HIV drug, wherein a test concentration of the anti-HIV drug is present at steps (a)-(c); at steps (b)-(c); or at step (c).

In one aspect of the invention there is provided a method for determining susceptibility for an anti-HIV drug comprising: (a) introducing a resistance test vector comprising a patient-derived segment and an indicator gene into a host cell; (b) culturing the host cell from step (a); (c) measuring an indicator in a target host cell wherein said indicator is a DNA or RNA structure; and (d) comparing the measurement of the indicator from step (c) with the measurement of the indicator when steps (a)-(c) are carried out in the absence of the anti-HIV drug, wherein a test concentration of the anti-HIV drug is present at steps (a)-(c); at steps (b)-(c); or at step (c).

In one aspect of the invention there is provided a method for determining susceptibility for an anti-HBV drug comprising: (a) introducing a resistance test vector comprising a patient-derived segment and an indicator gene into a host cell; (b) culturing the host cell from step (a); (c) measuring expression of the indicator gene in a target host cell; and (d) comparing the expression of the indicator gene from step (c) with the expression of the indicator gene measured when steps (a)-(c) are carried out in the absence of the anti-HBV drug, wherein a test concentration of the anti-HBV drug is present at steps (a)-(c); at steps (b)-(c); or at step (c).

In one aspect of the invention there is provided a method for determining susceptibility for an anti-HBV drug comprising: (a) introducing a resistance test vector comprising a patient-derived segment and an indicator gene into a host cell; (b) culturing the host cell from step (a); (c) measuring an indicator in a target host cell wherein said indicator is a DNA or RNA structure; and (d) comparing the measurement of the indicator from step (c) with the measurement of the indicator when steps (a)-(c) are carried out in the absence of the anti-HBV drug, wherein a test concentration of the anti-HBV drug is present at steps (a)-(c); at steps (b)-(c); or at step (c).

This invention also provides a method for determining anti-HIV drug resistance in a patient comprising: (a) developing a standard curve of drug susceptibility for an anti-HIV drug; (b) determining anti-HIV drug susceptibility in the patient using the susceptibility test described above; and (c) comparing the anti-HIV drug susceptibility in step (b) with the standard curve determined in step (a), wherein a decrease in anti-HIV susceptibility indicates development of anti-HIV drug resistance in the patient.

This invention also provides a method for determining anti-HBV drug resistance in a patient comprising: (a) developing a standard curve of drug susceptibility for an anti-HBV drug; (b) determining anti-HBV drug susceptibility in the patient using the susceptibility test described above; and (c) comparing the anti-HBV drug susceptibility in step (b) with the standard curve determined in step (a), wherein a decrease in anti-HBV susceptibility indicates development of anti-HBV drug resistance in the patient.

This invention also provides a method for evaluating the biological effectiveness of a candidate anti-viral drug compound comprising: (a) introducing a resistance test vector comprising a patient-derived segment and an indicator gene into a host cell; (b) culturing the host cell from step (a); (c) measuring expression of the indicator gene in a target host cell; and (d) comparing the expression of the indicator gene from step (c) with the expression of the indicator gene measured when steps (a)-(c) are carried out in the absence of the candidate anti-viral drug compound, wherein a test concentration of the candidate anti-viral drug compound is present at steps (a)-(c); at steps (b)-(c); or at step (c).

This invention also provides a method for evaluating the biological effectiveness of a candidate anti-viral drug compound comprising: (a) introducing a resistance test vector comprising a patient-derived segment and an indicator gene into a host cell; (b) culturing the host cell from step (a); (c) measuring an indicator in a target host cell wherein said indicator is a DNA or RNA structure; and (d) comparing the measurement of the indicator from step (c) with the measurement of the indicator when steps (a)-(c) are carried out in the absence of the candidate anti-viral drug compound, wherein a test concentration of the candidate anti-viral drug compound is present at steps (a)-(c); at steps (b)-(c); or at step (c).

The resistance test vector comprising the patient-derived viral segment(s) (e.g. HIV, HBV, etc.) and the indicator gene may additionally include one or more non-patient-derived segments. In one embodiment the resistance test vector is constructed from a genomic viral vector which may include a deletion in one or more genes. For example, in the case of HIV, env is deleted in a resistance test vector which otherwise preserves the mRNA expression and processing characteristics of the complete virus. Alternatively, the resistance test vector is constructed from a subgenomic viral vector which may include only one or a few viral genes which are typically the target of the anti-viral drug. For example in the case of HBV, one or more of the HBV genes encoding certain structural and enzymatic functions necessary for HBV DNA replication and virus particle formation (i.e. C, S and X genes) may be deleted from a resistance test vector which otherwise preserves mRNA expression and processing characteristics of the complete virus. The resistance test vector further comprises either the native enhancer/promoter of the particular virus or a foreign enhancer/promoter for the expression of the anti-viral target genes.

The expression of the indicator gene in the resistance test vector in the target cell is ultimately dependent upon the action of the patient-derived segment sequences. The indicator gene may be functional or non-functional. In the case of a non-functional indicator gene, the indicator gene is not efficiently expressed in a host cell transfected by the resistance test vector until it is converted into a functional indicator gene through the action of one or more of the patient-derived segment products. In one embodiment, the indicator gene is rendered non-functional through use of a permuted promoter, i.e. a promoter that, although in the same transcriptional orientation as the indicator gene, follows rather than precedes the coding sequence of the indicator gene. In addition, the orientation of the non-functional indicator gene is opposite to that of the viral promoters or LTRs. Thus the coding sequence of the non-functional indicator gene can neither be transcribed by the permuted promoter nor by the viral promoters. In the case of HIV, the indicator gene is rearranged as a consequence of reverse transcription so that the permuted promoter now precedes the indicator gene sequence, which as a result can be functionally expressed. In the case of HBV, the indicator gene is rearranged as a consequence of circularization of the genome during HBV replication. In a second embodiment, the indicator gene is rendered non-functional through use of a permuted coding region, i.e. an indicator gene coding region in which the 5' portion of the coding region follows rather than precedes the 3' portion of the coding region. In this configuration, no mRNA is expressed which can give rise to a functional indicator gene product. In the case of HIV, the indicator gene is rearranged as a consequence of reverse transcription so that the 5' coding region of the indicator gene now precedes the 3' coding region, and as a result the indicator gene can be functionally expressed. In the case of HBV, the indicator gene is rearranged as a result of circularization of the genome during HBV replication. In a third embodiment, the indicator gene is rendered non-functional through use of an inverted intron, i.e. an intron inserted into the coding sequence of the indicator gene with a transcriptional orientation opposite to that of the indicator gene. In addition, the indicator gene itself contains a functional promoter with the entire transcriptional unit oriented opposite to the viral promoters. Thus the non-functional indicator gene is in the wrong orientation to be transcribed by the viral LTRs in the case of HIV or the HBV enhancer-promoter and it cannot be functionally transcribed by its own promoter, as the inverted intron cannot be properly excised by splicing. However, in the case of retroviruses and hepadnaviruses, and HIV and HBV specifically, transcription by the viral promoters result in the formation of mRNA in which removal of the inverted intron can occur by splicing. In retroviruses, as a consequence of reverse transcription of the resulting spliced transcript and the integration of the resulting provirus into the host cell chromosome, the indicator gene can now be functionally transcribed by its own promoter. In HBV, as a consequence of reverse transcription of the resulting spliced transcript and circularization of the genomic DNA in the host cell, the indicator gene can now be functionally transcribed by its own promoter.

Resistance test vectors comprising a non-functional indicator gene can be used to carry out resistance tests in either a particle-based or non-particle-based assay. The particle based assay is based on resistance test vector viral particles, which are replication defective, being produced by the resistance test vector host cells. The trans-acting factors necessary for production of the resistance test vector viral particles are provided by the packaging expression vectors which are transfected into the packaging host cell. In contrast the non-particle based resistance test is performed by transfection of a single host cell with a resistance test vector in the absence of packaging expression vectors.

In the case of the functional indicator gene, the functional indicator gene is efficiently expressed in a first host cell transfected by the resistance test vector (referred to herein as a resistance test vector host cell). Thus, the function of the indicator gene in the resistance test vector host cell is not dependent on the patient-derived segment. However, the capacity of the indicator gene to be expressed in a second host cell (referred to herein as a target host cell) is dependent on the production of functional resistance test vector viral particles in the resistance test vector host cell. Thus, the activity of the indicator gene in the target host cells is dependent on the activity of the patient-derived segments.

In another aspect this invention is directed to anti-viral drug susceptibility and resistance tests for HIV/AIDS or HBV. Particular resistance test vectors of the invention for use in the HIV/AIDS anti-viral drug susceptibility and resistance test are identified as well as resistance test vector host cells. In yet another aspect this invention is directed to anti-viral drug susceptibility and resistance tests for hepatitis. Similarly in the case of HBV, particular resistance test vectors (also referred to herein as resistance test vector systems) of the invention for use in the HBV anti-viral drug susceptibility and resistance test are identified as well as resistance test vector host cells.

In yet another aspect this invention provides for the identification and assessment of the biological effectiveness of potential therapeutic anti-viral compounds for the treatment of viral diseases. In still another aspect the invention is directed to a host cell transfected with one or more vectors to assess drug susceptibility. In another aspect, the invention is directed to a novel resistance test vector comprising a patient-derived viral gene(s) and an indicator gene.

Figure 1A:
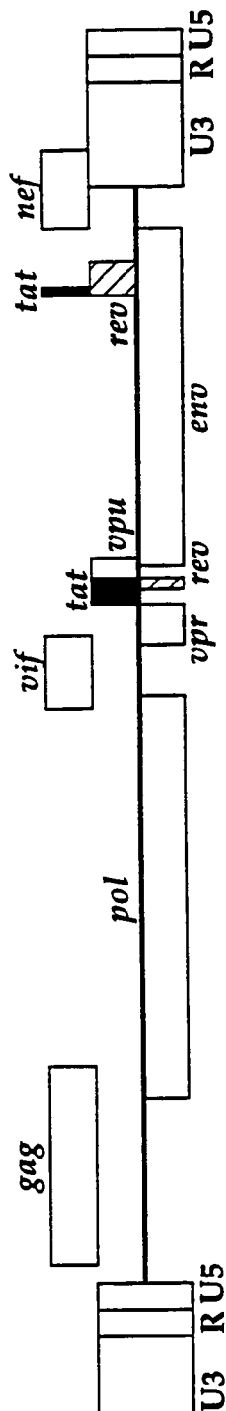
FIG. 1.A. Diagrammatic representation of the DNA genomic structure of HIV-1. Viral proteins are encoded in each of the three reading frames by the gag, pol, vif, vpr, tat, rev, vpu, env and nef genes. The RNA is transcribed from viral DNA and processed by viral and cellular enzymes, giving rise to both genomic viral RNA and mRNA. The U3, R and U5 elements of the viral long terminal repeat (LTR) are indicated.
Figure 1B:
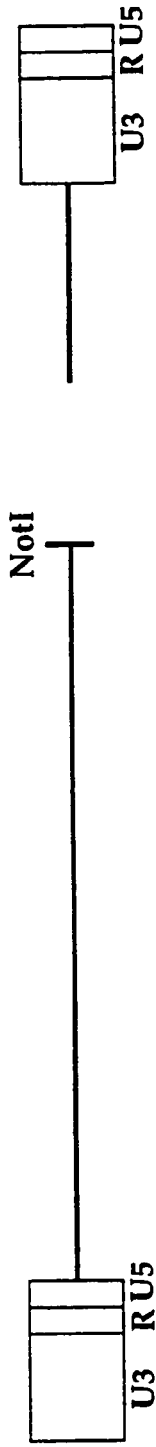
Figure 1C:

B. Generalized diagrammatic representation of the HIV genomic viral vector which contains the following elements in a 5' to 3' orientation: 1) an HIV-LTR U3 region, 2) an HIV-LTR R region, 3) an HIV-LTR U5 region 4) the coding regions of the HIV gag-pol, vif, vpr, tat, rev, vpu, deleted env, and nef genes, and 5) a 3' HIV-LTR.

C. Generalized diagrammatic representation of the HIV genomic viral vector which contains the following elements in a 5' to 3' orientation: 1) a CMV IE enhancer-promoter, 2) an HIV-LTR R region, 3) an HIV-LTR U5 region, 4) the coding regions of the HIV gag-pol, vif, vpr, tat, rev, vpu, deleted env, and nef genes, and 5) a 3' HIV-LTR.

D. Generalized diagrammatic representation of the HIV subgenomic viral vector which contains the following elements in a 5' to 3' orientation: 1) an HIV-LTR U3 region, 2) an HIV-LTR R region, 3) an HIV-LTR U5 region, 4) the coding region of the HIV gag-pol gene, and 5) a 3' HIV-LTR.

E. Generalized diagrammatic representation of the HIV subgenomic viral vector which contains the following elements in a 5' to 3' orientation: 1) a CMV IE enhancer-promoter, 2) an HIV-LTR R region, 3) an HIV-LTR U5 region, 4) the coding region of the HIV gag-pol gene, and 5) a 3' HIV-LTR.

FIG. 2.A. Diagrammatic representation of the DNA genomic structure of HIV-1.

B. Diagrammatic representation of the resistance test vector comprising a nonfunctional indicator gene comprising a permuted promoter having the following elements in a 5' to 3' orientation: 1) an HIV-LTR U3 region (pLG-lucPP-HS and pLG-lucPP-PB) or a CMV IE enhancer-promoter (pCG-lucPP-HS and pCG-lucPP-PB), 2) an HIV-LTR R region, 3) an HIV-LTR U5 region containing an inserted T7 phage RNA polymerase promoter (herein referred to as T7 promoter) with a transcriptional orientation opposite to that of the LTRs, 4) the coding regions of the HIV gag-pol, vif, vpr, tat, rev, vpu, deleted env, and nef genes, 5) a patient-derived segment(s) inserted into the patient sequence acceptor sites, 6) an indicator gene cassette inserted into the deleted env gene, and 7) a 3' HIV-LTR.

C. Diagrammatic representation showing the conversion of the non-functional indicator gene (permuted promoter) in the resistance test vector, described in 2(a), to a functional indicator gene by reverse transcriptase. The conversion to a functional indicator gene results from the repositioning of the T7 promoter relative to the indicator gene coding region.

D. Diagrammatic representation of the resistance test vector, based on the genomic indicator gene viral vector pCG(NF-lucP)1-PB/T7, comprising a nonfunctional indicator gene comprising a permuted promoter having the following elements in a 5' to 3' orientation: (1) a CMV IE enhancer-promoter, (2) an HIV-LTR R region, (3) an HIV-LTR U5 region into which has been inserted a T7 promoter with a transcriptional orientation opposite to that of the CMV promoter, (4) the coding regions of HIV gag-pol, vif, vpr, tat, rev, vpu, deleted env, and nef genes, (5) a patient-derived segment(s) inserted into the patient sequence acceptor sites, (6) a luciferase indicator gene cassette inserted into the deleted env gene, (7) 3' HIV LTR U3 and R regions, (8) the SV40 polyadenylation signal region, and (9) the SV40 origin of replication region.

E. Diagrammatic representation showing the conversion of the non-functional indicator gene (permuted promoter) in the resistance test vector, pCG(NF-lucP)1-PP/T7 described in 2(d), to a functional indicator gene by reverse transcriptase. The conversion to a functional indicator gene results from the repositioning of the T7 promoter relative to the indicator gene coding region.

FIG. 3.A. Diagrammatic representation of the DNA genomic structure of HIV-1.

B. Diagrammatic representation of the packaging expression vector pLTR-HIV3' which provides the vif, vpr, tat, rev, vpu and nef genes, each of which is expressed as a spliced subgenomic mRNA transcribed from the HIV LTR U3 region.

C. Diagrammatic representation of the packaging expression vector pCMV-HIV3' which provides the vif, vpr, tat, rev, vpu and nef genes, each of which is expressed as a spliced subgenomic mRNA transcribed from the CMV IE enhancer-promoter.

D. Diagrammatic representation of the packaging expression vector pVL-env4070A [pCXAS(4070A env)] which provides the amphotrophic MLV env gene product, by transcription from the CMV IE enhancer-promoter.

FIG. 4.A. Diagrammatic representation of the DNA genomic structure of HIV-1.

B. A generalized diagrammatic representation of the resistance test vectors comprising a nonfunctional indicator gene comprising a permuted coding region containing the following elements in a 5' to 3' orientation: 1) an HIV-LTR U3 region (pLG-lucPC-HS and pLG-lucPC-PB) or a first CMV IE enhancer-promoter (pCG-lucPC-HS and pCG-lucPC-PB), 2) the HIV-LTR R and U5 regions, 3) the coding regions of the HIV gag-pol, vif, vpr, tat, rev, vpu, deleted env, and nef genes, 4) a patient-derived segment(s) inserted into the patient sequence acceptor sites, 5) a first indicator gene cassette containing the 5' coding region of the luciferase gene, inserted into the deleted env gene, 6) a second indicator gene cassette containing the 3' coding region of the luciferase gene, inserted into a deleted 3' HIV-LTR U3 region, and 7) a 3' HIV-LTR R and U5 region.

C. Diagrammatic representation showing the conversion of the non-functional indicator gene (permuted coding region) in the resistance test vector, described in 4 (a), to a functional indicator gene by reverse transcriptase. Following reverse transcription and strand transfer, the luciferase 3' coding region is copied from the 3' LTR to the 5' LTR, permitting the transcription of mRNA which can be spliced to generate a functional luciferase coding region.

FIG. 5.A. Diagrammatic representation of the DNA genomic structure of HIV-1.

B. A generalized diagrammatic representation of the resistance test vectors comprising a nonfunctional indicator gene comprising an inverted intron containing the following elements in a 5' to 3' orientation: 1) an HIV-LTR U3 region (pLG-lucII-HS and pLG-lucII-PB) or a first CMV IE enhancer-promoter (pCG-lucII-HS and pCG-lucII-PB), 2) the HIV-LTR R and U5 regions, 3) the coding regions of the HIV gag-pol, vif, vpr, tat, rev, vpu, deleted env, and nef genes, 4) patient-derived segment(s) inserted into the patient sequence acceptor site, 5) an indicator gene cassette inserted into the deleted env gene, and 5) a 3' HIV-LTR.

C. Diagrammatic representation showing the conversion of the non-functional indicator gene (inverted intron) in the resistance test vector, described in 5(a), to a functional indicator gene by reverse transcriptase. The overall transcriptional orientation of the indicator gene cassette is opposite to that of the first CMV enhancer-promoter and viral LTRs, while the orientation of the artificial intron is the same as the latter elements. Transcription of the indicator gene by the second CMV enhancer-promoter does not lead to the production of functional transcripts as the inverted intron cannot be spliced in this orientation. Transcription of the indicator gene by the 5' viral LTR or the first CMV IE enhancer-promoter, however, leads to the removal of the inverted intron by RNA splicing, although the indicator gene is still not functionally expressed as the resulting transcript has an antisense orientation. Following the reverse transcription of this transcript and integration of the resultant proviral DNA, the indicator gene can be functionally transcribed by the second CMV enhancer-promoter as the inverted intron has been previously removed.

FIG. 6.A. Diagrammatic representation of the DNA genomic structure of HIV-1 is shown above (a) and (b).

B. A generalized diagrammatic representation of the resistant test vectors comprising a functional indicator gene having the following elements in a 5' to 3' orientation: 1) an HIV-LTR U3 region (pLG-luc-HS-1 and pLG-luc-PB-1) or a first CMV IE enhancer-promoter (pCG-luc-HS-1 and pCG-luc-PB-1), 2) the HIV-LTR R and U5 regions, 3) the coding region of the HIV gag-pol, vif, vpr, tat, rev, vpu, deleted env, and nef genes, 4) a functional indicator gene cassette inserted into the deleted env gene, with a transcriptional orientation opposite to the viral LTRs and 5) a 3' HIV-LTR.

C. A generalized diagrammatic representation of the resistance test vectors comprising a functional indicator gene cassette (pLG-luc-HS-2, pLG-luc-PB-2, pCG-luc-HS-2 and pCG-luc-PB-2) in which the transcriptional orientation of the indicator gene cassette is the same as the viral LTRs.

FIG. 7.A. Diagrammatic representation of the DNA genomic structure of HIV-1 is shown above (a) and (b).

B. Diagrammatic representation of the resistance test vector, based on the genomic indicator gene viral vector pCG-CXCN(F-lucP)2AA, comprising a functional indicator gene having the following elements in a 5' to 3' orientation: (1) a CMV IE enhancer-promoter region, (2) HIV LTR "R" and "U5" regions, (3) the coding regions of the HIV gag-pol, vif, vpr, 5' tat exon, 5' rev exon, vpu, deleted env, 3' tat exon, 3' rev exon, and nef genes, (4) "test" patient-derived segment(s) inserted into the patient sequence acceptor sites (ApaI, AgeI), (5) a functional indicator gene cassette (CXCN(lucP)) inserted into the deleted env gene, (6) HIV LTR "U3" and "R" regions, (7) the SV40 polyadenylation signal sequence region, and (8) the SV40 origin of replication region.

C. Diagramatic representation of the predicted integrated proviral structure of the resistance test vector, pCG-CXCN (F-lucP)2-AA, and the transcription of the functional indicator gene cassette in the target host cell.

D. Diagrammatic representation of the resistance test vector, based on the genomic indicator gene viral vector pCG-CXAT(F-lucP)2-AA, comprising a functional indicator gene having the following elements in a 5' to 3' orientation: (1) a CMV IE enhancer-promoter region, (2) HIV LTR "R" and "U5" regions, (3) the coding regions of the HIV gag-pol, vif, vpr, 5' tat exon, 5' rev exon, vpu, deleted env, 3' tat exon, 3' rev exon, and nef genes, (4) "test" patient-derived segment(s) inserted into the patient sequence acceptor sites (ApaI, AgeI), (5) the functional indicator gene cassette (CXAT(lucP)) inserted into the deleted env gene, (6) HIV LTR "U3" and "R" regions, (7) the SV40 polyadenylation signal sequence region, and (8) the SV40 origin of replication region.

E. Diagrammatic representation of the predicted integrated proviral structure of the resistance test vector, pCG-CXAT(F-lucP) 2-AA, and the transcription of the functional indicator gene cassette in the target host cell.

FIG. 8.A. Demonstration of drug susceptibility using the resistance test vectors, pCG-CXCN(F-lucP)2-AA and pCG-CXAT(F-lucP)2-AA. Data are presented as luciferase gene activity in target host cells as Relative Light Units (RLU) in the absence of AZT or in the presence of 5 mM AZT.

B. Drug susceptibility and resistance test performed with the resistance test vector, pCG-CXCN(F-lucP)2-AA containing pre-AZT treatment and post-AZT treatment "test" patient-derived segments. The resistance test vectors are derived from the genomic indicator gene viral vector, pCG-CXCN(F-lucP)2-AA. Data are presented as percent inhibition of luciferase gene activity in target host cells vs. AZT concentration ($\log_{10}$). pCG-CXCN(F-lucP)2-AA is plotted as solid boxes. pCG-CXCN(F-lucP)2-AA containing patient-derived segments prior to AZT treatment is plotted as solid circles and post-AZT treatment as solid triangles.

C. Drug susceptibility and resistance test performed with the resistance test vector, pCG-CXCN(F-lucP)2-AA containing the reverse transcriptase segment derived from the biologically active proviral clone, pNL4-3. Data are presented as percent inhibition of luciferase gene activity in target host cells vs. nevirapine concentration ($\log_{10}$) and is plotted as solid boxes.

D. Drug susceptibility and resistance test performed with the resistance test vector, pCG-CXCN(F-lucP)2-AA containing the protease segment derived from the biologically active proviral clone, pNL4-3. Data are presented as percent inhibition of luciferase gene activity in target host cells vs. indinavir concentration ($\log_{10}$) and is plotted as solid boxes.

Figure 9A:
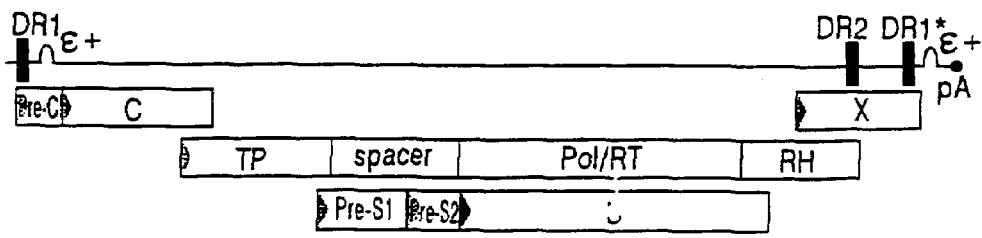

FIG. 9A. Diagrammatic representation of the RNA pregenomic structure of HBV. Pregenomic RNA is shown as a solid line. Direct repeat sequences (DR) are shown as closed rectangles. The positions of the encapsidation signal sequence is shown ($\epsilon$). The C, P, S, and X genes are shown as open rectangles. The terminal protein (TP), spacer, DNA polymerase/reverse transcriptase (pol/RT), and RNase H regions of the P gene are indicated. Sites of C, P, S, and X translation initiation are indicated by shaded triangles.

B. A generalized diagrammatic representation of the subgenomic indicator gene viral vector, pCS-HBV(NF-IG)II-(PSAS−), a component of the resistance test vector system, comprising an indicator gene cassette and an inverted intron containing the following elements in a 5' to 3' orientation: (1) the CMV IE enhancer-promoter region, (2) the 5' region of the HBV genome and the DR1 and 5' $\epsilon$ (the pre-C ORF translation initiation codon is eliminated), (3) a non-functional indicator gene cassette in which the indicator gene ORF contains an inverted intron, (4) the region of the HBV genome containing DR2, DR1*, the 3' $\epsilon$, and the 3' HBV polyadenylation (pA) signal region.

C. Diagrammatic representation of the covalently closed circular DNA (cccDNA) form of the subgenomic indicator gene viral vector, pCS-HBV(F-IG)II(PSAS−), containing a functional indicator gene cassette assembled as a result of HBV viral replication.

D. Diagrammatic representation of one example of a packaging vector, pPK-CPX, a component of the resistance test vector system comprising a patient-derived segment containing the following elements in a 5' to 3' orientation: (1) the CMV IE enhancer-promoter region, (2) the region of the HBV genome spanning from the C ORF translation initiation codon to the 3' pA signal and including the C, P, S, and X genes. The C gene of the packaging vector, pPK-CPX, is modified such that it does not contain the pre-C ORF sequences and does not express the S proteins (as shown by the X at the translation initiation sites).

E. Diagrammatic representation of an additional packaging vector, pPK-S, providing the S gene proteins, that is cotransfected with the resistance test vector system comprising the indicator gene viral vector, pCS-HBV(NF-IG)II-(PSAS−), and the packaging plasmid, pPK-CPX.

F. A generalized diagrammatic representation of the resistance test vector, pCS-HBV(NF-IG)II-(PSAS+), comprising a non-functional indicator gene with an inverted intron containing the following elements in a 5' to 3' orientation:

(1) the CMV IE enhancer-promoter region, (2) the 5' region of the HBV genome and the DR1 and 5' ε (the pre-C ORF translation initiation codon is eliminated), (3) indicator gene cassette (containing an inverted intron) within the region of the HBV genome which contains a patient-derived P gene segment, (4) the region of the HBV genome containing DR2, DR1*, the 3' ε, and the 3' HBV pA signal region.

G. Diagrammatic representation of the covalently closed circular DNA (cccDNA) form of the resistance test vector, pCS-HBV(F-IG)II-(PSAS+), containing a functional indicator gene cassette and a patient-derived P gene segment assembled as a result of HBV viral replication.

H. Diagrammatic representation of a packaging vector, pPK-CSX, providing the C, S and X gene proteins, that is cotransfected with the resistance test vector, pCS-HBV(NF-IG)-II-(PSAS+).

Figure 10A:
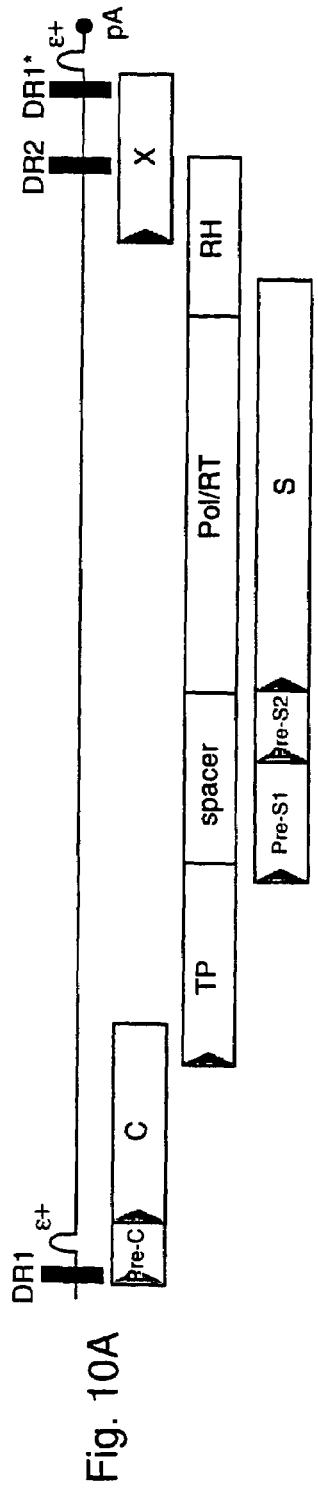
Figure 10B:
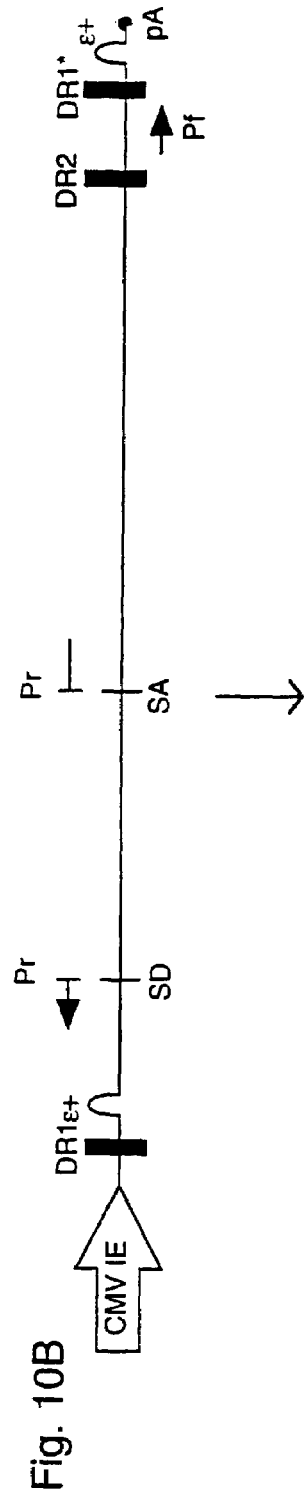
Figure 10C:
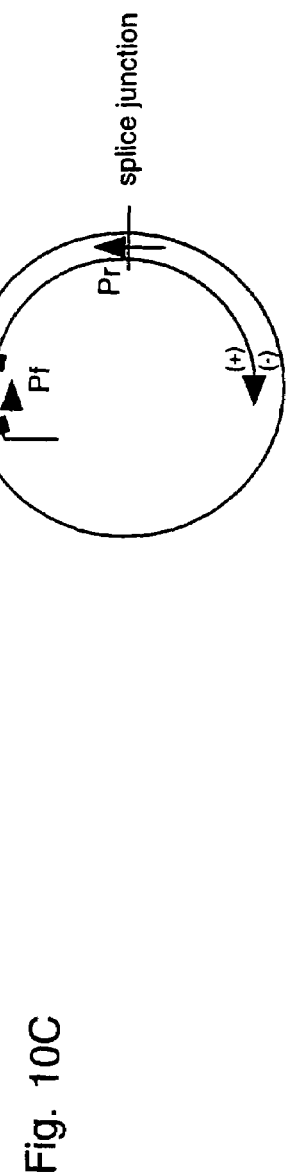

FIG. 10A. Diagrammatic representation of the RNA pregenomic structure of HBV.

B. Diagrammatic representation of an HBV indicator gene viral vector containing a non-functional indicator gene cassette. Primer binding sites for the amplification of a target DNA sequence are shown. The location and orientation of the forward primer (Pf) and reverse primer (Pr) binding sites do not constitute a functional amplification unit in the linear form of the vector that is used to transfect packaging host cells. The Pr binding site is designed to span the junction sequence that is generated by splicing of the pregenomic RNA.

C. Diagrammatic representation of the rc-DNA form of the indicator gene viral vector described in 10B. Primer binding sites for the amplification of a target DNA sequence are shown. The location and orientation of the Pf and Pr primer binding sites constitute a functional amplification unit in the plus strand DNA component of the rc-DNA form and the plus and minus strand DNA components of the cccDNA form of the vector that is generated by HBV DNA replication within the virus particles produced in packaging host cells. The Pr binding site is assembled by the splicing of the pregenomic RNA.

D. Diagrammatic representation of an HBV indicator gene viral vector containing a non-functional indicator gene cassette. Primer binding sites for the amplification of a target DNA sequence are shown. The location and orientation of the Pf and Pr binding sites constitute a functional amplification unit in the linear form of the vector that is used to transfect packaging host cells, but the Pf binding site is not adjacent to the binding site of the exonuclease detection probe (probe) in the unspliced linear form of the vector. This arrangement of Pf, Pr, and probe binding sites does not constitute an efficient exonuclease detection unit.

E. Diagrammatic representation of the rc-DNA form of the indicator gene viral vector described in 10D. Primer binding sites for the amplification of a target DNA sequence are shown. The location and orientation of the Pf and Pr primer binding sites constitute a functional amplification unit in the rc-DNA and cccDNA forms of the vector that are generated by HBV DNA replication in packaging host cells. The location of the Pf binding site is brought immediately adjacent to the binding site of the exonuclease detection probe (probe) in the rc-DNA and cccDNA forms of the vector. This arrangement of Pf, Pr, and probe binding sites constitute an efficient exonuclease detection unit.

F. Diagrammatic representation of an HBV indicator gene viral vector. Primer binding sites for the amplification of a target DNA sequence are shown. The location and orientation of the forward primer (Pf) and reverse primer (Pr) binding sites do not constitute a functional amplification unit in the linear form of the vector that is used to transfect packaging host cells.

G. Diagrammatic representation of the rc-DNA form of the indicator gene viral vector described in 10F. Primer binding sites for the amplification of a target DNA sequence are shown. The location and orientation of the Pf and Pr primer binding sites constitute a functional amplification unit in the plus strand DNA component of the rc-DNA form and the plus and minus strand DNA components of the cccDNA form of the vector that is generated by HBV DNA replication within the virus particles produced in packaging host cells.

Figure 11D:
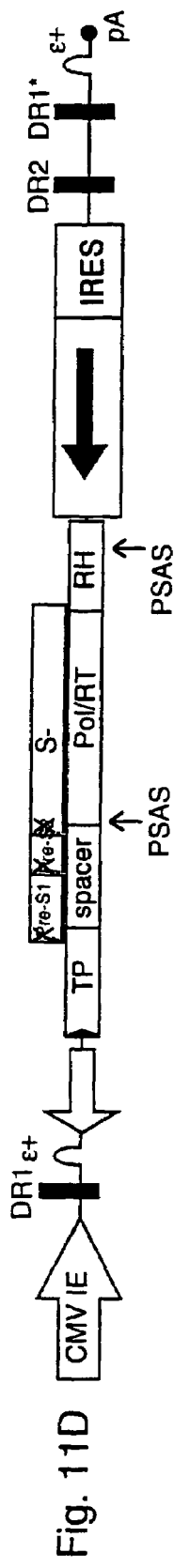

FIG. 11A. Diagrammatic representation of the RNA pregenomic structure of HBV.

Figure 9B:
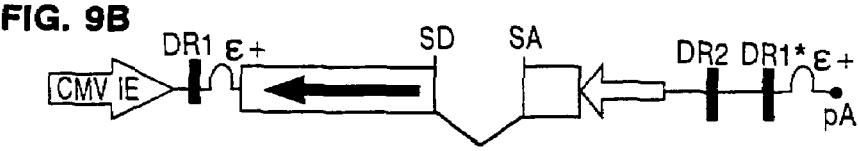
Figure 9C:
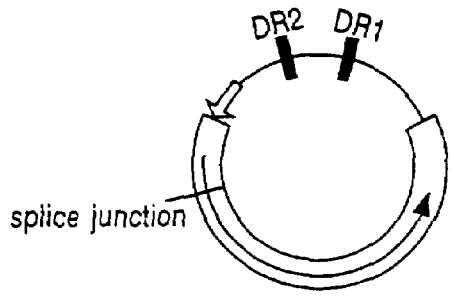
Figure 9D:
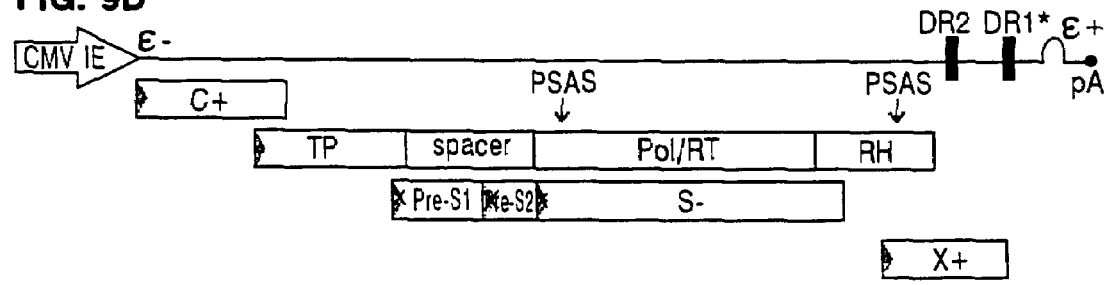
Figure 9E:
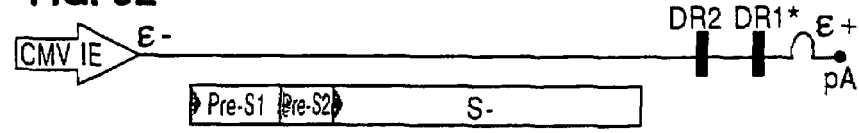

B. A generalized diagrammatic representation of the subgenomic indicator gene viral vector, pCS-HBV(NF-IG)PP-(PSAS−), a component of the resistance test vector system comprising a non-functional indicator gene with a permuted promoter containing the following elements in a 5' to 3' orientation: (1) the CMV IE enhancer promoter region, (2) the 5' region of the HBV genome and the DR1 and 5' ε (the pre-C ORF translation initiation codon is eliminated), (3) a non-functional indicator gene cassette assembled such that the promoter region is positioned 3', i.e. downstream, of the indicator gene ORF, (4) the 3' region of the HBV genome containing DR2, DR1*, the 3' ε, and the 3' HBV pA signal region (the pre-C ORF translation initiation codon is eliminated). The packaging vector, PPK-CPX, a component of the resistance test vector system comprising a patient-derived P gene segment is shown in FIG. 9D and the S packaging vector, pPK-S, is shown in FIG. 9E.

C. Diagrammatic representation of the covalently closed circular DNA (cccDNA) form of the subgenomic indicator gene viral vector, pCS-HBV(F-IG)PP(PSAS−), containing a functional indicator gene cassette assembled as a result of HBV viral replication.

D. A generalized diagrammatic representation of the resistance test vector, pCS-HBV(NF-IG) PP(PSAS+), comprising a non-functional indicator gene with a permuted promoter containing the following elements in a 5' to 3' orientation: (1) the CMV IE enhancer-promoter region, (2) the 5' region of the HBV genome and the DR1 and 5' copy of E (the pre-C ORF translation initiation codon is eliminated) (3) an enhancer-promoter region (permuted promoter), (4) the P gene containing the patient-derived segment (5) the indicator gene ORF (6) an internal ribosome entry site (IRES), and (7) the 3' region of the HBV genome containing DR2, DR1*, the 3' ε, and the 3' HBV pA signal region (the pre-C ORF translation initiation codon is eliminated). The packaging vector, pPK-CSX, providing the C, S and X genes is cotransfected with the resistance test vector, pCS-HBV(NF-IG)PP(PSAS+), and is shown in FIG. 9H.

E. Diagrammatic representation of the covalently closed circular DNA (cccDNA) form of the resistance test vector, pCS-HBV(F-IG)PP(PSAS+), containing a functional indicator gene cassette and a patient-derived P gene segment assembled as a result of HBV viral replication.

FIG. 12A. Diagrammatic representation of the RNA pregenomic structure of HBV.

B. A generalized diagrammatic representation of the subgenomic indicator gene viral vector, pCS-HBV(NF-IG)PP-TIS-(PSAS−), a component of the resistance test vector system comprising a non-functional indicator gene with a permuted promoter and translation initiation site containing the following elements in a 5' to 3' orientation: (1) the CMV IE enhancer-promoter region, (2) the 5' region of the HBV genome including the DR1 and 5' ε (the pre-C ORF translation initiation codon is eliminated), (3) an indicator gene ORF lacking a translation initiation site, (4) an enhancer-promoter region (permuted promoter) (5) the 3' region of the HBV genome containing DR2, pre-C ORF translation initiation codon, DR1*, the 3' ε, and the 3' HBV pA signal region. The packaging vector, pPK-CPX, a component of the resistance test vector system comprising a patient-derived segment is shown in FIG. 9D and the S packaging vector, pPK-S, is shown in FIG. 9E.

C. Diagrammatic representation of the covalently closed circular DNA (cccDNA) form of the subgenomic indicator gene viral vector, pCS-HBV(F-IG)PPTIS(PSAS−), containing a functional indicator gene cassette assembled as a result of HBV viral replication.

D. A generalized diagrammatic representation of the resistance test vector, pCS-HBV(NF-IG)PPTIS(PSAS+), comprising a non-functional indicator gene with a permuted promoter containing the following elements in a 5' to 3' orientation: (1) the CMV IE enhancer-promoter region, (2) the 5' region of the HBV genome including the DR1 and 5' ε (the pre-C ORF translation initiation codon is eliminated), (3) an indicator gene ORF lacking a translation initiation site, (4) the P gene containing the patient-derived segment, (5) an enhancer-promoter region (permuted promoter) (6) the 3' region of the HBV genome containing DR2, pre-C ORF translation initiation codon, DR1*, the 3' E, and the 3' HBV pA signal region. The packaging vector, pPK-CSX, providing the C, S and X genes is cotransfected with the resistance test vector, pCS-HBV(NF-IG)PPTIS(PSAS+), and is shown in FIG. 9H.

E. Diagrammatic representation of the covalently closed circular DNA (cccDNA) form of the resistance test vector, pCS-HBV(F-IG)PPTIS(PSAS+), containing a functional indicator gene cassette and a patient-derived P gene segment assembled as a result of HBV viral replication.

Figure 13A:
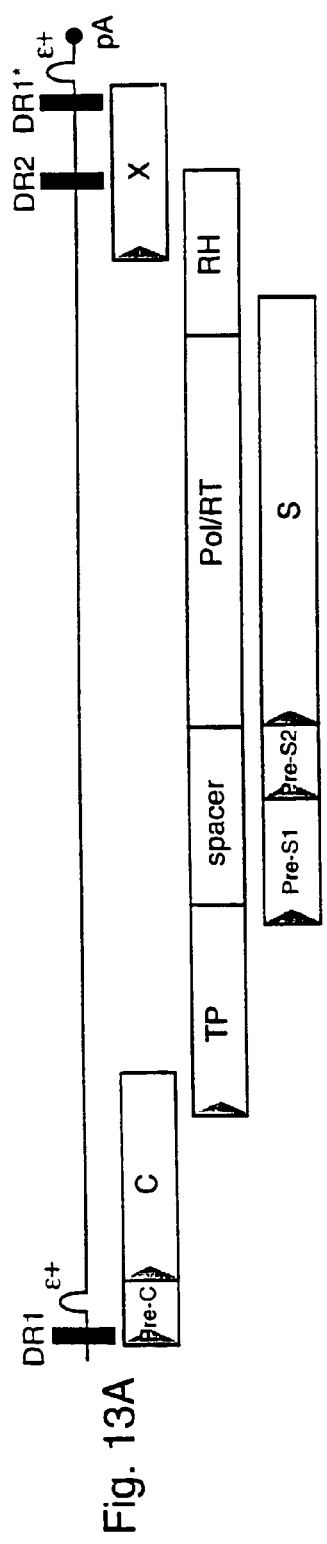

FIG. 13A. Diagrammatic representation of the RNA pre-genomic structure of HBV.

B. A generalized diagrammatic representation of the subgenomic indicator gene viral vector, pCS-HBV(NF-IG)PCR-(PSAS−), a component of the resistance test vector system comprising a non-functional indicator gene with a permuted coding region containing the following elements in a 5' to 3' orientation: (1) the CMV IE enhancer-promoter region, (2) the 5' region of the HBV genome including the DR1 and 5' ε (the pre-C ORF translation initiation codon is eliminated), (3) a non-functional indicator gene cassette assembled such that the promoter region and a 5' portion of the coding region are positioned 3', i.e. downstream, of the remaining 3' portion of the coding region, (4) the 3' region of the HBV genome containing DR2, DR1*, the 3' ε, and the 3' HBV pA signal region (the pre-C ORF translation initiation codon is eliminated). The packaging vector, pPK-CPX, a component of the resistance test vector system comprising a patient-derived P gene segment is shown in FIG. 9D and the S packaging vector, pPK-S, is shown in FIG. 9E.

C. Diagrammatic representation of the covalently closed circular DNA (cccDNA) form of the subgenomic indicator gene viral vector, pCS-HBV(F-IG)PCR(PSAS−), containing a functional indicator gene cassette assembled as a result of HBV viral replication.

D. A generalized diagrammatic representation of the resistance test vector, pCS-HBV(NF-IG) PCR(PSAS+), comprising a non-functional indicator gene with a permuted coding region containing the following elements in a 5' to 3' orientation: (1) the CMV IE enhancer-promotor region, (2) the 5' region of the HBV genome including the DR1 and 5' ε (the pre-C ORF translation initiation codon is eliminated), (3) the 3' portion of the indicator gene ORF beginning with a splice acceptor sequence in the reverse orientation, (4) the P gene containing the patient-derived segment, (5) an enhancer-promoter region, (6) the 5' portion of the indicator gene ORF ending in a splice donor sequence in the reverse orientation, (7) the 3' region of the HBV genome containing DR2, DR1*, the 3' ε, and the 3' HBV pA signal region (the pre-C ORF translation initiation codon is eliminated). The packaging vector, pPK-CSX, providing the C, S and X genes is cotransfected with the resistance test vector, pCS-HBV(NF-IG)PCR(PSAS+), and is shown in FIG. 9H.

E. Diagrammatic representation of the covalently closed circular DNA (cccDNA) form of the resistance test vector, pCS-HBV(F-IG)PCR(PSAS+), containing a functional indicator gene cassette and a patient-derived P gene segment assembled as a result of HBV viral replication.

FIG. 14A. Diagrammatic representation of the RNA pre-genomic structure of HBV.

B. A generalized diagrammatic representation of the subgenomic indicator gene viral vector component, pCS-HBV(F-IG)(PSAS−), a component of the resistance test vector system comprising a functional indicator gene cassette containing the following elements in a 5' to 3' orientation: (1) the CMV IE enhancer-promoter region, (2) the 5' region of the HBV genome including the DR1 and 5' ε (the pre-C ORF translation initiation codon is eliminated), (3) a functional indicator gene cassette, (4) the 3' region of the HBV genome containing DR2, DR1*, the 3' ε, and the 3' HBV pA signal region (the pre-C ORF translation initiation codon is eliminated). The packaging vector, PPK-CPX, a component of the resistance test vector system comprising a patient-derived P gene segment is shown in FIG. 9D and the S packaging vector, pPK-S, is shown in FIG. 9E.

C. Diagrammatic representation of the covalently closed circular DNA (cccDNA) form of the subgenomic indicator gene viral vector, pCS-HBV(F-IG)(PSAS−), containing a functional indicator gene.

D. A generalized diagrammatic representation of the resistance test vector, pCS-HBV(F-IG)(PSAS+), comprising a functional indicator gene containing the following elements in a 5' to 3' orientation: (1) the CMV IE enhancer promoter region, (2) the 5' region of the HBV genome including the DR1 and 5' ε (the pre-C ORF translation initiation codon is eliminated), (3) a functional indicator gene cassette, (4) the P gene containing the patient-derived segment, (5) the 3' region of the HBV genome containing DR2, DR1*, the 3' ε, and the 3' HBV pA signal region (the pre-C ORF translation initiation codon is eliminated). The packaging vector, pPK-CSX, providing the C, S and X genes, that is cotransfected with the resistance test vector, pCS-HBV(F-IG)(PSAS+), and is shown in FIG. 9H.

E. Diagrammatic representation of the covalently closed circular DNA (cccDNA) form of the resistance test vector, pCS-HBV(F-IG)(PSAS+), containing a functional indicator gene.

Figure 15:
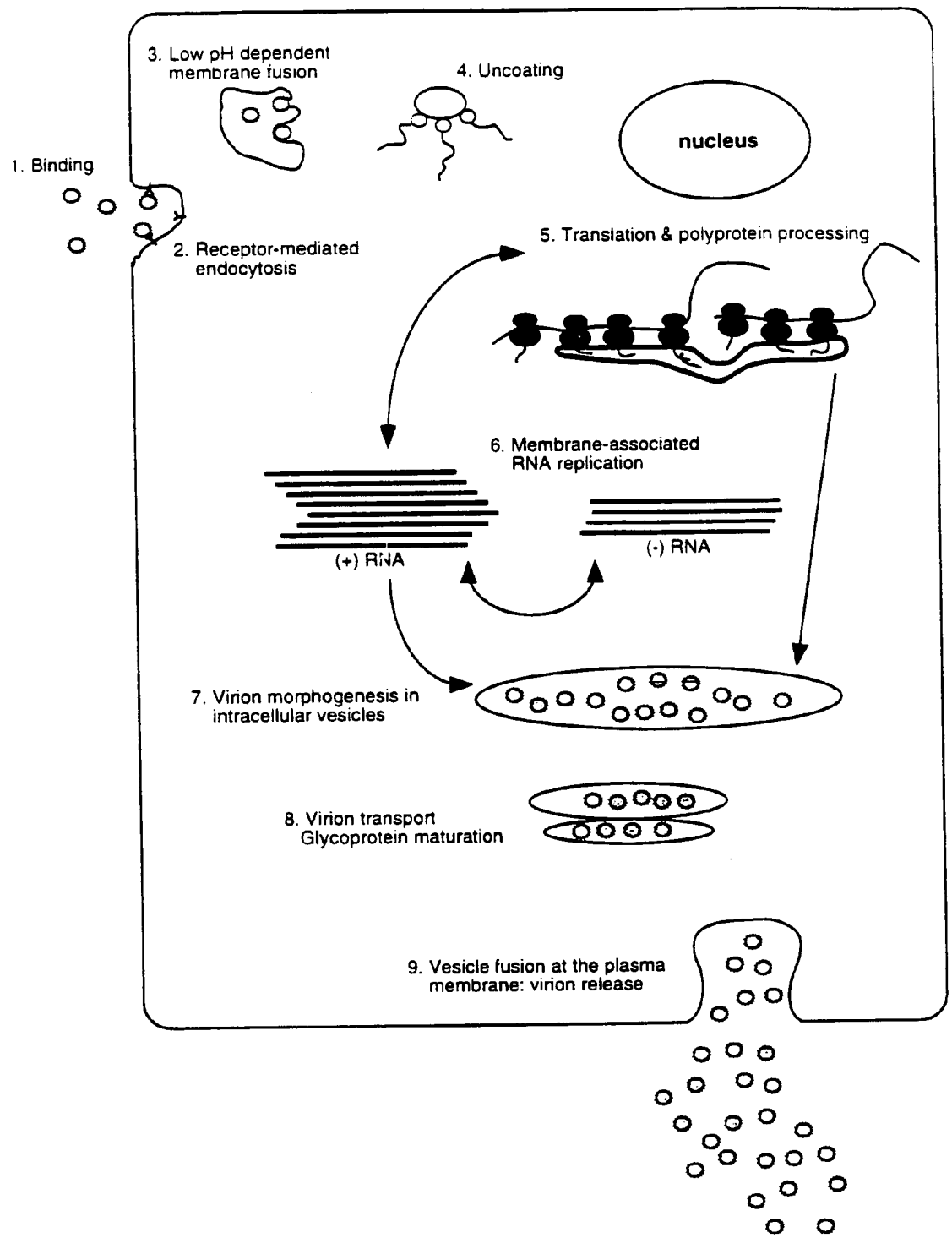

FIG. 15 HCV Replication

Schematic drawing of the replication cycle of HCV. Virions bind to the cell surface, via a specific interaction between a viral surface glycoprotein and a cell surface receptor (1). Following receptor-mediated endocytosis (2) and low pH dependent membrane fusion (3), the nucleocapsid core is released into the cytoplasm (4). Virion RNA is translated in close association with the endoplasmic reticulum, and the polyprotein is processed by specific endoproteolytic cleavages mediated by host signal peptidase in the ER, or one of two viral proteases (5). After enough of the non-structural proteins have been produced, the viral RNA is replicated through a negative strand intermediate, to generate more positive sense RNA for translation and packaging into new virions (6). Structural proteins and RNA assemble to form new viral particles which bud into the ER (7) and are secreted via the cellular pathway (8, 9) to release the progeny virions.

Figure 16:
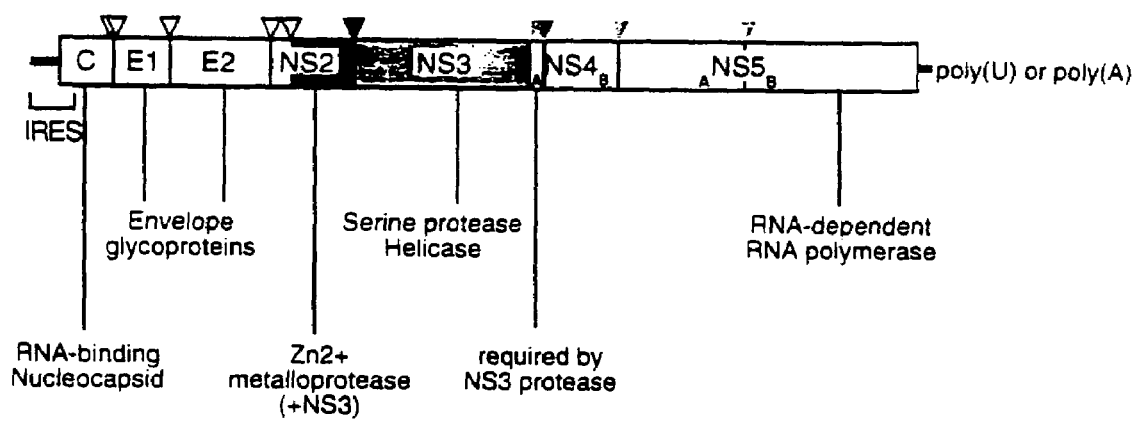

FIG. 16 HCV Genome Structure

Schematic diagram of the ~9.5 kb HCV RNA. The order of the individual HCV proteins is indicated in the HCV polyprotein, with putative functions associated indicated below. Cleavage sites for proteolytic processing are indicated by triangles (open triangles for host signal peptidase, black triangle for NS2/3, and grey triangles for NS3/4A). The internal ribosome entry site (IRES) is located at the 5' end of the RNA and comprises the entire untranslated region (UTR) and some sequences at the beginning of the C ORF. The 3' end of the RNA contains either a poly(A) or poly(U) tail, depending on the type of HCV.

FIG. 17 Resistance Test Vectors (luciferase fusion protein).

A. Diagrammatic representation of the resistance test vector (pXHCV-luc, where X is either CMV or T7), with patient sequence acceptor sites for transfer of patient derived segments indicated by arrows below the polyprotein (PSAS). The promoter and terminator sequences are indicated generically in this figure as well as in subsequent figures, as several different types of regulatory elements may be used (as described below). The luciferase reporter gene is expressed as a fusion protein with the HCV polyprotein and then cleaved off by the action of NS3/4A.

B. Method for transfection using DNA transfection of a resistance test vector (pCMVHCV-luc) containing the CMV IE promoter and SV40 polyadenylation signal. The RNA is transcribed in the nucleus of transfected cells by cellular RNA polymerases, then transported to the cytoplasm where translation and replication can occur.

C. Method for transfection using DNA transfection of a resistance test vector (pT7HCV-luc1) containing the T7 RNA polymerase promoter and T7 RNA polymerase terminator. The DNA is transfected into cells expressing T7 RNA polymerase (for example, after infection with recombinant vaccinia virus or by co-transfection with a T7 RNA polymerase expression plasmid); RNA is transcribed in the cytoplasm by T7 polymerase.

D. Method for transfection using RNA transfection of RNA derived from a resistance test vector (pT7HCV-luc2) containing the T7 RNA polymerase promoter and a restriction site placed at the 3' end for linearization of the DNA prior to transcription in vitro. The synthetic RNA is then transfected directly into cells and translation and replication can occur.

Figure 18:
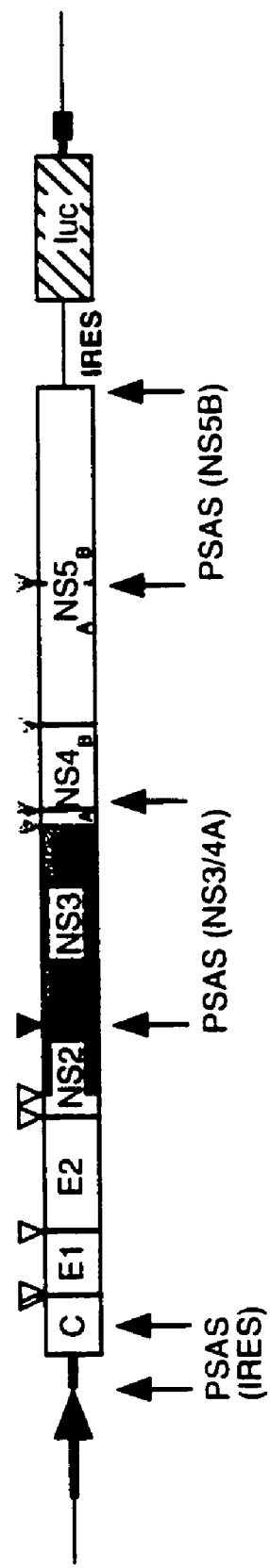

FIG. 18 Resistance Test Vectors (bicistronic luciferase expression).

Structure of the resistance test vector (pXHCV-IRESluc) containing an IRES element for luciferase translation. The IRES may be the native HCV IRES, or derived from other viruses which use such elements for internal initiation of their mRNAs. Expression of luciferase occurs by internal initiation of translation from the bicistronic RNA in the cytoplasm of transfected cells.

Figure 19:
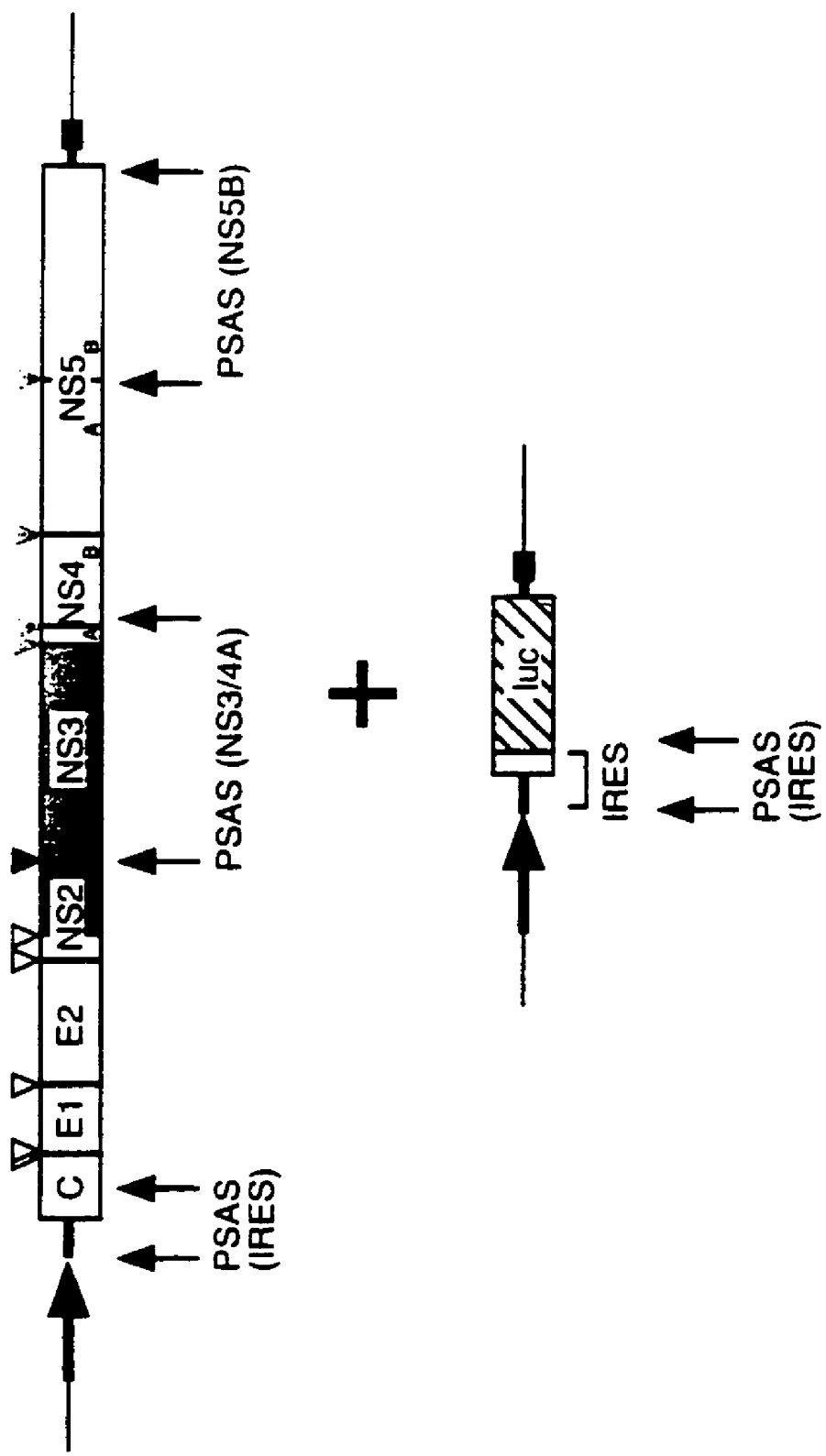

FIG. 19 Resistance Test Vectors (positive sense minigenomes).

Diagrammatic representation of the resistance test vectors (pXHCV and pXIRESluc) comprising a positive sense luciferase RNA minigenome. The two constructs are co-transfected into cells; HCV non-structural proteins expressed from pXHCV act on both RNAs to replicate and package them. The replicated RNA are packaged into progeny virions which can then be used for infection of fresh target cells; the target cells are also infected with HCV or transfected with pXHCV, and the luciferase minigenome is expressed.

Figure 20:
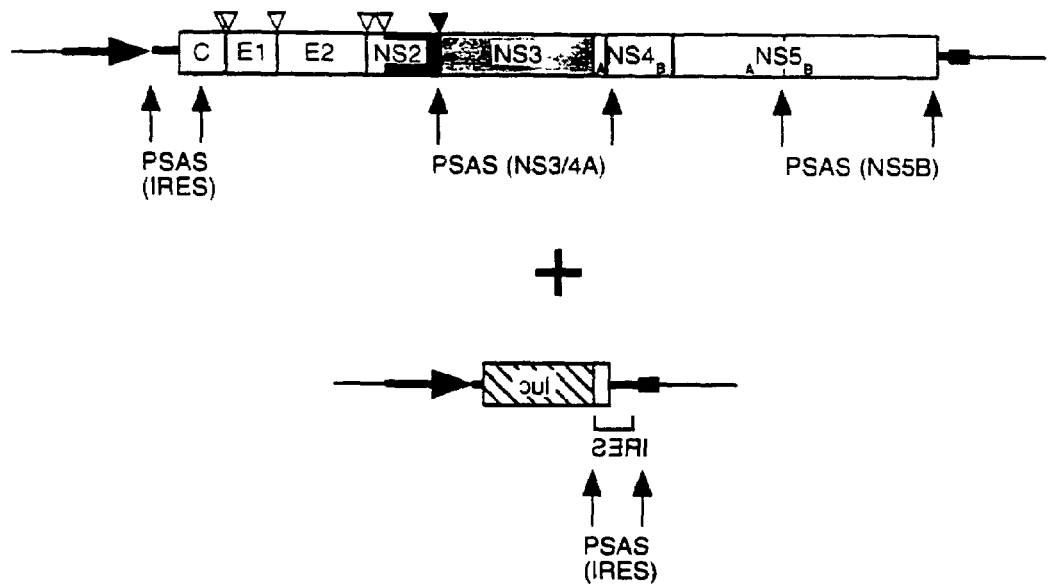

FIG. 20 Resistance Test Vectors (negative sense minigenomes).

Diagrammatic representation of the resistance test vector (pXHCV-ASIRESluc) comprising a negative sense RNA minigenome. The two constructs are co-transfected into cells; HCV non-structural proteins expressed from pXHCV act on both RNAs, leading to their replication. The replicated RNA are packaged into progeny virions which can then be used for infection of fresh target cells; the target cells are also infected with HCV or transfected with pXHCV, and the luciferase minigenome (now positive sense RNA) is expressed.

Figure 21:
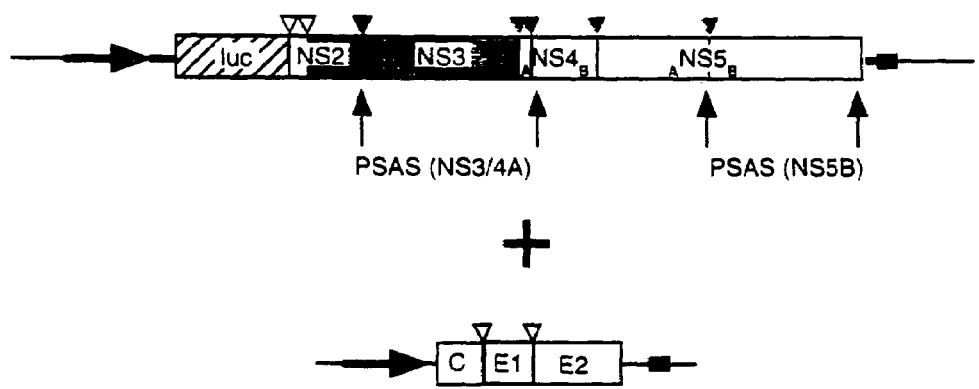

FIG. 21 Resistance Test Vectors (defective genome).

Diagrammatic representation of the resistance test vectors (pXluc-NSHCV and pXSHCV) expressing defective genomic RNAs. The two constructs are co-transfected into cells; non-structural proteins expressed from pXluc-NSHCV act to replicate the luc-NSHCV RNA; the newly replicated RNA is packaged into virions using structural proteins (C, E1 and E2) from pXSHCV. The progeny virions are then used to infected new cells.

Figure 22:
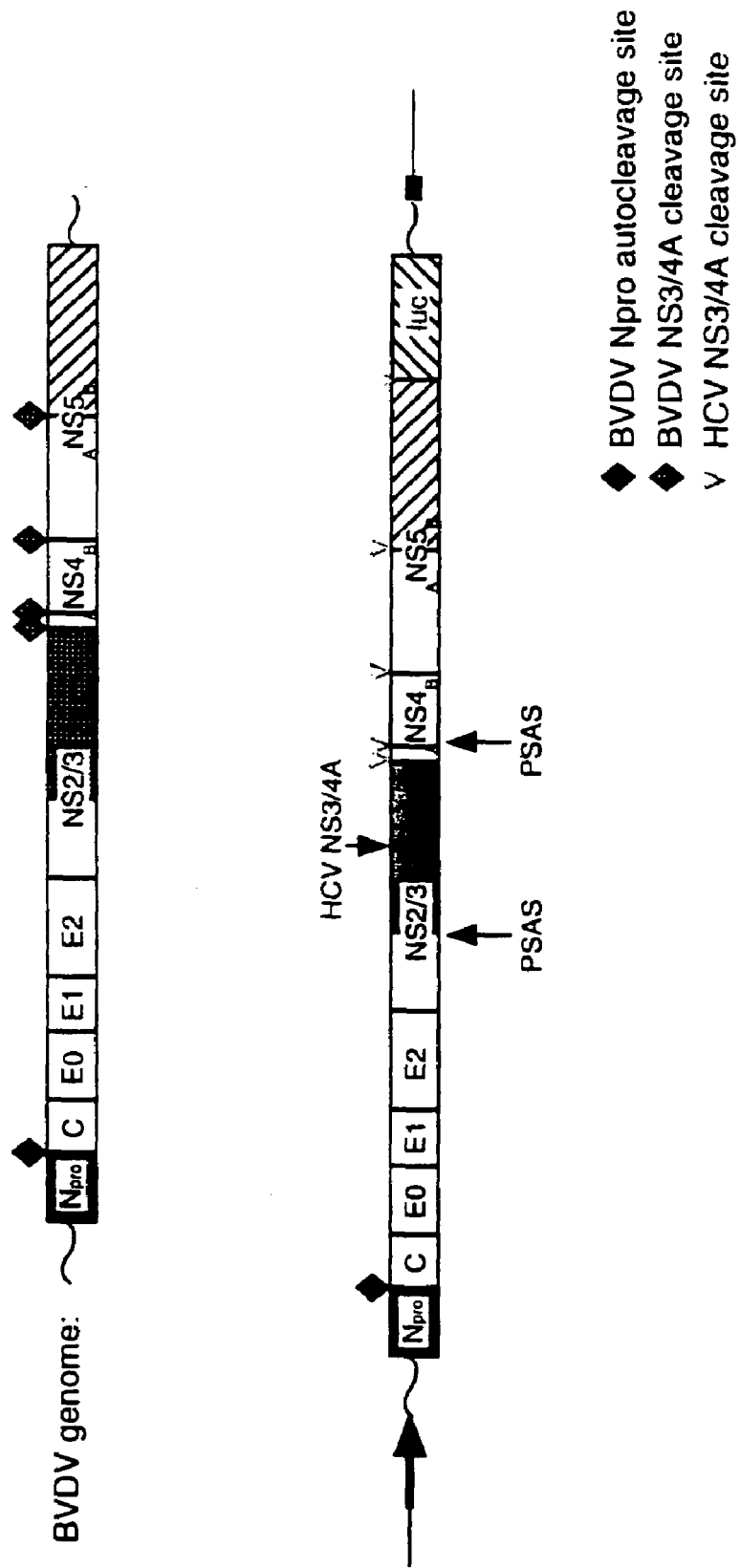

FIG. 22 Resistance Test Vectors (BVDV NS3/4A chimeras, luc fusion protein)

A diagrammatic representation of the genome of BVDV is shown at the top. HCV protease cleavage sites are indicated by grey triangles, and BVDV protease cleavage sites are represented by crosshatched diamonds (signal peptidase and NS2/3 protease cleavage sites are not shown). The resistance test vector pXBVDV(HCVNS3)luc contains the BVDV structural protein genes, BVDV NS2, HCV NS3/4A protease, and BVDV NS4B and NS5; the cleavage sites in the nonstructural protein region are altered so that they are recognized by the HCV NS3/4A protease. The luciferase reporter gene is expressed as a fusion with the chimeric polyprotein, and released by cleavage by HCV NS3/4A.

Figure 23:
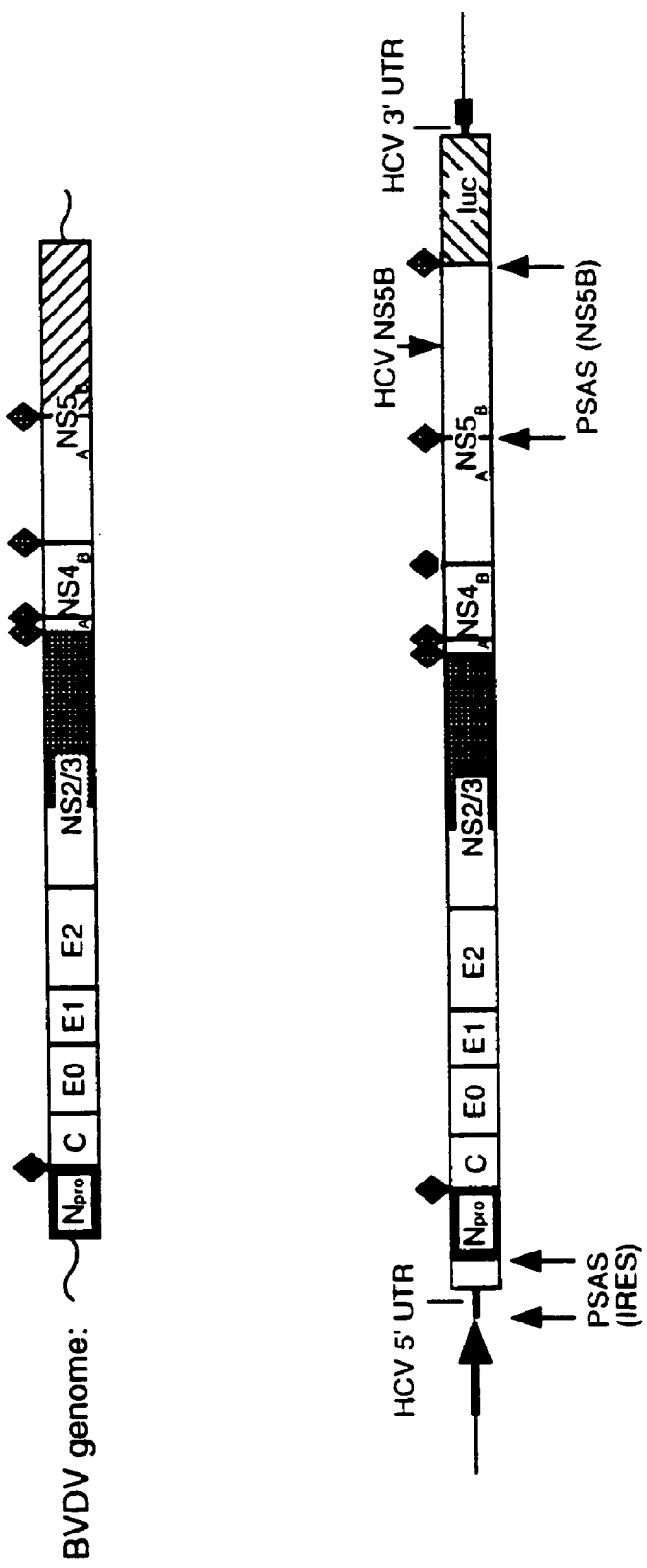
Figure 24A:
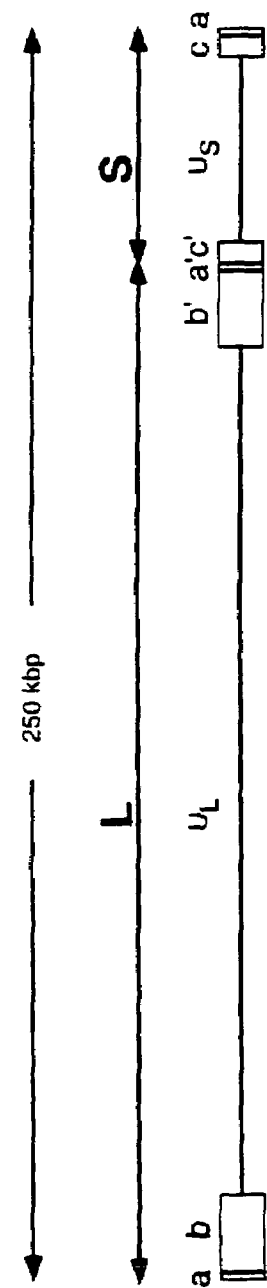
Figure 24B:
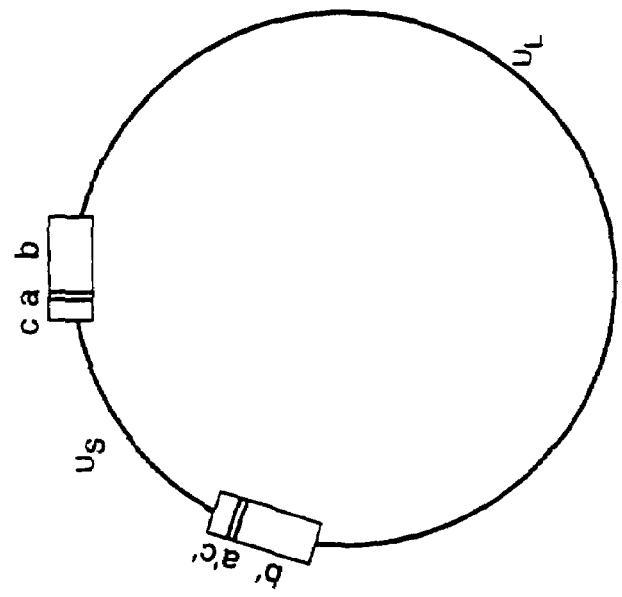

FIG. 23 Resistance Test Vectors (BVDV NS5B chimeras, luc fusion protein).

The resistance test vector pXBVDV(HCVNS5B)luc comprising the BVDV structural protein genes, BVDV NS2, NS3/4A protease, NS4B and NS5A, and HCV NS5B; the cis-acting regulatory elements recognized by the NS5B polymerase, located in the 3' UTR and 5' UTR and amino terminal region of the C ORF, are derived from HCV. The luciferase reporter gene is expressed as a fusion with the chimeric polyprotein, and released by cleavage by BVDV NS3/4A.

FIG. 24

A. Diagrammatic representation of the HCMV genome. The genome has terminal direct repeats designated as "a" which exist in 1-10 copies per genome. The "a" sequences are also present in an inverted orientation at the L-S junction (a'). Inverted repeats "b" and "c" are designated as blocks, "b'" and "c'" are used to designate the "b" and "c" repeats in the anti-sense orientation. $U_L$ and $U_S$ designate the unique regions of the L and S components of the genome. Blocks of ORFs are shown below the genome. Three genes that code for targets of anti-viral drugs, UL54, UL80 and UL97 are indicated by arrows. OriLYT refers to the HCMV lytic origin of replication.

B. Circularization of a monomeric HCMV genome following infection

FIG. 25

A. Diagrammatic representation of the HCMV genome.

B. Circularization of the HCMV genome following infection.

C. Four isomers of HCMV genome following inversion of the genome during replication. Arrows under the $U_L$ and $U_S$ segments emphasize the inversion of the L and S segments of the genome relative to each other.

FIG. 26

Diagrammatic representation of the HCMV genome. The $\beta_{2.7}$ transcript present in the "b" region of the genome is shown as it exists in the wild type HCMV (A) and as it is modified in the HCMV-$\beta_{2.7}$-F-IG (B).

FIG. 27

Diagrammatic representation of the amplicon plasmid lacking a functional indicator gene. ORF Gene X designates an anti-viral target (e.g. UL54, UL80, UL97) The large black arrow represents a promoter and the circle (pA+) indicates a polyadenylation signal. The promoter and polyadenylation signal can be derived from the HCMV genome and appropriate to the viral gene/drug target (gene X) or may be exogenous regulatory elements as described in the text. PSAS indicates patient sequence acceptor sites.

FIG. 28

Diagrammatic representation of the amplicon plasmid comprising a non-functional indicator gene which includes a permuted promoter. ORF Gene X designates an anti-viral target (e.g. UL54, UL80, UL97) The large black arrow represents a promoter and the round circle (pA+) indicates a polyadenylation signal. The promoter and polyadenylation signal can be derived from the HCMV genome and appropriate to the viral gene/drug target (gene X) or may be exogenous regulatory elements as described in the text. PSAS indicates patient sequence acceptor sites. This amplicon contains the permuted promoter cassettes as described in the text.

FIG. 29

Diagrammatic representation of the amplicon plasmid comprising a non-functional indicator gene with a permuted coding region. ORF Gene X designates an anti-viral target (e.g. UL54, UL80, UL97) The large black arrow represents a promoter and the circle (pA+) indicates a polyadenylation signal. The promoter and polyadenylation signal can be derived from the HCMV genome and appropriate to the viral gene/drug target (gene X) or may be exogenous regulatory elements as described in the text. PSAS indicates patient sequence acceptor sites. This amplicon contains the permuted coding region cassettes as described in the text.

FIG. 30

Diagrammatic representation of the four isomers of the HCMV genome present after viral replication and the relative position of the permuted coding region cassettes after rearrangement. Note that in panel C the 2 halves of the cassette are now in the proper orientation to direct expression of the reporter gene. The arrangement shown in panel B will also result in an appropriate juxtaposition of the 2 halves of the cassette following concatamerization of the rearranged genomes.

FIG. 31

Diagrammatic representation of amplicon plasmid comprising a functional indicator gene. ORF Gene X designates an anti-viral target (e.g. UL54, UL80, UL97) The large black arrow represents a promoter and the circle (pA+) indicates a polyadenylation signal. The promoter and polyadenylation signal can be derived from the HCMV genome and appropriate to the viral gene/drug target (gene X) or may be exogenous regulatory elements as described in the text. PSAS indicates patient sequence acceptor sites. This amplicon contains the functional indicator gene cassette as described in the text.

DETAILED DESCRIPTION OF THE INVENTION

In order that the invention described herein may be more fully understood, the following description is set forth.

The present invention provides a novel drug susceptibility and resistance assay comprising the steps of: (a) introducing a resistance test vector comprising a patient-derived segment and an indicator gene into a host cell; (b) culturing the host cell from step (a); (c) measuring expression of the indicator gene in a target host cell; and (d) comparing the expression of the indicator gene from step (c) with the expression of the indicator gene measured when steps (a)-(c) are carried out in the absence of the anti-viral drug, wherein a test concentration of the anti-viral drug is present at steps (a)-(c); at steps (b)-(c); or at step (c).

In one aspect of the invention there is provided a method for determining susceptibility for an anti-viral drug comprising: (a) introducing a resistance test vector comprising a patient-derived segment and an indicator gene into a host cell; (b) culturing the host cell from step (a); (c) measuring an indicator in a target host cell wherein said indicator is a DNA or RNA structure; and (d) comparing the measurement of the indicator from step (c) with the measurement of the indicator when steps (a)-(c) are carried out in the absence of the anti-viral drug, wherein a test concentration of the anti-viral drug is present at steps (a)-(c); at steps (b)-(c); or at step (c).

This invention also provides a method for determining anti-viral drug resistance in a patient comprising: (a) developing a standard curve of drug susceptibility for an anti-viral drug; (b) determining anti-viral drug susceptibility in the patient using either of the susceptibility tests described above; and (c) comparing the anti-viral drug susceptibility in step (b) with the standard curve determined in step (a), wherein a decrease in anti-viral susceptibility indicates development of anti-viral drug resistance in the patient.

This invention also provides a method for determining anti-viral drug resistance in a patient comprising: (a) determining anti-viral drug susceptibility in the patient at a first time according to either of the above methods, wherein the patient-derived segment is obtained from the patient at about said time; (b) determining anti-viral drug susceptibility of the same patient at a later time; and (c) comparing the anti-viral drug susceptibilities determined in step (a) and (b), wherein a decrease in anti-viral drug susceptibility at the later time compared to the first time indicates development or progression of anti-viral drug resistance in the patient.

The assay of this invention can be used for any viral disease where anti-viral drug susceptibility and resistance is a concern including, for example, HIV, herpes simplex virus, cytomegalovirus virus, varicella zoster virus, other human herpes (HIV) viruses, influenza A virus, respiratory syncytial virus, hepatitis A, B and C viruses, rhinovirus, and human papilloma virus. The foregoing are representative of certain viruses for which there is presently available anti-viral chemotherapy, and represent the viral families retroviridae, herpesviridae, orthomyxoviridae, pneumovirus and hepadnaviridae. The assay of this invention would be used with other viral infections arising from infections due to other viruses within these families as well as viral infections arising from viruses in other viral families. In addition, the drug susceptibility and resistance test of this invention is useful for screening for compounds to treat viral diseases for which there is no currently available therapy.

The structure, life cycle and genetic elements of the viruses which could be tested in the drug susceptibility and resistance test of this invention would be known to one of ordinary skill in the art. It is useful to the practice of this invention, for example, to understand the life cycle of a retrovirus, as well as the viral genes required for retrovirus rescue and infectivity. Retrovirally infected cells shed a membrane virus containing a diploid RNA genome. The virus, studded with an envelope glycoprotein (which serves to determine the host range of infectivity), attaches to a cellular receptor in the plasma membrane of the cell to be infected. After receptor binding, the viru is internalized and uncoated as it passes through the cytoplasm of the host cell. Either on its way to the nucleus or in the nucleus, the reverse transcriptase molecules resident in the viral core drive the synthesis of the double-stranded DNA provirus, a synthesis that is primed by the binding of a tRNA molecule to the genomic viral RNA. The double-stranded DNA provirus is subsequently integrated in the genome of the host cell, where it can serve as a transcriptional template for both mRNAs encoding viral proteins and virion genomic RNA, which will be packaged into viral core particles. On their way out of the infected cell, core particles move through the cytoplasm, attach to the inside of the plasma membrane of the newly infected cell, and bud, taking with them tracts of membrane containing the virally encoded envelope glycoprotein gene product. This cycle of infection—reverse transcription, transcription, translation, virion assembly, and budding—repeats itself over and over again as infection spreads.

The viral RNA and, as a result, the proviral DNA encode several cis-acting elements that are vital to the successful completion of the viral lifecycle. The virion RNA carries the viral promoter at its 3' end. Replicative acrobatics place the viral promoter at the 5' end of the proviral genome as the genome is reverse transcribed. Just 3' to the 5' retroviral LTR lies the viral packaging site. The retroviral lifecycle requires the presence of virally encoded transacting factors. The viral-RNA-dependent DNA polymerase (pol)-reverse transcriptase is also contained within the viral core and is vital to the viral life cycle in that it is responsible for the conversion of the genomic RNA to the integrative intermediate proviral DNA. The viral envelope glycoprotein, env, is required for viral attachment to the uninfected cell and for viral spread. There are also transcriptional trans-activating factors, so called transactivators, that can serve to modulate the level of transcription of the integrated parental provirus. Typically, replication-competent (non-defective) viruses are self-contained in that they encode all of these trans-acting factors. Their defective counterparts are not self-contained.

In the case of a DNA virus, such as a hepadnavirus, understanding the life cycle and viral genes required for infection is useful to the practice of this invention. The process of HBV entry has not been well defined. Replication of HBV uses an RNA intermediate template. In the infected cell the first step in replication is the conversion of the asymmetric relaxed circle DNA (rc-DNA) to covalently closed circle DNA (cccDNA). This process, which occurs within the nucleus of infected liver cells, involves completion of the DNA positive-strand synthesis and ligation of the DNA ends. In the second step, the cccDNA is transcribed by the host RNA polymerase to generate a 3.5 kB RNA template (the pregenome). This pregenome is complexed with protein in the viral core. The third step involves the synthesis of the first negative-sense DNA strand by copying the pregenomic RNA using the virally encoded P protein reverse transcriptase. The P protein also serves as the minus strand DNA primer. Finally, the synthesis of the second positive-sense DNA strand occurs by copying the first DNA strand, using the P protein DNA polymerase activity and an oligomer of viral RNA as primer. The pregenome also transcribes mRNA for the major structural core proteins.

The following flow chart illustrates certain of the various vectors and host cells which may be used in this invention. It is not intended to be all inclusive.

Vectors

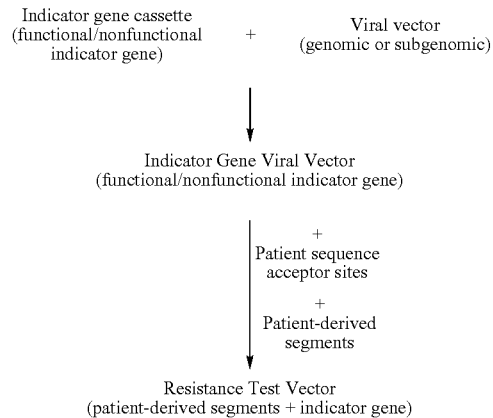

Host Cells

Packaging Host Cell—transfected with packaging expression vectors

Resistance Test Vector Host Cell—a packaging host cell transfected with a resistance test vector Target Host Cell—a host cell to be infected by a resistance test vector viral particle produced by the resistance test vector host cell Resistance Test Vector "Resistance test vector" means one or more vectors which taken together contain DNA or RNA comprising a patient-derived segment and an indicator gene. In the case where the resistance test vector comprises more than one vector the patient-derived segment may be contained in one vector and the indicator gene in a different vector. Such a resistance test vector comprising more than one vector is referred to herein as a resistance test vector system for purposes of clarity but is nevertheless understood to be a resistance test vector. The DNA or RNA of a resistance test vector may thus be contained in one or more DNA or RNA molecules. In one embodiment, the resistance test vector is made by insertion of a patient-derived segment into an indicator gene viral vector. In another embodiment, the resistance test vector is made by insertion of a patient-derived segment into a packaging vector while the indicator gene is contained ir a second vector, for example an indicator gene viral vector. As used herein, "patient-derived segment" refers to one or more viral segments obtained directly from a patient using various means, for example, molecular cloning or polymerase chain reaction (PCR) amplification of a population of patient-derived segments using viral DNA or complementary DNA (cDNA) prepared from viral RNA, present in the cells (e.g. peripheral blood mononuclear cells, PBMC), serum or other bodily fluids of infected patients. When a viral segment is "obtained directly" from a patient it is obtained without passage of the virus through culture, or if the virus is cultured, then by a minimum number of passages to essentially eliminate the selection of mutations in culture. The term "viral segment" refers to any functional viral sequence or viral gene encoding a gene product (e.g., a protein) that is the target of an anti-viral drug. The term "functional viral sequence" as used herein refers to any nucleic acid sequence (DNA or RNA) with functional activity such as enhancers, promoters, polyadenylation sites, sites of action of trans-acting factors, such as tar and RRE, packaging sequences, integration sequences, or splicing sequences. If a drug were to target more than one functional viral sequence or viral gene product then patient-derived segments corresponding to each said viral gene would be inserted in the resistance test vector. In the case of combination therapy where two or more anti-virals targeting two different functional viral sequences or viral gene products are being evaluated, patient-derived segments corresponding to each functional viral sequence or viral gene product would be inserted in the resistance test vector. The patient-derived segments are inserted into unique restriction sites or specified locations, called patient sequence acceptor sites, in the indicator gene viral vector or for example, a packaging vector depending on the particular construction being used as described herein.

As used herein, "patient-derived segment" encompasses segments derived from human and various animal species. Such species include, but are not limited to chimpanzees, horses, cattles, cats and dogs.

Patient-derived segments can also be incorporated into resistance test vectors using any of several alternative cloning techniques. For example, cloning via the introduction of class II restriction sites into both the plasmid backbone and the patient-derived segments or by uracil DNA glycosylase primer cloning.

The patient-derived segment may be obtained by any method of molecular cloning or gene amplification, or modifications thereof, by introducing patient sequence acceptor sites, as described below, at the ends of the patient-derived segment to be introduced into the resistance test vector. For example, in a gene amplification method such as PCR, restriction sites corresponding to the patient-sequence acceptor sites can be incorporated at the ends of the primers used in the PCR reaction. Similarly, in a molecular cloning method such as cDNA cloning, said restriction sites can be incorporated at the ends of the primers used for first or second strand cDNA synthesis, or in a method such as primer-repair of DNA, whether cloned or uncloned DNA, said restriction sites can be incorporated into the primers used for the repair reaction. The patient sequence acceptor sites and primers are designed to improve the representation of patient-derived segments. Sets of resistance test vectors having designed patient sequence acceptor sites provide representation of patient-derived segments that would be underrepresented in one resistance test vector alone.

Resistance test vectors are prepared by modifying an indicator gene viral vector (described below) by introducing patient sequence acceptor sites, amplifying or cloning patient-derived segments and inserting the amplified or cloned sequences precisely into indicator gene viral vectors at the patient sequence acceptor sites. The resistance test vectors are constructed from indicator gene viral vectors which are in turn derived from genomic viral vectors or subgenomic viral vectors and an indicator gene cassette, each of which is described below. Resistance test vectors are then introduced into a host cell. Alternatively, a resistance test vector (also referred to as a resistance test vector system) is prepared by introducing patient sequence acceptor sites into a packaging vector, amplifying or cloning patient-derived segments and inserting the amplified or cloned sequences precisely into the packaging vector at the patient sequence acceptor sites and co-transfecting this packaging vector with an indicator gene viral vector.

In one preferred embodiment, the resistance test vector may be introduced into packaging host cells together with packaging expression vectors, as defined below, to produce resistance test vector viral particles that are used in drug resistance and susceptibility tests that are referred to herein as a "particle-based test." In an alternative preferred embodiment, the resistance test vector may be introduced into a host cell in the absence of packaging expression vectors to carry out a drug resistance and susceptibility test that is referred to herein as a "non-particle-based test." As used herein a "packaging expression vector" provides the factors, such as packaging proteins (e.g. structural proteins such as core and envelope polypeptides), transacting factors, or genes required by replication-defective retrovirus or hepadnavirus. In such a situation, a replication-competent viral genome is enfeebled in a manner such that it cannot replicate on its own. This means that, although the packaging expression vector can produce the trans-acting or missing genes required to rescue a defective viral genome present in a cell containing the enfeebled genome, the enfeebled genome cannot rescue itself.

Indicator or Indicator Gene

"Indicator or indicator gene" refers to a nucleic acid encoding a protein, DNA or RNA structure that either directly or through a reaction gives rise to a measurable or noticeable aspect, e.g. a color or light of a measurable wavelength or in the case of DNA or RNA used as an indicator a change or generation of a specific DNA or RNA structure. Preferred examples of an indicator gene is the *E. coli* lacZ gene which encodes beta-galactosidase, the luc gene which encodes luciferase either from, for example, *Photonis pyralis* (the firefly) or *Renilla reniformis* (the sea pansy), the *E. coli* phoA gene which encodes alkaline phosphatase, green fluorescent protein and the bacterial CAT gene which encodes chloramphenicol acetyltransferase. Additional preferred examples of an indicator gene are secreted proteins or cell surface proteins that are readily measured by assay, such as radioimmunoassay (RIA), or fluorescent activated cell sorting (FACS), including, for example, growth factors, cytokines and cell surface antigens (e.g. growth hormone, I1-2 or CD4, respectively). "Indicator gene" is understood to also include a selection gene, also referred to as a selectable marker. Examples of suitable selectable markers for mammalian cells are dihydrofolate reductase (DHFR), thymidine kinase, hygromycin, neomycin, zeocin or *E. coli* gpt. In the case of the foregoing examples of indicator genes, the indicator gene and the patient-derived segment are discrete, i.e. distinct and separate genes. In some cases a patient-derived segment may also be used as an indicator gene. In one such embodiment in which the patient-derived segment corresponds to more than one viral gene which is the target of an anti-viral, one of said viral genes may also serve as the indicator gene. For example, a viral protease gene may serve as an indicator gene by virtue of its ability to cleave a chromogenic substrate or its ability to activate an inactive zymogen which in turn cleaves a chromogenic substrate, giving rise in each case to a color reaction. In all of the above examples of indicator genes, the indicator gene may be either "functional" or "non-functional" but in each case the expression of the indicator gene in the target cell is ultimately dependent upon the action of the patient-derived segment.

Functional Indicator Gene

In the case of a "functional indicator gene" the indicator gene may be capable of being expressed in a "packaging host cell/resistance test vector host cell" as defined below, independent of the patient-derived segment, however the functional indicator gene could not be expressed in the target host cell, as defined below, without the production of functional resistance test vector particles and their effective infection of the target host cell. In one embodiment of a functional indicator gene, the indicator gene cassette, comprising control elements and a gene encoding an indicator protein, is inserted into the indicator gene viral vector with the same or opposite transcriptional orientation as the native or foreign enhancer/promoter of the viral vector. One example of a functional indicator gene in the case of HIV or HBV, places the indicator gene and its promoter (a CMV IE enhancer/promoter) in the same or opposite transcriptional orientation as the HIV-LTR or HBV enhancer-promoter, respectively, or the CMV IE enhancer/promoter associated with the viral vector.

Non-Functional Indicator Gene

Alternatively the indicator gene, may be "non-functional" in that the indicator gene is not efficiently expressed in a packaging host cell transfected with the resistance test vector, which is then referred to a resistance test vector host cell, until it is converted into a functional indicator gene through the act on of one or more of the patient-derived segment products. An indicator gene is rendered non-functional through genetic manipulation according to this invention.

1. Permuted Promoter In one embodiment an indicator gene is rendered non-functional due to the location of the promoter, in that, although the promoter is in the same transcriptional orientation as the indicator gene, it follows rather than precedes the indicator gene coding sequence. This misplaced promoter is referred to as a "permuted promoter." In addition to the permuted promoter the orientation of the non-functional indicator gene is opposite to that of the native or foreign promoter/enhancer of the viral vector. Thus the coding sequence of the non-functional indicator gene can neither be transcribed by the permuted promoter nor by the viral promoters. The non-functional indicator gene and its permuted promoter is rendered functional by the action of one or more of the viral proteins. One example of a non-functional indicator gene with a permuted promoter in the case of HIV, places a T7 phage RNA polymerase promoter (herein referred to as T7 promoter) promoter in the 5' LTR in the same transcriptional orientation as the indicator gene. The indicator gene cannot be transcribed by the T7 promoter as the indicator gene cassette is positioned upstream of the T7 promoter. The non-functional indicator gene in the resistance test vector is converted into a functional indicator gene by reverse transcriptase upon infection of the target cells, resulting from the repositioning of the T7 promoter, by copying from the 5' LTR to the 3' LTR, relative to the indicator gene coding region. Following the integration of the repaired indicator gene into the target cell chromosome by HIV integrase, a nuclear T7 RNA polymerase expressed by the target cell transcribes the indicator gene. One example of a non-functional indicator gene with a permuted promoter in the case of HBV, places an enhancer-promoter region downstream or 3' of the indicator gene both having the same transcriptional orientation. The indicator gene cannot be transcribed by the enhancer-promoter as the indicator gene cassette is positioned upstream. The non-functional indicator gene in the resistance test vector is converted into a functional indicator gene by reverse transcription and circularization of the HBV indicator gene viral vector by the repositioning of the enhancer-promoter upstream relative to the indicator gene coding region.

A permuted promoter may be any eukaryotic or prokaryotic promoter which can be transcribed in the target host cell. Preferably the promoter will be small in size to enable insertion in the viral genome without disturbing viral replication. More preferably, a promoter that is small in size and is capable of transcription by a single subunit RNA polymerase introduced into the target host cell, such as a bacteriophage promoter, will be used. Examples of such bacteriophage promoters and their cognate RNA polymerases include those of phages T7, T3 and Sp6. A nuclear localization sequence (NLS) may be attached to the RNA polymerase to localize expression of the RNA polymerase to the nucleus where they may be needed to transcribed the repaired indicator gene. Such an NLS may be obtained from any nuclear-transported protein such as the SV40 T antigen. If a phage RNA polymerase is employed, an internal ribosome entry site (IRES) such as the EMC virus 5' untranslated region (UTR) may be added in front of the indicator gene, for translation of the transcripts which are generally uncapped. In the case of HIV, the permuted promoter itself can be introduced at any position within the 5' LTR that is copied to the 3' LTR during reverse transcription so long as LTR function is not disrupted, preferably within the U5 and R portions of the LTR, and most preferably outside of functionally important and highly conserved regions of U5 and R. In the case of HBV, the permuted promoter can be placed at any position that does not disrupt the cis acting elements that are necessary for HBV DNA replication. Blocking sequences may be added at the ends of the resistance test vector should there be inappropriate expression of the non-functional indicator gene due to transfection artifacts (DNA concatenation). In the HIV example of the permuted T7 promoter given above, such a blocking sequence may consist of a T7 transcriptional terminator, positioned to block readthrough transcription resulting from DNA concatenation, but not transcription resulting from repositioning of the permuted T7 promoter from the 5' LTR to the 3' LTR during reverse transcription.

2. Permuted Coding Region In a second embodiment, an indicator gene is rendered non-functional due to the relative location of the 5' and 3' coding regions of the indicator gene, in that, the 3' coding region precedes rather than follows the 5' coding region. This misplaced coding region is referred to as a "permuted coding region." The orientation of the non-functional indicator gene may be the same or opposite to that of the native or foreign promoter/enhancer of the viral vector, as mRNA coding for a functional indicator gene will be produced in the event of either orientation. The non-functional indicator gene and its permuted coding region is rendered functional by the action of one or more of the patient-derived segment products. A second example of a non-functional indicator gene with a permuted coding region in the case of HIV, places a 5' indicator gene coding region with an associated promoter in the 3' LTR U3 region and a 3' indicator gene coding region in an upstream location of the HIV genome, with each coding region having the same transcriptional orientation as the viral LTRs. In both examples, the 5' and 3' coding regions may also have associated splice donor and acceptor sequences, respectively, which may be heterologous or artificial splicing signals. The indicator gene cannot be functionally transcribed either by the associated promoter or viral promoters, as the permuted coding region prevents the formation of functionally spliced transcripts. The non-functional indicator gene in the resistance test vector is converted into a functional indicator gene by reverse transcriptase upon infection of the target cells, resulting from the repositioning of the 5' and 3' indicator gene coding regions relative to one another, by copying of the 3' LTR to the 5' LTR. Following transcription by the promoter associated with the 5' coding region, RNA splicing can join the 5' and 3' coding regions to produce a functional indicator gene product. One example of a non-functional indicator gene with a permuted coding region in the case of HBV, places a 3' indicator gene coding region upstream or 5' of the enhancer-promoter and the 0.5° coding region of the indicator gene. The transcriptional orientation of the indicator gene 5' and 3' coding regions are identical to one another, and the same as that of the indicator gene viral vector. However, as the indicator gene 5' and 3' coding regions are permuted in the resistance test vectors (i.e., the 5' coding region is downstream of the 3' coding region), no mRNA is transcribed which can be spliced to generate a functional indicator gene coding region. Following reverse transcription and circularization of the indicator gene viral vector, the indicator gene 3' coding region is positioned downstream or 3' to the enhancer-promoter and 5' coding regions thus permitting the transcription of mRNA which can be spliced to generate a functional indicator gene coding region.

3. Inverted Intron In a third embodiment, the indicator gene is rendered nor-functional through use of an "inverted intron," i.e. an intron inserted into the coding sequence of the indicator gene with a transcriptional orientation opposite to that of the indicator gene. The overall transcriptional orientation of the indicator gene cassette including its own, linked promoter, is opposite to that of the viral control elements, while the orientation of the artificial intron is the same as the viral control elements. Transcription of the indicator gene by its own linked promoter does not lead to the production of functional transcripts as the inverted intron cannot be spliced in this orientation. Transcription of the indicator gene by the viral control elements does, however, lead to the removal of the inverted intron by RNA splicing, although the indicator gene is still not functionally expressed as the resulting transcript has an antisense orientation. Following the reverse transcription of this transcript and integration of the resultant retroviral DNA, or the circularization of hepadnavirus DNA, the indicator gene can be functionally transcribed using its own linked promoter as the inverted intron has been previously removed. In this case, the indicator gene itself may contain its own functional promoter with the entire transcriptional unit oriented opposite to the viral control elements. Thus the non-functional indicator gene is in the wrong orientation to be transcribed by the viral control elements and it cannot be functionally transcribed by its own promoter, as the inverted intron cannot be properly excised by splicing. However, in the case of a retrovirus and HIV specifically and hepadnaviruses, and HBV specifically, transcription by the viral promoters (HIV LTR or HBV enhancer-promoter) results in the removal of the inverted intron by splicing. As a consequence of reverse transcription of the resulting spliced transcript and the integration of the resulting provirus into the host cell chromosome or circularization of the HBV vector, the indicator gene can now be functionally transcribed by its own promoter. The inverted intron, consisting of a splice donor and acceptor site to remove the intron, is preferably located in the coding region of the indicator gene in order to disrupt translation of the indicator gene. The splice donor and acceptor may be any splice donor and acceptor. A preferred splice donor-receptor is the CMV IE splice donor and the splice acceptor of the second exon of the human alpha globin gene ("intron A").

Indicator Gene Viral Vector—Construction

As used herein, "indicator gene viral vector" refers to a vector(s) comprising an indicator gene and its control elements and one or more viral genes. The indicator gene viral vector is assembled from an indicator gene cassette and a "viral vector," defined below. The indicator gene viral vector may additionally include an enhancer, splicing signals, polyadenylation sequences, transcriptional terminators, or other regulatory sequences. Additionally the indicator gene viral vector may be functional or nonfunctional. In the event that the viral segments which are the target of the anti-viral drug are not included in the indicator gene viral vector they are provided in a second vector. An "indicator gene cassette" comprises an indicator gene and control elements. "Viral vector" refers to a vector comprising some or all of the following: viral genes encoding a gene product, control sequences, viral packaging sequences, and in the case of a retrovirus, integration sequences. The viral vector may additionally include one or more viral segments one or more of which may be the target of an anti-viral drug. Two examples of a viral vector which contain viral genes are referred to herein as an "genomic viral vector" and a "subgenomic viral vector." A "genomic viral vector" is a vector which may comprise a deletion of a one or more viral genes to render the virus replication incompetent, but which otherwise preserves the mRNA expression and processing characteristics of the complete virus. In one embodiment for an HIV drug susceptibility and resistance test, the genomic viral vector comprises the HIV gag-pol, vif, vpr, tat, rev, vpu, and nef genes (some, most or all of env may be deleted). A "subgenomic viral vector" refers to a vector comprising the coding region of one or more viral genes which may encode the proteins that are the target(s) of the anti-viral drug. In the case of HIV, a preferred embodiment is a subgenomic viral vector comprising the HIV gag-pol gene. In the case of HBV a preferred embodiment is a subgenomic viral vector comprising the HBV P gene. In the case of HIV, two examples of proviral clones used for viral vector construction are: HXB2 (Fisher et al., (1986) *Nature*, 320, 367-371) and NL4-3, (Adachi et al., (1986) *J. Virol.*, 59, 284-291). In the case of HBV, a large number of full length genomic sequences have been characterized and could be used for construction of HBV viral vectors: GenBank Nos. M54923, M38636, J02203 and X59795. The viral coding genes may be under the control of a native enhancer/promoter or a foreign viral or cellular enhancer/promoter. A preferred embodiment for an HIV drug susceptibility and resistance test, is to place the genomic or subgenomic viral coding regions under the control of the native enhancer/promoter of the HIV-LTR U3 region or the CMV immediate-early (IE) enhancer/promoter. A preferred embodiment for an HBV drug susceptibility and resistance test, is to place the genomic or subgenomic viral coding regions under the control of the CMV immediate-early (IE) enhancer/promoter. In the case of an indicator gene viral vector that contains one or more viral genes which are the targets or encode proteins which are the targets of an anti-viral drug(s) then said vector contains the patient sequence acceptor sites. The patient-derived segments are inserted in the patient sequence acceptor site in the indicator gene viral vector which is then referred to as the resistance test vector, as described above.

"Patient sequence acceptor sites" are sites in a vector for insertion of patient-derived segments and said sites may be: 1) unique restriction sites introduced by site-directed mutagenesis into a vector; 2) naturally occurring unique restriction sites in the vector; or 3) selected sites into which a patient-derived segment may be inserted using alternative cloning methods (e.g. UDG cloning). In one embodiment the patient sequence acceptor site is introduced into the indicator gene viral vector. The patient sequence acceptor sites are preferably located within or near the coding region of the viral protein which is the target of the anti-viral drug. The viral sequences used for the introduction of patient sequence acceptor sites are preferably chosen so that no change, or a conservative change, is made in the amino acid coding sequence found at that position. Preferably the patient sequence acceptor sites are located within a relatively conserved region of the viral genome to facilitate introduction of the patient-derived segments. Alternatively, the patient sequence acceptor sites are located between functionally important genes or regulatory sequences. Patient-sequence acceptor sites may be located at or near regions in the viral genome that are relatively conserved to permit priming by the primer used to introduce the corresponding restriction site into the patient-derived segment. To improve the representation of patient-derived segments further, such primers may be designed as degenerate pools to accommodate viral sequence heterogeneity, or may incorporate residues such as deoxyinosine (I) which have multiple base-pairing capabilities. Sets of resistance test vectors having patient sequence acceptor sites that define the same or overlapping restriction site intervals may be used together in the drug resistance and susceptibility tests to provide representation of patient-derived segments that contain internal restriction sites identical to a given patient sequence acceptor site, and would thus be underrepresented in either resistance test vector alone.

Host Cells

The resistance test vector is introduced into a host cell. Suitable host cells are mammalian cells. Preferred host cells are derived from human tissues and cells which are the principle targets of viral infection. In the case of HIV these include human cells such as human T cells, monocytes, macrophage, dendritic cells, Langerhans cells, hematopoeitic stem cells or precursor cells, and other cells. In the case of HBV, suitable host cells include hepatoma cell lines (HepG2, Huh7), primary human hepatocytes, mammalian cells which can be infected by pseudotyped HBV, and other cells. Human derived host cells will assure that the anti-viral drug will enter the cell efficiently and be converted by the cellular enzymatic machinery into the metabolically relevant form of the anti-viral inhibitor. Host cells are referred to herein as a "packaging host cells," "resistance test vector host cells," or "target host cells." A "packaging host cell" refers to a host cell that provides the trans-acting factors and viral packaging proteins required by the replication defective viral vectors used herein, such as the resistance test vectors, to produce resistance test vector viral particles. The packaging proteins may be provided for by the expression of viral genes contained within the resistance test vector itself, a packaging expression vector(s), or both. A packaging host cell is a host cell which is transfected with one or more packaging expression vectors and when transfected with a resistance test vector is then referred to herein as a "resistance test vector host cell" and is sometimes referred to as a packaging host cell/resistance test vector host cell. Preferred host cells for use as packaging host cells for HIV include 293 human embryonic kidney cells (293, Graham, F. L. et al., J. Gen Virol. 36: 59, 1977), BOSC23 (Pear et al., Proc. Natl. Acad. Sci. 90, 8392, 1993), tsa54 and tsa201 cell lines (Heinzel et al., J. Virol. 62, 3738, 1988), for HBV HepG2 (Galle and Theilmann, L. Arzheim.—Forschy Drug Res. (1990) 40, 1380-1382), and Huh7 (Ueda, K et al. Virology (1989) 169, 213-216). A "target host cell" refers to a cell to be infected by resistance test vector viral particles produced by the resistance test vector host cell in which expression or inhibition of the indicator gene takes place. Preferred host cells for use as target host cells include human T cell leukemia cell lines including Jurkat (ATCC T1B-152), H9 (ATCC HTB-176), CEM (ATCC CCL-119), HUT78 (ATCC T1B-161), and derivatives thereof.

Drug Susceptibility and Resistance Tests

The drug susceptibility and resistance tests of this invention may be carried out in one or more host cells. Viral drug susceptibility is determined as the concentration of the anti-viral agent at which a given percentage of indicator gene expression is inhibited (e.g. the $IC_{50}$ for an anti-viral agent is the concentration at which 50% of indicator gene expression is inhibited). A standard curve for drug susceptibility of a given anti-viral drug can be developed for a viral segment that is either a standard laboratory viral segment or from a drug-naive patient (i.e. a patient who has not received any anti-viral drug) using the method of this invention. Correspondingly, viral drug resistance is a decrease in viral drug susceptibility for a given patient either by comparing the drug susceptibility to such a given standard or by making sequential measurement in the same patient over time, as determined by increased inhibition of indicator gene expression (i.e. decreased indicator gene expression).

In the first type of drug susceptibility and resistance test, resistance test vector viral particles are produced by a first host cell (the resistance test vector host cell) that is prepared by transfecting a packaging host cell with the resistance test vector and packaging expression vector(s). The resistance test vector viral particles are then used to infect a second host cell (the target host cell) in which the expression of the indicator gene is measured. Such a two cell system comprising a packaging host cell which is transfected with a resistance test vector, which is then referred to as a resistance test vector host cell, and a target cell are used in the case of either a functional or non-functional indicator gene. Functional indicator genes are efficiently expressed upon transfection of the packaging host cell and would require infection of a target host cell with resistance test vector host cell supernatart to carry out the test of this invention. Non-functional indicator genes with a permuted promoter, a permuted coding region, or an inverted intron are not efficiently expressed upon transfection of the packaging host cell and thus the infection of the target host cell can be achieved either by co-cultivation by the resistance test vector host cell and the target host cell or through infection of the target host cell using the resistance test vector host cell supernatant. In the second type of drug susceptibility and resistance test, a single host cell (the resistance test vector host cell) also serves as a target host cell. The packaging host cells are transfected and produce resistance test vector viral particles and some of the packaging host cells also become the target of infection by the resistance test vector particles. Drug susceptibility and resistance tests employing a single host cell type are possible with viral resistance test vectors comprising a non-functional indicator gene with a permuted promoter, a permuted coding region, or an inverted intron. Such indicator genes are not efficiently expressed upon transfection of a first cell, but are only efficiently expressed upon infection of a second cell, and thus provide an opportunity to measure the effect of the anti-viral agent under evaluation. In the case of a drug susceptibility and resistance test using a resistance test vector comprising a functional indicator gene, neither the co-cultivation procedure nor the resistance and susceptibility test using a single cell type can be used for the infection of target cells. A resistance test vector comprising a functional indicator gene requires a two cell system using filtered supernatants from the resistance test vector host cells to infect the target host cell.

In one embodiment of the invention in the case of HIV, a particle-based resistance tests are carried out with resistance test vectors derived from genomic viral vectors, i.e., pLG-lucPP-HS, pCG-lucPP-HS, pLG-lucPP-PB, pCG-lucPP-PB, pLG-lucPC-HS, pCG-lucPC-HS, pLG-lucPC-PB, pCG-lucPC-PB, pLG-lucII-HS, pCG-lucII-HS, pLG-lucII-PB, pCG-lucII-PB, and pCG-CXCN(F-lucP)2-AA which are cotransfected with the packaging expression vector pVL-env4070A (also referred to as pCXAS-4070Aenv). Alternatively, a particle-based resistance test may be carried out with resistance test vectors derived from subgenomic viral vectors, i.e., pLS-lucPP-HS, pCS-lucPP-HS, pLS-lucPP-PB, pCS-luc-PP-PB, pLS-lucPC-HS, pCS-lucPC-HS, pLS-lucPC-PB, pCS-luc-PC-PB, pLS-lucII-HS, pCS-lucII-HS, pLS-lucII-PB, and pCS-luc-II-PB) which are cotransfected with the packaging expression vector pVL-env4070A and either pLTR-HIV3' or pCMV-HIV3'. In another embodiment of the invention in the case of HIV, non-particle-based resistance tests are carried out using each of the above described resistance test vectors by transfection of selected host cells in the absence of packaging expression vectors.

In the case of the particle-based susceptibility and resistance test, resistance test vector viral particles are produced by a first host cell (the resistance test vector host cell) that is prepared by transfecting a packaging host cell with the resistance test vector and packaging expression vector(s). The resistance test vector viral particles are then used to infect a second host cell (the target host cell) in which the expression of the indicator gene is measured. In a second type of particle-based susceptibility and resistance test, a single host cell type (the resistance test vector host cell) serves both purposes: some of the packaging host cells in a given culture are transfected and produce resistance test vector viral particles and some of the host cells in the same culture are the target of infection by the resistance test vector particles thus produced. Resistance tests employing a single host cell type are possible with resistance test vectors comprising a non-functional indicator gene with a permuted promoter since such indicator genes are efficiently expressed upon infection of a permissive host cell, the are not efficiently expressed upon transfection of the same host cell type, and thus provide an opportunity to measure the effect of the anti-viral agent under evaluation. For similar reasons, resistance tests employing-two cell types may be carried out by co-cultivating the two cell types as an alternative to infecting the second cell type with viral particles obtained from the supernatants of the first cell type.

In the case of the non-particle-based susceptibility and resistance test, resistance tests are performed by transfection of a single host cell with the resistance test vector in the absence of packaging expression vectors. Non-particle based resistance tests are carried out using the resistance test vectors comprising non-functional indicator genes with either permuted promoters, permuted coding regions or inverted introns. These non-particle based resistance tests are performed by transfection of a single host cell type with each resistance test vector in the absence of packaging expression vectors. Although the non-functional indicator genes contained within these resistance test vectors are not efficiently expressed upon transfection of the host cells, there is detectable indicator gene expression resulting from non-viral particle-based reverse transcription. Reverse transcription and strand transfer results in the conversion of the permuted, non-functional indicator gene to a non-permuted, functional indicator gene.

As reverse transcription is completely dependent upon the expression of the pol gene contained within each resistance test vector, anti-viral agents may be tested for their ability to inhibit the pol gene products encoded by the patient-derived segments contained within the resistance test vectors. In the case of HIV, reverse transcription and strand transfer results in the conversion of the non-functional indicator gene to a functional indicator gene. As reverse transcription is completely dependent upon the expression of the patient-derived segment contained within each resistance test vector, anti-viral agents may be tested for their ability to inhibit the gene products encoded by the patient-derived segments contained within the resistance test vectors.

The packaging host cells are transfected with the resistance test vector and the appropriate packaging expression vector(s) to produce resistance test vector host cells. Individual anti-viral agents, including the reverse transcriptase inhibitors AZT, ddI, ddC, d4T and 3TC, and the protease inhibitors saquinavir, ritonavir and indinavir, as well as combinations thereof, are added to individual plates of packaging host cells at the time of their transfection, at an appropriate range of concentrations. Twenty-four to 48 hours after transfection, target host cells are infected by co-cultivation with resistance test vector host cells or with resistance test vector viral particles obtained from filtered supernatants of resistance test vector host cells. Each anti-viral agent, or combination thereof, is added to the target host cells prior to or at the time of infection to achieve the same final concentration of the given agent, or agents, present during the transfection.

Determination of the expression or inhibition of the indicator gene in the target host cells infected by co-cultivation or with filtered viral supernatants is made by assay of indicator gene expression, for example in the case where the indicator gene is the firefly luc gene, by measuring luciferase activity. The reduction in luciferase activity observed for target host cells infected with a given preparation of resistance test vector viral particles in the presence of a given antiviral agent, or agents, as compared to a control run in the absence of the antiviral agent, generally relates to the log of the concentration of the antiviral agent as a sigmoidal curve. This inhibition curve is used to calculate the apparent inhibitory concentration (IC) of that agent, or combination of agents, for the viral target product encoded by the patient-derived segments present in the resistance test vector.

In the case of a one cell susceptibility and resistance test, host cells are transfected with the resistance test vector and the appropriate packaging expression vector(s) to produce resistance test vector host cells. Individual antiviral agents, or combinations thereof, are added to individual plates of transfected cells at the time of their transfection, at an appropriate range of concentrations. Twenty-four to 72 hours after transfection, cells are collected and assayed for firefly luciferase activity. As transfected cells in the culture do not efficiently express the indicator gene, transfected cells in the culture, as well superinfected cells in the culture, can serve as target host cells for indicator gene expression. The reduction in luciferase activity observed for cells transfected in the presence of a given antiviral agent, or agents as compared to a control run in the absence of the antiviral agent(s), generally relates to the log of the concentration of the antiviral agent as a sigmoidal curve. This inhibition curve is used to calculate the apparent inhibitory concentration (IC) of an agent, or combination of agents, for the viral target product encoded by the patient-derived segments present in the resistance test vector.

Antiviral Drugs/Drug Candidates

The antiviral drugs being added to the test system are added at selected times depending upon the target of the antiviral drug. For example, in the case of HIV protease inhibitors, including saquinavir, ritonavir, indinavir, and nelfinavir, they are added to individual plates of packaging host cells at the time of their transfection with a resistance test vector, at an appropriate range of concentrations. HIV protease inhibitors are also added to the target host cells at the time of infection to achieve the same final concentration added during transfections. HIV reverse transcriptase inhibitors, including AZT, ddI, ddC, d4T, 3TC and nevaripine, are added to individual plates of target host cells at the time of infection by the resistance test vector viral particles, at a test concentration. Alternatively, the antiviral drugs may be present throughout the assay. The test concentration is selected from a range of concentrations which is typically between about 0.1 nM and about 100 μM and more specifically for each of the following drugs: AZT, from about 1 nM to about 5 μM; ddI, from about 1 nM to about 25 μM; 3TC, from about 1 nM to about 50 μM; d4T, from about 1 nM to about 25 μM; and, nevaripine, from about 1 nM to about 100 μM.

In another embodiment of this invention, a candidate antiviral compound is tested in the drug susceptibility and resistance test of this invention. The candidate antiviral compound is added to the test system at an appropriate concentration and at selected times depending upon the protein target of the candidate anti-viral. Alternatively, more than one candidate antiviral compound may be tested or a candidate antiviral compound may be tested in combination with an approved antiviral drug such as AZT, ddI, ddC, d4T, 3TC, saquinavir or a compound which is undergoing clinical trials such as ritonavir, or indinovir. The effectiveness of the candidate antiviral will be evaluated by measuring the expression or inhibition of the indicator gene. In another aspect of this embodiment, the drug susceptibility and resistance test may be used to screen for viral mutants. Following the identification of resistant mutants to either known anti-virals or candidate anti-virals the resistant mutants are isolated and the DNA is analyzed. A library of viral resistant mutants can thus be assembled enabling the screening of candidate anti-virals, alone or in combination. This will enable one of ordinary skill to identify effective anti-virals and design effective therapeutic regimens.

General Materials and Methods

Most of the techniques used to construct vectors, and transfect and infect cells, are widely practiced in the art, and most practitioners are familiar with the standard resource materials which describe specific conditions and procedures. However, for convenience, the following paragraphs may serve as a guideline.

"Plasmids" and "vectors" are designated by a lower case p followed by letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

Construction of the vectors of the invention employs standard ligation and restriction techniques which are well understood in the art (see Ausubel et al., (1987) Current Protocols in Molecular Biology, Wiley-Interscience or Maniatis et al., (1992) in Molecular Cloning: A laboratory Manual, Cold Spring Harbor Laboratory, N.Y.). Isolated plasmids, DNA sequences, or synthesized oligonucleotides are cleaved, tailored, and relegated in the form desired. The sequences of all DNA constructs incorporating synthetic DNA were confirmed by DNA sequence analysis (Sanger et al. (1977) *Proc. Natl. Acad. Sci.* 74, 5463-5467).

"Digestion" of DNA refers to catalytic cleavage of the DNA with a restriction enzyme that acts only at certain sequences, restriction sites, in the DNA. The various restriction enzymes used herein are commercially available and their reaction conditions, cofactors and other requirements are known to the ordinarily skilled artisan. For analytical purposes, typically 1 μg of plasmid or DNA fragment is used with about 2 units of enzyme in about 20 μl of buffer solution. Alternatively, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods of Enzymology* 65:499-560 (1980).

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 minutes at 20° C. in 50 mM Tris (ph7.6) 50 mM NaCl, 6 mM MgCl$_2$, 6 mM DTT and 5-10 μM dNTPs. The Klenow fragment fills in at 5' sticky ends but chews back protruding 3' single strands, even though the four dNTPs are present. If desired, selective repair can be performed by supplying only one of the dNTPs, or with selected dNTPs, within the limitations dictated by the nature of the sticky ends. After treatment with Klenow, the mixture is extracted with phenol/chloroform and ethanol precipitated. Treatment under appropriate conditions with S1 nuclease or Bal-31 results in hydrolysis of any single-stranded portion.

Ligations are performed in 15-50 μl volumes under the following standard conditions and temperatures: 20 mM Tris-Cl pH 7.5, 10 mM MgCl$_2$, 10 mM DTT, 33 mg/ml BSA, 10 mM-50 mM NaCl, and either 40 μM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 μg/ml total DNA concentrations (5-100 mM total end concentration). Intermolecular blunt end ligations (usually employing a 10-30 fold molar excess of linkers) are performed at 1 μM total ends concentration.

"Transient expression" refers to unamplified expression within about one day to two weeks of transfection. The optimal time for transient expression of a particular desired heterologous protein may vary depending on several factors including, for example, any transacting factors which may be employed, translational control mechanisms and the host cell. Transient expression occurs when the particular plasmid that has been transfected functions, i.e., is transcribed and translated. During this time the plasmid DNA which has entered the cell is transferred to the nucleus. The DNA is in a nonintegrated state, free within the nucleus. Transcription of the plasmid taken up by the cell occurs during this period. Following transfection the plasmid DNA may become degraded or diluted by cell division. Random integration within the cell chromatin occurs.

In general, vectors containing promoters and control sequences which are derived from species compatible with the host cell are used with the particular host cell. Promoters suitable for use with prokaryotic hosts illustratively include the beta-lactamase and lactose promoter systems, alkaline phosphatase, the tryptophan (trp) promoter system and hybrid promoters such as tac promoter. However, other functional bacterial promoters are suitable. In addition to prokaryotes, eukaryotic microbes such as yeast cultures may also be used. *Saccharomyces cerevisiae*, or common baker's yeast is the most commonly used eukaryotic microorganism, although a number of other strains are commonly available. Promoters controlling transcription from vectors in mammalian host cells may be obtained from various sources, for example, the genomes of viruses such as: polyoma, simian virus 40 (SV40), adenovirus, retroviruses, hepatitis B virus and preferably cytomegalovirus, or from heterologous mammalian promoters, e.g. b-actin promoter. The early and late promoters of the SV 40 virus are conveniently obtained as an SV40 restriction fragment which also contains the SV40 viral origin of replication. The immediate early promoter of the human cytomegalovirus is conveniently obtained as a HindIII E restriction fragment. Of course, promoters from the host cell or related species also are useful herein.

The vectors used herein may contain a selection gene, also termed a selectable marker. A selection gene encodes a protein, necessary for the survival or growth of a host cell transformed with the vector. Examples of suitable selectable markers for mammalian cells include the dihydrofolate reductase gene (DHFR), the ornithine decarboxylase gene, the multi-drug resistance gene (mdr), the adenosine deaminase gene, and the glutamine synthase gene. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. The second category is referred to as dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin (Southern and Berg (1982) *J. Molec. Appl. Genet.* 1, 327), mycophenolic acid (Mulligan and Berg (1980) *Science* 209, 1422), or hygromycin (Sugden et al. (1985) *Mol. Cell. Biol.* 5, 410-413). The three examples given above employ bacterial genes under eukaryotic control to convey resistance to the appropriate drug neomycin (G418 or genticin), xgpt (mycophenolic acid) or hygromycin, respectively.

"Transfection" means introducing DNA into a host cell so that the DNA is expressed, whether functionally expressed or otherwise; the DNA may also replicate either as an extrachromosomal element or by chromosomal integration. Unless otherwise provided, the method used herein for transformation of the host cells is the calcium phosphate co-precipitation method of Graham and van der Eb (1973) *Virology* 52, 456-457. Alternative methods for transfection are electroporation, the DEAE-dextran method, lipofection and biolistics (Kriegler (1990) Gene Transfer and Expression: A Laboratory Manual, Stockton Press).

Host cells may be transfected with the expression vectors of the present invention and cultured in conventional nutrient media modified as is appropriate for inducing promoters, selecting transformants or amplifying genes. Host cells are cultured in F12:DMEM (Gibco) 50:50 with added glutamine and without antibiotics. The culture conditions, such as temperature, pH and the like, are those previously used with the host cell selected for expression, and will be apparent to the ordinarily skilled artisan.

The following examples merely illustrate the best mode now known for practicing the invention, but should not be construed to limit the invention. All literature references are expressly incorporated by reference.

EXAMPLE 1

HIV Drug Susceptibility and Resistance Test Using Resistance Test Vectors Comprising Patient-Derived Segment(s) and a Non-Functional Indicator Gene with a Permuted Promoter Indicator Gene Viral Vector—Construction Indicator gene viral vectors containing a non-functional indicator gene with a permuted promoter were designed using both HIV genomic and subgenomic viral vectors comprising viral genes which are the target(s) of anti-viral drugs. The indicator gene viral vectors pLG-lucPP and pCG-lucPP are based on the genomic viral vectors pLG and pCG; each bears a deletion in the HIV env gene. Resistance test vectors derived from the genomic indicator gene viral vectors, pLG-lucPP and pCG-lucPP, contain a patient sequence acceptor site for insertion of the patient-derived segment and are used in conjunction with a packaging expression vector encoding the amphotrophic MLV 4070A env gene product. The indicator gene viral vectors pLS-lucPP and pCS-lucPP are based on the subgenomic viral vectors pLS and pCS; each encodes the HIV gag-pol gene only. Resistance test vectors derived from the subgenomic indicator gene viral vectors, pLS-lucPP and pCS-lucPP, contain a sequence acceptor site for insertion of patient-derived segment and are used in conjunction with a first packaging expression vector encoding the HIV vif, vpr, tat, rev, vpu and nef genes and a second packaging vector encoding the amphotrophic MLV 4070A env gene product.

HIV Viral Vectors—Genomic and Subgenomic

HIV viral vectors were designed using the sequences of the biologically active proviral clone, HXB2 (Fisher et al. (1986) *Nature* 320, 367-371). Two types of viral vector were designed: genomic viral vectors with deletions in a single gene such as env, but which otherwise preserve the mRNA expression and processing characteristics of the complete virus, and subgenomic viral vectors which may include only one or a few genes that are typically the specific targets of susceptibility and resistance testing, such as gag-pol, or which may lack viral genes altogether. Both types of vectors have a unique restriction site within the viral genome for the insertion of an indicator gene cassette as well as patient sequence acceptor sites, i.e. additional unique restriction sites near or within the anti-viral target gene (eg., pol) to permit the insertion of patient-derived HIV sequences. In addition, both types of vector were designed to incorporate either the native enhancer-promoter of the HIV-LTR U3 region, or a foreign enhancer-promoter from the CMV immediate-early (IE) region. Standard methods are employed for the construction of plasmid DNAs (Ausubel et al. (1987) Current Protocols in Molecular Biology, Wiley-Interscience). The sequences of all DNA constructs incorporating synthetic DNA are confirmed by DNA sequence analysis (Sanger et al. (1977) Proc. Natl. Acad. Sci. 74, 5463-5467).

HIV sequences are obtained from plasmid pBS-HIV (Page et al. (1990) J. Virol. 64, 5270-5276) which contains the HXB2 proviral DNA sequence on an HpaI to XbaI restriction fragment inserted into the polylinker of the pBluescript KS (+) plasmid cloning vector (Stratagene, San Diego, Calif.). As this proviral clone contains uncharacterized, flanking human DNA from the site of proviral integration, two steps of site-directed mutagenesis are employed to remove such sequences using plasmid pBS-HIV as a template. In step one, human sequences adjacent to the 5' LTR are removed using oligonucleotide 1 which contains the following sequences in a 5' to 3' direction: 1) a sequence complementary to the first 18 nucleotides of the integrated provirus, within the left U3 region, 2) a six nucleotide SmaI site, and 3) an 18 nucleotide sequence complementary to the region in pBluescript KS (+) just beyond the polylinker and phage T3 promoter. In step two, human sequences adjacent to the 5' LTR are removed using oligonucleotide 2 which contains the following sequences (5' to 3'): 1) an 18 nucleotide sequence complementary to the region in pBluescript KS (+) just beyond the PvuI site, within the LacZ gene, 2) a six nucleotide XbaI site, and 3) a sequence complementary to the last 18 nucleotides of the integrated provirus, within the right U5 region. The resulting plasmid is called pBS-HXB2.

Genomic and subgenomic viral vectors employing the HIV-LTR U3 region as an enhancer-promoter for the expression of anti-viral target genes (FIG. 1) are each derived from plasmid pBS-HXB2 by a single step of site-directed mutagenesis. The genomic viral vector pLG, which is deleted for the env gene, is prepared using oligonucleotide 3 which contains the following sequences (5' to 3'): 1) an 18 nucleotide sequence complementary to positions 7626 to 7643 of HXB2 within the env gene (all coordinates for HXB2 are by reference to GenBank, accession number K03455), 2) an 8 nucleotide NotI site, and 3) an 18 nucleotide sequence complementary to positions 6384 to 6401 of HXB2 within the env gene. The subgenomic viral vector pLS, which is deleted for the env, tat, rev, vif, vpr and vpu genes, is prepared using oligonucleotide 4 which contains the following sequences (5' to 3'): 1) an 18 nucleotide sequence complementary to positions 7626 to 7643 of HXB2 within the env gene, 2) an 8 nucleotide NotI site, and 3) an 18 nucleotide sequence complementary to positions 5109 to 5126 of HXB2 within the vif gene.

Genomic and subgenomic viral vectors which employ the CMV IE region as an enhancer-promoter for the expression of anti-viral target genes are derived from plasmids pLG and pLS, and are called pCG and pCS, respectively (FIG. 1). The genomic viral vector pCG is prepared in two steps. In the first step, an intermediate plasmid is prepared from two DNA fragments: 1) a vector fragment 11.2 kB prepared from digesting plasmid pLG with SmaI and treating the vector with alkaline phosphatase, and 2) a DNA fragment of 0.9 kB containing the CMV IE enhancer-promoter prepared by digesting plasmid pVL-1 (described below) with SmaI. Plasmids containing the CMV IE region in the same transcriptional orientation as the viral LTRs are identified by restriction mapping. In the second step, plasmid pCG is prepared from this intermediate plasmid by site-directed mutagenesis to join the CMV IE enhancer-promoter to the 5'-LTR region at a position permitting transcription initiation to occur at the beginning of the R region, using oligonucleotide 5 which contains the following sequences (5' to 3'): 1) an 18 nucleotide sequence complementary to positions 455 to 472 of HXB2 at the beginning of the R region, and 2) an 18 nucleotide sequence complementary to positions −18 to −1 of the CMV IE enhancer-promoter (coordinates referenced to Boshart et al. (1985) Cell 41, 521-530). The subgenomic viral vector pCS is derived from plasmid pCG and is prepared from two DNA fragments: 1) a vector DNA of 9.1 kB prepared by digesting plasmid pLS with SmaI and ClaI, and 2) a DNA fragment of 1.3 kB prepared by digesting plasmid pCG with SmaI and ClaI.

Genomic Indicator Gene Viral Vector—Permuted Promoter

The indicator gene viral vectors pLG-lucPP and pCG-lucPP, and resistance test vectors derived therefrom, contain the following elements in a 5' to 3' orientation (FIG. 2B): 1) an HIV-LTR U3 region (pLG-lucPP) or a CMV IE enhancer-promoter (pCG-lucPP), 2) an HIV-LTR R region, 3) an HIV-LTR U5 region containing an inserted T7 promoter with a transcriptional orientation opposite to that of the LTRs, 4) the coding regions of the HIV gag-pol, vif, vpr, tat, rev, vpu, deleted env, and nef genes, 5) an indicator gene cassette inserted into the deleted env gene, and 6) a 3' HIV-LTR. The same indicator gene cassette is inserted in pLG-lucPP and pCG-lucPP and contains the following elements: 1) an EMC 5'-UTR region which permits internal ribosome entry, 2) the complete coding region of the luciferase (luc) gene, and 3) a T7 transcriptional terminator. The indicator gene has a transcriptional orientation opposite to the HIV-LTR or CMV IE enhancer-promoter and therefore cannot be functionally transcribed by these elements. The indicator gene also cannot be transcribed by the T7 promoter as the indicator gene cassette is positioned upstream of the T7 promoter. Following reverse transcription and strand transfer, the T7 promoter is copied from the 5' LTR to the 3' LTR, permitting functional transcription of the indicator gene from the newly created T7 promoter by T7 RNA polymerase (FIG. 2C).

Plasmid plucPP, which contains the indicator gene cassette, is prepared in three steps. In the first step, plasmid pVL-EMC/T7 which contains a cassette flanked by unique NotI sites comprising the EMC 5'-UTR element and T7 transcriptional terminator, is prepared from two DNA fragments: 1) a vector DNA of 3.0 kB prepared by digesting plasmid pVL (described below) with NotI and treating the vector with alkaline phosphatase, and 2) a DNA fragment of 0.8 kB containing the EMC 5' UTR and T7 terminator prepared by PCR using plasmid pTM1 (Moss et al. (1990) Nature 348, 91-92) as a template and oligonucleotides 6 and 7 as primers, followed by digestion with NotI. Oligonucleotides 6 and 7 each incorporate a NotI restriction site. In the second step, plasmid pVL-luc, which contains the coding region of the firefly luciferase gene inserted into the mammalian expression vector pVL-1 (described below), is prepared from two DNA fragments: a vector DNA of 4.1 kB prepared by digesting plasmid pVL-1 with NruI and BglII, and 2) a DNA fragment of 1.7 kB containing the complete luciferase coding region, prepared by PCR using plasmid pGEM-luc (Promega, Madison, Wis.) as a template and oligonucleotides 8 and 9 as primers followed by digestion with NruI and BglII. Oligonucleotides 8 and 9 incorporate NruI and NcoI, and BglII and XhoI restriction sites, respectively. In the third step, plasmid plucPP, which contains the coding region of the luciferase gene inserted between the EMC 5'-UTR element and T7 transcriptional terminator, is prepared from two DNA fragments: 1) a vector DNA of 3.8 kB prepared by digesting plasmid pVL-EMC/T7 with NcoI and SalI, and 2) a DNA fragment of 1.7 kB containing the complete luciferase coding region, prepared by digesting plasmid pVL-luc with NcoI and XhoI.

Plasmid pLG-lucPP is prepared in two steps. In the first step, plasmid pLG-T7 is prepared by inserting a phage T7 promoter into the upstream HIV-LTR U5 region in plasmid pLG by site-directed mutagenesis using oligonucleotide 10 which contains the following sequences (5' to 3'): 1) an 18 nucleotide sequence complementary to positions 552 to 569 of HXB2 within the U5 region, 2) a 20 nucleotide sequence complementary to the T7 promoter, and 3) an 18 nucleotide sequence complementary to positions 534 to 551 of HXB2 within the U5 region. In the second step, plasmid pLG-lucPP is prepared from two DNA fragments: 1) a vector DNA of 11.2 kB prepared by digesting plasmid pLG-T7 with NotI and treating the resulting vector with alkaline phosphatase, and 2) a DNA fragment of 2.5 kB containing the luciferase indicator gene cassette prepared by digesting plasmid plucPP with NotI. Clones corresponding to pLG-lucPP, which contain the indicator gene cassette inserted into the viral vector with a transcriptional orientation opposite to that of the viral LTRs, are identified by restriction mapping.

Plasmid pCG-lucPP is prepared in two steps. In the first step, plasmid pCG-T7 is prepared by inserting a phage T7 promoter into the upstream HIV-LTR U5 region in plasmid pCG by site-directed mutagenesis using oligonucleotide 10. In the second step, plasmid pCG-lucPP is prepared from two DNA fragments: 1) a vector DNA of 11.7 kB prepared by digesting plasmid pCG-T7 with NotI and treating the resulting vector with alkaline phosphatase, and 2) a DNA fragment of 2.5 kB containing the luciferase indicator gene cassette prepared by digesting plasmid plucPP with NotI. Clones corresponding to pCG-lucPP, which contain the indicator gene cassette inserted into the viral vector with a transcriptional orientation opposite to that of the CMV IE enhancer-promoter and viral LTRs, are identified by restriction mapping.

Genomic Indicator Gene Viral Vector—Permuted Promoter Alternative Construction

The genomic indicator gene viral vector pCG-(NF-lucP) 1-PPT7 contains the following elements in a 5' to 3' orientation (FIG. 2D): 1) a CMV IE enhancer-promoter, 2) an HIV-LTR R region, 3) an HIV-LTR U5 region into which the T7 promoter with a transcriptional orientation opposite to that of the CMV promoter was inserted, 4) the coding regions of HIV gag-pol, vif, vpr, tat, rev, vpu, deleted env, and nef genes, 5) a luciferase indicator gene cassette inserted into the deleted env gene, 6) 3' HIV LTR U3 and R regions, 7) the SV40 polyadenylation signal sequence, and 8) the SV40 origin of replication region. The same indicator gene cassette is inserted in pCG-(NF-lucP)1 and contains the following elements: 1) an EMCV 5'-UTR region which permits internal ribosome entry, 2) the complete coding region of the luciferase (luc) gene, and 3) a T7 transcriptional terminator. The indicator gene has a transcriptional orientation opposite to the CMV IE enhancer-promoter and thus cannot be functionally transcribed by these elements. The indicator gene also cannot be transcribed by the T7 promoter as the indicator gene cassette is positioned upstream of the T7 promoter. Following reverse transcription and strand transfer, the T7 promoter is copied from the 5' LTR to the 3' LTR, permitting functional transcription from the newly created T7 promoter by T7 RNA polymerase.

The genomic indicator gene viral vector pCG-(NF-lucP) 1-PP/T7 is prepared from two DNA fragments: 1) a 9.7 kB vector fragment prepared by digesting pCG-(NF-lucP)1, described below, with NotI and AgeI, and 2) a 3.7 kB fragment containing the CMV IE enhancer-promoter, the HIV-LTR R region, the U5 region containing the T7 promoter, and the 5' portion of the gag-pol coding region, prepared by digesting pBS.NR.T7 with NotI and AgeI. Plasmids containing the proper elements are identified by restriction enzyme digestion.

The viral vector pCG-(NF-lucP)1 contains the following elements in a 5' to 3' orientation: 1) a CMV IE enhancer-promoter, 2) an HIV-LTR R and U5 regions, 3) the coding regions of HIV gag-pol, vif, vpr, tat, rev, vpu, deleted env, and nef genes, 4) a luciferase indicator gene cassette lacking a promoter was inserted into the deleted env gene, 5) 3' HIV LTR U3 and R regions, 6) the SV40 polyadenylation signal sequence, and 7) the SV40 origin of replication region. The indicator gene cassette contains the following elements: 1) an EMCV 5'-UTR region which permits internal ribosome entry, 2) the complete coding region of the luciferase gene, and 3) a T7 transcriptional terminator. The indicator gene has a transcriptional orientation opposite to the CMV IE enhancer-promoter and thus cannot be functionally transcribed by these elements.

pCG-(NF-lucP)1 was constructed from two DNA fragments: 1) an 11.1 kB vector fragment prepared by digesting plasmid pCG-CXAT(F-lucP)1 with BsmBI and treating the vector with alkaline phosphatase, and 2) a 2.3 kB fragment containing the luciferase indicator gene cassette prepared by digesting the expression vector pT7X(lucP), described below, with SgrAI. Plasmids containing the luciferase gene cassette inserted into the viral vector in a transcriptional orientation opposite to that of the viral transcription units were identified by restriction enzyme digestion. pCG-CXAT (F-lucP)1 was generated as described in Example 6 below. The luciferase indicator gene cassette plasmid, pT7X(lucP) contains the following elements in a 5' to 3' orientation: 1) a T7 promoter, 2) an SgrAI restriction site, 3) an EMCV 5'-UTR region which permits internal ribosome entry, 4) the complete coding region of the luciferase gene, inserted within the multiple cloning site region of pT7X, 5) a T7 transcriptional terminator, 6) an SgrAI restriction site. pT7X (lucP) was constructed from two DNA fragments: 1) a 2.7 kB vector fragment prepared by digesting pT7X, described below with BglII and XbaI, and 2) a 1.6 kB fragment containing the complete luciferase coding region, prepared by digesting pCXCN(F-lucP) with BglII and XbaI. Plasmids containing the luciferase gene were identified by restriction enzyme digestion.

The pT7X expression vector contains the following elements in a 5' to 3' orientation: 1) a T7 promoter, 2) an SgrAI restriction site, 3) an EMCV 5'-UTR region which permits internal ribosome entry, 4) multiple cloning sites with recognition sequences for restriction enzymes NcoI, BglII, NheI, XhoI, MluI, KpnI, and XbaI, 5) a T7 transcriptional terminator, 6) an SgrAI restriction site. pT7X was constructed from three DNA fragments: 1) a 2.0 kB vector fragment prepared by digesting pSP70 (Promega Corp.) with AatII and BspMI, 2) a 160 bp synthetic fragment containing the 3' portion of the EMCV 5' UTR, the multiple cloning sites, and the T7 terminator, prepared by phosphorylating oligonucleotides p8B (99) and p8C (100) with T4 polynucleotide kinase and ATP, then annealing and ligating them with oligonucleotides p8A (101) and p8D (102), and 3) a 560 bp fragment containing the T7 promoter and the 5' portion of the EMCV 5' UTR, prepared by digesting plasmid pCITE 1 (Novagen) with EcoRI, phosphorylating oligonucleotide p8AR− (103) with T4 polynucleotide kinase and ATP, then annealing with oligonucleotide p8AR+ (104) and ligating them to the EcoR1 digested pCITE 1 plasmid, followed by digestion with DsaI and isolation by gel electrophoresis. The 160 bp fragment contains the following elements in a 5' to 3' orientation: 1) a DsaI compatible cohesive end, 2) sequences identical to bases 1389 to 1428 of pTM1, 3) multiple cloning sites with recognition sequences for restriction enzymes NcoI, BglII, NheI, XhoI, MluI, KpnI, and XbaI, 4) a T7 transcriptional terminator, 5) recognition sites for restriction enzymes SgrAI and AscI and 6) a cohesive end compatible with the BspMI cohesive end from pSP70. The oligonucleotide pair P8AR+ (104) and p8AR− (103) contain the following elements, 1) an AatII compatible cohesive end, 2) a NotI restriction site, 3) a T7 promoter, 4) an SgrAI site, and 5) an EcoRI compatible cohesive which does not regenerate an EcoRI cleavage site when ligated to a compatible EcoRI cohesive end. Plasmids containing the proper elements were identified by restriction enzyme digestion, and the sequences of the synthetically generated portions confirmed by DNA sequencing.

Plasmid pBS.NR.T7 contains the following elements in a 5' to 3' orientation: 1) a CMV IE enhancer-promoter, 2) an HIV-LTR R region, 3) an HIV-LTR U5 region containing a T7 promoter with a transcriptional orientation opposite to that of the CMV promoter, and 4) the coding regions of HIV gag-pol. pBS.NR.T7 is constructed in two steps.

In the first step plasmid pBS.NR is constructed from two fragments: 1) a 2.9 kB vector fragment prepared from pBluescriptII KS+ by digestion with EcoRI and NotI, and 2) a 6.0 kB fragment containing the CMV IE enhancer-promoter, the HIV-LTR R and U5 regions, and the coding regions of HIV gag-pol prepared by digesting plasmid pCG-RTV1 with NotI and EcoRI. Plasmids containing the inserted fragment are identified by restriction digestion.

In the second step, single stranded DNA from plasmid pBS.NR is isolated and used as template in site-directed mutagenesis to insert the T7 promoter into the U5 region, using oligonucleotide MT7P (105) as the primer. Oligonucleotide MT7P (105) contains the following sequences in a 5' to 3' orientation: 1) 18 bases identical to bases 112 to 129 of the pNL4-3 isolate of HIV, 2) a 20 base pair sequence containing the inverted T7 promoter, and 3) 18 bases identical to positions 150 to 167 of the pNL4-3 isolate of HIV. This places the inverted T7 promoter in the middle of a 26 bp portion of the HIV-LTR U5 region that is not essential for infectivity (Vicenzi et al. (1994) *J. Virol.* 68, 7879-7890). Plasmids containing the inverted T7 promoter within the U5 region are identified by restriction digestion, and the sequence confirmed by DNA sequencing.

Subgenomic Indicator Gene Viral Vector—Permuted Promoter

The indicator gene viral vectors pLS-lucPP and pCS-lucPP, and resistance test vectors derived therefrom, contain the following elements in a 5' to 3' orientation (FIG. 2B): 1) an HIV-LTR U3 region (pLS-lucPP) or a CMV IE enhancer-promoter (pCS-lucPP), 2) an HIV-LTR R region, 3) an HIV-LTR U5 region containing an inserted T7 promoter with a transcriptional orientation opposite to that of the LTRs, 4) the coding region of the HIV gag-pol gene, 5) the indicator gene cassette, 6) an RRE element, from the HIV env gene containing a viral packaging sequence, and 7) a 3' HIV-LTR. The indicator gene cassette of pLS-lucPP and pCS-lucPP is the same as in pLG-lucPP and pCG-lucPP. As for the latter vectors, the indicator genes of pLS-lucPP and pCS-lucPP cannot be functionally transcribed until reverse transcription and strand transfer results in the copying of the T7 promoter from the 5' LTR to the 3' LTR (FIG. 2C).

Plasmid pLS-lucPP is prepared in two steps. In the first step, plasmid pLS-T7, which contains a phage T7 promoter inserted into the upstream HIV-LTR U5 region of plasmid pLS, is prepared from two DNA fragments: 1) a vector DNA of 9.1 kB prepared by digesting plasmid pLS with SmaI and ClaI, and 2) a DNA fragment of 0.8 containing the HIV-LTR with an R5 region containing an inserted T7 promoter, prepared by digesting plasmid pLG-T7 with SmaI and ClaI. In the second step, plasmid pLS-lucPP is prepared from two DNA fragments: 1) a vector DNA of 9.9 kB prepared by digesting plasmid pLS-T7 with NotI and treating the resulting vector with alkaline phosphatase, and 2) a DNA fragment of 2.5 kB containing the luciferase indicator gene cassette prepared by digesting plasmid plucPP with NotI. Clones corresponding to pLS-lucPP, which contain the indicator gene cassette inserted into the viral vector with a transcriptional orientation opposite to that of the viral LTRs, are identified by restriction mapping.

Plasmid pCS-lucPP is prepared from two DNA fragments: 1) a vector DNA of 11.6 kB prepared by digesting plasmid pLS-lucPP with SmaI and ClaI, and 2) a DNA fragment of 1.3 containing the CMV IE promoter fused to the R5 region with an inserted T7 promoter, prepared by digesting plasmid pCG-T7 with SmaI and ClaI.

Resistance Test Vectors—Construction

Figure 2A:
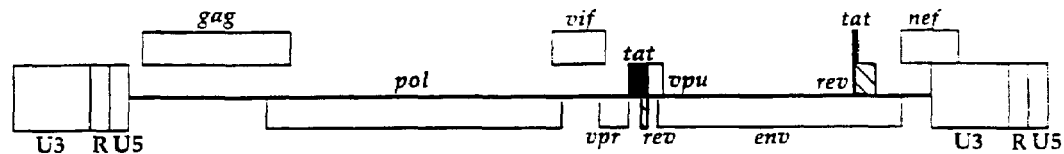
Figure 2B:
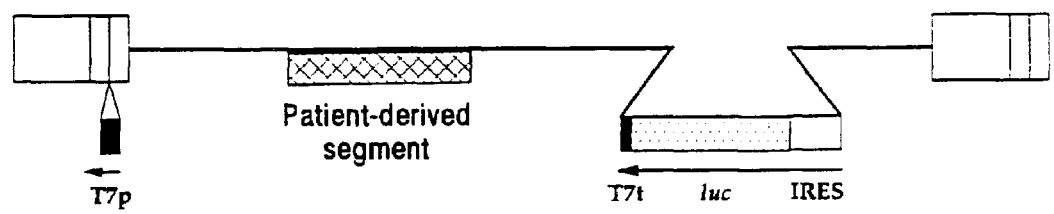
Figure 2C:
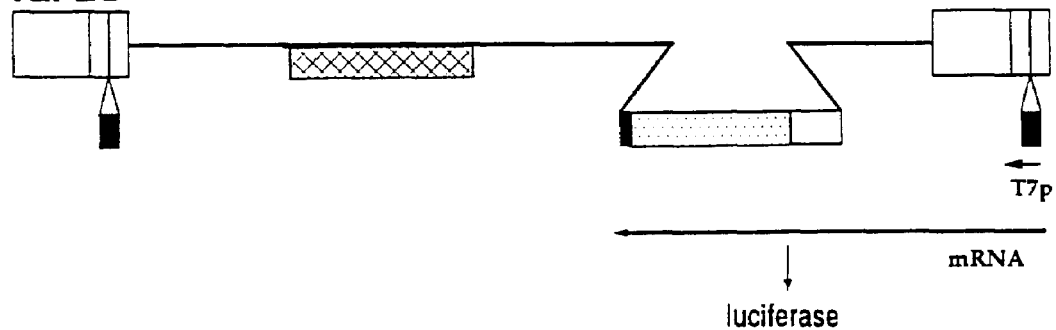
Figure 2D:
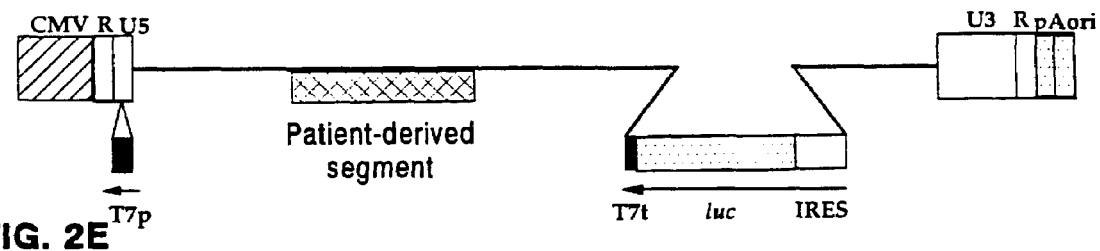
Figure 2E:
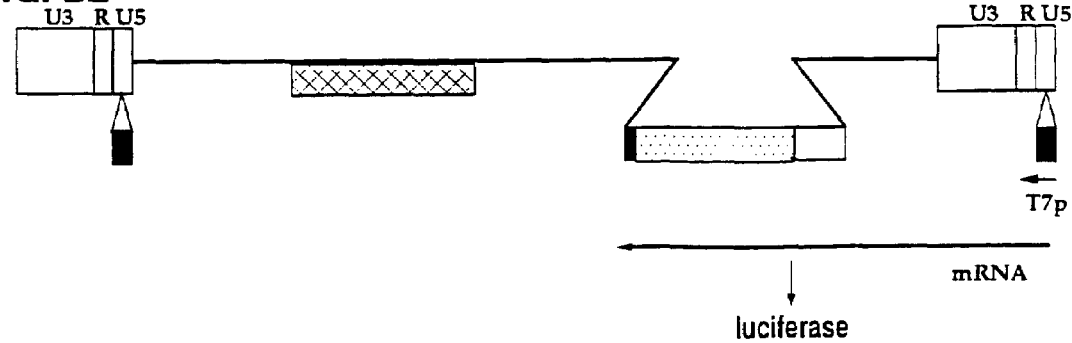

Resistance test vectors are prepared by 1) modifying the indicator gene viral vectors pLG-lucPP, pCG-lucPP, pLS-lucPP and pCS-lucPP by introducing unique restriction sites, called patient sequence acceptor sites, in or near the pol gene, 2) amplifying patient-derived segments corresponding to the HIV protease and reverse transcriptase coding regions by PCR using complementary DNA (cDNA) prepared from viral RNA or DNA present in the serum or cells of infected patients, and 3) inserting the amplified sequences precisely into indicator gene viral vectors at patient sequence acceptor sites (FIG. 2B). Two sets of patient sequence acceptor sites are introduced by site-directed mutagenesis into each of the four indicator gene viral vectors. The first set of patient sequence acceptor sites consist of a HpaI site and a SalI site which define an interval comprising the entire protease coding region and most of the reverse transcriptase coding region, resulting in plasmids pLG-lucPP-HS, pCG-lucPP-HS, pLS-lucPP-HS and pCS-lucPP-HS. The second set of patient sequence acceptor sites consist of a PvuI site and a BamHI site which define the same interval, resulting in plasmids pLG-lucPP-PB, pCG-lucPP-PB, pLS-lucPP-PB and pCS-lucPP-PB, respectively. Cognate pairs of resistance test vectors which define the same restriction site interval (eg., those derived from pLG-lucPP-HS and pLG-lucPP-PB) are used together in some resistance tests to improve the representation of those patient-derived segments that contain internal restriction sites identical to a given patient sequence acceptor site, and would thus be underrepresented in either resistance test vector alone.

Plasmid pLG-lucPP-HS is prepared by three consecutive steps of site-directed mutagenesis using plasmid pLG-lucPP as a template. The first two steps are for the purpose of introducing two new restriction sites, one of which (HpaI) is unique to, and one of which (SalI) is already is present once in each indicator gene viral vector. The third step is for the purpose of deleting the pre-existing SalI site in each vector to make the introduced SalI site unique. In step 1, a HpaI site is introduced immediately upstream of the mature coding region of the HIV protease at position 2243 using oligonucleotide 11 which contains the following sequences (5' to 3'): 1) an 18 nucleotide sequence complementary to positions 2249 to 2266 of HXB2, 2) a six nucleotide HpaI site, which leaves the gag protein sequence at this position unaltered and introduces a conservative amino acid change (Phe to Val) into the pol precursor sequence, and 3) an 18 nucleotide sequence complementary to positions 2225 to 2242 of HXB2. In step 2, a SalI site is introduced at the carboxy-terminal coding region of the HIV reverse transcriptase at position 4190 using oligonucleotide 12 which contains the following sequences (5' to 3'): 1) an 18 nucleotide sequence complementary to positions 4196 to 4213 of HXB2, 2) a six nucleotide SalI site which leaves the reverse transcriptase protein sequence at this position unaltered, and 3) an 18 nucleotide sequence complementary to positions 4172 to 4189 of HXB2. In step 3, the pre-existing SalI site within the vpr coding region at position 5785 of HXB2 is deleted using oligonucleotide 13 which contains the following sequences (5' to 3'): 1) an 18 nucleotide sequence complementary to positions 5791 to 5808 of HXB2, 2) the 6 nucleotide sequence GCCGAC which ablates the SalI site but leaves the vpr protein sequence at this position unaltered, 3) an 18 nucleotide sequence complementary to positions 5767 to 5784 of HXB2.

Plasmids pCG-lucPP-HS, pLS-lucPP-HS and pCS-lucPP-HS are derived from pLG-lucPP-HS as follows. Plasmid pCG-lucPP-HS is prepared from two DNA fragments: 1) a vector DNA of 12.9 kB prepared by digesting plasmid pLG-lucPP-HS with SmaI and ClaI, and 2) a DNA fragment of 1.3 kB prepared by digesting plasmid pCG-lucPP with SmaI and ClaI. Plasmid pLS-lucPP-HS is prepared from two DNA fragments: 1) a vector DNA of 11.1 kB prepared by digesting plasmid pLG-lucPP-HS with NdeI and XhoI, and 2) a DNA fragment of 1.3 kB prepared by digesting plasmid pLS-lucPP with NdeI and XhoI. Plasmid pCS-lucPP-HS is prepared from two DNA fragments: 1) a vector DNA of 11.6 kB prepared by digesting plasmid pLS-lucPP-HS with SmaI and ClaI, and 2) a DNA fragment of 1.3 kB prepared by digesting plasmid pCS-lucPP with SmaI and ClaI.

Plasmid pLG-lucPP-PB is prepared by four consecutive steps of site-directed mutagenesis using plasmid pLG-lucPP as a template. The first two steps are for the purpose of introducing two new restriction sites (PvuI and BamHI), each of which is already present once in each indicator gene viral vector. The third and fourth steps are for the purpose of deleting the pre-existing PvuI and BamHI sites in each vector to make the newly introduced sites unique. In step 1, a PvuI site is introduced immediately upstream of the mature coding region of the HIV protease at position 2221 using oligonucleotide 14 which contains the following sequences (5' to 3'): 1) an 18 nucleotide sequence complementary to positions 2227 to 2244 of HXB2, 2) a six nucleotide PvuI site, which leaves the gag and pol precursor protein sequences at this position unaltered, and 3) an 18 nucleotide sequence complementary to positions 2203 to 2220 of HXB2. In step 2, a BamHI site is introduced at the carboxy-terminal coding region of the HIV reverse transcriptase at position 4212 using oligonucleotide 15 which contains the following sequences (5' to 3'): 1) an 18 nucleotide sequence complementary to positions 4218 to 4235 of HXB2, 2) a six nucleotide BamHI site which leaves the reverse transcriptase protein sequence at this position unaltered, and 3) an 18 nucleotide sequence complementary to positions 4194 to 4211 of HXB2. In step 3, the pre-existing PvuI site within the b-lactamase coding region at position 2413 (coordinates references to GenBank, accession number X52331) is deleted using oligonucleotide 16 which contains the following sequences (5' to 3'): 1) an 18 nucleotide sequence complementary to positions 2395 to 2412 of pBluescript KS (+), 2) the 6 nucleotide sequence CAATCG which ablates the PvuI site but leaves the b-lactamase protein sequence at this position unaltered, and 3) an 18 nucleotide sequence complementary to positions 2419 to 2436 of pBluescript KS (+). In step 4, the pre-existing BamHI site within the HIV rev coding region at position 8474 of HXB2 is deleted using oligonucleotide 17 which contains the following sequences (5' to 3'): 1) an 18 nucleotide sequence complementary to positions 8480 to 8497 of HXB2, 2) the 6 nucleotide sequence GGATTC which ablates the BamHI site but leaves the HIV rev protein sequence at this position unaltered, and 3) an 18 nucleotide sequence complementary to positions 8456 to 8473 of HXB2.

Plasmids pCG-lucPP-PB, pLS-lucPP-PB and pCS-lucPP-PB are derived from pLG-lucPP-PB as follows. Plasmid pCG-lucPP-PB is prepared from two DNA fragments: 1) a vector DNA of 12.9 kB prepared by digesting plasmid pLG-lucPP-PB with SmaI and ClaI, and 2) a DNA fragment of 1.3 kB prepared by digesting plasmid pCG-lucPP with SmaI and ClaI. Plasmid pLS-lucPP-PB is prepared from three DNA fragments: 1) a vector DNA of 11.1 kB prepared by digesting plasmid pLG-lucPP-PB with NdeI and XhoI, 2) a DNA fragment of 0.5 kB prepared by digesting plasmid pLS-lucPP with NdeI and HindIII and 3) a DNA fragment of 0.8 kB prepared by digesting plasmid pLG-lucPP-PB with HindIII and XhoI. Plasmid pCS-lucPP-PB is prepared from two DNA fragments: 1) a vector DNA of 11.6 kB prepared by digesting plasmid pLS-lucPP-PB with SmaI and ClaI, and 2) a DNA fragment of 1.3 kB prepared by digesting plasmid pCS-lucPP with SmaI and ClaI.

Patient-derived segment(s) corresponding to the HIV protease and reverse transcriptase coding regions are amplified by the reverse transcription-polymerase chain reaction method (RT-PCR), using viral RNA isolated from the serum of HIV-infected patients. Two RT-PCR protocols are used as described. In the first method (Piatak et al. (1993) Science 259, 1749-1754), separate enzymes, Moloney murine leukemia virus reverse transcriptase (BRL, Bethesda, Md.) and Taq DNA polymerase (Roche Molecular Diagnostics, Ontario, Canada), are used for the preparation of cDNA and for the PCR reaction, respectively. In the second method (Mulder et al. (1994) J. Clin. Microbiol. 32, 292-300), a single enzyme, *Thermus thermophilus* (Tth) DNA polymerase, is used to carry both cDNA synthesis and the PCR reaction. Two primer pairs, consisting of oligonucleotides 18 and 19, and oligonucleotides 20 and 21, are employed for the amplification of patient-derived segments that can be inserted precisely into the indicator gene viral vectors containing the HpaI/SalI and PvuI/BamHI patient acceptor sites, respectively.

A first set of four resistance test vectors incorporating the first primer pair is constructed from the following two DNA preparations: 1) a vector DNA prepared from plasmid pLG-lucPP-HS, pCG-lucPP-HS, pLS-lucPP-HS or pCS-lucPP-HS, digested with HpaI and SalI, and 2) an amplified DNA product of 2.0 kB prepared by RT-PCR using viral RNA isolated from the serum of an HIV-infected individual as a template and oligonucleotides 18 and 19 as primers, followed by digestion with HpaI and SalI. A second set of four resistance test vectors incorporating the second primer pair are constructed from the following two DNA preparations: 1) a vector DNA prepared from plasmid pLG-lucPP-PB, pCG-lucPP-PB, pLS-lucPP-PB or pCS-lucPP-PB, digested with PvuI and BamHI, and 2) an amplified DNA product of 2.0 kB prepared by RT-PCR using viral RNA isolated from the serum of an HIV-infected individual as a template and oligonucleotides 18 and 19 as primers, followed by digestion with PvuI and BamHI. Oligonucleotides 18, 19, 20 and 21 incorporate HpaI, SalI, PvuI and BamHI restriction sites, respectively. To ensure that the plasmid DNA corresponding to each of the eight resulting resistance test vectors comprises a representative sample of the HIV viral quasi-species present in the serum of a given patient, at least one hundred independent E. coli transformants obtained in the construction of a given resistance test vector are used for the preparation of plasmid DNA.

To improve the representation of patient-derived segments, a third and fourth set of resistance test vectors are prepared using partially degenerate PCR primer pools, called oligonucleotides 22, 23, 24 and 25, which are based on the sequences of oligonucleotides 18, 19, 20 and 21, respectively. Each primer pool is synthesized in a manner that incorporates more than one nucleotide base (G, A, T or C) at the each of the 18 nucleotide positions located at the 3' end of the parent primer that display sequence variations among the different patient isolates cataloged in the Los Alamos HIV sequence database (Myers et al. (1993) Human Retroviruses and AIDS 1993, Los Alamos National Laboratory, Los Alamos, N. Mex.). The third set of four resistance test vectors is constructed using vectors prepared from plasmid pLG-lucPP-HS, pCG-lucPP-HS, pLS-lucPP-HS or pCS-lucPP-HS, with amplified patient sequences prepared with oligonucleotides 22 and 23; the fourth set of four resistance test vectors is constructed using vectors prepared from plasmid pLG-lucPP-PB, pCG-lucPP-PB, pLS-lucPP-PB or pCS-lucPP-PB, with amplified patient sequences prepared with oligonucleotides 24 and 25. Oligonucleotides 22, 23, 24 and 25 incorporate HpaI, SalI, PvuI and BamHI restriction sites, respectively.

Host Cells—Preparation

Packaging Host Cells and Resistance Test Vector Host Cells

Resistance test vectors are used to prepare resistance test vector host cells from packaging host cells expressing viral packaging proteins. The packaging proteins may be provided for by the expression of viral genes contained within the resistance test vector itself, a packaging expression vector(s), or both. Either transient or stable transfection of the packaging host cell may be employed to produce the packaging proteins. A packaging expression vector encoding an amphotrophic MLV env gene product enables production in a resistance test vector host cell of resistance test vector viral particles which can efficiently infect human target cells. Resistance test vectors derived from plasmids pLG-lucPP-HS, pLG-lucPP-PB, pCG-lucPP-HS and pCG-lucPP-PB encode all HIV genes with the exception of env, and are used to produce resistance test vector host cells. The pVL-env4070A packaging expression vector which encodes the amphotrophic MLV 4070A env gene product is used with the foregoing genomic-based resistance test vectors to enable production in the resistance test vector host cell of resistance test vector viral particles. Resistance test vectors derived from plasmids pLS-lucPP-HS, pLS-lucPP-PB, pCS-lucPP-HS and pCS-lucPP-PB encode the HIV gag-pol gene products only, and are used to prepare resistance test vector host cells. The pVL-env4070A which provides env, and either the pLTR-HIV3' or the pCMV-HIV3' packaging expression vectors, each of which provides the HIV vif, vpr, tat, rev, vpu and nef genes are used with the foregoing subgenomic based resistance test vectors to enable production in the resistance test vector host cells of resistance test vector viral particles.

Plasmids pLTR-HIV3' and pCMV-HIV3' are each derived by removing most of the gag-pol coding region from the genomic viral vectors pLG and pCG, respectively. Plasmid pLTR-HIV3' (FIG. 3B) is prepared by site-directed mutagenesis using plasmid pLG as a template with oligonucleotide 26 which contains the following sequences (5' to 3'): 1) an 18 nucleotide sequence complementary to positions 4712 to 4729 of HXB2 within the pol gene, and 2) an 18 nucleotide sequence complementary to positions 925 to 942 of HXB2 within the gag gene. Plasmid pCMV-HIV3' (FIG. 3C) is prepared from two DNA fragments: 1) a vector fragment of 6.8 kB prepared by digesting plasmid pLTR-HIV3' with SmaI and ClaI, and 2) a DNA fragment of 1.3 kB prepared by digesting plasmid pCG with SmaI and ClaI.

Plasmid pVL-env4070A (FIG. 3D) is constructed from two DNA fragments: 1) a vector fragment of 4.3 kB prepared by digestion of the pVL-2 mammalian expression vector with NruI and BglII, and 2) a DNA fragment of 2.0 kB containing the complete coding region of the MLV4070A env gene product (nucleotides 37 to 2001, coordinates given in GenBank, accession number M33469, Ott et al. (1990) J. Virol. 64, 757-766) prepared by PCR using plasmid pCRI-Pamgag-2 (Danos and Mulligan (1988) Proc. Natl. Acad. Sci. 85, 6460) as a template with oligonucleotides 27 and 28 as primers, followed by digestion with NruI and BglII. Oligonucleotide 27 incorporates a unique NruI site followed by a consensus sequence for mammalian translation initiation (e.g., Kozak (1991) J. Biol. Chem, 266, 19867-19870), while oligonucleotide 28 incorporates a unique BglII site.

The mammalian expression vector pVL-2 contains the following elements in a 5' to 3' direction: the CMV IE promoter/enhancer, the CMV IE first exon splice donor, the human $\alpha 1$ globin second exon splice acceptor, a cloning site polylinker, the polyadenylation site of the SV40 T antigen gene, and the SV40 origin of replication. Plasmid pVL-2 is constructed in four steps as follows. In the first step, plasmid pVL is prepared by replacing the cloning site polylinker and phage T7 and T3 promoters of plasmid pBluescript II KS (+) with a cloning site polylinker containing BssHII, NotI, SmaI, HindIII, SphI, SmaI, EcoRI, NruI, ApaI, BglII, NheI, NotI, XhoI, and BssHII restriction sites. pVL is constructed from two DNA fragments: 1) a vector fragment of 3.0 kB prepared by cutting plasmid pBluescript II KS (+) with BssHII, and treating the resulting vector with alkaline phosphatase, and 2) a DNA fragment prepared by annealing overlapping oligonucleotides 29 and 30, extending with Klenow DNA polymerase and digesting with BssHII. Plasmids containing the HindIII to XhoI sites in a 5' to 3' order relative to the pBluescript II KS (+) plasmid map (GenBank accession number X52327) are identified by restriction mapping analysis. In the second step, an intermediate plasmid is prepared from plasmid pVL by inserting the CMV IE enhancer-promoter and first exon splice donor, and the human $\alpha 1$ globin second exon splice acceptor. This intermediate plasmid is prepared from three DNA fragments: 1) a vector fragment of 3.0 kB prepared by digesting plasmid pVL with HindIII and EcoRI, 2) a DNA fragment of 0.9 kB containing a CMV IE promoter-enhancer and first exon splice donor (nucleotides −674 to −19, coordinates referenced to Boshart et al. (1985) Cell 41, 521-530), prepared by PCR using the plasmid pCM5027 containing the PstI m-fragment from HCMV strain AD169 (Boshart et al., Ibid) as template with oligonucleotides 31 and 32 as primers, followed by digestion with HindIII and SphI, and 3) a DNA fragment of 0.1 kB containing the human α1 globin second exon splice acceptor (nucleotides 6808 to 6916, coordinates by reference to GenBank, accession number J00153) prepared by PCR using plasmid ppSVaHP (Treisman et al. (1983) *Proc. Natl. Acad. Sci.* 80, 7428-7432) as a template with oligonucleotides 33 and 34 as primers, followed by digestion with SphI and EcoRI. Oligonucleotides 31, 32, 33 and 34 incorporate HindIII, SphI, SphI and EcoRI restriction sites at their respective ends. In the third step, plasmid pVL-1 is prepared by inserting the SV40 T antigen polyadenylation site into this intermediate plasmid. Plasmid pVL-1 is prepared from two DNA fragments: 1) a vector fragment of 4.0 kB prepared by cutting the intermediate plasmid with BglII and NheI, and 2) a DNA fragment of 0.2 kB containing the SV40 T antigen polyadenylation site (nucleotides 2770 to 2533 of SV40, coordinates by reference to Reddy et al. (1978) *Science* 200, 494-502) prepared by PCR using plasmid pSV2 (Southern and Berg (1982) *J. Mol. Appl. Gen.* 1, 327-341) as template with oligonucleotides 35 and 36 as primers, followed by digestion with BglII and NheI. Oligonucleotides 35 and 36 incorporate unique BglII and NheI restriction sites at their respective ends. In the fourth step, plasmid pVL-2 is prepared by inserting the SV40 origin of replication into plasmid pVL-1. Plasmid pVL-2 is prepared from two DNA fragments: 1) a vector fragment of 4.2 kB prepared by digesting plasmid pVL-1 with NheI and XhoI, and 2) a DNA fragment of 0.2 kB containing the SV40 origin of replication (nucleotides 5725 to 5578 of SV40, Ibid) prepared by PCR using plasmid pSV2 as template with oligonucleotides 37 and 38 as primers, followed by digestion with NheI and SalI. Oligonucleotides 37 and 38 incorporate unique NheI and SalI restriction sites at their respective ends.

Target Host Cells

Target host cells used for resistance tests carried out with resistance test vectors derived from plasmids pLG-lucPP-HS, pLG-lucPP-PB, pCG-lucPP-HS, pCG-lucPP-PB, pLS-lucPP-HS, pLS-lucPP-PB, pCS-lucPP-HS or pCS-lucPP-PB are prepared from the human embryonic kidney cell line 293 and the Jurkat leukemic T cell line (American Type Culture Collection, Rockville, Md.). Each cell line is stably transfected with an expression vector encoding a variant phage T7 RNA polymerase. This variant contains an SV40 T antigen nuclear localization signal (NLS) fused in frame to the N-terminus of the T7 RNA polymerase, permitting its transport into, and function in, the cell nucleus (Lieber et al. (1989) *Nucleic Acids Res.* 17, 8485-8493). The non-functional indicator gene in the resistance test vector is converted into a functional indicator gene by reverse transcriptase upon infection of the target cells, resulting from the repositioning of the T7 promoter relative to the indicator gene coding region. Following the integration of the repaired indicator gene into the target cell chromosome by HIV integrase, the nuclear T7 RNA polymerase expressed by the target cell is capable of functionally transcribing the indicator gene.

Plasmid pVL-T7RNAP-NLS is used to direct the expression of a variant T7 RNA polymerase linked to an NLS, in human and other mammalian cells and cell lines. pVL-T7RNAP-NLS is prepared from three DNA fragments: 1) a vector fragment of 4.3 kB prepared by digestion of the plasmid pVL-2 with EcoRI and BglII, 2) a DNA fragment of 2.6 kB encoding T7 RNA polymerase amino acid residues 34 to 883 (nucleotides 267 to 2817, coordinates by reference to GenBank, accession number M38308, Grachev and Pletnev (1984) *Bioorg. Khim.* 10, 824-843) prepared by PCR using plasmid pT7-G1 (Deng et al. (1994) *Gene* 143, 245-249) as a template with oligonucleotides 39 and 40 as primers, followed by digestion with NruI and BglII, and 3) a synthetic DNA fragment encoding the first three amino acids of SV40 T antigen followed by amino acids 118 to 133 of the SV40 large T antigen containing the NLS (Lieber et al., Ibid), prepared by annealing the overlapping oligonucleotides 41 and 42, extending with Klenow DNA polymerase and digesting with EcoRI and NruI. Oligonucleotides 39, 40, 41, 42 incorporate NruI, BglII, EcoRI and NruI restrictions site, respectively.

Plasmid pVL-Neo is employed as a selectable marker for the establishment of stable transfectants of human and other mammalian cells and cell lines by co-transfection. pVL-Neo directs the expression of neomycin phosphotransferase and confers resistance to the antibiotic G418. Plasmid pVL-Neo is prepared from two DNA fragments: 1) a vector fragment of 4.3 kB prepared by digesting plasmid pVL-2 with EcoRI and BglII, and 2) a DNA fragment of 0.8 kB containing the complete Neo coding region (nucleotides 1551 to 2345 of the Tn5 transposon sequence, coordinates given in GenBank accession number U00004, Beck et al. (1982) *Gene* 19, 327-336) prepared by PCR using plasmid pSV2neo (Southern and Berg (1982) *J. Mol. Appl. Gen.* 1, 327-341) as a template with oligonucleotides 43 and 44 as primers, followed by digestion with EcoRI and BglII. Oligonucleotide 43 incorporates a unique EcoRI site followed by a consensus sequence for mammalian translation initiation, while oligonucleotide 44 incorporates a unique BglII site.

pVL-T7RNAP is introduced by stable transfection into 293 cells by the calcium phosphate coprecipitation method (Wigler et al. (1979) *Cell* 16, 777) and into Jurkat cells by electroporation (Irving et al. (1991) *Cell* 64, 891-901). 293 cells are maintained in DMEM medium (JRH Biosciences) supplemented with 1 g/L glucose, 10% donor calf serum (Tissue Culture Biologics). Jurkat cells are maintained in RPMI 1640 medium supplemented with 10% fetal bovine serum (Irvin Scientific), glutamine, penicillin and streptomycin. Transfection cocktails for 293 cells and Jurkat cells each contain a mixture of 10 micrograms of pVL-T7RNAP and the selectable marker pVL-Neo in a mass ratio of 10:1 to 20:1. Twenty-four to 48 hours following transfection, cells are replated in the same media containing the antibiotic G418 (GIBCO, Grand Island, N.Y.). Independent 293 cell clones resistant to G418 are picked directly from selection plates after two weeks and are expanded for analysis. Independent Jurkat cell clones resistant to G418 are obtained by limiting dilution after two to three weeks of drug selection and are expanded for analysis.

G418-resistant 293 and Jurkat cell clones are screened for their level of expression of T7 RNA polymerase by determining the level of steady-state T7 RNA polymerase-specific mRNA synthesized by the cells using the Northern blot hybridization method (Ausubel et al. (1987) Current Protocols in Molecular Biology, Wiley-Interscience). 293 and Jurkat cell clones expressing optimal levels of the T7 RNA polymerase are then identified by determining their ability to support T7 RNA polymerase-specific transcription in transient transfections with plasmid pEMCLucbgAn (Deng et al. (1991) *Gene* 109, 193-201) in which the transcription of the luciferase gene is directed by a T7 promoter. 293 and Jurkat clones supporting the highest levels of luciferase gene expression are chosen for further use; these are referred to as 293/T7RNAP-NLS cells and Jurkat/T7RNAP-NLS cells, respectively.

Drug Susceptibility and Resistance Tests

Resistance tests are carried out with resistance test vectors based on indicator gene viral vectors pLG-lucPP-HS, pLG-lucPP-PB, pCG-lucPP-HS, pCG-lucPP-PB, pLS-lucPP-HS, pLS-lucPP-PB, pCS-lucPP-HS or pCS-lucPP-PB, using either two types of host cell or one type of host cell. In the first type of resistance test, resistance test vector viral particles are produced by a first host cell (the resistance test vector host cell) that is prepared by transfecting a packaging host cell with the resistance test vector and packaging expression vector(s). The resistance test vector viral particles are then used to infect a second host cell (the target host cell) in which the expression of the indicator gene is measured. In the second type of resistance test, a single host cell type (the resistance test vector host cell) serves both purposes: some of the packaging host cells in a given culture are transfected and produce resistance test vector viral particles and some of the host cells in the same culture are the target of infection by the resistance test vector particles thus produced. Resistance tests employing a single host cell type are possible with resistance test vectors comprising a non-functional indicator gene with a permuted promoter: while such indicator genes are efficiently expressed upon infection of a permissive host cell, they are not efficiently expressed upon transfection of the same host cell type, and thus provide an opportunity to measure the effect of the anti-viral agent under evaluation. For similar reasons, resistance tests employing two cell types may be carried out by co-cultivating the two cell types as an alternative to infecting the second cell type with viral particles obtained from the supernatants of the first cell type.

Susceptibility and Resistance Test—Two Cell

Resistance test vector host cells are prepared by the cotransfection of a resistance test vector and the appropriate packaging expression vector(s) using either the 293 cell line, the tsa54 or tsa201 cell lines (Heinzel et al. (1988) *J. Virol.* 62, 3738), or the BOSC 23 cell line (Pear et al. (1993) *Proc. Natl. Acad. Sci.* 90, 8392) as packaging host cells. Resistance test vectors constructed by inserting patient-derived segment into pLG-lucPP-HS, pCG-lucPP-HS, pLG-lucPP-PB and pCG-lucPP-PB are cotransfected with the packaging expression vector pVL-env4070A, while resistance test vectors prepared by inserting patient-derived segments into pLS-lucPP-HS, pCS-lucPP-HS, pLS-lucPP-PB and pCS-lucPP-PB are cotransfected with the packaging expression vectors pVL-env4070A and either pLTR-HIV3' or pCMV-HIV3'. Jurkat/T7RNAP-NLS cells are employed as target host cells.

Packaging host cells are grown in DMEM media, 1 g/L glucose, 10% donor calf serum and passaged at a 1:10 dilution every three days. Cells are plated 48 hours prior to transfection at $1 \times 10^6$ cells per 10 cm plate. Cells are transfected by the calcium phosphate coprecipitation method using 5 to 10 mg each of the resistance test vector and the appropriate packaging expression vector(s) to produce resistance test vector host cells. Individual anti-viral agents, including the reverse transcriptase inhibitors AZT, ddI, ddC, d4T and 3TC, and the protease inhibitors saquinavir, ritonavir and indinavir, as well as combinations thereof, are added to individual plates of transfected cells at the time of their transfection, at an appropriate range of concentrations. Twenty-four to 48 hours after transfection, target host cells are infected by co-cultivation with resistance test vector host cells or with viral particles obtained from filtered supernatants of resistance test vector host cells. Each anti-viral agent, or combination thereof, is added to the target host cells at the time of infection to achieve the same final concentration of the given agent, or agents, present during the transfection.

For infection by co-cultivation, media is removed from a 10 cm plate of resistance test vector host cells prepared by transfection 24 to 48 hours earlier, and 0.5 to $1.0 \times 10^6$ Jurkat/T7RNAP-NLS target cells are added to the plate in Jurkat cell media containing the anti-viral agent at the appropriate concentration. Target cells are co-cultivated with the resistance test vector host cells for 24 hours, then removed and added to freshly prepared resistance test vector host cells for a second co-cultivation in Jurkat cell media containing the anti-viral agent(s) at the appropriate concentration. Twenty-four hours later, the target host cells are harvested from the second co-cultivation, collected by centrifugation, washed three times with ice-cold phosphate-buffered saline (PBS), and assayed for luciferase activity. For infection with filtered supernatants, media is removed from a 10 cm plate of resistance test vector host cells prepared by transfection 24 to 48 hours earlier. The media is filtered through a 0.45 mm filter at the time of harvest, frozen at $-70°$ C., and thawed before transduction. Jurkat/T7RNAP-NLS cells (0.5 to $1.0 \times 10^6$) are added to 5 ml of an equal mixture of Jurkat cell media and the filtered supernatant, made up to 8 mg/ml of polybrene (Sigma, St. Louis, Mich.) and the appropriate concentration of the anti-viral agent(s). Twenty-four to 48 hours post-infection, the target host cells are collected by centrifugation, washed three times with ice-cold phosphate-buffered saline, and assayed for indicator gene expression. Target host cells infected by co-cultivation or with filtered viral supernatants are assayed for firefly luciferase activity as described (Ausubel et al. (1987) Current Protocols in Molecular Biology, Wiley-Interscience). The reduction in luciferase activity observed for target host cells infected with a given preparation of resistance test vector viral particles in the presence of a given anti-viral agent, or agents, as compared to a control run in the absence of the anti-viral agent, generally relates to the log of the concentration of the anti-viral agent as a sigmoidal curve. This inhibition curve is used to calculate the apparent inhibitory concentration (IC) of that agent, or combination of agents, for the viral target product encoded by the patient-derived segments present in the resistance test vector.

Susceptibility and Resistance Test—One Cell

Resistance test vector host cells are prepared by the cotransfection of a resistance test vector and the appropriate packaging expression vector(s) using either 293/T7RNAP-NLS cells or Jurkat/T7RNAP-NLS cells as packaging host cells. Resistance test vectors constructed by inserting patient-derived segments into pLG-lucPP-HS, pCG-lucPP-HS, pLG-lucPP-PB and pCG-lucPP-PB are cotransfected with the packaging expression vector pVL-env4070A, while resistance test vectors prepared by inserting patient-derived segments into pLS-lucPP-HS, pCS-lucPP-HS, pLS-lucPP-PB and pCS-lucPP-PB are cotransfected with the packaging expression vectors pVL-env4070A and either pLTR-HIV3' or pCMV-HIV3'.

Cells are transfected using 5 to 10 mg each of the resistance test vector and the appropriate packaging expression vector(s) to produce resistance test vector host cells. 293/T7RNAP-NLS cells are transfected by the calcium phosphate coprecipitation method and Jurkat/T7RNAP- NLS cells are transfected by electroporation. Individual anti-viral agents, or combinations thereof, are added to individual plates of transfected cells at the time of their transfection, at an appropriate range of concentrations. Twenty-four to 72 hours after transfection, cells are collected by centrifugation, washed three times with ice-cold phosphate-buffered saline, and assayed for firefly luciferase activity as described. As transfected cells in the culture do not efficiently express the indicator gene, transfected cells in the culture, as well superinfected cells in the culture, can serve as target host cells for indicator gene expression. The reduction in luciferase activity observed for cells transfected in the presence of a given anti-viral agent, or agents as compared to a control run in the absence of the anti-viral agent(s), generally relates to the log of the concentration of the anti-viral agent as a sigmoidal curve. This inhibition curve is used to calculate the apparent inhibitory concentration (IC) of that agent, or combination of agents, for the viral target product encoded by the patient-derived segments present in the resistance test vector.

EXAMPLE 2

HIV Drug Susceptibility and Resistance Tests Using Resistance Test Vectors Comprising Patient-Derived Segments and a Non-Functional Indicator Gene with a Permuted Coding Region Indicator Gene Viral Vector—Construction The genomic indicator gene viral vectors with patient sequence acceptor sites, pLG-lucPC-HS, pLG-lucPC-PB, pCG-lucPC-HS and pCG-lucPC-PB, and resistance test vectors derived therefrom, each contain the following elements in a 5' to 3' orientation (FIG. 4B): 1) an HIV-LTR U3 region (pLG-lucPC-HS and pLG-lucPC-PB) or a first CMV IE enhancer-promoter (pCG-lucPC-HS and pCG-lucPC-PB), 2) the HIV-LTR R and U5 regions, 3) the coding regions of the HIV gag-pol, vif, vpr, tat, rev, vpu, deleted env, and nef genes, 4) a first indicator gene cassette containing the 5' coding region of the luciferase gene, inserted into the deleted env gene, 5) a second indicator gene cassette containing the 3' coding region of the luciferase gene, inserted into a deleted 3' HIV-LTR U3 region, and 6) a 3' HIV-LTR R and U5 region. pLG-lucPC-HS and pCG-lucPC-HS contain unique HpaI and SalI patient sequence acceptor sites at nucleotides 2243 and 4190 of HXB2, respectively; pLG-lucPC-PB and pCG-lucPC-PB contain unique PvuI and BamHI patient sequence acceptor sites at nucleotides 2221 and 4212 of HXB2, respectively (see Example 1 for details). The first indicator gene cassette contains: 1) a second CMV enhancer-promoter, 2) the 5' coding region of the luciferase gene (amino acids 1 to 446), and 3) a CMV IE splice donor. The second indicator gene cassette contains: 1) an _-globin gene second exon splice acceptor, 2) the 3' coding region of the luciferase gene (amino acids 447 to 550), and 3) an SV40 polyadenylation site. The transcriptional orientation of the luciferase 5' and 3' coding regions are identical to one another, and opposite to that of the first CMV enhancer-promoter and viral LTRs. However, as the luciferase 5' and 3' coding regions are permuted in the resistance test vectors (ie., the 5' coding region is downstream of the 3' coding region), no mRNA is transcribed which can be spliced to generate a functional luciferase coding region. Following reverse transcription and strand transfer, the luciferase 3' coding region is copied from the 3' LTR to the 5' LTR, permitting the transcription of mRNA which can be spliced to generate a functional luciferase coding region (FIG. 4C).

The subgenomic indicator gene viral vectors with patient sequence acceptor sites, pLS-lucPC-HS, pLS-lucPC-PB, pCS-lucPC-HS and pCS-lucPC-PB, and resistance test vectors derived therefrom, each contain the following elements in a 5' to 3' orientation (FIG. 4B): 1) an HIV-LTR U3 region (pLS-lucPC-HS and pLS-lucPC-PB) or a first CMV IE enhancer-promoter (pCS-lucPC-HS and pCS-lucPC-PB), 2) the HIV-LTR R and U5 regions, 3) the coding region of the HIV gag-pol gene, 4) a first indicator gene cassette containing the 5' coding region of the luciferase gene, 5) an RRE element from the HIV env gene containing a viral packaging sequence, 6) a second indicator gene cassette containing the 3' coding region of the luciferase gene, inserted into a deleted 3' HIV-LTR U3 region, and 7) a 3' HIV-LTR R and U5 region. pLS-lucPC-HS and pCS-lucPC-HS contain unique HpaI and SalI patient sequence acceptor sites at nucleotides 2243 and 4190 of HXB2, respectively; pLS-lucPC-PB and pCS-lucPC-PB contain unique PvuI and BamHI patient sequence acceptor sites at nucleotides 2221 and 4212 of HXB2, respectively. The first indicator gene cassette contains: 1) a second CMV enhancer-promoter, 2) the 5' coding region of the luciferase gene (amino acids 1 to 446), and 3) a CMV IE splice donor. The second indicator gene cassette contains: 1) an α-globin gene second exon splice acceptor, 2) the 3' coding region of the luciferase gene (amino acids 447 to 550), and 3) an SV40 polyadenylation site. As the luciferase 5' and 3' coding regions are permuted in the resistance test vectors, reverse transcription and strand transfer must occur to generate non-permuted luciferase 5' and 3' coding regions, permitting the transcription of mRNA which can be spliced to generate a functional luciferase coding region (FIG. 4C).

Plasmid pVL-luc5', which contains the first indicator gene cassette, is prepared in three steps. In the first two steps, the artificial intron contained in pVL-1 consisting of the CMV IE splice donor and α-globin gene splice acceptor is subjected to site-directed mutagenesis to create restriction sites which upon digestion yield a DNA fragment whose 5' and 3' termini correspond precisely to the start and end of the artificial intron. In step one, site-directed mutagenesis is carried out with pVL-1 using oligonucleotide 45 which contains the following sequences (5' to 3'): 1) the 18 nucleotide sequence which precedes the CMV IE splice donor, 2) a TAC trinucleotide sequence corresponding to first half of the SnaBI restriction site, and 3) the 18 nucleotide sequence at the beginning of the artificial intron. As the sequence of the first three nucleotides of the intron is GTA, the resulting plasmid pVL-SnaBI contains a SnaBI restriction site which upon digestion releases the 5' sequence of the intron as a blunt DNA end. In step two, site-directed mutagenesis is carried out with pVL-SnaBI using oligonucleotide 46 which contains the following sequences (5' to 3'): 1) the 18 nucleotide sequence at the end of the artificial intron, 2) a CTG trinucleotide sequence corresponding to last half of the PvuII restriction site, and 3) the 18 nucleotide sequence following the _-globin splice acceptor. As the sequence of the last three nucleotides of the intron is CAG, the resulting plasmid pVL-SnaBI/PvuII contains a PvuII restriction site which upon digestion releases the 3' sequence of the intron as a blunt DNA end. In the third step, plasmid pVL-luc5' is prepared from two DNA fragments: 1) a vector DNA of 5.3 kB prepared by digesting plasmid pVL-luc with EcoRV and NheI, and treating the resulting vector with Klenow DNA polymerase and alkaline phosphatase, and 2) a DNA fragment of 0.1 kB containing the CMV IE splice donor, prepared by digesting plasmid pVL-SnaBI/PvuII with SnaBI and SmaI. Clones corresponding to pVL-luc5', which contain the CMV IE splice donor inserted in the correct orientation into the luciferase coding region, are identified by restriction mapping.

Plasmid pVL-luc3', which contains the second indicator gene cassette, is prepared in three steps. In step one, plasmid pBS-LTR, in which the 3'LTR of pBS-HXB2 is subcloned, is prepared from two DNA fragments: 1) a vector DNA of 3.0 kB prepared by digesting plasmid pBluescript II KS (+) with XhoI and XbaI, and 2) a DNA fragment of 0.8 kB containing the 3'LTR, prepared by digesting pBS-HXB2 with XhoI and XbaI. In step two, plasmid pBS-LTR-luc3', which contains the 3' coding region of luciferase followed by an SV40 polyadenylation site, inserted into the deleted 3'LTR, is prepared from two fragments: 1) a vector DNA of 3.5 kB prepared by digesting pBS-LTR with EcoRV, and treating the resulting vector with alkaline phosphatase, and 2) a DNA fragment of 0.5 kB containing the 3' luciferase coding region and SV40 polyA site, prepared by digesting plasmid pVL-luc with EcoRV and NheI, followed by treatment of the resulting fragment with Klenow DNA polymerase. Clones having the 3' luciferase coding region inserted in the correct orientation (ie., opposite to the direct of transcription in the 3'LTR) are identified by restriction mapping. In step three, plasmid pVL-luc3' is prepared from two DNA fragments: 1) a vector DNA of 4.0 kB prepared by digesting plasmid pBS-LTR-luc3' with EcoRV, followed by treatment of the resulting vector with alkaline phosphatase, and 2) a DNA fragment of 0.1 kB containing the α-globin gene second exon splice acceptor, prepared by digesting plasmid pVL-SnaBI/PvuII with PvuII and SmaI. Clones corresponding to pVL-luc3', which contain the α-globin second exon splice acceptor inserted in the correct orientation into the luciferase coding region, are identified by restriction mapping.

Plasmids pLG-lucPC-HS, pLG-lucPC-PB, pLS-lucPC-HS and pLS-lucPC-PB are prepared by the same three step procedure. In step one, plasmids pLG-lucDP-HS, pLG-lucDP-PB, pLS-lucDP-HS and pLS-lucDP-PB are prepared from two DNA fragments: 1) a vector DNA prepared by digesting plasmids pLG-lucPP-HS, pLG-lucPP-PB, pLS-lucPP-HS, pLS-lucPP-PB, respectively, with SmaI and ClaI, and 2) a DNA fragment of 0.8 kB prepared by digesting plasmid pLG with SmaI and ClaI. In step two, plasmids pLG-luc5'-HS, pLG-luc5'-PB, pLS-luc5'-HS and pLS-luc5'-PB are prepared from two DNA fragments: 1) a vector DNA prepared by digesting plasmids pLG-lucDP-HS, pLG-lucDP-PB, pLS-lucDP-HS and pLS-lucDP-PB, respectively, and treating the resulting vectors with alkaline phosphatase, and 2) a DNA fragment of 2.5 kB containing the first indicator gene cassette prepared by digesting pVL-luc5' with NotI. Clones which contain the first indicator gene cassette inserted into the viral vector with a transcriptional orientation opposite to that of the viral LTRs are identified by restriction mapping. In step three, plasmids pLG-lucPC-HS, pLG-lucPC-PB, pLS-lucPC-HS and pLS-lucPC-PB are prepared from two DNA fragments: 1) a vector DNA prepared by digesting plasmids pLG-luc5'-HS, pLG-luc5'-PB, pLS-luc5'-HS and pLS-luc5'-PB, respectively, with XhoI and XbaI, and 2) a DNA fragment of 1.1 kB containing the second indicator gene cassette, prepared by digesting plasmid pVL-luc3' with XhoI and XbaI.

Plasmids pCG-lucPC-HS, pCG-lucPC-PB, pCS-lucPC-HS and pCS-lucPC-PB are each prepared from two DNA fragments: 1) a vector DNA prepared by digesting either plasmids pLG-lucPC-HS, pLG-lucPC-PB, pLS-lucPC-HS and pLS-lucPC-PB, respectively, with SmaI and ClaI, and 2) a DNA fragment of 1.3 kB prepared by digesting plasmid pCG with SmaI and ClaI.

Resistance Test Vector—Construction

Resistance test vectors containing a non-functional indicator gene with a permuted coding region were designed using the HIV genomic and subgenomic viral vectors comprising anti-viral target genes described in Example 1.

Resistance test vectors are prepared from plasmids pLG-lucPC-HS, pLG-lucPC-PB, pCG-lucPC-HS, pCG-lucPC-PB, pLS-lucPC-HS, pLS-lucPC-PB, pCS-lucPC-HS and pCS-lucPC-PB (FIG. 4B), by the procedure described in Example 1. Resistance test vectors are constructed with vectors prepared from plasmids pLG-lucPC-HS, pCG-lucPC-HS, pLS-lucPC-HS or pCS-lucPC-HS using amplified patient sequences prepared with oligonucleotides 18 and 19, and with oligonucleotides 22 and 23. Resistance test vectors are constructed with vectors prepared from plasmids pLG-lucPC-PB, pCG-lucPC-PB, pLS-lucPC-PB or pCS-lucPC-PB using amplified patient sequences prepared with oligonucleotides 20 and 21, and with oligonucleotides 24 and 25.

Drug Susceptibility and Resistance Test

Resistance tests are carried out by the procedures described in Example 1 as follows. Resistance test vectors prepared from plasmids pLG-lucPC-HS, pLG-lucPC-PB, pCG-lucPC-HS and pCG-lucPC-PB lack a functional HIV env gene, and are used in conjunction with the packaging expression vector pVL-env4070A. Resistance test vectors prepared from plasmids pLS-lucPC-HS, pLS-lucPC-PB, pCS-lucPC-HS and pCS-lucPC-PB encode the HIV gag-pol gene products only, and are used in conjunction with pVL-env4070A, and either the pLTR-HIV3' or pCMV-HIV3' packaging expression vectors. In resistance tests carried out using two host cell types, the 293 cell line, the tsa54 cell line, the tsa201 cell line, or the BOSC 23 cell line are employed as packaging host cells, and unmodified Jurkat cells are employed as target cells. As the non-functional indicator genes with permuted coding regions contained within these resistance test vectors are not efficiently expressed upon transfection of the packaging host cells, infection of target host cells is carried out either by co-cultivation with packaging host cells, or by using virus from the packaging host cell supernatant. For similar reasons, resistance tests carried out with these resistance test vectors may employ a single host cell type. Resistance tests using a single host cell type are carried out using either 293, tsa54, tsa201, BOSC 23 or Jurkat cells.

EXAMPLE 3

HIV Drug Susceptibility and Resistance Test Using Resistance Test Vectors Comprising Patient-Derived Segment(s) and a Non-Functional Indicator Gene with an Inverted Intron Resistance test vectors containing a non-functional indicator gene with an inverted intron were designed using the HIV genomic and subgenomic viral vectors comprising anti-viral target genes described in Example 1.

Indicator Gene Viral Vectors—Inverted Intron

Figures 5A, 5B, 5C:
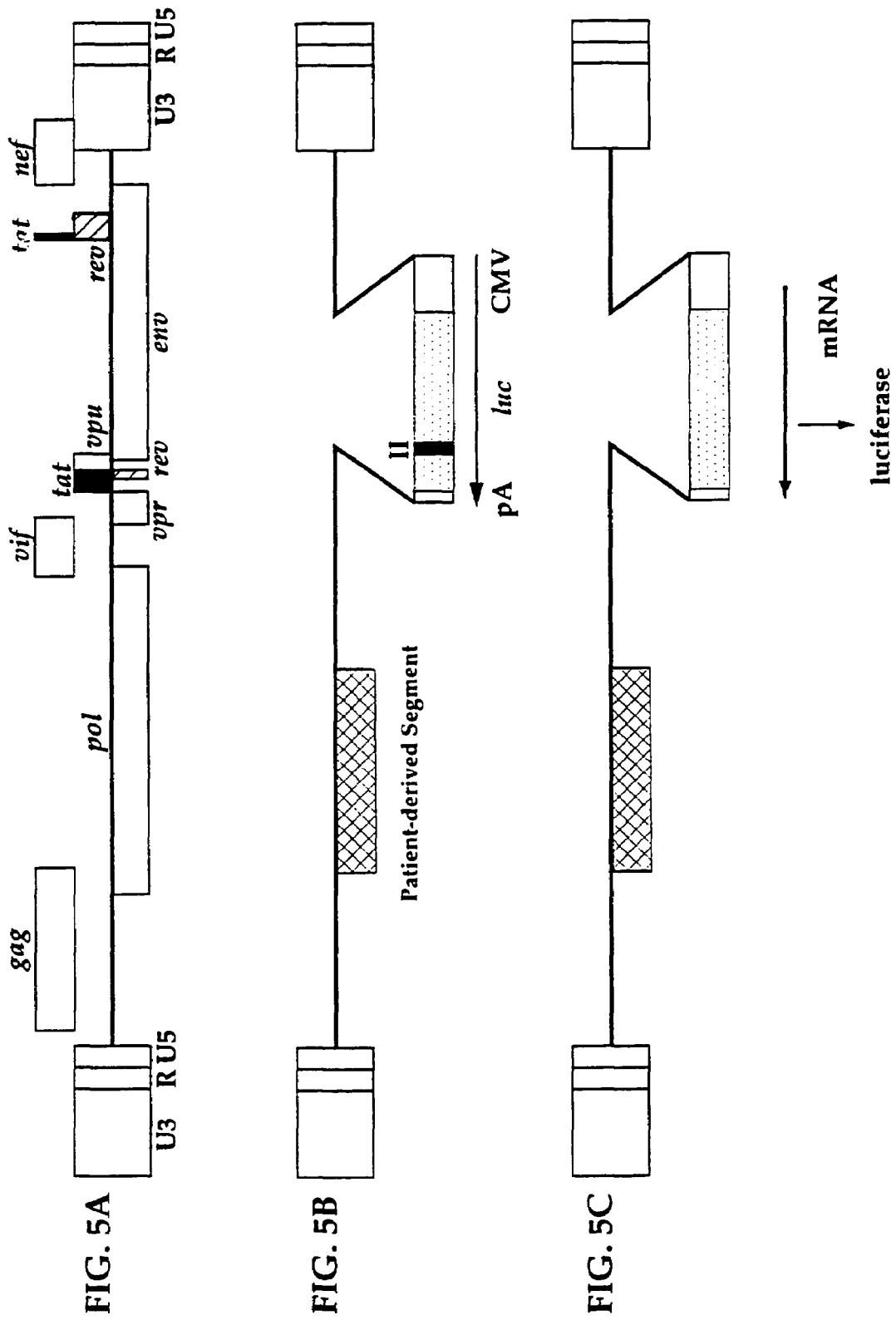

The genomic indicator gene viral vectors with patient sequence acceptor sites, pLG-lucII-HS, pLG-lucII-PB, pCG-lucII-HS and pCG-lucII-PB, and resistance test vectors derived therefrom, each contain the following elements in a 5' to 3' orientation (FIG. 5B): 1) an HIV-LTR U3 region (pLG-lucII-HS and pLG-lucII-PB) or a first CMV IE enhancer-promoter (pCG-lucII-HS and pCG-lucII-PB), 2) the HIV-LTR R and U5 regions, 3) the coding regions of the HIV gag-pol, vif, vpr, tat, rev, vpu, deleted env, and nef genes, 4) an indicator gene cassette inserted into the deleted env gene, and 5) a 3' HIV-LTR. pLG-lucII-HS and pCG-lucII-HS contain unique HpaI and SalI patient sequence acceptor sites at nucleotides 2243 and 4190 of HXB2, respectively; pLG-lucII-PB and pCG-lucII-PB contain unique PvuI and BamHI patient sequence acceptor sites at nucleotides 2221 and 4212 of HXB2, respectively (see Example 1 for details). The indicator gene cassette contains 1) a second CMV enhancer-promoter, 2) the coding region of the luciferase gene interrupted by an inverted artificial intron, and 3) an SV40 polyadenylation sequence. The overall transcriptional orientation of the indicator gene cassette is opposite to that of the first CMV enhancer-promoter and viral LTRs, while the orientation of the artificial intron is the same as the latter elements. Transcription of the indicator gene by the second CMV enhancer-promoter does not lead to the production of functional transcripts to the inverted intron cannot be spliced in this orientation. Transcription of the indicator gene by the 5' viral LTR or the first CMV IE enhancer-promoter, however, leads to the removal of the inverted intron by RNA splicing, although the indicator gene is still not functionally expressed as the resulting transcript has an antisense orientation. Following the reverse transcription of this transcript and integration of the resultant proviral DNA, the indicator gene can be functionally transcribed by the second CMV enhancer-promoter as the inverted intron has been previously removed (FIG. 5C).

The subgenomic indicator gene viral vectors with patient sequence acceptor sites, pLS-lucII-HS, pLS-lucII-PB, pCS-lucII-HS and pCS-lucII-PB, and resistance test vectors derived therefrom, each contain the following elements in a 5' to 3' orientation (FIG. 5B): 1) an HIV-LTR U3 region (pLS-lucII-HS and pLS-lucII-PB) or a first CMV IE enhancer-promoter (pCS-lucII-HS and pCS-lucII-PB), 2) the HIV-LTR R and U5 regions, 3) the coding region of the HIV gag-pol gene, 4) the indicator gene cassette, 5) an RRE element from the HIV env gene containing a viral packaging sequence, and 6) a 3' HIV-LTR. pLS-lucII-HS and pCS-lucII-HS contain unique HpaI and SalI patient sequence acceptor sites at nucleotides 2243 and 4190 of HXB2, respectively; pLS-lucII-PB and pCS-lucII-PB contain unique PvuI and BamHI patient sequence acceptor sites at nucleotides 2221 and 4212 of HXB2, respectively. The indicator gene cassette contains 1) a second CMV enhancer-promoter, 2) the coding region of the luciferase gene interrupted by an inverted artificial intron, and 3) an SV40 polyadenylation sequence. As is the case for the pLG-lucII and pCG-lucII genomic viral vectors, the indicator genes of pLS-lucII and pCS-lucII cannot be functionally transcribed until after the inverted intron is removed and reverse transcription and proviral integration occur (FIG. 5C).

Plasmid pVL-lucII, which contains the indicator gene cassette, in which the artificial intron from pVL-SnaBI/PvuII is inserted into the luciferase coding region in an inverted orientation, is prepared from two. DNA fragments: 1) a vector fragment of 5.8 kB prepared by digesting pVL-luc with EcoRV and treating the resulting vector with alkaline phosphatase, and 2) a DNA fragment of 0.2 kB corresponding precisely to the artificial intron sequence prepared by digesting pVL-SnaBI/PvuII with SnaI and PvuII. Clones corresponding to pVL-lucII which contain the artificial intron inserted into the luciferase coding region in an inverted orientation are identified by restriction mapping.

Plasmids pLG-lucII-HS, pLG-lucII-PB, pLS-lucII-HS and pLS-lucII-PB are prepared from two DNA fragments: 1) a vector DNA prepared by digesting plasmids pLG-lucDP-HS, pLG-lucDP-PB, pLS-lucDP-HS and pLS-lucDP-PB, respectively, and treating the resulting vectors with alkaline phosphatase, and 2) a DNA fragment of 3.2 kB containing the luciferase indicator gene cassette prepared by digesting pVL-lucII with NotI. Clones which contain the correct plucII indicator gene cassette inserted into the viral vector with a transcriptional orientation opposite to that of the viral LTRs are identified by restriction mapping and are used for the preparation of resistance test vectors.

Plasmids pCG-lucII-HS, pCG-lucII-PB, pCS-lucII-HS and pCS-lucII-PB are each prepared from two DNA fragments: 1) a vector DNA prepared by digesting plasmids pLG-lucII-HS, pLG-lucII-PB, pLS-lucII-HS and pLS-lucII-PB, respectively, with SmaI and ClaI, and 2) a DNA fragment of 1.3 kB prepared by digesting plasmid pCG with SmaI and ClaI.

Resistance Test Vector—Construction

Resistance test vectors are prepared from plasmids pLG-lucII-HS, pLG-lucII-PB, pCG-lucII-HS, pCG-lucII-PB, pLS-lucII-HS, pLS-lucII-PB, pCS-lucII-HS and pCS-lucII-PB (FIG. 5B), by the procedure described in Example 1. Resistance test vectors are constructed with vectors prepared from plasmids pLG-lucII-HS, pCG-lucII-HS, pLS-lucII-HS or pCS-lucII-HS using amplified patient sequences prepared with oligonucleotides 18 and 19, and with oligonucleotides 22 and 23. Resistance test vectors are constructed with vectors prepared from plasmids pLG-lucII-PB, pCG-lucII-PB, pLS-lucII-PB or pCS-lucII-PB using amplified patient sequences prepared with oligonucleotides 20 and 21, and with oligonucleotides 24 and 25.

Drug Susceptibility and Resistance Test

Resistance tests are carried out by the procedures described in Example 1 as follows. Resistance test vectors prepared from plasmids pLG-lucII-HS, pLG-lucII-PB, pCG-lucII-HS and pCG-lucII-PB lack a functional HIV env gene, and are used in conjunction with the packaging expression vector pVL-env4070A. Resistance test vectors prepared from plasmids pLS-lucII-HS, pLS-lucII-PB, pCS-lucII-HS and pCS-lucII-PB encode the HIV gag-pol gene products only, and are used in conjunction with pVL-env4070A, and either the pLTR-HIV3' or PCMV-HIV3' packaging expression vectors. In resistance tests carried out using two host cell types, the 293 cell line, the tsa54 cell line, the tsa201 cell line, or the BOSC 23 cell line are employed as packaging host cells, and unmodified Jurkat cells are employed as target cells. As the non-functional indicator genes with inverted introns contained within these resistance test vectors are not efficiently expressed upon transfection of the packaging host cells, infection of target host cells is carried out either by co-cultivation with packaging host cells, or by using virus from the packaging host cell supernatant. For similar reasons, resistance tests carried out with these resistance test vectors may employ a single host cell type. Resistance tests using a single host cell type are carried out using either 293, tsa54, tsa201, BOSC 23 or Jurkat cells.

EXAMPLE 4

Non-Particle Based HIV Drug Susceptibility and Resistance Test Using Resistance Test Vectors Comprising Patient-Derived Segment(s) and a Non-Functional Indicator Gene Drug Susceptibility and Resistance Test Non-particle based resistance tests are carried out using the resistance test vectors comprising non-functional indicator genes with either permuted promoters, permuted coding regions or inverted introns, described in Examples 1, 2 and 3. These non-particle based resistance tests are performed by transfection of a single host cell type with each resistance test vector in the absence of packaging expression vectors. Although the non-functional indicator genes contained within these resistance test vectors are not efficiently expressed upon transfection of the host cells, there is detectable indicator gene expression resulting from non-viral particle-based reverse transcription. Reverse transcription and strand transfer results in the conversion of the permuted, non-functional indicator gene to a non-permuted, functional indicator gene. As reverse transcription is completely dependent upon the expression of the pol gene contained within each resistance test vector, anti-viral agents may be tested for their ability to inhibit the pol gene products encoded by the patient-derived segments contained within the resistance test vectors. Non-particle based resistance tests are carried out by the general procedures described in Example 1 with the following modifications: 1) Resistance test vectors are transfected into the appropriate host cells, 2) anti-viral agents, or combinations thereof, are added at appropriate concentrations to individual cultures of transfected host cells immediately after transfection, 3) host cells are harvested 24 to 72 hours following transfection and assayed for luciferase activity. The reduction in luciferase activity observed for host cells transfected with a given resistance test vector in the presence of a given anti-viral agent, or agents, as compared to a control run in the absence of the anti-viral agent(s) is used to calculate the apparent inhibitory content (Ki) of that agent, or combination of agents, for the viral target gene product encoded by the patient-derived segments present in the resistance test vector.

Resistance Test Vector—Construction

For non-particle based resistance tests with resistance test vectors comprising a non-functional indicator gene with a permuted promoter, resistance test vectors are prepared as described in. Example 1 using plasmids pLG-lucPP-HS, pLG-lucPP-PB, pCG-lucPP-HS, pCG-lucPP-PB, pLS-lucPP-HS, pLS-lucPP-PB, pCS-lucPP-HS or pCS-lucPP-PB. Each resistance test vector is transfected into host cells expressing a cytoplasmic T7 RNA polymerase (eg., 293/T7RNAP cells or Jurkat/T7RNAP cells). Such host cells are prepared by the stable transfection of 293 cells and Jurkat cells as described in Example 1, using plasmid pVL-T7RNAP, which directs the expression of a cytoplasmic phage T7 RNA polymerase in human and other mammalian cells and cell lines. pVL-T7RNAP is constructed from the following two DNA fragments: 1) a vector fragment of 4.3 kB prepared by digestion of the mammalian expression vector pVL-2 with EcoRI and BglII, and 2) a DNA fragment of 2.6 kB containing the complete coding region of the T7 RNA polymerase (nucleotides 166 to 2815, coordinates given in GenBank accession number M38308, Grachev and Pletnev (1984) *Bioorg. Khim.* 10, 824-843) prepared by PCR using plasmid pT7-G1 as a template with oligonucleotides 47 and 40 as primers, followed by digestion with EcoRI and BglII. Oligonucleotide 47 incorporates a unique EcoRI site followed by a consensus sequence for eukaryotic translation initiation (e.g., Kozak (1991) *J. Biol. Chem,* 266, 19867-19870), while oligonucleotide 40 incorporates a unique BglII site.

For non-particle based resistance tests with resistance test vectors comprising a non-functional indicator gene with a permuted coding region or inverted intron, resistance test vectors are prepared as described in Example 1 using plasmids pLG-lucPC-HS, pLG-lucPC-PB, pCG-lucPC-HS, pCG-lucPC-PB, pLS-lucPC-HS, pLS-lucPC-PB, pCS-lucPC-HS, pCS-lucPC-PB, pLG-lucII-HS, pLG-lucII-PB, pCG-lucII-HS, pCG-lucII-PB, pLS-lucII-HS, pLS-lucII-PB, pCS-lucII-HS or pCS-lucII-PB. Each resistance test vector is transfected into either 293, tsa54, tsa201, BOSC 23 or Jurkat cells.

EXAMPLE 5

HIV Drug Susceptibility and Resistance Test Using Resistance Test Vectors Comprising Patient-Derived Segment(s) and a Functional Indicator Gene Indicator Gene Viral Vector—Functional Indicator Gene The genomic indicator gene viral vectors with patient sequence acceptor sites, plasmids pLG-luc-HS-1, pLG-luc-HS-2, pLG-luc-PB-1, pLG-luc-PB-2, pCG-luc-HS-1, pCG-luc-HS-2, pCG-luc-PB-1 and pCG-luc-PB-2, and resistance test vectors derived therefrom, each contain the following elements in a 5' to 3' orientation (FIG. 6): 1) an HIV-LTR U3 region (pLG-luc-HS-1, pLG-luc-HS-2, pLG-luc-PB-1 and pLG-luc-PB-2) or a first CMV IE enhancer-promoter (pCG-luc-HS-1, pCG-luc-HS-2, pCG-luc-PB-1 and pCG-luc-PB-2), 2) the HIV-LTR R and U5 regions, 3) the coding regions of the HIV gag-pol, vif, vpr, tat, rev, vpu, deleted env, and nef genes, 4) an indicator gene cassette inserted into the deleted env gene, and 5) a 3' HIV-LTR. pLG-luc-HS-1, pLG-luc-HS-2, pCG-luc-HS-1 and pCG-luc-HS-2 contain unique HpaI and SalI patient sequence acceptor sites at nucleotides 2243 and 4190 of HXB2, respectively; pLG-luc-PB-1, pLG-luc-PB-2, pCG-luc-PB-1 and pCG-luc-PB-2 contain unique PvuI and BamHI patient sequence acceptor sites at nucleotides 2221 and 4212 of HXB2, respectively (see Example 1 for details). The indicator gene cassettes of each plasmid contain 1) a second CMV enhancer-promoter, 2) the coding region of the luciferase gene, and 3) an SV40 polyadenylation sequence. The indicator gene cassettes of pLG-luc-HS-1, pLG-luc-PB-1, pCG-luc-HS-1 and pCG-luc-PB-1 are inserted into the vector with a transcriptional orientation opposite to the viral LTRs or first CMV enhancer-promoter (FIG. 6B), while the indicator gene cassettes of pLG-luc-HS-2, pLG-luc-PB-2, pCG-luc-HS-2 and pCG-luc-PB-2 are inserted into the vector with the same orientation (FIG. 6C).

The subgenomic indicator gene viral vectors with patient sequence acceptor sites, plasmids pLS-luc-HS-1, pLS-luc-HS-2, pLS-luc-PB-1, pLS-luc-PB-2, pCS-luc-HS-1, pCS-luc-HS-2, pCS-luc-PB-1 and pCS-luc-PB-2, and resistance test vectors derived therefrom, each contain the following elements in a 5' to 3' orientation (FIG. 6): 1) an HIV-LTR U3 region (pLS-luc-HS-1, pLS-luc-HS-2, pLS-luc-PB-1 and pLS-luc-PB-2) or a first CMV IE enhancer-promoter (pCS-luc-HS-1, pCS-luc-HS-2, pCS-luc-PB-1 and pCS-luc-PB-2), 2) the HIV-LTR R and U5 regions, 3) the coding region of the HIV gag-pol gene, 4) the indicator gene cassette, 5)

an RRE element from the HIV env gene containing a viral packaging sequence, and 6) a 3' HIV-LTR. pLS-luc-HS-1, pLS-luc-HS-2, pCS-luc-HS-1 and pCS-luc-HS-2 contain unique HpaI and SalI patient sequence acceptor sites at nucleotides 2243 and 4190 of HXB2, respectively; pLS-luc-PB-1, pLS-luc-PB-2, pCS-luc-PB-1 and pCS-luc-PB-2 contain unique PvuI and BamHI patient sequence acceptor sites at nucleotides 2221 and 4212 of HXB2, respectively. The indicator gene cassettes of each plasmid contain 1) a second CMV enhancer-promoter, 2) the complete coding region of the luciferase gene, and 3) an SV40 polyadenylation sequence. The indicator gene cassettes of pLS-luc-HS-1, pLS-luc-PB-1, pCS-luc-HS-1 and pCS-luc-PB-1 are inserted into the vector with a transcriptional orientation opposite to the viral LTRs or first CMV enhancer-promoter (FIG. 6B), while the indicator gene cassettes of pLS-luc-HS-2, pLS-luc-PB-2, pCS-luc-HS-2 and pCS-luc-PB-2 are inserted into the vector with the same orientation (FIG. 6C).

Plasmids pLG-luc-HS-1 and pLG-luc-HS-2, pLG-luc-PB-1 and pLG-luc-PB-2, pCG-luc-HS-1 and pCG-luc-HS-2, pCG-luc-PB-1 and pCG-luc-PB-2, pLS-luc-HS-1 and pLS-luc-HS-2, pLS-luc-PB-1 and pLS-luc-PB-2, pCS-luc-HS-1 and pCS-luc-HS-2, pCS-luc-PB-1 and pCS-luc-PB-2 are each prepared from two DNA fragments: 1) a vector DNA prepared by digesting either pLG-lucII-HS, pLG-lucII-PB, pCG-lucII-HS, pCG-lucII-PB, pLS-lucII-HS, pLS-lucII-PB, pCS-lucII-HS and pCS-lucII-PB, respectively with NotI and treating the resulting vectors with alkaline phosphatase, and 2) a DNA fragment of 3.0 kB containing the luciferase indicator gene cassette prepared by digesting pVL-luc with NotI. Clones containing the indicator gene cassette inserted into a given viral vector in both transcriptional orientations relative to the viral LTRs are identified by restriction mapping (eg., pLG-luc-HS-1 and pLG-luc-HS-2).

Resistance Test Vector—Construction

Resistance test vectors containing a functional indicator gene were designed using the HIV genomic and subgenomic viral vectors comprising anti-viral target genes described in Example 1. Resistance test vectors are prepared from the above plasmids (FIG. 6) by the procedure described in Example 1. Resistance test vectors are constructed with vectors prepared from plasmids pLG-luc-HS-1, pLG-luc-HS-2, pCG-luc-HS-1, pCG-luc-HS-2, pLS-luc-HS-1, pLS-luc-HS-2, pCS-luc-HS-1 or pCS-luc-HS-1 using amplified patient sequences prepared with oligonucleotides 18 and 19, and with oligonucleotides 22 and 23. Resistance test vectors are constructed with vectors prepared from plasmids pLG-luc-PB-1, pLG-luc-PB-2, pCG-luc-PB-1, pCG-luc-PB-2, pLS-luc-PB-1, pLS-luc-PB-2, pCS-luc-PB-1 or pCS-luc-PB-1 using amplified patient sequences prepared with oligonucleotides 20 and 21, and with oligonucleotides 24 and 25.

Drug Susceptibility and Resistance Test

Resistance tests are carried out by the procedures described in Example 1 as follows. Resistance test vectors prepared from plasmids pLG-luc-HS-1, pLG-luc-HS-2, pLG-luc-PB-1, pLG-luc-PB-2, pCG-luc-HS-1, pCG-luc-HS-2, pCG-luc-PB-1 and pCG-luc-PB-2 lack a functional HIV env gene, and are used in conjunction with the packaging expression vector pVL-env4070A. Resistance test vectors prepared from plasmids pLS-luc-HS-1, pLS-luc-HS-2, pLS-luc-PB-1, pLS-luc-PB-2, pCS-luc-HS-1, pCS-luc-HS-2, pCS-luc-PB-1 and pCS-luc-PB-2 encode the HIV gag-pol gene products only, and are used in conjunction with pVL-env4070A, and either the pLTR-HIV3' or pCMV-HIV3' packaging expression vectors. Resistance tests are carried out with two host cell types, using the 293 cell line, the tsa54 cell line, the tsa201 cell line, or the BOSC 23 cell line as packaging host cells, and using unmodified Jurkat cells as target cells. The infection of target cells with these or other resistance test vectors containing functional indicator genes is carried out employing the procedure for infection with resistance test vector viral particles from the filtered supernatants obtained from resistance test vector indicator host cells, as described in Example 1. In contrast to resistance test vectors comprising non-functional indicator gene viral vectors with a permuted promoter or an inverted intron, those comprising a functional indicator genes are typically able to express their indicator genes in the transfected packaging host cells. Neither the co-cultivation procedure, nor the resistance test using a single cell type can therefore be readily adapted for the infection of target cells using resistance test vectors with functional indicator genes, as it would be difficult to distinguish between indicator gene expression in infected target host cells and the transfected packaging host cells.

All publications and patent applications cited in this specification are herein incorporated by reference in their entirety as if each individual publication or patent application were specifically and individually indicated to be incorporated by reference.

As will be apparent to those skilled in the art to which the invention pertains, the present invention may be embodied in forms other than those specifically disclosed above, for example to carry out the drug susceptibility and resistance test on other viruses, without departing from the spirit or essential characteristics of the invention. The particular embodiments of the invention described above, are, therefore to be considered as illustrative and not restrictive. The scope of the present invention is as set forth in the appended claims rather than being limited to the examples contained in the foregoing description.

EXAMPLE 6

Figure 3A:
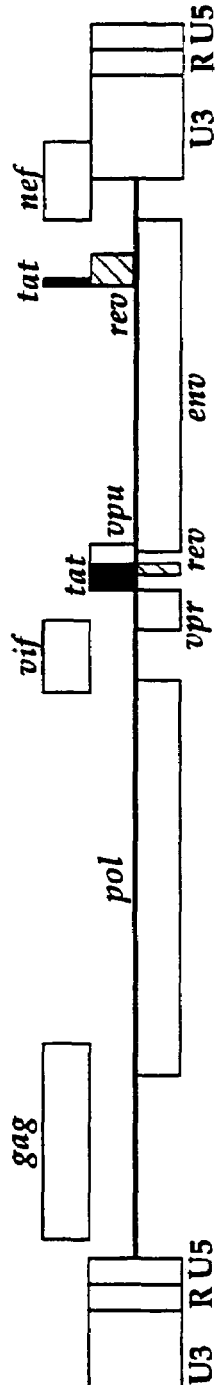
Figure 3B:
Figure 3C:
Figure 3D:
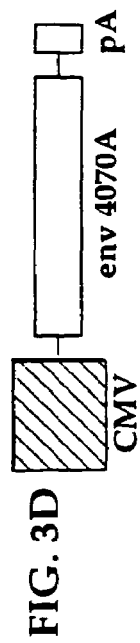

HIV Drug Susceptibility and Resistance Test Using Resistance Test Vectors Comprising Patient-Derived Segment(s) and a Functional Indicator Gene Indicator Gene Viral Vector—Construction The genomic indicator gene viral vector, pCG-CXCN(F-lucP)2 containing a functional indicator gene was made using a genomic HIV viral vector pCG which has a deletion in the HIV env gene. The genomic indicator gene viral vector, pCG-CXCN(F-lucP)2 was used to generate resistance test vectors by the insertion of patient-derived sequences into the patient sequence acceptor sites. Infectious virus particles carrying the resistance test vector were produced using a packaging expression vector encoding the amphotrophic murine leukemia virus (A-MuLV) 4070A env gene product (FIG. 3D).

The genomic indicator gene viral vector pCG-CXCN(F-lucP)2 and resistance test vectors derived the refrom, each contain the following elements in a 5' to 3' orientation (FIG. 7B): 1) a CMV IE enhancer-promoter region, 2) HIV LTR R and U5 regions, 3) the coding regions of the HIV gag-pol, vif, vpr, tat, rev, vpu, deleted env, and nef genes, 4) a luciferase indicator gene cassette inserted into the deleted env gene, 5) 3' HIV LTR U3 and R regions, 6) the SV40 polyadenylation signal sequence region, and 7) the SV40 origin of replication region. The resistance test vector pCG-CXCN(F-lucP)2-AA contains unique ApaI and AgeI patient sequence acceptor sites.

The luciferase indicator gene cassette, CXCN(lucP), inserted in the deleted env gene contains each of the following elements in a 5' to 3' direction: 1) a CMV IE enhancer-promoter region, and 2) the coding region of the firefly (*Photinus pyralis*) luciferase gene inserted into a multiple cloning site region. The luciferase indicator gene cassette was inserted into the genomic viral vector pCG in the same transcriptional orientation as the first CMV IE and HIV-R-U5 promoter enhancer region.

Genomic Indicator Gene Viral Vector—pCG-CXCN(F-luc)2

The indicator gene viral vector pCG-CXCN(F-luc)2 was prepared from two DNA fragments: 1) an 11.1 kB vector fragment was prepared by digesting plasmid pCG (described below) with XmaI and treating the vector with alkaline phosphatase, and 2) a 2.5 kB fragment containing the luciferase indicator gene cassette prepared by digesting the expression vector pCXCN(lucP) (described below) with SgrAI. Plasmids containing the luciferase gene cassette inserted into the viral vector in the same transcriptional orientation as the viral transcription units were identified by restriction enzyme digestion.

Genomic HIV Viral Vector—pCG

The genomic viral vector, pCG, was derived from the HIV proviral plasmid, pNL4-3 (GenBank Accession No. M19921, Adachi et. al. (1986) *J. Virol.* 59:284-291). In pCG, the HIV 5' LTR U3 region has been replaced with the CMV immediate-early (IE) enhancer-promoter region. The pCG vector contains unique ApaI and AgeI patient sequence acceptor sites. pCG also has a unique XmaI restriction site within the deleted env gene for insertion of an indicator gene cassette.

pCG was assembled from three component pieces. The first piece (plasmid p1.3) consisted of the CMV IE promoter enhancer region fused to the R region of the 5' HIV LTR, and the U5 and gag-pol regions. The second piece (plasmid p2) consisted of the 5' tat and 5' rev exons, the deleted env region containing a unique XmaI insertion site, the 3' tat and 3' rev exons and the 5' region of the nef gene. The third piece (plasmid 3A) consisted of the 3' region of the nef gene, the 3' LTR U3 and R regions, the SV40 polyadenylation signal sequence region and the SV40 origin of replication region.

Plasmid pCG was assembled in two steps. In the first step, an intermediate plasmid was prepared from two DNA fragments: 1) a 6.5 kB fragment containing the CMV IE enhancer-promoter region, which is fused to the HIV R-U5 sequence (at position 1 of R), and the gag and pol open reading frames of HIV and 2) a 3.6 kB fragment containing the env coding region bearing a 1.2 kB deletion into which was inserted an XmaI restriction site. The 6.5 kB fragment was prepared by digesting plasmid 1.3 (p1; described below) with EcoRI and PvuI. The 3.6 kB fragment was prepared by digesting plasmid p2 (described below) with EcoRI and PvuI. Intermediate plasmids with the correct structure were identified by restriction enzyme digestion. In the second step, plasmid pCG was assembled from two DNA fragments: 1) a 9.5 kB fragment containing the CMV IE enhancer-promoter fused to HIV R-U5 sequence and the gag, pol and deleted env coding regions and 2) a 2.6 kB fragment containing the nef coding region and the U3-R sequence of the HIV LTR followed by the SV40 polyadenylation signal region and the SV40 origin of replication region. The 9.5 kB fragment was prepared by digesting the intermediate plasmid (described above) with XhoI and PvuI. The 2.6 kB fragment was prepared by digesting plasmid p3A (described below) with XhoI and PvuI. Plasmids with the correct pCG structure were identified by restriction enzyme digestion.

Plasmid p1.3 containing the CMV IE enhancer-promoter, the 5' R and U5 regions of HIV and the gag and pol coding regions, was prepared in two steps. In the first step, an intermediate plasmid p1.2 was prepared from two DNA fragments: 1) a 2.4 kB vector fragment prepared by digesting plasmid pSP72 (Promega Corp.) with EcoRI and SstI, and 2) a 5.2 kB fragment containing the 3' portion of the HIV R sequence, followed by the U5 and gag and pol coding regions. The 5.2 kB fragment was prepared by digesting plasmid pNL4-3 (GenBank Accession No. M19921) with SstI and EcoRI. Plasmids with the correct structure were identified by restriction enzyme digestion. Plasmid p1.3 was prepared from two DNA fragments: 1) a 7.1 kB vector fragment containing the gag and pol coding regions, prepared by digesting plasmid p1.2, described above, with AatII and BssHII, and 2) a 1 kB fragment containing the CMV IE promoter-enhancer fused to the R region of HIV (at position 1 of R), prepared by digesting a PCR-generated fragment with BstXI and BssHII. This fragment was generated in two steps. In the first step, a 0.7 kB fragment was generated using plasmid pCMV-EBNA as the template, and oligonucleotides A1 (48) and p1SS–(49)) as primers. Oligonucleotide A1 (48) has the recognition sequence for the type II restriction enzyme BstXI that results in an AatII compatible end following digestion of the PCR product with BstXI. Oligonucleotide p1SS–(49) contains sequences complementary to positions –18 to –1 of the CMV IE enhancer-promoter (coordinates referenced to Boshart et al. [1985]), followed by sequences complementary to positions 1 to 33 of the pNL4-3 isolate of HIV. After gel isolation, this fragment was used as a double stranded primer, together with B2(50) to generate the 1 kB fragment, using plasmid p1.2 as the template. Plasmids with the correct structure were identified by restriction enzyme digestion and the DNA sequence of the PCR-generated region was confirmed by DNA sequencing.

Plasmid p2 contains the coding regions for the tat and rev proteins, a deleted env coding region containing an XmaI site for inserting the indicator gene expression cassette, and the 5' portion of the nef coding region. It was prepared from three DNA fragments: 1) a 2.9 kB vector fragment prepared by digesting pBluescript II KS+ (Stratagene) with EcoRI and XhoI, 2) a 0.6 kB fragment that contains the 5' tat and rev exons and the 5' portion of the env coding region prepared by digesting pNL4-3 with EcoRI and NdeI, and 3) a 1.3 kB fragment that contains the 3' portion of the env coding region and was adapted to have cohesive ends compatible with XhoI and NdeI generated cohesive ends. This fragment was prepared as follows: 1) oligonucleotides 2NM–(53) and 2BX+(54) were treated with T4 polynucleotide kinase (NEB) and then were annealed separately with 2NM+(55) and 2BX–(56), respectively; 2) the annealed oligonucleotides were ligated to a 1.2 kB 3' env fragment prepared by digesting pNL4-3 with MfeI and BsmBI. The annealed oligonucleotides 2NM+(55) and 2NM–(53) contain the following sequences (5' to 3'): 1) an NdeI compatible cohesive overhang, 2) an XmaI restriction site, flanked by Bson BI sties such that Bson BI, and SuaI all cleave at the same position, 3) a 35 bp sequence identical to bases 7157 to 7191 of NL4-3 within the env gene, and 4) an MfeI-compatible cohesive end. The annealed oligonucleotides 2BX+(54) and 2BX–(56) contain the following sequences (5' to 3') 1) a BsmBI compatible cohesive end, 2) sequences identical to bases 8392 to 8433 of NL4-3, except for a single C to A base change at position 8396 to disrupt the BsmBI restriction site while not changing the encoded amino acid sequences, and 3) an XhoI compatible cohesive overhang. Plasmids containing the proper structure were identified by restriction digestion, and the DNA sequence of the synthetically-generated regions were verified by DNA sequencing.

Plasmid p3A contains the 3' portion of the nef coding region, the U3 and R sequences of HIV, and the polyadenylation signal and origin of replication regions of SV40. It was prepared from three DNA fragments: 1) a 2.3 kB vector fragment prepared by digesting plasmid pSP70 (Promega) with XhoI and BspMI, 2) a 0.8 kB fragment containing the 3' portion of nef, U3 and the 5' portion of R prepared by digesting plasmid pNL4-3 with XhoI and HindIII, and 3) a 420 bp fragment containing the 3' portion of R and the polyadenylation signal and origin of replication regions of SV40. The 420 bp fragment was prepared from 13 oligonucleotides 3.1-3.13, (57-70). All of the oligonucleotides, except p3.1 and p3.13, were treated with T4 Polynucleotide Kinase and ATP, and then all were annealed and ligated. The 420 bp ligation product was isolated by gel electrophoresis. The 420 bp fragment contains the following elements in a 5' to 3' orientation: 1) a Hind III compatible cohesive end; 2) sequences identical to bases 9152 to 9173 of pNL4-3; 3) an XbaI restriction site; 4) sequences identical to bases 2770 to 2533 of SV40 containing the T antigen polyadenylation site; 5) an SgrAI and an AscI restriction site; 6) sequences identical to bases 5725 to 5578 of SV40, containing the origin of replication; 7) AscI and BspMI restriction sites, and a cohesive end compatible with the BspMI cohesive end in pSP70 (Promega). Plasmids containing the proper elements were identified by restriction digestion, and the DNA sequence of the synthetically-generated region was confirmed by DNA sequencing.

Luciferase Indicator Gene Cassette—pCXCN(lucP)

The luciferase indicator gene cassette, pCXCN(lucP), contains the coding region of the firefly (*Photinus pyralis*) luciferase gene inserted into the mammalian expression vector pCXCN. pCXCN(lucP) was prepared from two DNA fragments: 1) a vector DNA of 3 kB prepared by digesting pCXCN with BglII and XbaI, and 2) a fragment of 1.6 kB containing the complete luciferase coding region prepared by digesting plasmid p4AlucPSgrAI(−) (described below) with BglII and XbaI.

The pCXCN expression vector contains the following sequence components in the 5' to 3' orientation: 1) the CMV IE enhancer-promoter; 2) multiple cloning sites consisting of the recognition sequences for restriction enzymes BglII, NheI, XhoI, EcoRI, MluI, KpnI, XbaI; 3) the SV40 origin of replication region. pCXCN was constructed from two DNA fragments: 1) a 1424 bp fragment generated by digesting plasmid pCXCS (described below) with XbaI and PvuI, 2) a 1610 bp fragment generated by digesting p3C (described below) with PvuI and XbaI. The pCXCS expression vector contains the following sequence components in the 5' to 3' orientation: 1) the CMV IE enhancer-promoter; 2) multiple cloning sites consisting of the recognition sequences for restriction enzymes BglII, NheI, XhoI, EcoRI, MluI, KpnI, XbaI; 3) the SV40 polyadenylation signal sequence region; 4) the SV40 origin of replication region. The expression vector pCXCS was constructed from three DNA fragments: 1) an 1840 bp fragment generated by digesting plasmid p3A (described above) with XbaI and PvuI, 2) a 1200 bp fragment generated by digesting plasmid p1.1 (described below) with PvuI and SstI, and 3) a 200 bp fragment generated by digesting plasmid p4C (described below) with SstI and XbaI. Plasmid p1.1 contains the CMV IE enhancer-promoter region inserted into the pSP72 (Promega) multiple cloning site region. p1A was assembled by ligating the following two fragments: 1) a 0.7 kB fragment that contains the CMV IE enhancer-promoter and is flanked by AatII and SstI overhangs, and 2) a 2.4 kB vector fragment prepared by digesting pSP72 with AatII and SstI. The 0.7 kB fragment was made as follows: oligonucleotide 1AH−(51) was kinased and annealed to the oligonucleotide 1AH+(52) to form an AatII to HindIII linker. The annealed oligonucleotide linker pair was then ligated to a 0.7 kB fragment generated by digesting pCMV-EBNA with HindIII and SstI. Plasmids with the correct structure were identified by restriction enzyme analysis. Plasmid p4C contains the CMV IE promoter-enhancer, but differs from plasmid 4A, described below, in that it does not contain the artificial intron A sequence. This plasmid was assembled using the following two fragments: 1) a 5.1 kB vector fragment, containing the 5' portion of the CMV IE promoter-enhancer, generated by digesting plasmid pCINeo (Promega) with SstI and NheI; 2) a synthetic 153 bp fragment with SstI and NheI compatible single stranded DNA overhangs, containing the 3' end of the CMV IE enhancer-promoter. The 153 bp fragment was constructed by assembling 5 synthetic oligonucleotides 4A1(78), 4A2(79), 4A4(80), 4C1(88), and 4C2 (89). All of the oligonucleotides except 4A1 and 4C2 were phosphorylated using T4 polynucleotide kinase in the presence of ATP and then were annealed and ligated. The ligation product corresponding to 153 bp was separated by gel electrophoresis and purified. Correct plasmids were identified by restriction enzyme digestion. Synthetic DNA sequences were confirmed by DNA sequencing.

Plasmid p4A-lucP-SgrAI(−) contains the complete coding sequence of luciferase that was mutated to eliminate an SgrAI site but not alter the encoded amino acid sequence of the luciferase protein. Plasmid p4A-lucP-SgrAI(−) was derived from p4A-lucP (described below) by site-directed mutagenesis, using single-stranded p4A-lucP DNA as template and oligonucleotide 75 as the mutagenic primer. Plasmids lacking the SgrAI site were identified by restriction digestion and the sequence confirmed by DNA sequencing.

Plasmid p4A-lucP was prepared from two DNA fragments: 1) a 5.4 kB vector fragment prepared by digesting plasmid p4A (described below) with BglII and XbaI; and 2) a 1.6 kB fragment containing the luciferase gene that was obtained by digesting plasmid p5B (described below) with BglII and XbaI.

Plasmid p4A contains the CMV IE promoter-enhancer linked to artificial intron A (CMV IE splice donor/α-globin splice acceptor). Plasmid p4A was assembled using the following two fragments: 1) a 5.1 kB vector fragment, containing the 5' end of the CMV IE promoter-enhancer, generated by digesting plasmid pCINeo (Promega) with SstI and NheI; 2) a synthetic 309 bp fragment with SstI and NheI single stranded DNA overhangs, containing the 3' end of the CMV IE enhancer-promoter and the artificial intron A sequence. The 309 bp fragment was constructed by assembling 10 synthetic oligonucleotide sequences 4A1-10(78-87). All of the oligonucleotides except 4A1 and 4A10 were phosphorylated using T4 polynucleotide kinase in the presence of ATP and then were annealed and ligated. The ligation product corresponding to 309 bp was separated by gel electrophoresis and purified. Correct plasmids were identified by restriction enzyme digestion. Synthetic DNA sequences were confirmed by DNA sequencing.

Plasmid p5B was prepared from three DNA fragments: 1) a 2.4 kB vector fragment prepared by digesting pSP72

(Promega) with HindIII and XbaI; 2) a 1.6 kB fragment containing the complete firefly luciferase coding region prepared by digesting plasmid pGL3-control (Promega) with NcoI and XbaI; and 3) a synthetic DNA fragment of 19 bp having HindIII and NcoI cohesive ends prepared by treating oligonucleotide sequence G5' (−)(90) with T4 polynucleotide kinase and ATP and then annealing it with oligonucleotide sequence G5'(+)(91). Plasmids with the correct structure were identified by restriction enzyme digestion, and the sequence of the synthetic insert was confirmed by DNA sequencing.

Resistance Test Vectors—Construction

Figure 7A:
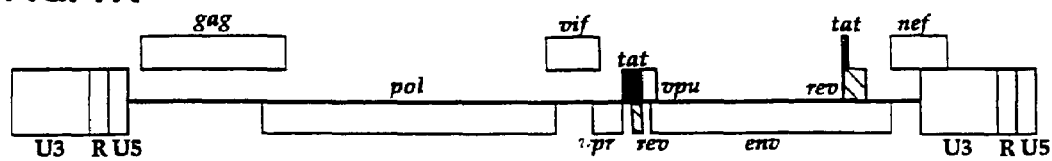
Figure 7B:
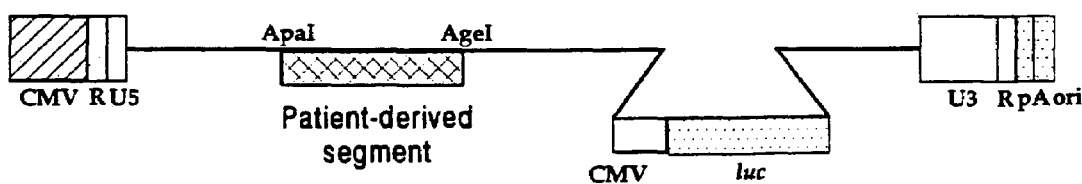
Figure 7C:
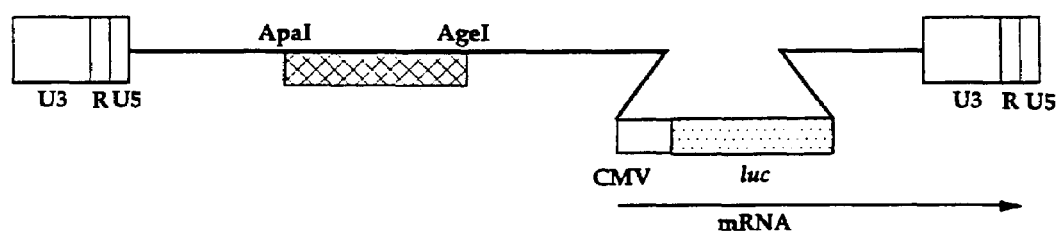
Figure 7D:
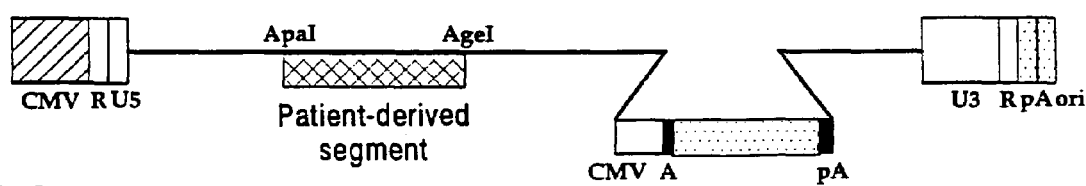
Figure 7E:
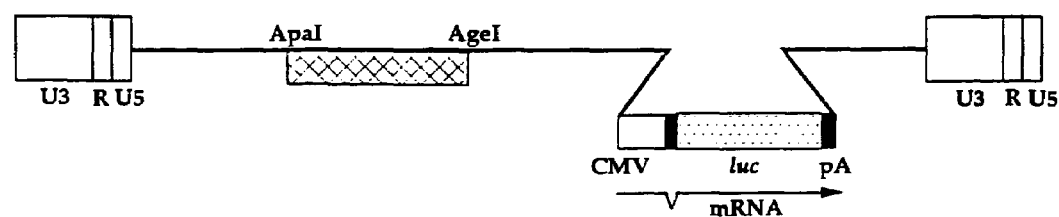

Resistance test vectors were prepared by 1) either modifying the indicator gene viral vector pCG-CXCN(F-lucP)2 by introducing unique patient sequence acceptor sites or by selecting unique patient sequence acceptor sites such as ApaI and AgeI, which define an interval comprising the entire protease coding region and most of the reverse transcriptase coding region; 2) amplifying "test" patient-derived segments, as described below, corresponding to the HIV protease (PR) and reverse transcriptase (RT) coding regions by RT-PCR using complementary DNA (cDNA) prepared from viral RNA obtained from the serum of infected patients, and 3) inserting the amplified sequences precisely into the indicator gene viral vector at the unique patient sequence acceptor sites (FIG. 7B).

In these experiments patient-derived segment(s) corresponding to the HIV protease and reverse transcriptase coding regions were "test" patient-derived segments in that they were reference strains of HIV-1 from the NIH AIDS Research and Reference Reagent Program and/or were mutants of wild type HIV-1 made by site directed mutagenesis amplified by the reverse transcription-polymerase chain reaction method (RT-PCR) using viral RNA isolated from viral particles present in the serum of HIV-infected individuals. Isolation of viral RNA was performed using standard procedures (e.g. RNAgents Total RNA Isolation System, Promega, Madison Wis. or RNAzol, Tel-Test, Friendswood, Tex.). The RT-PCR protocol was divided into two steps. A retroviral reverse transcriptase [e.g. Moloney MuLV reverse transcriptase (Roche Molecular Systems, Inc., Branchburg, N.J.), or avian myeloblastosis virus (AMV) reverse transcriptase, (Boehringer Mannheim, Indianapolis, Ind.)] was used to copy viral RNA into cDNA. The cDNA was then amplified using a thermostable DNA polymerase [e.g. Taq (Roche Molecular Systems, Inc., Branchburg, N.J.), Tth (Roche Molecular Systems, Inc., Branchburg, N.J.), PrimeZyme (isolated from *Thermus brockianus*, Biometra, Gottingen, Germany)] or a combination of thermostable polymerases as described for the performance of "long PCR" (Barnes, W. M., (1994) *Proc. Natl. Acad. Sci, USA* 91, 2216-2220) [e.g. Expand High Fidelity PCR System (Taq+Pwo), (Boehringer Mannheim. Indianapolis, Ind.) OR GeneAmp XL PCR kit (Tth+Vent), (Roche Molecular Systems, Inc., Branchburg, N.J.)].

The primers, ApaI primer (PDSApa) (76) and AgeI primer (PDSAge) (77) used to amplify the "test" patient-derived segments contained sequences resulting in ApaI and AgeI recognition sites being introduced into the 5' and 3' termini of the PCR product, respectively.

Resistance test vectors incorporating the "test" patient-derived segments were constructed from the following two DNA preparations: 1) a vector DNA prepared from the indicator gene viral vector pCG-CXCN(F-lucP)2, digested with ApaI and AgeI, and 2) an amplified DNA product of 1.5 kB prepared by RT-PCR using viral RNA as a template and oligonucleotides PDSApa (76) and PDSAge (77) as primers, followed by digestion with ApaI and AgeI. To ensure that the plasmid DNA corresponding to the resultant resistance test vector comprises a representative sample of the HIV viral quasi-species present in the serum of a given patient, many independent *E. coli* transformants obtained in the construction of a given resistance test vector were used for the preparation of plasmid DNA.

Host Cells

Packaging Host Cells and Resistance Test Vector Host Cells

A packaging expression vector encoding an amphotrophic MuLV 4070A env gene product enables production in a resistance test vector host cell of resistance test vector viral particles which can efficiently infect human target cells. Resistance test vectors derived from genomic indicator gene viral vectors encode all HIV genes with the exception of env, and were used to transfect a packaging host cell (once transfected the host cell is referred to as a resistance test vector host cell). The pCXAS packaging expression vector which encodes the amphotrophic MuLV 4070A env gene product is used with the resistance test vector to enable production in the resistance test vector host cell of resistance test vector viral particles.

Resistance test vectors were constructed by inserting an ApaI/AgeI "test" patient-derived segment into pCG-CXCN (F-lucP)2 and cotransfecting with the packaging expression vector pCXAS(4070A-env) (described below) into the 293 cell line, (Heinzel et al. (1988) *J. Virol.* 62, 3738), which was used as packaging host cells.

Envelope Gene Expression Vector—pCXAS(4070A-env)

The envelope protein of the amphotropic murine leukemia virus 4070A was expressed transiently in packaging host cells by transfection of the mammalian expression vector pCXAS(4070A-env). The parent expression vector pCXAS contains the following sequence components in the 5' to 3' orientation: 1) the CMV IE enhancer-promoter; 2) artificial intron A (CMV IE splice donor/α-globin splice acceptor); 3) multiple cloning sites consisting of the recognition sequences for restriction enzymes PvuII, BglII, NheI, XhoI, EcoRI MluI, KpnI, XbaI; 4) the SV40 polyadenylation signal sequence region; 5) the SV40 origin of replication region. pCXAS was constructed from three DNA fragments: 1) an 1840 bp fragment generated by digesting plasmid p3A (described above) with XbaI and PvuI, 2) a 342 bp fragment generated by digesting plasmid 4A (described above) with SstI and XbaI, and 3) a 1200 bp fragment generated by digesting plasmid p1.1 (described above) with PvuI and SstI. Plasmid pCXAS(4070A-env) (FIG. 3D) was constructed from two DNA fragments: 1) a vector fragment of 3.3 kB prepared by digestion of the pCXAS mammalian expression vector with BglII and XbaI, and 2) a DNA fragment of 2.0 kB containing the complete coding region of the MuLV 4O7OA env gene product; GenBank Accession No. M33469; Ott et al. (1990) *J. Virol.* 64, 757-766)] obtained by digestion of plasmid p7.3 (described below) with BglII and XbaI.

Plasmid p7.3 contains the A-MuLV envelope gene as a BglII to XbaI fragment and was constructed in 3 steps. In the first step, plasmid p7.1 which contains the 5' end of the 4070A envelope sequence was constructed using DNA fragments obtained from pSV-A-MLVenv (Landau N., et al., (1991) *J. Virol.* 65 162-169) and pBluescriptII KS+ (Stratagene, San Diego, Calif.). Plasmid p7.1 was constructed as follows: a 1 kB DNA fragment, obtained by digestion of pSV-A-MLV-env with XbaI and EcoRI, was digested with PflMI to generate a 610 bp PflMI/EcoRI fragment; oligonucleotide E5'(−)(92) was kinased and annealed to oligonucleotide E5'(+)(93) to create a synthetic DNA fragment with an internal BglII recognition sequence and HindIII and PflMI overhangs at the 5' and 3' ends, respectively. The annealed oligonucleotides together with the 610 bp PflMI/EcoRI fragment were ligated to a 3 kB vector fragment that was obtained by digestion of pBluescriptII KS+ with HindIII and EcoRI. In the second step, a plasmid which is referred to as 7.2 and contains the middle and 3' regions of the 4070A env sequence was constructed using DNA fragments obtained from pSV-A-MLVenv (N. Landau, Ibid.), pLC/63 (Chattopadhyay S. K. (1981) *J. Virol.* 39 777-791, GenBank accession number M33469), and pBluescriptII KS+ (Stratagene, San Diego, Calif.). Plasmid p7.2 was constructed as follows: pSV-A-MLVenv was digested with EcoRI and ClaI to obtain a 1.3 kB fragment representing the middle region of the env sequence; pLC/63 was digested with ClaI and NheI to obtain a 170 bp fragment representing the 3' end of the env sequence; and the 1.3 kB EcoRI/ClaI fragment together with the 170 bp ClaI/NheI fragment were ligated to a 3 kB vector fragment obtained by digestion of pBluescriptII KS+ with EcoRI and SpeI (note: NheI and SpeI digestions create compatible overhangs). In the third step, plasmid 7.3 which contains the complete coding region of the 4070A env gene was assembled using DNA fragments obtained from plasmid 7.1 and plasmid 7.2. Plasmid 7.3 was constructed as follows: a 1.45 kB fragment containing the 3' region of the env sequence was prepared from plasmid 7.2 by digestion with EcoRI and XbaI; a 3.5 kB fragment containing the PBSKS+ vector sequences and the 5' region of the env gene was prepared by digestion of plasmid 7.1 with EcoRI and XbaI; and the two fragments were ligated together.

Target Host Cells

Resistance tests performed with resistance test vectors derived from genomic indicator gene viral vectors pCG-CXCN(F-lucP)2 were carried out using target host cells consisting of the human embryonic kidney cell line 293 (Cell Culture Facility, UC San Francisco, SF, Calif.) or the Jurkat leukemic T-cell line (Arthur Weiss, UC San Francisco, SF, Calif.).

Drug Susceptibility and Resistance Tests

Resistance tests were carried out with resistance test vectors based on the indicator gene viral vector pCG-CXCN (F-lucP)2 using two host cell types. Resistance test vector viral particles were produced by a first host cell (the resistance test vector host cell) that was prepared by transfecting a packaging host cell with the resistance test vector and the packaging expression vector. The resistance test vector viral particles were then used to infect a second host cell (the target host cell) in which the expression of the indicator gene is measured.

AZT Drug Susceptibility/Resistance Tests

The resistance test vectors pCG-CXCN(F-lucP)2-AA containing a functional luciferase gene cassette was constructed and host cells were transfected with the resistance test vector DNA. The resistant test vectors contained "test" patient-derived reverse transcriptase sequences that were either susceptible or resistant to the nucleoside reverse transcriptase inhibitor, AZT (Sigma). The resistance test vector viral particles produced by transfecting the resistance test vector DNA into host cells were used to infect target host cells grown either in the absence of AZT or in the presence of increasing concentrations of the drug (ranging from approximately 0.0001 μM to 1000 μM). The amount of luciferase activity produced in infected target host cells in the presence of drug was compared to the amount of luciferase produced in infected target host cells in the absence of drug. Drug resistance was measured as the amount of drug required to inhibit by 50% the luciferase activity detected in the absence of drug (inhibitory concentration 50%, $IC_{50}$). The $IC_{50}$ values were determined by plotting percent drug inhibition vs. $\log_{10}$ drug concentration.

Figure 8B:
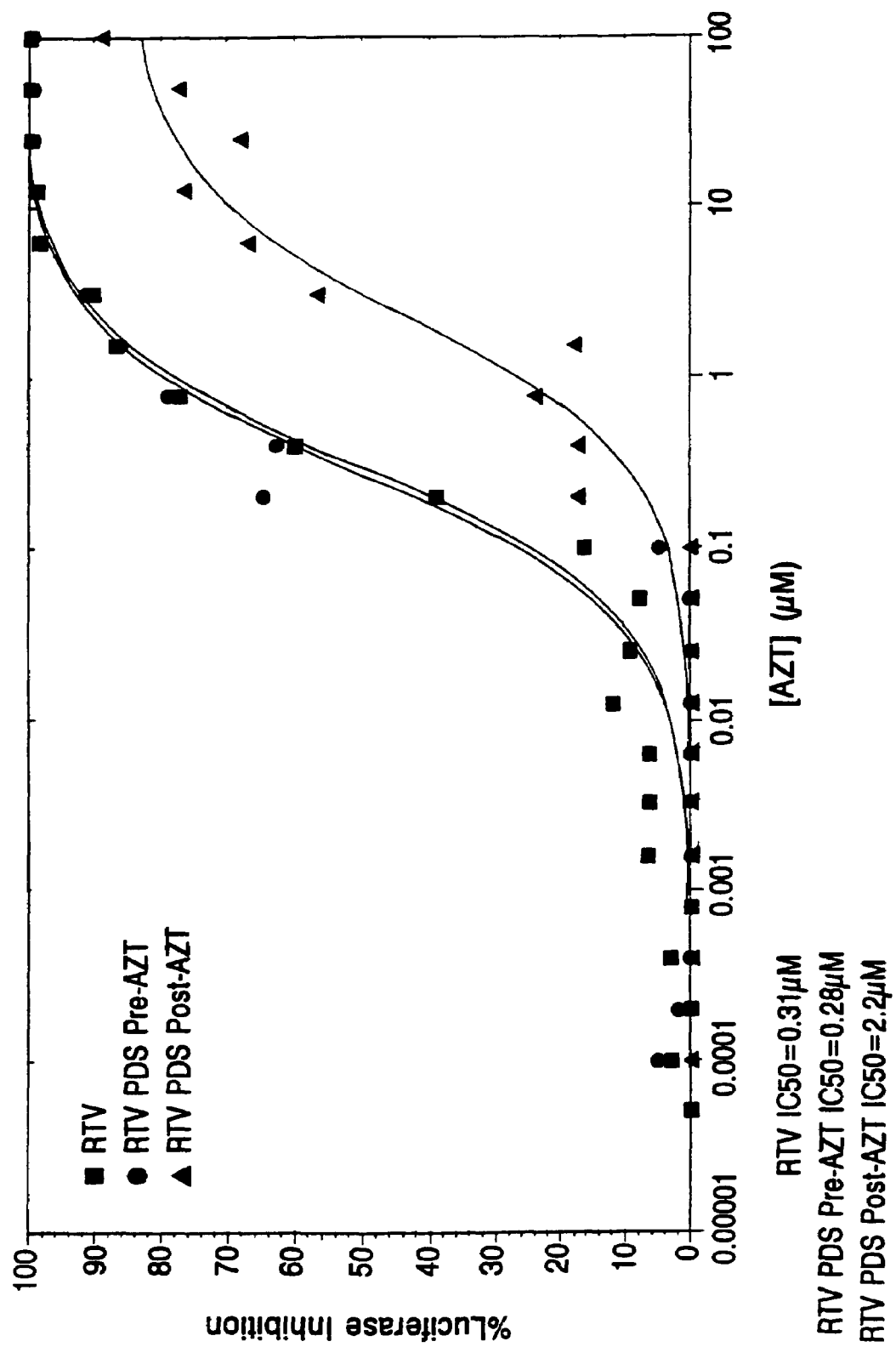
Figure 8D:
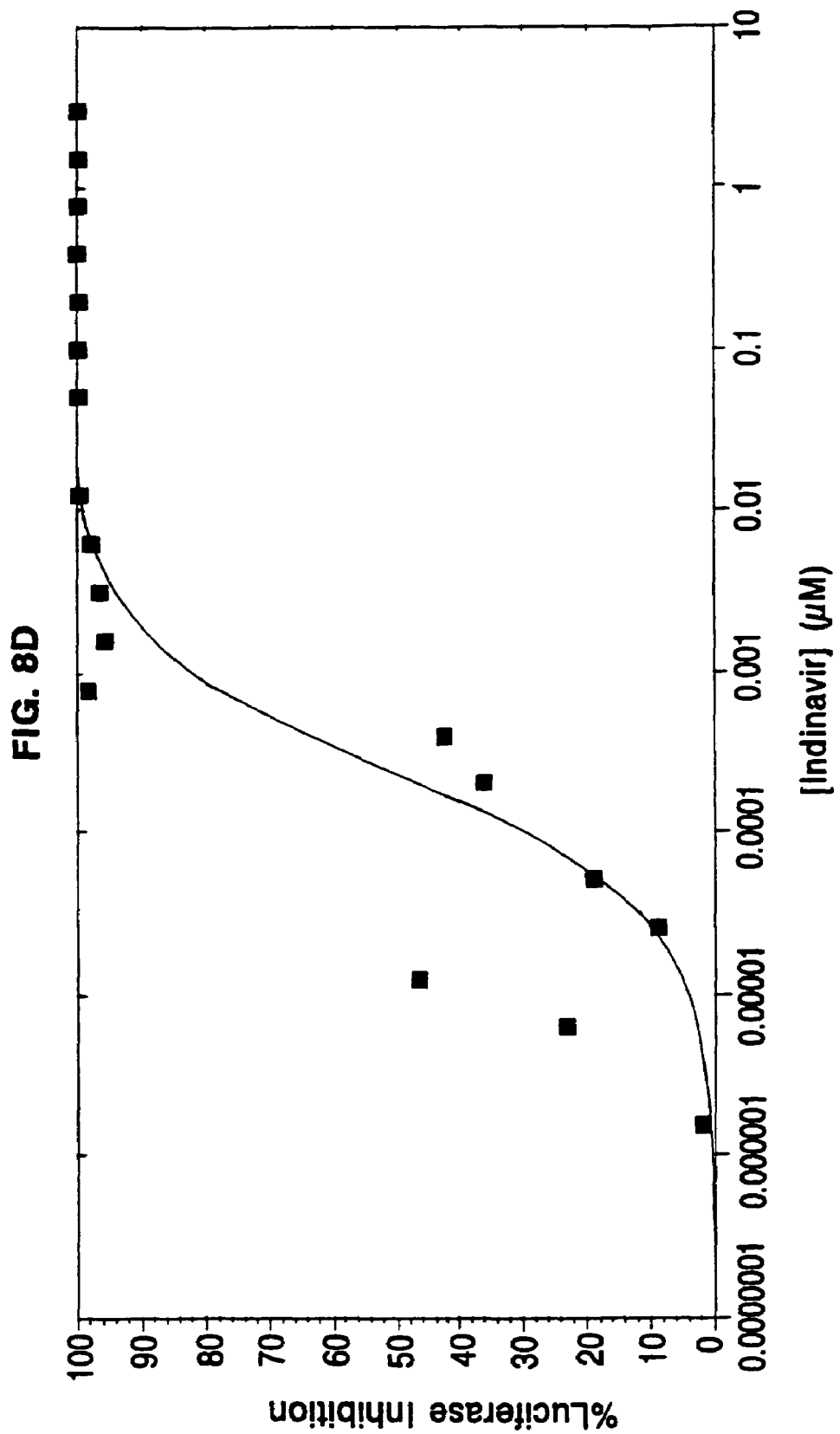

Host cells (293) were seeded in 10-cm-diameter dishes and were transfected several days after plating with resistance test vector plasmid DNA and the envelope expression vector pCXAS(4070A-env). Transfections were performed using a calcium-phosphate precipitation procedure. The cell culture media containing the DNA precipitate was replaced with fresh medium, from one to 24 hours, after transfection. Cell culture media containing resistance test vector viral particles was harvested one to four days after transfection and was passed through a 0.45-mm filter before being stored at −80° C. HIV capsid protein (p24) levels in the harvested cell culture media were determined by an EIA method as described by the manufacturer (SIAC; Frederick, Md.). Six to forty-eight hours before infection, target cells (293 and 293/T) were plated in cell culture media containing no AZT or serial two fold dilutions of AZT beginning at 1001M and ending at 0.00005 μM. The AZT concentrations were maintained throughout the infection. Target host cells were inoculated with 90 μl of transfected resistance test vector host cell supernatant. Control infections were performed using cell culture media from mock transfections (no DNA) or transfections containing the resistance test vector plasmid DNA without the envelope expression plasmid DNA (pCXAS (4070A-env)). One to twenty-four hours after the inoculation, fresh medium was added to each well. Twelve to thirty-six hours later the media was completely replaced with fresh media. One to three or more days after infection the media was removed and cell lysis buffer (Promega) was added to each well. Cell lysates were diluted 100 fold in lysis buffer and each diluted cell lysate was assayed for luciferase activity (FIG. 8A). The inhibitory effect of AZT was determined using the following equation:

$$\% \text{ luciferase inhibition} = 1 - (\text{RLUluc}_{[AZT]} \div \text{RLUluc})$$

where $\text{RLUluc}_{[AZT]}$ is the Relative Light Unit of luciferase activity in infected cells in the presence of AZT and RLUluc is the Relative Light Unit of luciferase activity in infected cells in the absence of AZT. $IC_{50}$ values were obtained from the sigmoidal curves that were generated from the data by plotting the percent inhibition of luciferase activity vs. the $\log_{10}$ drug concentration. The AZT inhibition curves are shown in (FIG. 8B).

Nevirapine Drug Susceptibility/Resistance Test

The resistant test vector, based on the indicator gene viral vector pCG-CXCN(F-lucP)2, contained the reverse transcriptase sequence derived from the biologically active proviral clone, pNL4-3, that is susceptible to the non-nucleoside reverse transcriptase inhibitor, nevirapine (BI-RG-587, Boehringer Ingleheim). Transfection of host packaging cells and infection of host target cells were performed as described for the AZT drug susceptibility/resistance tests as described above. Nevirapine susceptibility/resistance was evaluated using nevirapine concentrations ranging from 0.0001 μM to 100 μM. The nevirapine inhibition curve was determined as described above for AZT and is shown in FIG. 8C.

Indinavir Drug Susceptibility/Resistance Tests

The resistant test vector, based on the indicator gene viral vector pCG-CXCN(F-lucP)2, contained the protease sequence derived from the biologically active proviral clone, pNL4-3, that is susceptible to the protease inhibitor, indinavir (MK-639, Merck). Transfection of host packaging cells and infection of host target cells were performed as described for the AZT drug susceptibility/resistance test except that the protease inhibitor, indinavir, was present in the transfected packaging host cell cultures as well as the infected target host cell cultures, as described above. Indinavir susceptibility/resistance was evaluated using indinavir concentrations ranging from 1.5 pM to 3 µM. The indinavir inhibition curve was determined as described above for AZT and is shown in FIG. 8D.

EXAMPLE 7

HIV Drug Susceptibility and Resistance Test Using Resistance Test Vectors Comprising Patient-Derived Segment(s), and a Functional Luciferase Indicator Gene Cassette Indicator Gene Viral Vector—Construction The genomic indicator gene viral vector pCG-CXAT(F-lucP)2 is identical to pCG-CXCN(F-lucP)2 with the exception of the luciferase indicator gene cassette. The resistance test vector based on the genomic indicator gene viral vector comprises patient sequence acceptor sites and a luciferase indicator gene cassette inserted into the deleted env gene cassette which contains the following elements in a 5' to 3' orientation (FIG. 7D): 1) a CMV IE enhancer-promoter region; 2) artificial intron A (CMV IE splice donor/α-globin splice acceptor); 3) the coding region of the firefly (*Photinus pyralis*) luciferase gene inserted into a multiple cloning site, and 4) the thymidine kinase gene polyadenylation signal region from Herpes Simplex Virus type 1 (HSV-1) (GenBank Accession No. M11414, Cole and Stacy (1985) *Mol. Cell Biol.* 5, 2104-2113). The luciferase indicator gene cassette was inserted into the genomic viral vector pCG in the same transcriptional orientation as the first CMV IE promoter-enhancer region.

Genomic Indicator Gene Viral Vector

The indicator gene viral vector pCG-CXAT(F-lucP)2 was prepared from two DNA fragments: 1) a 11.1 kB vector fragment prepared by digesting plasmid pCG with XmaI and treating the vector with alkaline phosphatase, and 2) a 2.8 kB fragment containing the luciferase indicator gene cassette prepared by digesting the expression vector pCXAT(lucP) (described below) with SgrAI. Plasmids containing the luciferase gene cassette inserted into the viral vector in the same transcriptional orientation as the viral transcription units were identified by restriction enzyme digestion. Plasmids containing the luciferase gene cassette inserted into the viral vector in the reverse transcriptional orientation as the viral transcription units were identified by restriction enzyme digestion for use elsewhere (see e.g. Example 1).

Luciferase Indicator Gene Cassette—pCXAT(lucP)

The luciferase indicator gene cassette, pCXAT(lucP) contains the coding region of the firefly (*Photinus pyralis*) luciferase gene inserted into the expression vector pCXAT (described below). pCXAT(lucP) was constructed from a vector DNA of 3.3 kB prepared by digesting pCXAT with BglII and XbaI, and a fragment of 1.6 kB containing the complete luciferase coding region prepared by digesting p4AlucPSgrAI (–) (described in Example 6) with BglII and XbaI.

The pCXAT expression vector contains the following sequences in the 5' to 3' orientation: 1) the CMV IE enhancer-promoter; 2) artificial intron A (CMV IE splice donor/α-globin splice acceptor); 3) multiple cloning sites consisting of recognition sequences for restriction enzymes PvuII, BglII, NheI, XhoI, EcoRI, MluI, KpnI, and XbaI; 4) the thymidine kinase gene polyadenylation signal region from HSV-1, and 5) the SV40 origin of replication region. pCXAT was constructed from two DNA fragments: 1) a 1.6 kB fragment prepared by digesting plasmid pCXAS with XbaI and PvuI, and 2) a 1.7 kB fragment prepared by digesting plasmid p3B (described below) with PvuI and XbaI. Plasmid p3B contains the 3' portion of the nef coding region, the U3 and R sequences of HIV, the HSV-1 thymidine kinase gene polyadenylation signal region, and 5) the SV40 origin of replication region. It was constructed from two DNA fragments: 1) a 3.2 kB vector fragment prepared by digesting plasmid p3A with Xba I and SgrAI, and 2) a 140 bp synthetic fragment containing the thymidine kinase gene polyadenylation signal region from HSV-1. The 140 bp fragment was prepared from 5 oligonucleotides, TKT 1-TKT 5 (94-98). TKT 2, TKT 3, and TKT 4 were phosphorylated with T4 polynucleotide kinase and ATP, and then annealed and ligated, together with TKT 1 (94) and TKT 5 (98). The 140 bp ligation product was isolated by gel electrophoresis. The 140 bp fragment contains the following elements in a 5' to 3' orientation 1) an XbaI compatible cohesive end, 2) sequences identical to bases 24 to 150 of the HSV-1 thymidine kinase gene polyadenylation signal region, and 3) an SgrAI compatible cohesive end.

Resistance Test Vectors Construction

Resistance test vectors were prepared as described in Example 6 except the genomic indicator gene viral vector pCG-CXAT(F-lucP)2 was used instead of pCG-CXCN(F-lucP) 2. The packaging host cells, resistance test vector host cells and target host cells were also as described in Example 6. The AZT drug susceptibility was carried out at an AZT concentration of 5 µM as described in Example 6 and the results are shown in FIG. 8A.

EXAMPLE 8

Hepatitis Drug Susceptibility and Resistance Test Using Resistance Test Vectors Comprising Patient-Derived Segment(s) and a Non-Functional Indicator Gene Containing an Inverted Intron Indicator Gene Viral Vector—Construction Indicator gene viral vectors containing a non-functional indicator gene with an inverted intron were designed using HBV subgenomic viral vectors comprising viral genes which are the target(s) of anti-viral drugs. The indicator gene viral vectors pCS-HBV(NF-IG)II-(PSAS–), are based on the subgenomic viral vector pCS-HBV. The indicator gene viral vector contains a non-functional indicator gene cassette containing an inverted intron and all of the cis-acting regulatory elements that are necessary for HBV DNA replication (i.e. DR1, 5'ϵ DR2, DR1*, 3'pA) but lacks the HBV gene sequences (i.e. C, P, S, X genes) that provide the trans-acting structural and enzymatic functions that are necessary for HBV DNA replication and virus particle formation (FIG. 9B). The C, P, S and X genes and patient sequence acceptor sites are contained within a packaging vector pPK-CPX (described below, FIG. 9D) and pPK-S (described below, FIG. 9E). In this embodiment the indicator gene viral vector pCS-HBV(NF-IG)II-(PSAS−) and the packaging vector pPK-CPX constitute a resistance test vector system. The non-functional indicator gene viral vector pCS-HBV(NF-IG)II-(PSAS−) contains the following elements in a 5' to 3' orientation: (1) the CMV IE enhancer promoter region, (2) the 5' region of the HBV genome and the DR1 and 5' copy of the encapsidation signal region ($\epsilon$) (the pre-C ORF translation initiation codon is eliminated), (3) a non-functional indicator gene cassette in which the indicator gene ORF contains an inverted intron, (4) the region of the HBV genome containing DR2, DR1*, the 3' $\epsilon$, and the 3' HBV polyadenylation (pA) signal region. The non-functional indicator gene expression cassette is comprised of some or all of the following elements arranged in the 5' to 3' orientation: (1) a transcriptional enhancer-promoter region, (2) an intron, (3) an indicator gene containing an inverted intron, (4) a transcriptional polyadenylation signal sequence (e.g. SV40) (HSV-1 thymidine kinase gene). The indicator gene expression cassette has a transcriptional orientation opposite to the HBV sequence elements (FIG. 9B). However, the intron within the indicator gene ORF has the same transcriptional orientation as the HBV sequence elements.

In a second embodiment, the non-functional indicator gene viral vector, pCS-HBV(NF-IG)II(PSAS+), contains a non-functional indicator gene cassette containing an inverted intron, all of the cis-acting regulatory elements that are necessary for HBV DNA replication, and some or all of the HBV gene sequences (i.e. C, P, S, X genes) that provide the trans-acting structural and enzymatic functions that are necessary for HBV DNA replication and virus particle formation (FIG. 9F). Resistance test vectors derived from the indicator gene viral vector pCS-HBV(NF-IG)II(PSAS+) contain patient sequence acceptor sites (PSAS) and are used in conjunction with the packaging vector, pPK-CSX (FIG. 9H). In this embodiment the indicator gene viral vector may also provide some or all of the packaging functions, such as P. The structural and enzymatic activities that are not provided by the indicator gene viral vector, but that are necessary for HBV DNA replication and virus particle formation, are provided using additional packaging vector(s) pPK-CSX (described below, FIG. 9H). In this embodiment, the non-functional indicator gene viral vector, pCS-HBV(NF-IG)II (PSAS+) contains the following elements in a 5' to 3' orientation: (1) the CMV IE enhancer-promoter region, (2) the 5' region of the HBV genome and the DR1 and 5' $\epsilon$ (the pre-C ORF translation initiation codon is eliminated), (3) an indicator gene cassette, containing an inverted intron, positioned within the region of the HBV genome which may contain some or all of the C, P, S, and X genes as well as a patient-derived P gene segment, (4) the region of the HBV genome containing DR2, DR1*, the 3' $\epsilon$, and the 3' the HBV pA signal region. Within the non-functional indicator gene viral vector, pCS-HBV(NF-IG)II-(PSAS+) the indicator gene expression cassette has a transcriptional orientation opposite to the HBV sequence elements (FIG. 9F). However, the intron within the indicator gene ORF has the same transcriptional orientation as the HBV sequence elements.

In transfected cells the packaging vectors (FIGS. 9D, 9E and 9H) provide, in trans, the structural and enzymatic functions that are necessary for HBV DNA replication and virus particle formation, but that are not provided by the resistance test vector or the indicator gene viral vector. In the embodiment in which an indicator gene viral vector such as pCS-HBV(NF-IG)PP-(PSAS−)is co-transfected with a packaging vector, such as pPK-CPX, the combination of those vectors constitute a resistance test vector system, it is the packaging vector that contains patient sequence acceptor sites for insertion of the patient-derived P gene segment (described above). The packaging vector pPK-CPX contains the following elements in a 5' to 3' orientation: (1) the CMV IE enhancer-promoter region, (2) the region of the HBV genome spanning from the C ORF translation initiation codon to the 3' pA signal and including the C, P, S, and X genes. The C gene of the packaging vectors is modified such that it does not contain and/or express the pre-C ORF sequences and does not express the S proteins (described below).

In HBV, RNA that encodes C and/or P proteins is preferentially packaged, in cis, and consequently could interfere with the efficient packaging of the resistance test vector containing a non-functional indicator gene or a non-functional indicator gene viral vector RNA that does not encode C and P proteins. Two steps are taken to prevent the encapsidation of RNA produced from packaging vectors and to improve the encapsidation efficiency of the resistance test vector or non-functional indicator gene viral vector RNA. First, the RNA produced by packaging vectors does not contain the 5' encapsidation signal region ($\epsilon$) (FIGS. 9D, 9E and 9H). Second, in cases where either the C gene and/or P gene packaging functions are provided by the resistance test vector or non-functional indicator gene viral vector, packaging vectors, such as pPK-S or pPK-CSK, that do not express the C and/or P gene products are used (FIGS. 9E and 9H).

Resistance Test Vectors—Construction

Resistance test vectors are prepared by 1) modifying the indicator gene viral vector pCS-HBV(NF-IG)II-(PSAS−) by introducing unique restriction sites, called patient sequence acceptor sites (PSAS) in the P gene region, 2) amplifying patient-derived segments corresponding to the HBV drug target, e.g. reverse transcriptase or DNA polymerase, by the amplification of viral DNA present in the serum or cells of infected patients, and 3) inserting the amplified sequences precisely into the indicator gene viral vectors at patient sequence acceptor sites (FIG. 9F). Alternatively, resistance test vector systems are prepared by 1) modifying the packaging vectors, pPK-CPX, by introducing patient sequence acceptor sites in the P gene, 2) amplifying patient-derived segments corresponding to the HBV drug target, e.g. reverse transcriptase or DNA polymerase, by amplification using viral DNA present in the serum or cells of infected patients, and 3) inserting the amplified sequences precisely into the packaging vectors at patient sequence acceptor sites (FIG. 9D). In one embodiment, the 5' PSAS is situated near the border of the spacer and RT domains of the P protein (immediately downstream of the S protein translation initiation site) and the 3' PSAS is situated near the C-terminal end of the RNase H domain of the P protein. Insertion of a patient-derived P gene segment into the patient sequence acceptor sites results in the formation of a chimeric P gene sequence in which the TP and spacer domains are encoded by the vector P gene sequence while the reverse transcriptase/polymerase and RNase H domains are encoded by the patient-derived segments (FIGS. 9D and 9F).

In HBV the entire S gene ORF overlaps the P gene ORF but is expressed using a different reading frame (Nassal, M. and Schaller, H. (1993) *Trends in Microbiology* 1, 221-228). Thus, HBV P gene sequences (reverse transcriptase and RNase H domains) obtained from patients also contain the corresponding patient S gene sequences. Expression of the patient-derived S gene region from the overlapping S gene ORF is prevented by eliminating the three S gene ORF (pre-S1, pre-S2, and S) translation initiation sites and/or introducing in-frame termination codons in the pCS-HBV (NF-IG)II-(PSAS+) or pPK-CPK vectors (FIGS. 9F and 9D). S gene expression is provided, in trans, using a separate packaging vector that provides well-characterized S gene products (FIGS. 9E and 9H). The modifications that eliminate S gene expression are performed without introducing changes to the overlapping amino acid sequences that are encoded by the terminal protein (TP) or spacer domains of the P gene.

Drug Susceptibility and Resistance Tests

Drug susceptibility and resistance tests are carried out with a resistance test vector based on indicator gene viral vectors pCS-HBV(NF-IG)II-(PSAS+) or with a resistance test vector system based on an indicator gene viral vector, pCS-HBV(NF-IG)II-(PSAS−) and a packaging vector, pPK-CPX, using either one type of host cell or two types of host cell. Co-transfection of packaging host cells either with a resistance test vector, such as pCS-HBV(NF-IG)II-(PSAS+) and a packaging vector, pPK-CSX, or with an indicator gene viral vector, such as pCS-HBV(NF-IG)II-(PSAS−) and packaging vector-containing patient-derived segment, such as pPK-CPX, (i.e. resistance test vector system) produces HBV viral particles containing an encapsidated indicator gene "pregenome" RNA, which as a result of splicing of the inverted intron, contains a functional indicator gene. (FIGS. 9B and 9C).

Replicate transfections are performed on a series of packaging host cell cultures maintained either in the absence of the anti-viral drug or in increasing concentrations of the anti-HBV drug (e.g., an HBV P protein reverse transcriptase or polymerase inhibitor). After maintaining the packaging host cells for up to several days in the presence or absence of the anti-HBV drug the level of drug susceptibility or resistance can be assessed either directly in the host packaging cell lysates, or in isolated HBV particles obtained by harvesting the host packaging cell culture media. Alternative approaches can be used to evaluate drug susceptibility and resistance in the cell lysates and the isolated HBV particles.

In one embodiment, referred to as the one cell assay, drug susceptibility or resistance is assessed by measuring indicator gene expression e.g. luciferase activity in the transfected packaging host cells in the presence or absence of anti-viral drug. A reduction in luciferase activity observed for cells transfected in the presence of a given anti-viral agent, or combination of agents as compared to a control run in the absence of the anti-viral agent(s), generally relates to the log of the concentration of the anti-viral agent as a sigmoidal curve.

In a second embodiment, referred to as the two cell assay, drug susceptibility or resistance is assessed by measuring indicator gene expression, e.g. luciferase activity, in the target host cells following infection or transfection with HBV particles or HBV particle DNA, respectively. HBV viral particles obtained from packaging host cells are used to infect the target host cells or DNA from those particles is used to transfect target host cells. At the time of infection or transfection the appropriate concentration of the anti-viral drug is added to the cell culture. Up to several days following the infection or transfection, the target host cells are lysed and indicator gene expression is measured. A reduction in indicator gene expression will be observed for cells transfected or infected in the presence of drugs which inhibit HBV replication, for example by inhibiting either the reverse transcriptase (− strand DNA) or the DNA polymerase (+ strand DNA) activities of the HBV P protein as compared to a control run in the absence of drug.

In a third embodiment, referred to as the DNA structure indicator assay, drug susceptibility or resistance is assessed by measuring the level of HBV DNA replication that has occurred within the transfected packaging host cells or within the virus particles produced by the packaging host cells. In transfected host cells the HBV subgenomic viral vector is transcribed and the RNA transcript is packaged as "pregenomic" RNA. During virus maturation, the pregenomic RNA is converted to the relaxed circular form of the genomic DNA (rc-DNA) consisting of a complete minus strand and partial plus strand DNA copy. In a subsequent step, the rc-DNA is converted to a covalently closed circular DNA form (cccDNA). To measure HBV DNA replication, amplification primers are designed to amplify an HBV DNA structure that is formed by the splicing of pregenomic RNA and the conversion of this spliced RNA to the rc-DNA and cccDNA forms.

Formation of the correct amplification target structure within HBV particles requires successful completion of HBV DNA replication resulting in the formation of rc-DNA and cccDNA. Anti-viral drugs that inhibit HBV DNA replication (reverse transcription and DNA polymerase activities) will limit the formation of the DNA target sequence, which in turn, can be measured as a decrease in the amplified DNA product using a number of quantitative amplification assays. In one example (FIG. 10B), the binding site of the reverse primer (Pr) is separated into two components by an intron sequence that is inserted into an indicator gene ORF in the same transcriptional orientation as the HBV sequences. The primer binding site of the forward primer (Pf) is located within the region of the viral vector that is flanked by the DR2 and DR1* sequences. In the linear HBV vector the Pf and Pr primers direct DNA synthesis in opposite directions and are oriented outward with respect to each other. In this case, the Pr primer directs DNA synthesis in the upstream direction (toward the 5' copy of $\epsilon$) and the Pf primer directs DNA synthesis in the downstream direction (toward the 3' $\epsilon$). This arrangement of primers and template does not constitute a functional amplification unit in the linear indicator gene viral vector. Furthermore, the Pr binding site is not intact in the linear unspliced vector and thus Pr will not anneal to the target DNA. In contrast, the Pf and Pr primers assume an inward orientation with respect to each other in the relaxed circle form of HBV DNA found in mature virions and splicing of the RNA pregenome has assembled an intact Pr primer binding site. Both primers now direct DNA synthesis toward the single copy of DR1 within the plus strand copy of rc-DNA and in either plus or minus strand or cccDNA. This arrangement of primers and template constitutes a functional amplification unit (FIG. 10C).

In an alternative embodiment of the DNA sequence indicator assay (FIG. 10D) the 5' exonuclease activity of the amplification enzyme (e.g. Taq polymerase) is measured rather than the production of amplified DNA (C. Heid et al., 1996. *Genome Research* 6:986-994). The 5' exonuclease activity is measured by monitoring the nucleolytic cleavage of a fluorescently tagged oligonucleotide probe that is capable of binding to the amplified DNA template region flanked by the Pf and Pr binding sites. The performance of this assay is dependent on the close proximity of the 3' end of the upstream primer (Pf) to the 5' end of the oligonucleotide probe. When the Pf primer is extended it displaces the 5' end of the oligonucleotide probe such that the 5' exonuclease activity of the polymerase cleaves the oligonucleotide probe. The purpose of the intron is to distance the Pf binding site sufficiently far away from the 5' end of the exonuclease probe sequence to essentially eliminate detectable exonuclease digestion of the probe oligonucleotide in the unspliced target template. Removing the intron by splicing serves to position the 3' end of the Pf binding site immediately upstream of the probe 5' binding site. The latter rearrangement enables the quantitative detection of exonuclease activity of the amplified target template (FIG. 10E).

Drug Screening

Drug screening is carried out using an indicator gene viral vector containing a non-functional indicator gene cassette with an inverted intron and a packaging vector(s). In transfected packaging host cells, the indicator gene viral vector produces an encapsidation competent ($\epsilon$+) RNA transcript containing the indicator gene. The packaging vector(s) provide, in trans, the structural and/or enzymatic viral functions that are not provided by the resistance test vector, but that are necessary for viral DNA replication and particle formation. Upon co-transfection of packaging host cells, the indicator gene viral vector and packaging vectors give rise to HBV viral particles containing an encapsidated indicator gene viral vector "pregenome" RNA, which as a result of splicing of the inverted intron, contains a functional indicator gene.

Drug screening is performed as follows: indicator gene viral vector and packaging vector DNA is used to transfect the packaging host cells. Replicate transfections are performed on a series of packaging host cell cultures maintained either in the absence or presence of potential antiviral compounds (e.g., candidate HBV P protein reverse transcriptase or polymerase inhibitors). After maintaining the packaging host cells for up to several days in the presence or absence of the candidate anti-viral drugs the level of inhibition of DNA replication is assessed either directly in the packaging host cell lysates, or in isolated HBV particles obtained by harvesting the host packaging cell culture media. Either DNA detection or indicator gene activity methods, described above, can be used to evaluate potential anti-HBV drug candidates.

EXAMPLE 9

Hepatitis Drug Susceptibility and Resistance Test Using Resistance Test Vectors Comprising Patient-Derived Segment(s) and a Non-Functional Indicator Gene Containing a Permuted Promoter Indicator Gene Viral Vector—Construction Indicator gene viral vectors containing a non-functional indicator gene with a permuted promoter were designed using an HBV subgenomic viral vector comprising viral genes which are the target(s) of anti-viral drugs. The indicator gene viral vectors, pCS-HBV(NF-IG)PP-(PSAS–), are based on the subgenomic viral vector pCS-HBV. The indicator gene viral vector, pCS-HBV(NF-IG)PP-(PSAS–), contains a non-functional indicator gene cassette with a permuted promoter and all of the cis-acting regulatory elements that are necessary for HBV DNA replication (i.e. DR1, 5'$\epsilon$, DR2, DR1*, 3'pA) but lacks the HBV gene sequences (i.e. C, P, S, X genes) that provide the trans-acting structural and enzymatic functions that are necessary for HBV DNA replication and virus particle formation (FIG. 11B). The C, P and X and patient sequence acceptor sites are contained within a packaging vector pPK-CPX (described in Example 8, see FIG. 9D). The S gene is contained within a packaging vector pPK-S (described in Example 8, see FIG. 9E). In this embodiment, the indicator gene viral vector, pCS-HBV(NF-IG)PP-(PSAS–) and the packaging vector pPK-CPX constitute a resistance test vector system. The non-functional indicator gene viral vector, pCS-HBV(NF-IG)PP-(PSAS–), contains the following elements in a 5' to 3' orientation: (1) the CMV IE enhancer promoter region, (2) the 5' region of the HBV genome and the DR1 and 5' $\epsilon$ (the pre-C ORF translation initiation codon is eliminated), (3) a non-functional indicator gene cassette assembled such that the promoter region is positioned 3', i.e. downstream, of the indicator gene ORF, (4) the 3' region of the HBV genome containing DR2, DR1*, the 3' $\epsilon$, and the 3' HBV pA signal region (the pre-C ORF translation initiation codon is eliminated). The non-functional indicator gene expression cassette is comprised of some or all of the following elements arranged in the 5' to 3' orientation: (1) an internal ribosome entry site (IRES), (2) an indicator gene, which may contain an inverted intron, and (3) a transcriptional polyadenylation signal sequence (e.g. HSV-1 thymidine kinase gene, SV40) (4) an enhancer-promoter region. Within the non-functional indicator gene viral vector, the indicator gene expression cassette has a transcriptional orientation either opposite to or the same as the HBV sequence elements. In cases where the indicator gene ORF contains an intron, the intron has the same transcriptional orientation as the HBV sequence elements.

Figure 1D:
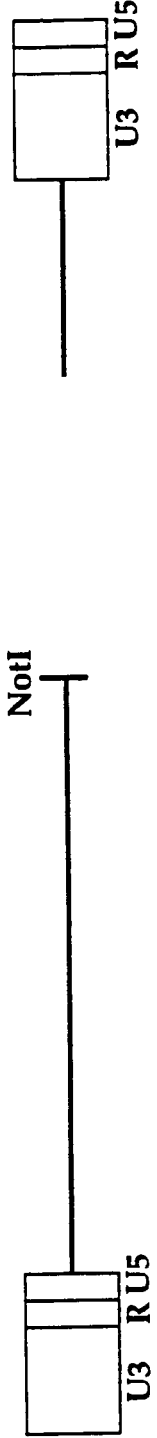
Figure 1E:
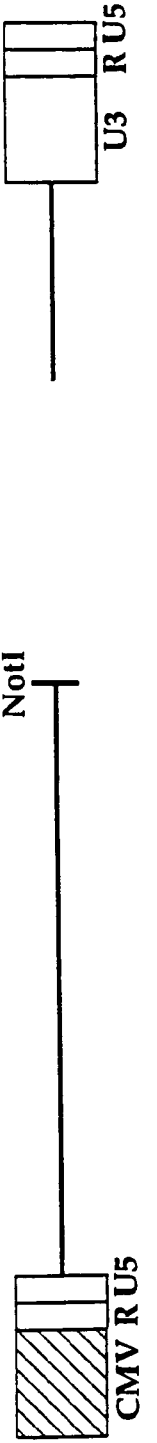

In a second embodiment, the non-functional indicator gene viral vector contains a non-functional indicator gene cassette containing a permuted promoter region, all of the cis-acting regulatory elements that are necessary for HBV DNA replication, and some or all of the HBV gene sequences (i.e. C, P, S, X genes) that provide the trans-acting structural and enzymatic functions that are necessary for HBV DNA replication and virus particle formation, pCS-HBV(NF-IG)PP-(PSAS+) (FIG. 1D). Resistance test vectors derived from the indicator gene viral vector, pCS-HBV (NF-IG)PP-(PSAS+), contain patient sequence acceptor sites and are used in conjunction with the packaging vector pPK-CSK (FIG. 9H). In this embodiment the indicator gene viral vector may also provide some or all of the packaging functions. Furthermore, in this embodiment the structural and enzymatic activities that are not provided by the indicator gene viral vector, but that are necessary for HBV DNA replication and virus particle formation, are provided using additional packaging vectors. In this embodiment, the non-functional indicator gene viral vector, pCS-HBV(NF-IG)PP-(PSAS+), contains the following elements in a 5' to 3' orientation: (1) the CMV IE enhancer-promoter region, (2) the 5' region of the HBV genome and the DR1 and 5' $\epsilon$ (the pre-C ORF translation initiation codon is eliminated), (3) an enhancer-promoter region (permuted promoter), (4) the P gene containing patient-derived segment (5) the indicator gene ORF (6) an internal ribosome entry site (IRES), and (7) the 3' region of the HBV genome containing DR2, DR1*, the 3' $\epsilon$, and the 3' HBV pA signal region (the pre-C ORF translation initiation codon is eliminated). Within the non-functional indicator gene viral vector, the indicator gene expression cassette has a transcriptional orientation either in the reverse or forward direction with respect to the HBV sequence elements. In cases where the indicator gene contains an inverted intron, the intron has a transcriptional orientation the same as to the HBV sequence elements.

Resistance Test Vector—Construction

Resistance test vectors containing a non-functional indicator gene with a permuted promoter were designed using the HBV subgenomic viral vector comprising anti-viral target genes as described in Example 8. The indicator gene viral vector or the packaging vector is modified to include patient sequence acceptor sites (PSAS) for the insertion of P gene containing patient-derived segments (PDS) (described in Example 8, see FIGS. 9D and 9F). The expression of the patient-derived S gene is eliminated as described in Example 8 (see FIG. 9D). Uniform S gene expression is provided, in trans, using a separate packaging vector that provides well-characterized S gene products (FIG. 9E).

Drug Susceptibility and Resistance Test

Drug susceptibility and resistance tests are carried out with a resistance test vector based on indicator gene viral vectors, pCS-HBV(NF-IG)PP-(PSAS+), or with a resistance test vector system comprising an indicator gene viral vector, pCS-HBV(NF-IG)PP-(PSAS−) and a packaging vector, pPK-CPX, using either one type of host cell or two types of host cell. Upon co-transfection of packaging host cells, either with a resistance test vector and a packaging vector or with an indicator gene viral vector and packaging vectors (i.e. resistance test vector system) HBV viral particles are produced containing an encapsidated indicator gene "pre-genome" RNA containing a non-functional indicator gene. Within the transfected host cells, the non-functional indicator gene with the permuted promoter is converted to a functional indicator gene during the HBV DNA replication process (FIGS. 11B and 11C).

Drug susceptibility and resistance tests are performed as described in Example 8 (above). The resistance or susceptibility of patient-derived reverse transcriptase and/or DNA polymerase activities to various anti-viral drugs can be measured by measuring the levels of indicator gene expression in transfected or infected host cells. Alternatively, resistance or susceptibility can be measured by quantitating the amount of HBV DNA replication that has taken place. The latter can be performed using quantitative DNA amplification assays. In one example of this type of assay, (FIGS. 10F and 10G) the primer binding site of the reverse primer (Pr) is located in the region downstream of the 5' $\epsilon$. The primer binding site of the forward primer (Pf) is located within the region flanked by the DR2 and DR1* sequences. In the linear HBV vector the Pf and Pr primers direct DNA synthesis in opposite directions. In this case, the Pr primer directs DNA synthesis in the upstream direction (toward the 5' $\epsilon$) and the Pf primer directs DNA synthesis in the downstream direction (toward the 3' $\epsilon$). This primer configuration does not constitute a functional amplification unit in the linear copy of the viral vector that is used for transfection. In contrast, the Pf and Pr primers assume an orientation toward each other in the rc-DNA form that is found in mature virions. Both primers now direct DNA synthesis toward the single copy of DR1 within the plus strand copy of rc-DNA. This arrangement of primers and template constitutes a functional amplification unit.

Drug Screening

Drug screening using an indicator gene viral vector that contains a non-functional indicator gene with a permuted promoter is performed essentially as described in Example 8 above.

EXAMPLE 10

Hepatitis Drug Susceptibility and Resistance Test Using Resistance Test Vectors Comprising Patient-Derived Segments and a Non-Functional Indicator Gene Containing a Permuted Promoter and Translation Initiation Sites Indicator Gene Viral Vector Indicator gene viral vectors containing a non-functional indicator gene with a permuted promoter and translation initiation site, pCS-HBV(NF-IG)PPTIS were designed using HBV subgenomic viral vector comprising viral genes which are the target(s) of anti-viral drugs. The indicator gene viral vectors pCS-HBV(NF-IG)PPTIS(PSAS−), are based on the subgenomic viral vector pCS-HBV. The indicator gene viral vector contains a non-functional indicator gene cassette with permuted promoter and translation initiation regions, and all of the cis-acting regulatory elements that are necessary for HBV DNA replication (i.e. DR1, 5'$\epsilon$, DR2, DR1*, 3'pA) but lacks the HBV gene sequences (i.e. C, P, S, X genes) that provide the trans-acting structural and enzymatic functions that are necessary for HBV DNA replication and virus particle formation (FIG. 12B). The C, P and X genes and patient sequence acceptor sites are contained within a packaging vector pPK-CPX (Example 8, FIG. 9D). The S gene is contained in the packaging vector, pPK-S, (Example 8, FIG. 9E). In this embodiment the indicator gene viral vector pCS-HBV(NF-IG)PPTIS(PSAS−) and the packaging vector pPK-CPX constitute a resistance test vector system. The non-functional indicator gene viral vector, pCS-HBV(NF-IG)PPTIS(PSAS−), contains the following elements in a 5' to 3' orientation: (1) the CMV IE enhancer-promoter region, (2) the 5' region of the HBV genome including the DR1 and 5' $\epsilon$ (the pre-C ORF translation initiation codon is eliminated), (3) an indicator gene ORF lacking a translation initiation site, (4) an enhancer-promoter region (permuted promoter) (5) the 3' region of the HBV genome containing DR2, a functional pre-C ORF translation initiation codon, DR1*, the 3' $\epsilon$, and the 3' HBV pA signal region. The non-functional indicator gene cassette is comprised of some or all of the following elements arranged in a 5' to 3' orientation: (1) an indicator gene ORF that does not contain an in-frame translation initiation site, (2) a transcriptional polyadenylation signal sequence (e.g. HSV-1 thymidine kinase gene, SV40), (3) an enhancer-promoter region. Within the non-functional indicator gene viral vector, pCS-HBV(NF-IG)PPTIS (PSAS−) the indicator gene expression cassette transcriptional orientation is the same as the HBV sequence elements. In cases where the indicator gene ORF contains an intron, the intron has a transcriptional orientation the same as the HBV sequence elements.

Figure 12D:
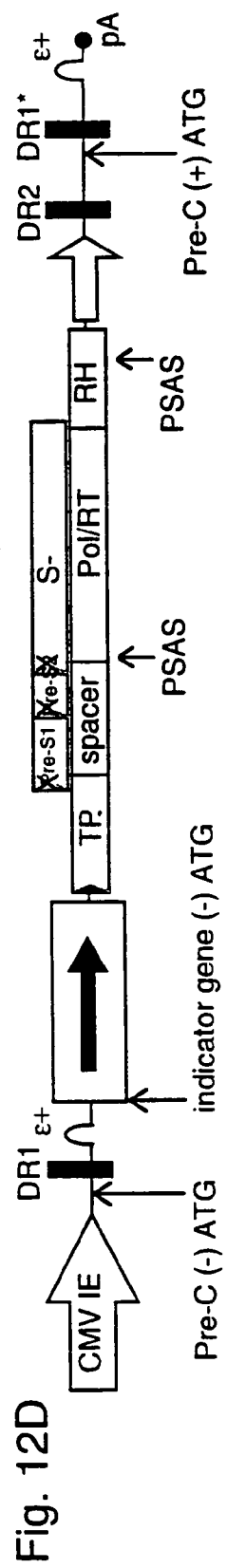
Figure 12E:
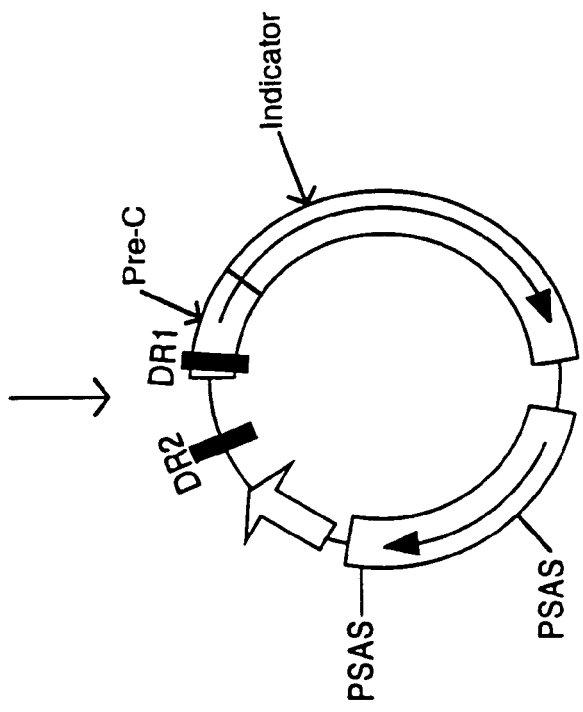

In a second embodiment, the non-functional indicator gene viral vector contains a non-functional indicator gene cassette containing a permuted promoter and translation initiation regions, all of the cis-acting regulatory elements that are necessary for HBV DNA replication, and some or all of the HBV gene sequences (i.e. C, P, S, X genes) that provide the trans-acting structural and enzymatic functions that are necessary for HBV DNA replication and virus particle formation, pCS-HBV(NF-IG)PPTIS(PSAS+) (FIG. 12D). The structural and enzymatic activities that are not provided by the indicator gene viral vector, but that are necessary for HBV DNA replication and virus particle formation, are provided using additional packaging vectors pPK-CSX (described in Example 8, see FIG. 9E). The C, S and X genes are contained within the packaging vector pPK-CSX (described in Example 8, see FIG. 9H). In this embodiment, the non-functional indicator gene viral vector, pCS-HBV(NF-IG)PPTIS(PSAS+), contains the following elements in a 5' to 3' orientation (FIG. 12D): (1) the CMV IE enhancer-promoter region, (2) the 5' region of the HBV genome including the DR1 and 5' ε (the pre-C ORF translation initiation codon is eliminated), (3) an indicator gene ORF lacking a translation initiation site, (4) the P gene containing patient-derived segment, (5) an enhancer-promoter region (permuted promoter) (6) the 3' region of the HBV genome containing DR2, pre-C ORF translation initiation codon, DR1*, the 3 ε, and the 3' HBV pA signal region. Within the non-functional indicator gene viral vector, the indicator gene expression cassette has a transcriptional orientation the same as the HBV sequence elements. In cases where the indicator gene contains an inverted intron, the intron has a transcriptional orientation the same as the HBV sequence elements.

Resistance Test Vectors—Construction

Resistance test vectors containing a non-functional indicator gene with a permuted promoter were designed using the HBV subgenomic viral vector comprising anti-viral target genes as described in Example 8. The indicator gene viral vector or the packaging vector is modified to include patient sequence acceptor sites (PSAS) for the insertion of P gene containing patient-derived segments (PDS) (described in Example 8, see FIGS. 9D and 9F). The expression of the patient-derived S gene is eliminated as described in Example 8 (see FIG. 9D). Uniform S gene expression is provided, in trans, using a separate packaging vector that provides well-characterized S gene products (FIG. 9E).

Drug Susceptibility and Resistance Test

Drug susceptibility and resistance tests are carried out by the procedures described in Examples 8 and 9. Non-functional indicator gene is converted to functional indicator gene during HBV replication (FIGS. 12B and 12C).

Drug Screening

Drug screening using an indicator gene viral vector that contains a non-functional indicator gene with permuted promoter and translation initiation regions is performed essentially as described in Examples 8 and 9 (above).

EXAMPLE 11

Figure 13B:
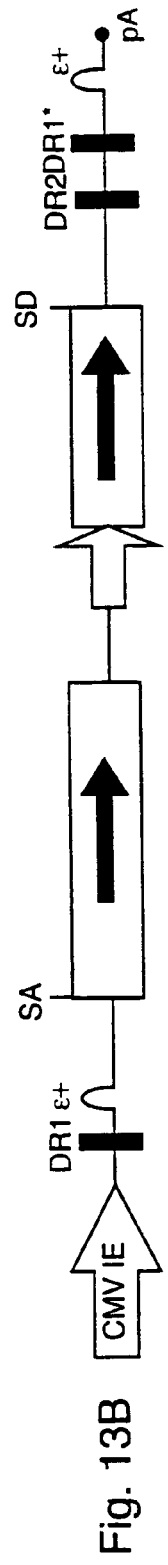
Figure 13C:
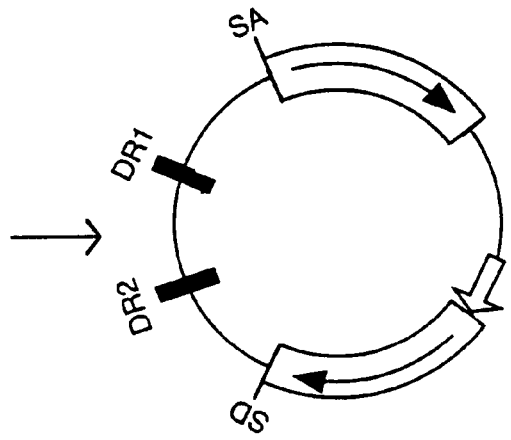

Hepatitis Drug Susceptibility and Resistance Test Using Resistance Test Vectors Comprising Patient-Derived Segments and a Non-Functional Indicator Gene with Permuted Coding Regions Indicator Gene Viral Vector—Constuction Indicator gene viral vectors containing a non-functional indicator gene with permuted coding region were designed using HBV subgenomic viral vectors comprising viral genes which are the target(s) of anti-viral drugs. The indicator gene viral vectors pCS-HBV(NF-IG)PCR(PSAS−), are based on the subgenomic viral vector pCS-HBV. The indicator gene viral vector contains a non-functional indicator gene cassette with a permuted coding region, and all of the cis-acting regulatory elements that are necessary for HBV DNA replication (i.e. DR1, 5'ε, DR2, DR1*, 3'pA) but lacks the HBV gene sequences (i.e. C, P, S, X genes) that provide the trans-acting structural and enzymatic functions that are necessary for HBV DNA replication and virus particle formation (FIG. 13B). The C, P and X genes and patient sequence acceptor sites are contained within a packaging vector, pPK-CPX and the S gene is provided by the packaging vector pPK-S (described in Example 8, see FIGS. 9D and 9E). In this embodiment the indicator gene viral vector pCS-HBV(NF-IG)PCR(PSAS−) and the packaging vector pPK-CPX constitute a resistance test vector system. The non-functional indicator gene viral vector, pCS-HBV(NF-IG)PCR(PSAS−), contains the following elements in a 5' to 3' orientation: (1) the CMV IE enhancer-promoter region, (2) the 5' region of the HBV genome including the DR1 and 5' ε (the pre-C ORF translation initiation codon is eliminated), (3) a non-functional indicator gene cassette assembled such that the promoter region and a 5' portion of the coding region are positioned 3', i.e. downstream, of the remaining 3' portion of the coding region, (4) the 3' region of the HBV genome containing DR2, DR1*, the 3' ε, and the 3' HBV pA signal region (the pre-C ORF translation initiation codon is eliminated). The non-functional indicator gene cassette is comprised of some or all of the following elements arranged in the 5' to 3' orientation: (1) the 3' region of an intron ending in a splice acceptor sequence (2) the 3' region of an indicator (reporter) ORF or selectable marker ORF, (3) a transcriptional polyadenylation signal sequence (e.g. HSV-1 thymidine kinase gene, SV40), (4) an enhancer-promoter region, (5) the 5' region of an indicator gene ORF, (6) the 5' region of an intron beginning in a splice donor sequence. Within the non-functional indicator gene viral vector, the indicator gene expression cassette has a transcriptional orientation either the same or opposite the HBV sequence elements. In cases where the indicator gene ORF contains an intron, the intron is oriented in the same orientation with respect to the HBV sequence elements.

Figures 13D, 13E:
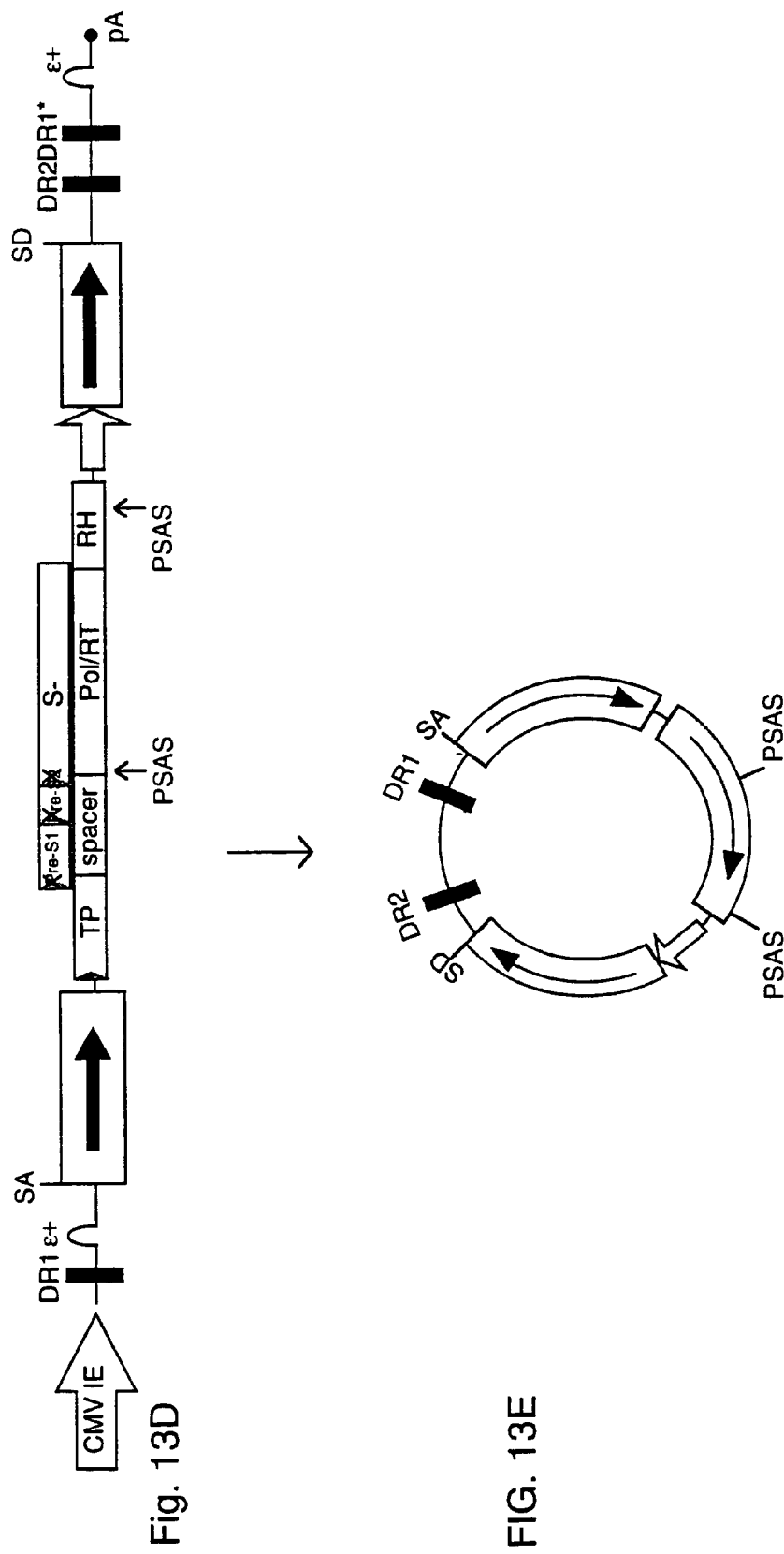

In a second embodiment, the non-functional indicator gene viral vector contains a non-functional indicator gene cassette containing a permuted coding region, all of the cis-acting regulatory elements that are necessary for HBV DNA replication, and some or all of the HBV gene sequences (i.e. C, P, S, X genes) that provide the trans-acting structural and enzymatic functions that are necessary for HBV DNA replication and virus particle formation pCS-HBV(NF-IG)PCR(PSAS+) (FIG. 13D). Resistance test vectors derived from the indicator gene viral vector pCS-HBV (NF-IG)PCR(PSAS+) contain patient sequence acceptor sites (PSAS) and are used in conjunction with the packaging vector pPK-CSK (described in Example 8, see FIG. 9H). In this embodiment the indicator gene viral vector may also provide some or all of the packaging functions. In this embodiment the structural and enzymatic activities that are not provided by the indicator gene viral vector, but that are necessary for HBV DNA replication and virus particle formation, are provided using additional packaging vectors. In this embodiment, the non-functional indicator gene viral vector contains the following elements in a 5' to 3' orientation: (1) the CMV IE enhancer promoter region, (2) the region of the HBV genome immediately downstream of the pre-C ORF translation initiation codon and the DR1 and 5' ε, (3) the indicator gene cassette containing a region of the HBV genome which may contain some or all of the C, P, S, and X genes, (4) the region of the HBV genome containing DR2, DR1*, the 3' ε, and the 3' HBV pA signal region (the pre-C ORF initiation codon has been eliminated). Within the non-functional indicator gene viral vector, pCS-HBV(NF-IG)PCR(PSAS+) the indicator gene expression cassette has a transcriptional orientation either the same or opposite to HBV sequence elements. In cases where the indicator gene contains an inverted intron, the intron is oriented in the same orientation with respect to the HBV sequence elements.

Resistance Test Vectors—Construction

Resistance test vectors containing a non-functional indicator gene with a permuted coding region were designed using the HBV subgenomic viral vector comprising anti-viral target genes as described in Example 8. The indicator gene viral vector or the packaging vector is modified to include patient sequence acceptor sites (PSAS) for the insertion of P gene containing patient-derived segments (PDS) (described in Example 8, see FIGS. 9D and 9F). The expression of the patient-derived S gene is eliminated as described in Example 8 (see FIG. 9D). Uniform S gene expression is provided, in trans, using a separate packaging vector that provides well-characterized S gene products (FIG. 9E).

Drug Susceptibility and Resistance Tests

Drug susceptibility and resistance tests are carried out by the procedures described in Examples 8 and 9. The non-functional indicator gene is converted to a functional indicator gene during HBV replication (FIGS. 13B and 13C).

Drug Screening

Drug screening using an indicator gene viral vector that contains a non-functional indicator gene with permuted promoter and translation initiation regions is performed essentially as described in Examples 8 and 9 (above).

EXAMPLE 12

Hepatitis Drug Susceptibility and Resistance Test Using Resistance Test Vector Comprising Patient-Derived Segment(s) and a Functional Indicator Gene Indicator Gene Viral Vector—Construction Indicator gene viral vectors containing a functional indicator gene were designed using HBV subgenomic viral vectors comprising viral genes which are the target(s) of anti-viral drugs. The indicator gene viral vectors pCS-HBV (F-IG)(PSAS−), are based on the subgenomic viral vector pCS-HBV. The indicator gene viral vector, pCS-HBV(F-IG) (PSAS−), contains a functional indicator gene cassette and all of the cis-acting regulatory elements that are necessary for HBV DNA replication (i.e. DR1, 5'ϵ, DR2, DR1*, 3'pA) but lacks the HBV gene sequences (i.e. C, P, S, X genes) that provide the trans-acting structural and enzymatic functions that are necessary for HBV DNA replication and virus particle formation (FIG. 14B). The C, P and X genes and patient sequence acceptor sites are contained within a packaging vector pPK-CPX and the S gene is contained within the packaging vector, pPK-S, (described below see FIGS. 9D and 9E). In this embodiment the indicator gene viral vector pCS-HBV(F-IG)(PSAS−) and the packaging vector pPK-CPX constitute a resistance test vector system. The functional indicator gene viral vector pCS-HBV(F-IG) (PSAS−) contains the following elements in a 5' to 3' orientation: (1) the CMV IE enhancer-promoter region, (2) the 5' region of the HBV genome including the DR1 and 5' ϵ (the pre-C ORF translation initiation codon is eliminated), (3) a functional indicator gene cassette, (4) the 3' region of the HBV genome containing DR2, DR1*, the 3' ϵ, and the 3' HBV pA signal region (the pre-C ORF translation initiation codon is eliminated). The indicator gene expression cassette is comprised of some or all of the following elements arranged in the 5' to 3' orientation: (1) a transcriptional enhancer-promoter region, (2) an intron, (3) an indicator gene ORF or selectable marker gene ORF, (4) a transcriptional polyadenylation signal sequence (e.g. SV40) or unidirectional (HSV-1 thymidine kinase gene). The indicator gene expression cassette has a transcriptional orientation the same as or opposite to the HBV sequence elements.

In a second embodiment, the indicator gene viral vector contains a functional indicator gene cassette, all of the cis-acting regulatory elements that are necessary for HBV DNA replication, and some or all of the HBV gene sequences (i.e. C, P, S, X genes) that provide the trans-acting structural and enzymatic functions that are necessary for HBV DNA replication and virus particle formation pCS-HBV(F-IG)(PSAS+) (FIG. 14D). Resistance test vectors derived from the indicator gene viral vector pCS-HBV(F-IG)(PSAS+) contain patient sequence acceptor sites (PSAS) and are used in conjunction with the packaging vector pPK-CSK. In this embodiment the indicator gene viral vector also provides some or all of the packaging functions. The structural and enzymatic activities that are not provided by the indicator gene viral vector, but that are necessary for HBV DNA replication and virus particle formation, are provided using additional packaging vectors pPK-CSX (described in Example 8, see FIG. 9H). In this embodiment, the functional indicator gene viral vector contains the following elements in a 5' to 3' orientation: (1) the CMV IE enhancer promoter region, (2) the region of the HBV genome immediately downstream of the pre-C ORF translation initiation codon and the DR1 and 5' ϵ, (3) a functional indicator gene cassette within the region of the HBV genome that contains some or all of the C, P, S, and X genes, (4) the region of the HBV genome containing DR2, DR1*, the 3' ϵ, and the 3' HBV pA signal region. Within the indicator gene viral vector, the indicator gene expression cassette has a transcriptional orientation either opposite to or the same as the HBV sequence elements.

Resistance Test Vector—Construction

Resistance test vectors containing a non-functional indicator gene with a permuted promoter were designed using the HBV subgenomic viral vector comprising anti-viral target genes as described in Example 8. The indicator gene viral vector or the packaging vector is modified to include patient sequence acceptor sites (PSAS) for the insertion of P gene containing patient-derived segments (PDS) (described in Example 8, see FIGS. 9D and 9F). The expression of the patient-derived S gene is eliminated as described in Example 8 (see FIG. 9D). Uniform S gene expression is provided, in trans, using a separate packaging vector that provides well-characterized S gene products (FIG. 9E).

Drug Susceptibility and Resistance Test

Drug susceptibility and resistance test are carried out with a resistance test vector based on a functional indicator gene viral vector, pCS-HBV(F-IG)(PSAS+) or with a resistance test vector system based on an indicator gene viral vector, pCS-HBV(F-IG)(PSAS−) and a packaging vector(s). In transfected packaging host cells, the indicator gene viral vector produces an encapsidation competent (ϵ+) RNA transcript containing a functional indicator gene cassette. The packaging vector(s) provide, in trans, the structural and/or enzymatic viral functions that are not provided by the functional indicator gene viral vector, but that are necessary for viral DNA replication and particle formation. Upon co-transfection of packaging host cells, the indicator gene viral vector and packaging vectors are capable of forming HBV particles containing an encapsidated indicator gene viral vector "pregenome" RNA containing a functional indicator gene cassette.

In this example, the indicator gene viral vector contains a functional indicator gene cassette and therefore can produce indicator gene activity in transfected cells in the absence of HBV DNA replication (FIG. 14). In the case of a functional indicator gene, the inhibition of HBV DNA replication by drugs can be evaluated by harvesting the virus particles produced in the packaging host cell and using the particles (or particle DNA) to infect (or transfect) a target host cell. Alternatively, DNA replication can be measured directly in virus particles isolated from packaging host cells by using the DNA as an indicator. A drug which inhibits HBV DNA replication will reduce the formation of virus particles containing the "mature" rc-DNA form of the functional indicator gene viral vector. Consequently, the functional indicator gene will not be efficiently transferred to the target host cells during infection/transfection and the amount of indicator gene viral vector cccDNA and indicator gene activity in these cells will be reduced. The detection of indicator gene expression in target host cells in a two cell assay is performed as described in Example 8. The detection of rc-DNA in virus particles is performed using DNA as an indicator as described in Example 9 and illustrated in FIGS. 10F and 10G.

Drug Screening

Drug screening using an indicator gene viral vector that contains a non-functional indicator gene with permuted promoter and translation initiation regions is performed essentially as described in Examples 8 and 9 (above).

Oligonucleotides

```
 1) 5'-AGTGAATTAGCCCTTCCACCCGGGTCGAGCTTGGCGTAATCA-3'
    (42-mer) (SEQ ID NO:1)

2) 5'-CTGTTGGGAAGGGCGATCTCTAGATGCTAGAGATTTTCCACA-3'
    (42-mer) (SEQ ID NO:2)

3) 5'-CTCCTCCTCCAAGTCTGAGCGGCCGCCTTTAGCATCTGATGCAC-3'
    (44-mer) (SEQ ID NO:3)

4) 5'-CTCCTCCTCCAAGTCTGAGCGGCCGCCATATGGTGTTTTACTAA-3'
    (44-mer) (SEQ ID NO:4)

5) 5'-GGTCTAACCAGAGAGACCCGGTTCACTAAACGAGCT-3'
    (36-mer) (SEQ ID NO:5)

6) 5'-GAATTCGCGGCCGCAATTCCGCCCCTCTCCCT-3'
    (32-mer) (SEQ ID NO:6)

7) 5'-GTTAACGCGGCCGCGATATAGTTCCTCCTTTC-3'
    (32-mer) (SEQ ID NO:7)

8) 5'-GAATTCTCGCGACCATGGAAGACGCCAAAAAC-3'
    (32-mer) (SEQ ID NO:8)

9) 5'-GTTAACAGATCTCTCGAGTTACAATTTGGACTTTCC-3'
    (36-mer) (SEQ ID NO:9)

10) 5'-AGACGGGCACACACTACTTAATACGACTCACTATAGGG
       TGAAGCACTCAAGGCAAG-3'
    (56-mer) (SEQ ID NO:10)

11) 5'-AAGAGTGACCTGAGGGAAGTTAACGGATACAGTTCCTTGTCT-3'
    (42-mer) (SEQ ID NO:11)

12) 5'-TCCAGCACTGACTAATTTGTCGACTTGTTCATTTCCTCCAAT-3'
    (42-mer) (SEQ ID NO:12)

13) 5'-TAACGCCTATTCTGCTATGCCGACACCCAATTCTGAAAATGG-3'
    (42-mer) (SEQ ID NO:13)

14) 5'-AAGGATACAGTTCCTTGTCGATCGGCTCCTGCTTCTGAGGGG-3'
    (42-mer) (SEQ ID NO:14)

15) 5'-CTAAAAATAGTACTTTCCGGATCCCAGCACTGACTAATTTAT-3'
    (42-mer) (SEQ ID NO:15)

16) 5'-TTAGCTCCTTCGGTCCTCCAATCGTTGTCAGAAGTAAGTTGG-3'
    (42-mer) (SEQ ID NO:16)

17) 5'-GTCCCAGATAAGTGCCAAGGATTCGTTCACTAATCGAATGGA-3'
    (42-mer) (SEQ ID NO:17)

18) 5'-GAATTCGTTAACTTCCCTCAGATCACTCTTTGG-3'
    (33-mer) (SEQ ID NO:18)

19) 5'-GTTAACGTCGACTTGTTCATTTCCTCCAAT-3'
    (30-mer) (SEQ ID NO:19)
```

-continued 20) 5'-GAATTCCGATCGACAAGGAACTGTATCCTTTAACTTCCC
    TCAGATCACTCTTTGG-3'
    (55-mer) (SEQ ID NO:20)

21) 5'-GTTAACGGATCCCAGCACTGACTAATTTATCTACTTGTTC
    ATTTCCTCCAAT-3'
    (52-mer) (SEQ ID NO:21)

22) 5'-GAATTCGTTAACTTCCCTCA (G/A) ATC (A/C) CTCTTTGG-3'
    (33-mer pool) (SEQ ID NO:22)

23) 5'-GTTAACGTCGACTT (G/T) (T/C) TCATTTCCTCC (A/T) AT-3'
    (30-mer pool) (SEQ ID NO:23)

24) 5'-GAATTCCGATCGACAAGGAACTGTATCCTTTAACTTCCC
    TCA (G/A) ATC (A/C) CTCTTTGG-3'
    (55-mer pool) (SEQ ID NO:24)

25) 5'-GTTAACGGATCCCAGCACTGACTAATTTATCTACTT (G/T)
    (T/C) TCATTTCCTCC (A/T) AT-3'
    (52-mer pool) (SEQ ID NO:25)

26) 5'-ATCTCTTACCTGTCCTATCTAACAGGCCAGGATTAA-3'
    (36-mer) (SEQ ID NO:26)

27) 5'-GAATTCTCGCGACCACCATGGCGCGTTCAACGCTC-3'
    (35-mer) (SEQ ID NO:27)

28) 5'-GTTAACAGATCTTCATGGCTCGTACTCTAT-3'
    (30-mer) (SEQ ID NO:28)

29) 5'-GAATTCGCGCGCAAGCGGCCGCAACCCGGGAAAAGCTT
    AAGCATGCAACCCGGGAAGAATTCAATCGCGAAA-3'
    (72-mer) (SEQ ID NO:29)

30) 5'-GTTAACGCGCGCTTCTCGAGTTGCGGCCGCTTGCTAGCTT
    AGATCTTTGGGCCCTTTCGCGATTGAATTCTT-3'
    (72-mer) (SEQ ID NO:30)

31) 5'-GAATTCAAGCTTGGCCATTGCATACGTTGT-3'
    (30-mer) (SEQ ID NO:31)

32) 5'-GTTAACGCATGCATAAGAAGCCAA-3'
    (24-mer) (SEQ ID NO:32)

33) 5'-GAATTCGCATGCTCCCCTGCTCCGACCCGG-3'
    (30-mer) (SEQ ID NO:33)

34) 5'-GTTAACGAATTCTCCTGCGGGGAGAAGCAG-3'
    (30-mer) (SEQ ID NO:34)

35) 5'-GAATTCAGATCTGCCATACCACATTTGTAG-3'
    (30-mer) (SEQ ID NO:35)

36) 5'-GTTAACGCTAGCTCCAGACATGATAAGATA-3'
    (30-mer) (SEQ ID NO:36)

37) 5'-GAATTCGCTAGCATCCCGCCCCTAACTCCG-3'
    (30-mer) (SEQ ID NO:37)

38) 5'-GTTAACGTCGACGCAAAAGCCTAGGCCTCC-3'
    (30-mer) (SEQ ID NO:38)

39) 5'-GAATTCTCGCGAACAGTTGGCCCT-3'
    (24-mer) (SEQ ID NO:39)

40) 5'-GTTAACAGATCTTTACGCGAACGCGAAGTC-3'
    (30-mer) (SEQ ID NO:40)

41) 5'-GTTAACGAATTCTTGCAAAAAGCTTTGCAAGATGGATA
    AAGTTTTTAGAAACTCCAGTAGGACTCC-3'
    (66-mer) (SEQ ID NO:41)

42) 5'-GAATTCTCGCGATCTAGACGTTCTACCTTTCTCTTCTT
    TTTTGGAGGAGTCCTACTGGAGTTT-3'
    (63-mer) (SEQ ID NO:42)

43) 5'-GTTAACGAATTCCCACCATGATTGAACAAGATGGA-5'
    (35-mer) (SEQ ID NO:43)

44) 5'-GAATTCAGATCTTCAGAAGAACTCGTCAAG-3'
   (30-mer) (SEQ ID NO:44)

45) 5'-CCCCGTGCCAAGAGTGACTACGTAAGTACCGCCTATAGA-3'
   (39-mer) (SEQ ID NO:45)

46) 5'-CTCTGCTTCTCCCCGCAGCTGGAGAATTCAATCGCGAAA-3'
   (39-mer) (SEQ ID NO:46)

47) 5'-GTTAACGAATTCCCACCATGAACACGATTAACATC-5'
   (35-mer) (SEQ ID NO:47)

48) 5'-CAGGATCCAGACGTCTGGCGGCCGCCGGTGAAGCTTGGCCCATTGCATACG-3'
   (51-mer) (SEQ ID NO:48)

49) 5'-CCAGGCTCAGATCTGGTCTAACCAGAGAGACCCGGTTCACTAAACGAGCT-3'
   (51-mer) (SEQ ID NO:49)

50) 5'-CCCATCTCTCTCCTTCTAGC-3'
   (20-mer) (SEQ ID NO:50)

51) 5'-AGCTTCACCGGCGGCCGCGACGT-3'
   (23-mer) (SEQ ID NO:51)

52) 5'-CGCGGCCGCCGGTGA-3'
   (15-mer) (SEQ ID NO:52)

53) 5'-AATTGTCCCTCATATCGCCTCCTCCAGGTCTGAAGATCTCGTCTCCCCGGG
   GAGACGCA-3'
   (59-mer) (SEQ ID NO:53)

54) 5'-AGAATGAGAAGAGCTGAGCCAGCAGCAGATGGGGTGGGAGCAGTATC-3'
   (47-mer) (SEQ ID NO:54)

55) 5'-TATGCGTCTCCCCGGGGAGACGAGATCTTCAGACCTGGAGGAGGCGATATG
   AGGGAC-3'
   (57-mer) (SEQ ID NO:55)

56) 5'-TCGAGATACTGCTCCCACCCCATCTGCTGCTGGCTCAGCTCTTCTCA-3'
   (47-mer) (SEQ ID NO:56)

57) 5'-AGCTTGCCTTGAGTGCTTCAATCTAGAGCCATACCACATTTGTAGAGGTTT
   TACTTGCTTTAAAAAACCT-3'
   (70-mer) (SEQ ID NO:57)

58) 5'-AACCTCTACAAATGTGGTATGGCTCTAGATTGAAGCACTCAAGGCA-3'
   (46-mer) (SEQ ID NO:58)

59) 5'-CCCACACCTCCCCCTGAACCTGAAACATAAAATGAATGCAATTGTTGTTAT
   TAACTTGTTTATTGCAG-3'
   (68-mer) (SEQ ID NO:59)

60) 5'-ACAACAATTGCATTCATTTTATGTTTCAGGTTCAGGGGGAGGTGTGGGAGG
   TTTTTTAAAGCAAGTAA-3'
   (68-mer) (SEQ ID NO:60)

61) 5'-CTTATAATGGTTACAAATAAAGCAATAGCATCACAAATTTCACAAATAAAG
   CATTTTTTTCACTGCAT-3'
   (68-mer) (SEQ ID NO:61)

62) 5'-TATTTGTGAAATTTGTGATGCTATTGCTTTATTTGTAACCATTATAAGCTG
   CAATAAACAAGTTAATA-3'
   (68-mer) (SEQ ID NO:62)

63) 5'-TATTTGTGAAATTTGTGATGCTATTGCTTTATTTGTAACCATTATAAGCTG
   CAATAAACAAGTTAATA-3'
   (68-mer) (SEQ ID NO:63)

64) 5'-CCAGACATGATAAGATACATTGATGAGTTTGGACAAACCACAACTAGAATG
   CAGTGAAAAAAATGCTT-3'
   (68-mer) (SEQ ID NO:64)

65) 5'-CCCTAACTCCGCCCAGTTCCGCCCATTCTCCGCCCCATGGCTGACTAATTT
   TTTTTATTTATGCAGAGGCCGAGGCCGC-3'
   (79-mer) (SEQ ID NO:65)

66) 5'-TTAGTCAGCCATGGGGCGGAGAATGGGCGGAACTGGGCGGAGTTAGGGGCG
   GGATGGCGCGCCGGTGT-3'
   (68-mer) (SEQ ID NO:66)

-continued 67) 5'-CTCGGCCTCTGAGCTATTCCAGAAGTAGTGAGGAGGCTTTTTTGGAGGCCT
AGGCTTTTGCGGCGCGCCACCTGCATTA-3'
(79-mer) (SEQ ID NO:67)

68) 5'-GCCTCCTCACTACTTCTGGAATAGCTCAGAGGCCGAGGCGGCCTCGGCCTC
TGCATAAATAAAAAAAA-3'
(68-mer) (SEQ ID NO:68)

69) 5'-TCATTAATGCAGGTGGCGCGCCGCAAAAGCCTAGGCCTCCAAAAAA-3'
(46-mer) (SEQ ID NO:69)

70) 5'-CTAGAGGGGGAGGCTAACTGAAACACGGAAGGAGACAATACCGGAAGGAAC
CCGCGCTATGACGGCA-3'
(67-mer) (SEQ ID NO:70)

71) 5'-ATAAAAAGACAGAATAAAACCCACGGGTGTTGGGTCGTTTGTTCATAAACC
CGGGCTTCGGTCCCA-3'
(66-mer) (SEQ ID NO:71)

72) 5'-CTTCCGGTATTGTCTCCTTCCGTGTTTCAGTTAGCCTCCCCCT-3'
(43-mer) (SEQ ID NO:72)

73) 5'-GTGGGTTTTATTCTGTCTTTTTATTGCCGTCATAGCGCGGGTTC-3'
(44-mer) (SEQ ID NO:73)

74) 5'-CCGGTGGGACCGAAGCCCGGGTTTATGAACAAACGACCCAACACCC-3'
(46-mer) (SEQ ID NO:74)

75) 5'-AACGGCGGCGGGAAGTTCTCCTGCGTCATCGTCGGGAAGA-3'
(40-mer) (SEQ ID NO:75)

76) 5'-CATGTTGCAGGGCCCCTAGGAAAAAGGGCTGTTGGAAATGTG-3'
(42-mer) (SEQ ID NO:76)

77) 5'-CACTCCATGTACCGGTTCTTTTAGAATYTCYCTG-3'
(34-mer) (SEQ ID NO:77)

78) 5'-CGTTTAGTGAACCGTCAGATCGCCTGGAGACGCCATCCACGCTGTTTTGAC
CTCCATAGAAGACAC-3'
(66-mer) (SEQ ID NO:78)

79) 5'-AACAGCGTGGATGGCGTCTCCAGGCGATCTGACGGTTCACTAAACGAGCT-3'
(50-mer) (SEQ ID NO:79)

80) 5'-CGGGACCGATCCAGCCTCCGCGGCCGGGAACGGTGCATTGGAACGCGGATT
CCCCGTGCCAAGAGTTAC-3'
(69-mer) (SEQ ID NO:80)

81) 5'-TCCGCGTTCCAATGCACCGTTCCCGGCCGCGGAGGCTGGATCGGTCCCGGT
GTCTTCTATGGAGGTCAA-3'
(69-mer) (SEQ ID NO:81)

82) 5'-GTAAGTACCGCCTATAGAGTCTATAGGCCCACCCCCTTGGCTTCTTATGCA
TGCTCCCCTGCTCCG-3'
(66-mer) (SEQ ID NO:82)

83) 5'-AAGAAGCCAAGGGGTGGGCCTATAGACTCTATAGGCGGTACTTACGTAAC
TCTTGGCACGGGGAA-3'
(66-mer) (SEQ ID NO:83)

84) 5'-ATCCGGGCTCCTCGCCCGCCCGGACCCACAGGCCACCCTCAACCGTCCTGG
CCCCGGACC-3'
(60-mer) (SEQ ID NO:84)

85) 5'-GAGGGTGGCCTGTGGGTCCGGGCGGGCGAGGAGCCCGGATCGGAGCAGGGG
AGCATGCAT-3'
(60-mer) (SEQ ID NO:85)

86) 5'-CAAACCCCACCCCTCACTCTGCTTCTCCCCGCAGCTGAGATCTG-3'
(44-mer) (SEQ ID NO:86)

87) 5'-CTAGCAGATCTCAGCTGCGGGAGAAGCAGAGTGAGGGGTGGGGTTTGGG
TCCGGGGCCAGGACGGTT-3'
(68-mer) (SEQ ID NO:87)

88) 5'-CGGGACCGATCCAGCCTCCGCGGCCGGGAACGGTGCATTGGAACGCGGAT
TCCCCGTGCCAAGAGTTACCTGAGATCT-3'
(78-mer) (SEQ ID NO:88)

-continued 89) 5'-CTAGCAGATCTCAGGTAACTCTTGGCACGGGGAA-3'
    (34-mer) (SEQ ID NO:89)

90) 5'-CATGGTGGTAGATCTCACA-3'
    (19-mer) (SEQ ID NO:90)

91) 5'-AGCTTGTGAGATCTACCAC-3'
    (16-mer) (SEQ ID NO:91)

92) 5'-AGATCTCACACACA-3'
    (14-mer) (SEQ ID NO:92)

93) 5'-AGCTTGTGTGTGAGATCTCCT-3'
    (21-mer) (SEQ ID NO:93)

94) 5'-CTAGAGGGGAGGCTAACTGAAACACGGAAGGAGACAATACCGGAAGGAAC
    CCGCGCTATGACGGCA-3'
    (67-mer) (SEQ ID NO:94)

95) 5'-ATAAAAAGACAGAATAAAACCCACGGGTGTTGGGTCGTTTGTTCATAAACC
    CGGGCTTCGGTCCCA-3'
    (66-mer) (SEQ ID NO):95)

96) 5'-CTTCCGGTATTGTCTCCTTCCGTGTTTCAGTTAGCCTCCCCCT-3'
    (43-mer) (SEQ ID NO:96)

97) 5'-GTGGGTTTTATTCTGTCTTTTTATTGCCGTCATAGCGCGGGTTC-3'
    (44-mer) (SEQ ID NO:97)

98) 5'-CCGGTGGGACCGAAGCCCGGGTTTATGAACAAACGACCCAACACCC-3'
    (46-mer) (SEQ ID NO:98)

99) 5'-GAGGCCCCAAGGGGTTATGCTATCTAGAGGTACCACGCGTGAATTCTCGAGGC
    TAGCAGATCTCCATGGTATTATCGTGTTTTTCAAAGGAAAACCACGTCCC-3'
    (103-mer) (SEQ ID NO:99)

100) 5'-GCATAACCCCTTGGGGCCTCTAAACGGGTCTTGAGGGGTTTTTTGCTCACC
    GGCGCGCCACCTGCATTA-3'
    (69-mer) (SEQ ID NO:100)

101) 5'-CACGGGGACGTGGTTTTCCTTTGAAAAACACGATAATACCATGGAGATCT
    GCTAGCCTCGAGAATTCACGCGTGGTACCTCTAGATA-3'
    (87-mer) (SEQ ID NO:101)

102) 5'-TCATTAATGCAGGTGGCGCGCCGGTGAGCAAAAAACCCCTCAAGACC
    CGTTTA-3'
    (53-mer) (SEQ ID NO:102)

103) 5'-AATTACACCGGCGTCGCCCTATAGTGAGTCGTATTAGCGGCCGCGACGT-3'
    (49-mer) (SEQ ID NO:103)

104) 5'-CGCGGCCGCTAATACGACTCACTATAGGGCGACGCCGGTGT-3'
    (41-mer) (SEQ ID NO:104)

105) 5'-GTCTGTTGTGTGACTCTGCCCTATAGTGAGTCGTATTACCCTTTTAGTCAG
    TGTGG-3'
    (56-mer) (SEQ ID NO:105)

Second Series of Experiments

The following flow chart illustrates certain of the various vectors and host cells which may be used in this invention. It is not intended to be all inclusive.

Vectors

Indicator gene cassette (functional/nonfunctional indicator gene) + Viral vector (genomic or subgenomic)

↓

Indicator Gene Viral Vector (functional/nonfunctional indicator gene)

+
Patient sequence acceptor sites
+
Patient-derived segments

↓

Resistance Test Vector (patient-derived segments + indicator gene)

Host Cells

Packaging Host Cell—transfected with packaging expression vectors

Resistance Test Vector Host Cell—a packaging host cell transfected with a resistance test vector Target Host Cell—a host cell to be infected by a resistance test vector viral particle produced by the resistance test vector host cell. The component of the resistance test vector system that contains the indicator gene can be delivered to the target host cell at the time of infection or may be stably integrated into the target host cell chromosomal DNA.

Resistance Test Vector

"Resistance test vector" means one or more vectors which taken together contain DNA or RNA comprising a patient-derived segment and an indicator gene. In the case where the resistance test vector comprises more than one vector the patient-derived segment may be contained in one vector and the indicator gene in a different vector. Such a resistance test vector comprising more than one vector is referred to herein as a resistance test vector system for purposes of clarity but is nevertheless understood to be a resistance test vector. The DNA or RNA of a resistance test vector may thus be contained in one or more DNA or RNA molecules. In one embodiment, the resistance test vector is made by insertion of a patient-derived segment into an indicator gene viral vector. In another embodiment, the resistance test vector is made by insertion of a patient-derived segment into a packaging vector while the indicator gene is contained in a second vector, for example an indicator gene viral vector. As used herein, "patient-derived segment" refers to one or more viral segments obtained directly from a patient using various means, for example, molecular cloning or polymerase chain reaction (PCR) amplification of a population of patient-derived segments using viral DNA or complementary DNA (cDNA) prepared from viral RNA, present in the cells (e.g. peripheral blood mononuclear cells, PBMC), serum or other bodily fluids of infected patients. When a viral segment is "obtained directly" from a patient it is obtained without passage of the virus through culture, or if the virus is cultured, then by a minimum number of passages to essentially eliminate the selection of mutations in culture. The term "viral segment" refers to any functional viral sequence or viral gene encoding a gene product (e.g., a protein) that is the target of an anti-viral drug. The term "functional viral sequence" as used herein refers to any nucleic acid sequence (DNA or RNA) with functional activity such as enhancers, promoters, polyadenylation sites, sites of action of trans-acting factors, internal ribosome entry sites (IRES), translation frameshift sites, packaging sequences, integration sequences, or splicing sequences. If a drug were to target more than one functional viral sequence or viral gene product then patient-derived segments corresponding to each said viral gene would be inserted in the resistance test vector. In the case of combination therapy where two or more anti-virals targeting two different functional viral sequences or viral gene products are being evaluated, patient-derived segments corresponding to each functional viral sequence or viral gene product would be inserted in the resistance test vector. The patient-derived segments are inserted into unique restriction sites or specified locations, called patient sequence acceptor sites, in the indicator gene viral vector or for example, a packaging vector depending on the particular construction being used as described herein.

As used herein, "patient-derived segment" encompasses segments derived from human and various animal species. Such species include, but are not limited to chimpanzees and other primates, horses, cattles, cats and dogs.

Patient-derived segments can also be incorporated into resistance test vectors using any of several alternative cloning techniques. For example, cloning via the introduction of class II restriction sites into both the plasmid backbone and the patient-derived segments or by uracil DNA glycosylase primer cloning, or by site specific recombination, or by exonuclease overhang cloning.

The patient-derived segment may be obtained by any method of molecular cloning or gene amplification, or modifications thereof, by introducing patient sequence acceptor sites, as described below, at the ends of the patient-derived segment to be introduced into the resistance test vector. For example, in a gene amplification method such as PCR, restriction sites corresponding to the patient-sequence acceptor sites can be incorporated at the ends of the primers used in the PCR reaction. Similarly, in a molecular cloning method such as cDNA cloning, said restriction sites can be incorporated at the ends of the primers used for first or second strand cDNA synthesis, or in a method such as primer-repair of DNA, whether cloned or uncloned DNA, said restriction sites can be incorporated into the primers used for the repair reaction. The patient sequence acceptor sites and primers are designed to improve the representation of patient-derived segments. Sets of resistance test vectors having designed patient sequence acceptor sites provide representation of patient-derived segments that would be underrepresented in one resistance test vector alone.

Resistance test vectors systems are prepared by modifying an indicator gene viral vector (described below), or packaging vector, by introducing patient sequence acceptor sites, amplifying or cloning patient-derived segments and inserting the amplified or cloned sequences precisely into indicator gene viral vectors, or packaging vectors, at the patient sequence acceptor sites. Resistance test vector systems that are constructed from indicator gene viral vectors are in turn derived from genomic viral vectors or subgenomic viral vectors and an indicator gene cassette, each of which is described below. Resistance test vector systems that are constructed from packaging indicator vectors are in turn derived from genomic packaging vectors or subgenomic packaging vectors and an indicator gene cassette, each of which is described below. Resistance test vectors are then introduced into a host cell. Alternatively, a resistance test vector (also referred to as a resistance test vector system) is prepared by introducing patient sequence acceptor sites into a packaging vector, amplifying or cloning patient-derived segments and inserting the amplified or cloned sequences precisely into the packaging vector at the patient sequence acceptor sites and co-transfecting this packaging vector with an indicator gene viral vector.

In one preferred embodiment, the resistance test vector may be introduced into packaging host cells together with packaging expression vectors, as defined below, to produce resistance test vector viral particles that are used in drug resistance and susceptibility tests that are referred to herein as a "particle-based test." In an alternative preferred embodiment, the resistance test vector may be introduced into a host cell in the absence of packaging expression vectors to carry out a drug resistance and susceptibility test that is referred to herein as a "non-particle-based test."

As used herein a "packaging expression vector" provides the factors, such as packaging proteins (e.g. structural proteins such as core and envelope polypeptides), transacting factors, or genes required by replication-defective virus. In such a situation, a replication-competent viral genome is enfeebled in a manner such that it cannot replicate on its own. This means that, although the packaging expression vector can produce the trans-acting or missing genes required to rescue a defective viral genome present in a cell containing the enfeebled genome, the enfeebled genome cannot rescue itself.

Indicator or Indicator Gene

"Indicator or indicator gene" refers to a nucleic acid encoding a protein, DNA or RNA structure that either directly or through a reaction gives rise to a measurable or noticeable aspect, e.g. a color or light of a measurable wavelength or in the case of DNA or RNA used as an indicator a change or generation of a specific DNA or RNA structure. Preferred examples of an indicator gene is the *E. coli* lacZ gene which encodes beta-galactosidase, the luc gene which encodes luciferase either from, for example, *Photonis pyralis* (the firefly) or *Renilla reniformis* (the sea pansy), the *E. coli* phoA gene which encodes alkaline phosphatase, green fluorescent protein, the bacterial CAT gene which encodes chloramphenicol acetyltransferase, and the bacterial β-lactamase gene. Additional preferred examples of an indicator gene are secreted proteins or cell surface proteins that are readily measured by assay, such as radioimmunoassay (RIA), or fluorescent activated cell sorting (FACS), including, for example, growth factors, cytokines and cell surface antigens (e.g. growth hormone, Il-2 or CD4, respectively). "Indicator gene" is understood to also include a selection gene, also referred to as a selectable marker. Examples of suitable selectable markers for mammalian cells are dihydrofolate reductase (DHFR), thymidine kinase or *E. coli* gpt or genes that codes for resistance to the antibiotics hygromycin, neomycin, puromycin or zeocin. In the case of the foregoing examples of indicator genes, the indicator gene and the patient-derived segment are discrete, i.e. distinct and separate genes. In some cases a patient-derived segment may also be used as an indicator gene. In one such embodiment in which the patient-derived segment corresponds to more than one viral gene which is the target of an anti-viral, one of said viral genes may also serve as the indicator gene. For example, the HCV protease gene may serve as an indicator gene by virtue of its ability to cleave a chromogenic substrate or its ability to activate an inactive zymogen which in turn cleaves a chromogenic substrate, giving rise in each case to a color reaction. In a second example, the HCMV phosphotransferase gene may serve as an indicator gene by virtue of its ability to phosphorylate a substrate thereby up-regulating or down-regulating its activity. In all of the above examples of indicator genes, the indicator gene may be either "functional" or "non-functional" but in each case the expression of the indicator gene in the target cell is ultimately dependent upon the action of the patient-derived segment.

Functional Indicator Gene

In the case of a "functional indicator gene" the indicator gene may be capable of being expressed in a "packaging host cell/resistance test vector host cell" as defined below, independent of the patient-derived segment, however the functional indicator gene could not be expressed in the target host cell, as defined below, without the production of functional resistance test vector particles and their effective infection of the target host cell. In one embodiment of a functional indicator gene, the indicator gene cassette, comprising control elements and a gene encoding an indicator protein, is inserted into the indicator gene viral vector, or packaging viral vector, with the same or opposite transcriptional orientation as the native or foreign enhancer/promoter of the viral vector. One example of a functional indicator gene in the case of HCV, places the indicator gene and its promoter (a CMV IE enhancer/promoter) in the same or opposite transcriptional orientation as the HCV enhancer-promoter, respectively, or the T7 phage RNA polymerase promoter (herein referred to as T7 promoter) associated with the viral vector.

Non-Functional Indicator Gene

Alternatively the indicator gene, may be "non-functional" in that the indicator gene is not efficiently expressed in a packaging host cell transfected with the resistance test vector, which is then referred to a resistance test vector host cell, until it is converted into a functional indicator gene through the action of one or more of the patient-derived segment products. An indicator gene is rendered non-functional through genetic manipulation according to this invention.

1. Permuted Promoter In one embodiment an indicator gene is rendered non-functional due to the location of the promoter, in that, although the promoter is in the same transcriptional orientation as the indicator gene, it follows rather than precedes the indicator gene coding sequence. This misplaced promoter is referred to as a "permuted promoter." The non-functional indicator gene and its permuted promoter is rendered functional by the action of one or more of the viral proteins. One example of a non-functional indicator gene with a permuted promoter in the case of HCMV, places a promoter in the "b" region and the IRES, coding and terminating regions of the indicator gene in the c'/and/or adjacent $U_S$ region. The non-functional indicator gene in the resistance test vector is converted into a functional indicator gene inversion of the $U_L/U_S$ junction upon infection of the target cells, resulting from the repositioning of the CMV IE promoter relative to the indicator gene coding region. Following the inversion, properly arranged indicator genes are expressed in the target cell.

A permuted promoter may be any eukaryotic or prokaryotic promoter which can be transcribed in the target host cell. In one example, the CMV IE promoter/enhancer region can be used. In a second example the promoter will be small in size to enable insertion in the viral genome without disturbing viral replication. More preferably, a promoter that is small in size and is capable of transcription by a single subunit RNA polymerase introduced into the target host cell, such as a bacteriophage promoter, will be used. Examples of such bacteriophage promoters and their cognate RNA polymerases include those of phages T7, T3 and Sp6. A nuclear localization sequence (NLS) may be attached to the RNA polymerase to localize expression of the RNA polymerase to the nucleus where they may be needed to transcribed the repaired indicator gene. Such an NLS may be obtained from any nuclear-transported protein such as the SV40 T antigen. If a phage RNA polymerase is employed, an internal ribosome entry site (IRES) such as the EMC virus 5' untranslated region (UTR) may be added in front of the indicator gene, for translation of the transcripts which are generally uncapped. In the case of HCMV, the permuted promoter can be introduced at any position that does not disrupt the cis acting elements that are necessary for HCMV DNA replication. Blocking sequences may be added at the ends of the resistance test vector should there be inappropriate expression of the non-functional indicator gene due to transfection artifacts (DNA concatenation). In the HCMV example of the permuted T7 promoter given above, such a blocking sequence may consist of a T7 transcriptional terminator, positioned to block readthrough transcription resulting from DNA concatenation.

2. Permuted Coding Region In a second embodiment, an indicator gene is rendered non-functional due to the relative location of the 5' and 3' coding regions of the indicator gene, in that, the 3' coding region precedes rather than follows the 5' coding region. This misplaced coding region is referred to as a "permuted coding region." The orientation of the non-functional indicator gene may be the same or opposite to that of the native or foreign promoter/enhancer of the viral vector, as mRNA coding for a functional indicator gene will be produced in the event of either orientation. The non-functional indicator gene and its permuted coding region is rendered functional by the action of one or more of the patient-derived segment products. An example of a non-functional indicator gene with a permuted coding region in the case of HCMV, places a 5' indicator gene coding region with an associated promoter in the b region and a 3' indicator gene coding region in the c' region and/or adjacent $U_S$ region of the HCMV genome, with the coding region having the opposite transcriptional orientation. In both examples, the 5' and 3' coding regions may also have associated splice donor and acceptor sequences, respectively, which may be heterologous or artificial splicing signals. The indicator gene cannot be functionally transcribed either by the associated promoter or viral promoters, as the permuted coding region prevents the formation of functional transcripts. The non-functional indicator gene in the resistance test vector is converted into a functional indicator gene by inversion of the $U_L/U_S$ junction upon infection of the target cells, resulting from the repositioning of the 5' and 3' indicator gene coding regions relative to one another. Following transcription by the promoter associated with the 5' coding region, RNA with appropriately arranged 5' and 3' coding regions produce a functional indicator gene product.

3. Negative strand RNA coding region—In a third embodiment, an indicator gene is rendered non-functional by virtue of the fact that it is expressed from RNA that is negative sense with respect to the viral encoded gene products. Expression of luciferase from mini-genome RNAs containing the luc gene in reverse orientation requires negative strand RNA made during virus replication (FIG. 19).

Indicator Gene Viral Vector—Construction

As used herein, "indicator gene viral vector" refers to a vector(s) comprising an indicator gene and its control elements and one or more viral genes. The indicator gene viral vector is assembled from an indicator gene cassette and a "viral vector," defined below. The indicator gene viral vector may additionally include an enhancer, splicing signals, polyadenylation sequences, transcriptional terminators, or other regulatory sequences. Additionally the indicator gene viral vector may be functional or nonfunctional. In the event that the viral segments which are the target of the anti-viral drug (which for drug resistance and susceptibility testing are patient derived) are not included in the indicator gene viral vector they are provided in a second vector, which may be a packaging viral vector. An "indicator gene cassette" comprises an indicator gene and control elements. "Viral vector" refers to a vector comprising some or all of the following: viral genes encoding a gene product, control sequences, viral packaging sequences. The viral vector may additionally include one or more viral segments one or more of which may be the target of an anti-viral drug. Two examples of a viral vector which contain viral genes are referred to herein as an "genomic viral vector" and a "subgenomic viral vector." A "genomic viral vector" is a vector which may comprise a deletion of a one or more viral genes to render the virus replication incompetent, but which otherwise preserves the mRNA expression and processing characteristics of the complete virus.

In one embodiment for an HCV drug susceptibility and resistance test, the genomic viral vector comprises C, E1, E2, NS2, NS3, NS4, and NS5. In one embodiment for an HCMV drug susceptibility and resistance test, the genomic viral vector comprises viruses deleted in one or a few genes such as JL54, UL80, UL97. A "subgenomic viral vector" refers to a vector comprising the coding region of one or more viral genes which may encode the proteins that are the target(s) of the anti-viral drug. In the case of HCV, a preferred embodiment is a subgenomic viral vector comprising the HCV NS2, NS3, NS4, NS5 genes (FIG. 20). In the case of HCMV, a preferred embodiment is a subgenomic viral vector comprising the HCMV amplicon plasmids containing one or a few viral genes such as UL54, UL80, UL90. Examples of viral clones used for viral vector construction are: Towne, Toledo, and AD169. The viral coding genes may be under the control of a native enhancer/promoter or a foreign viral or cellular enhancer/promoter. A preferred embodiment for an HCV drug susceptibility and resistance test, is to place the genomic or subgenomic viral coding regions under the control of the T7 promoter. A preferred embodiment for an HCMV drug susceptibility and resistance test, is to place the genomic or subgenomic viral coding regions under the control of the endogenous HCMV promoters. In the case of an indicator gene viral vector that contains one or more viral genes which are the targets or encode proteins which are the targets of an anti-viral drug(s) then said vector contains the patient sequence acceptor sites. The patient-derived segments are inserted in the patient sequence acceptor site in the indicator gene viral vector which is then referred to as the resistance test vector, as described above.

"Patient sequence acceptor sites" are sites in a vector for insertion of patient-derived segments and said sites may be: 1) unique restriction sites introduced by site-directed mutagenesis into a vector; 2) naturally occurring unique restriction sites in the vector; or 3) selected sites into which a patient-derived segment may be inserted using alternative cloning methods (e.g. UDG cloning, exonuclease overhang cloning), 4) site specific recombination target sites. In one embodiment the patient sequence acceptor site is introduced into the indicator gene viral vector. The patient sequence acceptor sites are preferably located within or near the coding region of the viral protein which is the target of the anti-viral drug. The viral sequences used for the introduction of patient sequence acceptor sites are preferably chosen so that no change, or a conservative change, is made in the amino acid coding sequence found at that position. Preferably the patient sequence acceptor sites are located within a relatively conserved region of the viral genome to facilitate introduction of the patient-derived segments. Alternatively, the patient sequence acceptor sites are located between functionally important genes or regulatory sequences. Patient-sequence acceptor sites may be located at or near regions in the viral genome that are relatively conserved to permit priming by the primer used to introduce the corresponding restriction site into the patient-derived segment. To improve the representation of patient-derived segments further, such primers may be designed as degenerate pools to accommodate viral sequence heterogeneity, or may incorporate residues such as deoxyinosine (I) which have multiple base-pairing capabilities. Sets of resistance test vectors having patient sequence acceptor sites that define the same or overlapping restriction site intervals may be used together in the drug resistance and susceptibility tests to provide representation of patient-derived segments that contain internal restriction sites identical to a given patient sequence acceptor site, and would thus be underrepresented in either resistance test vector alone.

Host Cells

The resistance test vector is introduced into a host cell. Suitable host cells are mammalian cells. Preferred host cells are derived from human tissues and cells which are the principle targets of viral infection. In the case of HCV these include human cells such as hepatocytes, hepatoma cell lines and other cells. In the case of HCMV, suitable host cells include MRC5, HF, human foreskin fibroblasts and other cells. Human derived host cells will assure that the anti-viral drug will enter the cell efficiently and be converted by the cellular enzymatic machinery into the metabolically relevant form of the anti-viral inhibitor. Host cells are referred to herein as a "packaging host cells," "resistance test vector host cells," or "target host cells." A "packaging host cell" refers to a host cell that provides the trans-acting factors and viral packaging proteins required by the replication defective viral vectors used herein, such as the resistance test vectors, to produce resistance test vector viral particles. The packaging proteins may be provided for by the expression of viral genes contained within the resistance test vector itself, a packaging expression vector(s), or both. A packaging host cell is a host cell which is transfected with one or more packaging expression vectors and when transfected with a resistance test vector is then referred to herein as a "resistance test vector host cell" and is sometimes referred to as a packaging host cell/resistance test vector host cell. Preferred host cells for use as packaging host cells for HCV include huh7, HepG2. Preferred host cells for use as packaging host cells for HCMV include MRC5 and HF. A "target host cell" refers to a cell to be infected by resistance test vector viral particles produced by the resistance test vector host cell in which expression or inhibition of the indicator gene takes place. Preferred host cells for use as target host cells for HCV include HepG2 (Hiramatsu et al. (1997), *J. Viral Hepatol.* 4(suppl. 1), 61-67), Huh7 (Yoo et al. (1995), *J. Virol.* 69, 32-38), Vero (Valli et al. (1997) *Res. Virol.* 148, 181-186), Molt4Ma (Shimizu et al. (1992), *PNAS* 89, 5477-5481), HPBMa (Shimizu et al. (1993), *PNAS* 90, 6037-6041; Shimizu and Yoshikura (1994), *J. Virol.* 68, 8406-8408; Shimizu et al. (1994), *J. Virol.* 68, 1494-1500), MT-2 (Mizutani et al. (1996), *J. Virol.* 70, 7219-7223). Preferred host cells for use as target host cells for HCMV include MRC5 and HF.

Drug Susceptibility and Resistance Tests

The drug susceptibility and resistance tests of this invention may be carried out in one or more host cells. Viral drug susceptibility is determined as the concentration of the anti-viral agent at which a given percentage of indicator gene expression is inhibited (e.g. the IC50 for an anti-viral agent is the concentration at which 50% of indicator gene expression is inhibited). A standard curve for drug susceptibility of a given anti-viral drug can be developed for a viral segment that is either a standard laboratory viral segment or from a drug-naive patient (i.e. a patient who has not received any anti-viral drug) using the method of this invention. Correspondingly, viral drug resistance is a decrease in viral drug susceptibility for a given patient either by comparing the drug susceptibility to such a given standard or by making sequential measurement in the same patient over time, as determined by increased inhibition of indicator gene expression (i.e. decreased indicator gene expression).

In the first type of drug susceptibility and resistance test, resistance test vector viral particles are produced by a first host cell (the resistance test vector host cell) that is prepared by transfecting a packaging host cell with the resistance test vector and packaging expression vector(s). The resistance test vector viral particles are then used to infect a second host cell (the target host cell) in which the expression of the indicator gene is measured. Such a two cell system comprising a packaging host cell which is transfected with a resistance test vector, which is then referred to as a resistance test vector host cell, and a target cell are used in the case of either a functional or non-functional indicator gene. Functional indicator genes are efficiently expressed upon transfection of the packaging host cell and would require infection of a target host cell with resistance test vector host cell supernatant to carry out the test of this invention. Non-functional indicator genes with a permuted promoter, a permuted coding region, or an negative sense strand indicator RNA, are not efficiently expressed upon transfection of the packaging host cell and thus the infection of the target host cell can be achieved either by co-cultivation by the resistance test vector host cell and the target host cell or through infection of the target host cell using the resistance test vector host cell supernatant. In the second type of drug susceptibility and resistance test, a single host cell (the resistance test vector host cell) also serves as a target host cell. The packaging host cells are transfected and produce resistance test vector viral particles and some of the packaging host cells also become the target of infection by the resistance test vector particles. Drug susceptibility and resistance tests employing a single host cell type are possible with viral resistance test vectors comprising a non-functional indicator gene with a permuted promoter, a permuted coding region, or negative sense strand indicator RNA. Such indicator genes are not efficiently expressed upon transfection of a first cell, but are only efficiently expressed upon infection of a second cell, and thus provide an opportunity to measure the effect of the anti-viral agent under evaluation. In the case of a drug susceptibility and resistance test using a resistance test vector comprising a functional indicator gene, neither the co-cultivation procedure nor the resistance and susceptibility test using a single cell type can be used for the infection of target cells (is this true for HCMV). A resistance test vector comprising a functional indicator gene requires a two cell system using filtered supernatants from the resistance test vector host cells to infect the target host cell.

In one embodiment of the invention in the case of HCV, a particle-based resistance tests are carried out with resistance test vectors derived from genomic viral vectors, i.e., pXHCV-luc; pXHCV-IRESluc; pXHCV/pxIRESluc; pXHCV/pXASIRESluc; pXluc-NSHCV/pXsHCV; pXB-VDV(HCVNS3)luc; pXBVDV(HCVNS5B)luc. In one embodiment of the invention in the case of HCMV, a particle-based resistance tests are carried out with resistance test vectors derived from genomic viral vectors, i.e., pA-CMV-VS-geneX; pA-CMV-CS-geneX; pA-CMV-VS-geneX-(NF-IG)PP/pA-CMV-CS-geneX-(NF-IG)PP; pA-CMV-VS-geneX-(NF-IG) PCR/pA-CMV-CS-geneX-(NF-IG) PCR; pA-CMV-VS-geneX-F-IG/pA-CMV-CS-geneX-F-IG, which are cotransfected with the packaging expression vector HCMV$\beta_{2.7}$FIG/$\Delta$geneX or HCMV$\Delta$geneX.

In the case of the particle-based susceptibility and resistance test, resistance test vector viral particles are produced by a first host cell (the resistance test vector host cell) that is prepared by transfecting a packaging host cell with the resistance test vector and packaging expression vector(s). The resistance test vector viral particles are then used to infect a second host cell (the target host cell) in which the expression of the indicator gene is measured. In a second type of particle-based susceptibility and resistance test, a single host cell type (the resistance test vector host cell) serves both purposes: some of the packaging host cells in a given culture are transfected and produce resistance test vector viral particles and some of the host cells in the same culture are the target of infection by the resistance test vector particles thus produced. Resistance tests employing a single host cell type are possible with resistance test vectors comprising a non-functional indicator gene with a permuted promoter since such indicator genes are efficiently expressed upon infection of a permissive host cell, they are not efficiently expressed upon transfection of the same host cell type, and thus provide an opportunity to measure the effect of the anti-viral agent under evaluation. For similar reasons, resistance tests employing two cell types may be carried out by co-cultivating the two cell types as an alternative to infecting the second cell type with viral particles obtained from the supernatants of the first cell type.

The packaging host cells are transfected with the resistance test vector and the appropriate packaging expression vector(s) to produce resistance test vector host cells. Individual anti-viral agents for HCV, including the protease inhibitors, IRES inhibitors, and the polymerase inhibitors as well as combinations thereof, are added to individual plates of packaging host cells at the time of their transfection, at an appropriate range of concentrations. Twenty-four to 48 hours after transfection, target host cells are infected by co-cultivation with resistance test vector host cells or with resistance test vector viral particles obtained from filtered supernatants of resistance test vector host cells. Each anti-viral agent, or combination thereof, is added to the target host cells prior to or at the time of infection to achieve the same final concentration of the given agent, or agents, present during the transfection.

Determination of the expression or inhibition of the indicator gene in the target host cells infected by co-cultivation or with filtered viral supernatants is made by assay of indicator gene expression, for example in the case where the indicator gene is the firefly luc gene, by measuring luciferase activity. The reduction in luciferase activity observed for target host cells infected with a given preparation of resistance test vector viral particles in the presence of a given antiviral agent, or agents, as compared to a control run in the absence of the antiviral agent, generally relates to the log of the concentration of the antiviral agent as a sigmoidal curve. This inhibition curve is used to calculate the apparent inhibitory concentration (IC) of that agent, or combination of agents, for the viral target product encoded by the patient-derived segments present in the resistance test vector.

In the case of a one cell susceptibility and resistance test, host cells are transfected with the resistance test vector and the appropriate packaging expression vector(s) to produce resistance test vector host cells. Individual antiviral agents, or combinations thereof, are added to individual plates of transfected cells at the time of their transfection, at an appropriate range of concentrations. At an appropriate time after transfection, cells are collected and assayed for firefly luciferase activity. As transfected cells in the culture do not efficiently express the indicator gene, transfected cells in the culture, as well superinfected cells in the culture, can serve as target host cells for indicator gene expression. The reduction in luciferase activity observed for cells transfected in the presence of a given antiviral agent, or agents as compared to a control run in the absence of the antiviral agent(s), generally relates to the log of the concentration of the antiviral agent as a sigmoidal curve. This inhibition curve is used to calculate the apparent inhibitory concentration (IC) of an agent, or combination of agents, for the viral target product encoded by the patient-derived segments present in the resistance test vector.

Antiviral Drugs/Drug Candidates

The antiviral drugs being added to the test system are added at selected times depending upon the target of the antiviral drug. For example, in the case of HCV protease inhibitors, they are added to individual plates of packaging host cells at the time of their transfection with a resistance test vector, at an appropriate range of concentrations. HCV protease inhibitors may also be added to the target host cells at the time of infection to achieve the same final concentration added during transfections. For HCMV, phosphotransferase, DNA polymerase and protease inhibitors, including GCV, cidofovir, foscarnet are added to individual plates of target host cells at the time of transfection/infection by the resistance test vector viral particles, at a test concentration. Alternatively, the antiviral drugs may be present throughout the assay. The test concentration is selected from a range of concentrations which is designed to give a satisfactory inhibition profile for resistant and sensitive isolates.

In another embodiment of this invention, a candidate antiviral compound is tested in the drug susceptibility and resistance test of this invention. The candidate antiviral compound is added to the test system at an appropriate concentration and at selected times depending upon the protein target of the candidate anti-viral. Alternatively, more than one candidate antiviral compound may be tested or a candidate antiviral compound may be tested in combination with an approved antiviral drug such as GCV for HCMV or a compound which is undergoing clinical trials. The effectiveness of the candidate antiviral will be evaluated by measuring the expression or inhibition of the indicator gene. In another aspect of this embodiment, the drug susceptibility and resistance test may be used to screen for viral mutants. Following the identification of resistant mutants to either known anti-virals or candidate anti-virals the resistant mutants are isolated and the DNA is analyzed. A library of viral resistant mutants can thus be assembled enabling the screening of candidate anti-virals, alone or in combination. This will enable one of ordinary skill to identify effective anti-virals and design effective therapeutic regimens.

General Materials and Methods

Most of the techniques used to construct vectors, and transfect and infect cells, are widely practiced in the art, and most practitioners are familiar with the standard resource materials which describe specific conditions and procedures. However, for convenience, the following paragraphs may serve as a guideline.

"Plasmids" and "vectors" are designated by a lower case p followed by letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

Construction of the vectors of the invention employs standard ligation and restriction techniques which are well understood in the art (see Ausubel et al., (1987) Current Protocols in Molecular Biology, Wiley-Interscience or Maniatis et al., (1992) in Molecular Cloning: A laboratory Manual, Cold Spring Harbor Laboratory, N.Y.). Isolated plasmids, DNA sequences, or synthesized oligonucleotides are cleaved, tailored, and relegated in the form desired. The sequences of all DNA constructs incorporating synthetic DNA were confirmed by DNA sequence analysis (Sanger et al. (1977) Proc. Natl. Acad. Sci. 74, 5463-5467).

"Digestion" of DNA refers to catalytic cleavage of the DNA with a restriction enzyme that acts only at certain sequences, restriction sites, in the DNA. The various restriction enzymes used herein are commercially available and their reaction conditions, cofactors and other requirements are known to the ordinarily skilled artisan. For analytical purposes, typically 1 µg of plasmid or DNA fragment is used with about 2 units of enzyme in about 20 µl of buffer solution. Alternatively, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in Methods of Enzymology 65:499-560 (1980).

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 minutes at 200 C in 50 mM Tris (pH7.6) 50 mM NaCl, 6 mM MgCl2, 6 mM DTT and 5-10 micromole dNTPs. The Klenow fragment fills in at 5' sticky ends but chews back protruding 3' single strands, even though the four dNTPs are present. If desired, selective repair can be performed by supplying only one of the dNTPs, or with selected dNTPs, within the limitations dictated by the nature of the sticky ends. After treatment with Klenow, the mixture is extracted with phenol/chloroform and ethanol precipitated. Treatment under appropriate conditions with S1 nuclease or Bal-31 results in hydrolysis of any single-stranded portion.

Ligations are performed in 15-50 µl volumes under the following standard conditions and temperatures: 20 mM Tris-Cl pH 7.5, 10 mM MgCl2, 10 mM DTT, 33 mg/ml BSA, 10 mM-50 mM NaCl, and either 40 µM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 µg/ml total DNA concentrations (5-100 mM total end concentration). Intermolecular blunt end ligations (usually employing a 10-30 fold molar excess of linkers) are performed at 1 µM total ends concentration.

"Transient expression" refers to unamplified expression within about one day to two weeks of transfection. The optimal time for transient expression of a particular desired heterologous protein may vary depending on several factors including, for example, any transacting factors which may be employed, translational control mechanisms and the host cell. Transient expression occurs when the particular plasmid that has been transfected functions, i.e., is transcribed and translated. During this time the plasmid DNA which has entered the cell is transferred to the nucleus. The DNA is in a nonintegrated state, free within the nucleus. Transcription of the plasmid taken up by the cell occurs during this period. Following transfection the plasmid DNA may become degraded or diluted by cell division. Random integration within the cell chromatin occurs.

In general, vectors containing promoters and control sequences which are derived from species compatible with the host cell are used with the particular host cell. Promoters suitable for use with prokaryotic hosts illustratively include the beta-lactamase and lactose promoter systems, alkaline phosphatase, the tryptophan (trp) promoter system and hybrid promoters such as tac promoter. However, other functional bacterial promoters are suitable. In addition to prokaryotes, eukaryotic microbes such as yeast cultures may also be used. *Saccharomyces cerevisiae*, or common baker's yeast is the most commonly used eukaryotic microorganism, although a number of other strains are commonly available. Promoters controlling transcription from vectors in mammalian host cells may be obtained from various sources, for example, the genomes of viruses such as: polyoma, simian virus 40 (SV40), adenovirus, retroviruses, hepatitis B virus and preferably cytomegalovirus, or from heterologous mammalian promoters, e.g. β-actin promoter. The early and late promoters of the SV 40 virus are conveniently obtained as an SV40 restriction fragment which also contains the SV40 viral origin of replication. The immediate early promoter of the human cytomegalovirus is conveniently obtained as a HindIII E restriction fragment. Of course, promoters from the host cell or related species also are useful herein.

The vectors used herein may contain a selection gene, also termed a selectable marker. A selection gene encodes a protein, necessary for the survival or growth of a host cell transformed with the vector. Examples of suitable selectable markers for mammalian cells include the dihydrofolate reductase gene (DHFR), the ornithine decarboxylase gene, the multi-drug resistance gene (mdr), the adenosine deaminase gene, and the glutamine synthase gene. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. The second category is referred to as dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin (Southern and Berg (1982) J. Molec. Appl. Genet. 1, 327), mycophenolic acid (Mulligan and Berg (1980) Science 209, 1422), or hygromycin (Sugden et al. (1985) Mol. Cell. Biol. 5, 410-413). The three examples given above employ bacterial genes under eukaryotic control to convey resistance to the appropriate drug neomycin (G418 or genticin), xgpt (mycophenolic acid) or hygromycin, respectively.

"Transfection" means introducing DNA into a host cell so that the DNA is expressed, whether functionally expressed or otherwise; the DNA may also replicate either as an extrachromosomal element or by chromosomal integration. Unless otherwise provided, the method used herein for transformation of the host cells is the calcium phosphate co-precipitation method of Graham and van der Eb (1973) Virology 52, 456-457. Alternative methods for transfection are electroporation, the DEAE-dextran method, lipofection and biolistics (Kriegler (1990) Gene Transfer and Expression: A Laboratory Manual, Stockton Press).

Host cells may be transfected with the expression vectors of the present invention and cultured in conventional nutrient media modified as is appropriate for inducing promoters, selecting transformants or amplifying genes. Host cells are cultured in F12:DMEM (Gibco) 50:50 with added glutamine and without antibiotics. The culture conditions, such as temperature, pH and the like, are those previously used with the host cell selected for expression, and will be apparent to the ordinarily skilled artisan.

The following examples merely illustrate the best mode now known for practicing the invention, but should not be construed to limit the invention. All literature references are expressly incorporated by reference.

EXAMPLE 1

Figures 17A, 17B:
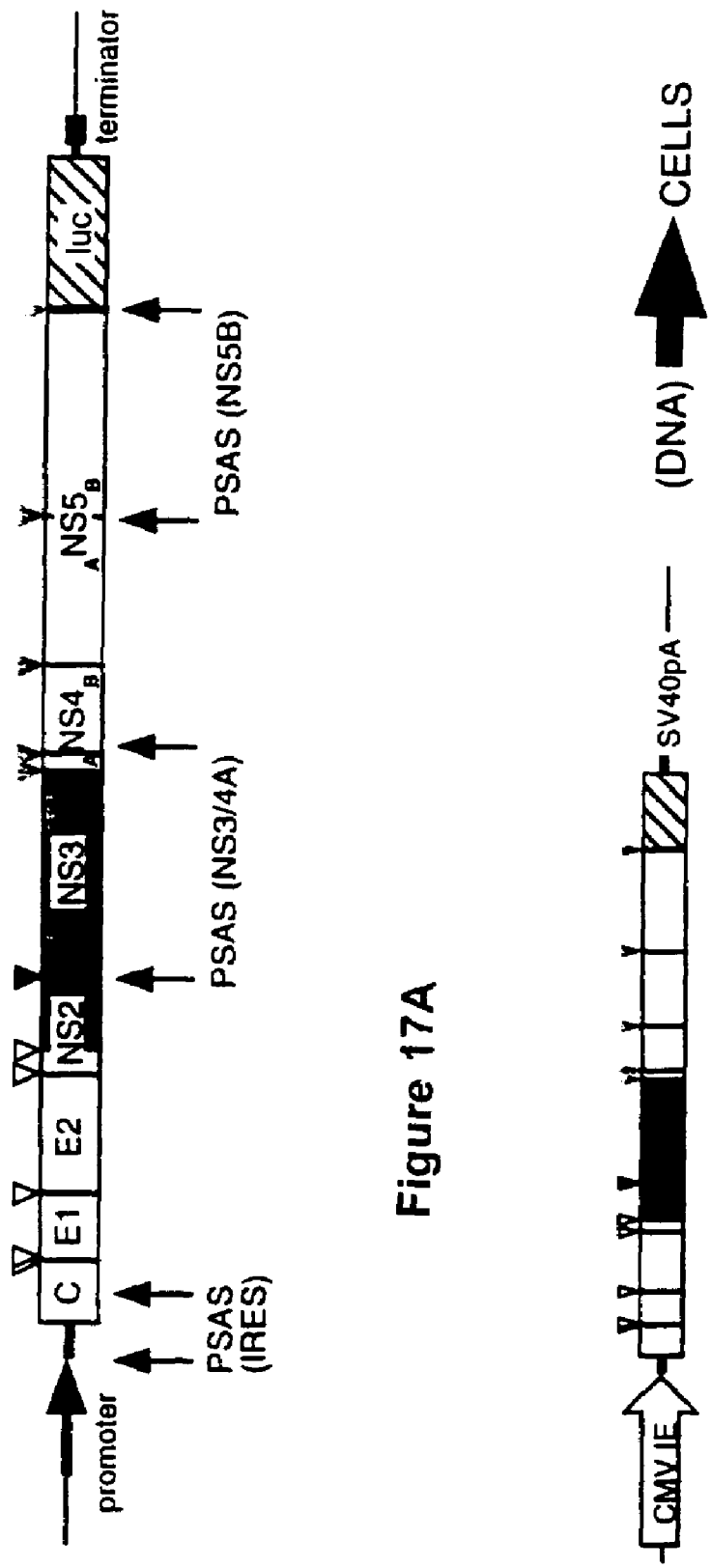
Figure 17C:
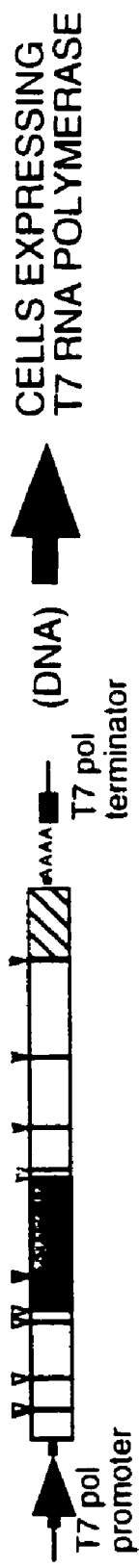
Figure 17D:
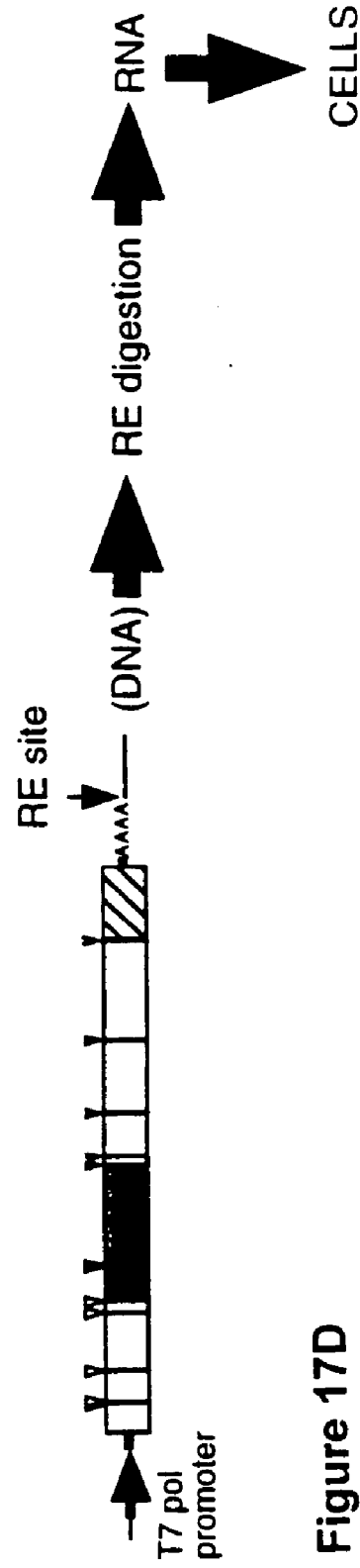

HCV Drug Susceptibility and Resistance Test Using Resistance Test Vectors Comprising Patient-Derived Segment(s) and a Functional Indicator Gene Fused to the HCV Polyprotein Indicator Gene Viral Vector—Construction The indicator gene viral vector (IGVV) pXHCV-luc was designed using HCV genomic viral vectors containing a functional indicator gene fused to the HCV polyprotein. The IGVV is constructed by inserting the open reading frame for the indicator gene in a cDNA construct containing the entire HCV genome producing an in-frame fusion protein. The IGVV also contains all the cis-acting regulatory elements in the 5' and 3' untranslated regions (UTRs) required for replication, transcription, and translation of the HCV RNA. In one embodiment, the luciferase open reading frame is placed immediately downstream of the NS5 coding region, with a spacer region containing the recognition sequence for the NS3/4A protease (FIG. 17A). An example of such a cleavage site is TEDVVCC-SMSYTWT, representing the junction between NS5A and NS5B (Grakoui et al 1993, J. Virol. 67:2832; Steinkuühler et al., 1996, J. Virol. 70:6694). The expected cleavage products are HCV NS5B containing a C-terminal extension (e.g., TEDVVCC), and luciferase containing an N-terminal extension (e.g., SMSYTWT). In a second embodiment, the luciferase open reading frame is placed between the NS5A and NS5B open reading frames, with an NS5A-5B cleavage sequence at both the N-terminal NS5A-luc and C-terminal luc-NS5B junctions. The luciferase protein produced from this construct contains an N-terminal SMSYTWT and a C-terminal TEDVVCC extension. In a third embodiment, the luciferase open reading frame is placed between the NS4B and NS5A open reading frames, with an NS4B-5A cleavage sequence (SECTTPC-SGSWLRD) at both the N-terminal NS4B-luc and C-terminal luc-NS5A junctions. The luciferase protein produced from this construct contains an N-terminal SGSWLRD and a C-terminal SECTTPC extension. In a fourth embodiment, the luciferase open reading frame is placed between the NS4A and NS4B open reading frames, with an NS4A-4B cleavage sequence (FDEMEEC-SQHLPYI) at both the N-terminal NS4A-luc and C-terminal luc-NS4B junctions. The luciferase protein produced from this construct contains an N-terminal SQHLPYI and a C-terminal FDEMEEC extension. The short extensions at the N and C-termini of luciferase or at the C-terminus of NS5B do not dramatically affect activity.

The viral vector is assembled from a full length cDNA construct of HCV, which consists of (in the 5' to 3' orientation) the 5' UTR, the open reading frame for the 3010 amino acid polyprotein, and the 3' UTR. The polyprotein contains within it the capsid (C) open reading frame, the envelope glycoprotein genes (E1 and E2), the NS2 (a cis-acting auto-protease that cleaves the polyprotein at a specific site at the NS2-NS3 junction), NS3 (helicase and serine protease), NS4A (required as a cofactor for NS3 activity), NS4B, NS5A, and NS5B (the RNA-dependent RNA polymerase) open reading frames. The luciferase open reading frame is also contained within the polyprotein open reading frame, located variously as described above.

In one embodiment, the IGVV contains a eukaryotic promoter at the 5' end of the HCV sequences for the production of RNA in transfected cells, and a transcription terminator at the 3' end. Examples of transcription promoters include, but are not limited to, the CMV intermediate-early promoter, or the SV40 promoter; examples of transcription terminators include, but are not limited to, the transcription terminator/polyadenylation signals found in SV40 or the human β-globin gene (see FIG. 17B). In a second embodiment, the promoter is a promoter for bacteriophage RNA polymerases such as T7, T3, or SP6, and the terminator is a sequence signalling termination of transcription that is recognized by the polymerase, or a self-cleaving ribozyme (e.g. see Chowrira et al. 1994, J. Biol. Chem. 269: 25864). The IGVV is transfected as DNA into cells expressing the RNA polymerase in the cytoplasm. Such expression is achieved by several methods including cotransfection with a polymerase expression vector, infection with a recombinant vaccinia virus expressing the polymerase (Fuerst et al. 1986, PNAS 83:8122), or by previously establishing a cell line permanently expressing the polymerase (see FIG. 17C). The IGVV additionally contains a poly-A or poly-U sequence immediately following the HCV 3' terminus, so that the transcribed RNA contains a poly-A or poly-U tail at the 3' end. In a third embodiment, the IGVV with a bacteriophage RNA polymerase promoter at the 5' end and a terminator sequence at the 3' end is transcribed in vitro and the nucleic acid representing the IGVV is transfected as RNA. The terminator may be a specific sequence recognized by the bacteriophage RNA polymerase as a termination site or a self-cleaving ribozyme (see chowrira et al. (1994) *J. Biol. Chem.* 269, 25856-25864). Alternatively, the terminator is a restriction endonuclease site allowing for linearization of the DNA template prior to transcription (see FIG. 17D). In this case the vector also contains a poly-A or poly-U sequence at the 3' end.

In transfected cells, the RNA is translated, using an internal initiation mechanism via the internal ribosome entry sequence (IRES), to yield the HCV polyprotein-luc fusion protein. Release of active luciferase from the HCV polyprotein fusion is dependent on the action of NS3/4A, itself expressed from the genomic RNA. High level expression takes place when the genomic RNA is replicated and amplified in the transfected cells, which is dependent on the action of the viral polymerase NS5B as well as the viral proteases NS2 and NS3/4A. In the case where the luciferase is inactive when it is part of the large HCV polyprotein, activity can be measured directly in the transfected cells since release of active luciferase is dependent on HCV RNA replication (one cell assay). In the case where luciferase has significant activity as a fusion protein, progeny virions will be collected and used to infect new target cells (two cell assay). Transfer of the IGVV RNA from the transfected cells to the infected target cells is dependent on replication and encapsidation of the RNA in the transfected cells, which in turn is dependent on the correct expression, processing and activity of the HCV viral structural and non-structural proteins. To augment the efficiency of transfer (i.e. packaging of the IGVV RNA into new virions) the target cells may be simultaneously infected with wild-type HCV virus or transfected with wild type HCV RNA or cDNA expression constructs. To further augment the replication and packaging of the IGVV RNA, input RNAs (see FIG. 17D) are cotransfected with purified NS5B protein (i.e. as RNP complexes), so that transcription can commence immediately upon uptake into the cells. This strategy or variation of it has been applied to the negative-stranded RNA viruses such as influenza virus (Enami and Palese 1991, J. Virol. 65: 2711-2713), rabies virus (Schnell et al. 1994, EMBO J. 13: 4195-4203), and vesicular stomatitis virus (Lawson et al. 1995, PNAS 92: 4477-4481).

Resistance Test Vectors—Construction

A resistance test vector (RTV) is constructed from the indicator gene viral vector by replacing a region of the HCV genome corresponding to the protein which is the anti-viral drug target (e.g. NS3/4A, NS5B, or the IRES) with the corresponding region derived from viruses and/or RNA present in the blood and/or cells of an infected patient (patient-derived segment, or PDS). In one embodiment, in the case of an NS3/4A protease inhibitor, the IGVV is modified by introducing unique restriction sites, called patient sequence acceptor sites (PSAS), in or near the NS3/4A genes (nucleotides 3418-5473 of the H strain of HCV). The patient derived segment obtained from the patient derived virus is then transferred into the PSAS in the IGVV (FIG. 17A). The wild-type NS3/4A region is removed from the IGVV by digestion with restriction endonucleases recognizing the patient sequence acceptor sites; these sequences are then replaced with DNA fragments generated by RT/PCR from patient-derived viral RNA obtained from plasma or serum or cells. The PCR products are generated using primers which contain the restriction endonuclease sites required for generation of compatible cohesive ends for cloning into the digested IGVV. RT and PCR primer binding sites are selected, and primer sequences designed, to enable amplification of as many different subtypes of HCV as possible. In a second embodiment, in the case of an inhibitor of the NS5B RDRP, the sequences spanning the NS5B open reading frame (nucleotides 7601-9373 of the H strain of HCV) are removed from the IGVV at unique patient sequence acceptor sites; these sequences are then replaced with the corresponding PDS generated by RT/PCR from patient viral RNA obtained from plasma or serum or cells. In a third embodiment, in the case of IRES inhibitors, the sequences spanning the IRES (nucleotides 1-709 of the H strain of HCV) are removed from the IGVV at unique patient sequence acceptor sites; these sequences are then replaced with corresponding PDS generated by RT/PCR from patient viral RNA obtained from plasma or serum or cells. The foregoing methods are applicable to other targets of anti-HCV drugs by identifying the gene encoding the target of the drug in the IGVV; introducing unique patient sequence acceptor sites into the IGVV; and replacing the target gene with a PDS.

Drug Susceptibility and Resistance Tests

Drug resistance and susceptibility tests are carried out with a resistance test vector prepared as described above (either as DNA or RNA) by transfection, using either a one cell assay or a two cell assay. Transfection of host cells with a resistance test vector produces HCV viral particles containing an encapsidated indicator gene RNA.

Replicate transfections are performed on a series of packaging host cell cultures maintained either in the absence of the anti-viral drug or in increasing concentrations of the anti-HCV drug (e.g., an HCV NS3/4A protease inhibitor, NS5B polymerase inhibitor, or IRES inhibitor). After maintaining the packaging host cells for several days in the presence or absence of the anti-HCV drug the level of drug susceptibility or resistance can be assessed by measuring indicator gene expression either directly in the host packaging cell lysates or in isolated HCV particles obtained by harvesting the host packaging cell culture media. Alternative approaches can be used to evaluate drug susceptibility and resistance in the cell lysates and the isolated HCV particles.

In one embodiment, referred to as the one cell assay, drug susceptibility or resistance is assessed by measuring luciferase expression or activity in the transfected packaging host cells in the presence or absence of anti-viral drug. A reduction in luciferase activity observed for cells transfected in the presence of a given anti-viral agent, or combination of agents as compared to a control run in the absence of the anti-viral agent(s), is used to calculate the inhibiting constant ($K_i$) of that agent or to generate a sigmoid curve relating the log of the concentration of the anti-viral agent to luciferase activity.

In a second embodiment, referred to as the two cell assay, drug susceptibility or resistance is assessed by measuring luciferase gene expression and/or activity, in the target host cells following infection with HCV particles obtained by transfecting host cells. At the time of transfection or infection, depending on the drug target, the appropriate concentration of the anti-viral drug is added to the host or target cell cultures. Several days following the infection, the target host cells are lysed and luciferase expression is measured. A reduction in luciferase expression will be observed for cells infected in the presence of drugs which inhibit HCV replication, for example by inhibiting either the protease (NS3/4A) or RDRP(NS5B) activities of HCV as compared to a control run in the absence of drug.

In a third embodiment, in which changes in RNA structure are used as an indicator, drug susceptibility or resistance is assessed by measuring the level of HCV RNA replication that has occurred within the transfected host cells. In host cells transfected with the DNA of the HCV viral vector, RNA is transcribed (or alternatively, the RNA is transcribed in vitro and transfected directly) as positive (mRNA) sense RNA, which can then serve as a template for the production of negative sense cRNA by the action of NS5B polymerase. Alternatively, positive sense RNA is transfected, which is translated and serves as a template for negative sense cRNA synthesis. To measure HCV RNA replication, RNA is isolated from the transfected cells and treated with DNAse to remove residual input DNA (the DNAse treatment would not be absolutely required if the cells were transfected with positive sense RNA). An RT primer is designed to hybridize specifically to negative sense HCV RNA to prime the synthesis of positive sense cDNA; after RNAse digestion to prevent reverse transcription of positive sense RNA using the PCR primers, the cDNA is amplified by PCR.

Formation of the amplification target cDNA of positive sense within the transfected cells follows initiation of HCV RNA replication resulting in the formation of negative sense RNA. Anti-viral drugs that inhibit HCV RNA replication (RNA-dependent RNA polymerase activity), or production of an active form of the polymerase (by the NS3/4A protease), will limit the formation of the RNA target sequence, which is measured as a decrease in the amplified DNA product using any one of a number of quantitative amplification assays.

In an alternative embodiment in which changes in RNA structure are used as the indicator, the 5' exonuclease activity of the amplification enzyme (e.g. Taq polymerase) is measured rather than the production of amplified DNA (Heid et al., 1996, Genome Research 6:986-994). The 5' exonuclease activity is measured by monitoring the nucleolytic cleavage of a fluorescently tagged oligonucleotide probe capable of binding to the amplified DNA template region flanked by the PCR primer binding sites. The performance of this assay is dependent on the close proximity of the 3' end of the upstream primer to the 5' end of the oligonucleotide probe. When the primer is extended it displaces the 5' end of the oligonucleotide probe such that the 5' exonuclease activity of the polymerase cleaves the oligonucleotide probe.

Drug Screening

Drug screening is carried out using an indicator gene viral vector containing a functional indicator gene fused to the HCV polyprotein. In transfected host cells, the indicator gene viral vector produces an RNA transcript containing the indicator gene (or alternatively, the RNA is transcribed in vitro and transfected directly). Translation of this RNA, or of mRNA produced as a result of replication and transcription by the viral RDRP (NS5B), produces the structural and enzymatic viral functions that are necessary for viral RNA replication and particle formation. The transfected cells give rise to HCV viral particles containing an encapsidated indicator gene viral vector RNA, which also contains the functional indicator gene fused to the HCV polyprotein gene.

Drug screening is performed as follows: indicator gene viral vector DNA or RNA is used to transfect host cells. Replicate transfections are performed on a series of packaging host cell cultures maintained either in the absence or presence of potential anti-viral compounds (e.g., candidate HCV NS3/4A protease or NS5B polymerase inhibitors). After maintaining the transfected host cells for up to several days in the presence or absence of the candidate anti-viral drugs the level of inhibition of RNA replication is assessed by measuring indicator gene expression either directly in the transfected host cell lysates, or in isolated HCV particles obtained by harvesting the host transfected cell culture media, or in target cells which are infected with the isolated HCV particles. Either RNA detection or indicator gene activity methods, described above, can be used to evaluate potential anti-HCV drug candidates.

EXAMPLE 2

HCV Drug Susceptibility and Resistance Test Using Resistance Test Vectors Comprising Patient-Derived Segment(s) and a Functional Indicator Gene Expressed from an Internal Ribosomal Initiation Sequence Indicator Gene Viral Vector—Construction Initiation of translation of the HCV polyprotein occurs via a cap-independent internal initiation mechanism. The 5' end of the viral RNA, comprising the untranslated region (UTR) and the first 369 nucleotides of the C open reading frame, contains a sequence and/or structure which directs cap-independent translation initiation (Tsukiyama-Kohara et al, J. Virol. 66:1476, 1992; Wang et al, J. Virol. 67:3338, 1993; Lu and Wimmer, PNAS 93:1412, 1996). Other viruses such as poliovirus (PV) (Pelletier and Sonenberg (1988), *Nature*, 334, 320-325), encephalomyocarditis virus (EMCV) (Jang et al. (1989), *J. Virol.* 63, 1651-1660), rhinovirus (RV) (Rohll et al. (1994), *J. Virol.* 68, 4384-4391), hepatitis A virus (HAV) (Brown et al. (1994), *J. Virol.* 68, 1066-1074; Glass et al. (1993) *Virol.* 193, 842-852), as well as the pestivirus, bovine viral diarrhea virus (BVDV) (Poole et al. (1995) *Virology,* 189, 285-292) to which HCV is closely related, employ similar mechanisms for translation initiation, although the sequences which serve as the internal ribosome entry site (IRES) are different for each virus. Some cellular mRNAs are also known to initiate translation internally via an IRES (Macejak and Sarnow (1991), *Nature,* 353, 90-94). These RNA elements have been shown to be capable of directing translation initiation when located in between two open reading frames, as well as at the 5' end of RNAs. These bicistronic RNAs can be used to obtain expression of two proteins from the same RNA by independently directing the translation of both open reading frames.

Indicator gene viral vectors containing a functional IG expressed from an internal ribosomal initiation sequence are constructed by inserting the open reading frame for an indicator gene, for example, luciferase, in a cDNA construct, containing the entire HCV genome, as a second cistronic element preceded by an IRES. Insertion of the IRES (either the native HCV 5' UTR or that of another virus) and luciferase downstream of the HCV polyprotein provides for luciferase gene expression independently of that of HCV proteins (see FIG. 18). Note that when testing for resistance to a drug that inhibits the function of the HCV IRES, the IRES used for expression of luciferase must be derived from a virus other than HCV, which is not affected by the drug. The IGVV thus contains the following elements in a 5' to 3' orientation: a promoter sequence, the HCV 5' UTR, the complete HCV polyprotein coding sequence, an IRES, the luciferase coding region, the HCV 3' UTR, and a transcription terminator.

In one embodiment, the IGVV contains a eukaryotic promoter at the 5' end of the HCV sequences for the production of RNA in transfected cells, and a transcription terminator at the 3' end. Examples of transcription promoters include, but are not limited to, the CMV intermediate-early promoter, or the SV40 promoter; examples of transcription terminators include, but are not limited to, the transcription terminator/polyadenylation signals found in SV40 or the human β-globin gene (see FIG. 17B). In a second embodiment, the promoter is a promoter for bacteriophage RNA polymerases such as T7, T3, or SP6, and the terminator is a sequence signalling termination of transcription that is recognized by the polymerase, or a self-cleaving ribozyme. The IGVV is transfected as DNA into cells expressing the RNA polymerase in the cytoplasm. Such expression is achieved by several methods including cotransfection with a polymerase expression vector, infection with a recombinant vaccinia virus expressing the polymerase, or by previously establishing a cell line permanently expressing the polymerase (see FIG. 17C). The IGVV additionally contains a poly-A or poly-U sequence immediately following the HCV 3' terminus, so that the transcribed RNA contains a poly-A or poly-U tail at the 3' end. In a third embodiment, the IGVV with a bacteriophage RNA polymerase promoter at the 5' end and a terminator sequence at the 3' end is transcribed in vitro and the nucleic acid representing the IGVV is transfected as RNA. The terminator may be a specific sequence recognized by the bacteriophage RNA polymerase as a termination site or a self-cleaving ribozyme. Alternatively, the terminator is a restriction endonuclease site allowing for linearization of the DNA template prior to transcription (see FIG. 17D). In this case the vector also contains a poly-A or poly-U sequence at the 3' end.

Resistance Test Vectors—Construction

Resistance test vectors containing a functional indicator gene expressed from an internal ribosomal initiation sequence are constructed from IGVVs described above and patient-derived HCV sequences as described in Example 1. The IGVV is modified to include PSAS for the insertion of NS3/4A, NS5B, or IRES containing PDS (described in Example 1, see FIG. 17A).

Drug Susceptibility and Resistance Tests

Drug resistance and susceptibility tests are carried out with a resistance test vector prepared as described above (either as DNA or RNA) by transfection, using either a one cell or two cell assay. Transfection of host cells with a resistance test vector produces HCV viral particles containing an encapsidated indicator gene RNA. Drug resistance and susceptibility tests are performed as described in Example 1.

Drug Screening

Drug screening using an IGVV containing a functional indicator gene expressed from an internal ribosomal initiation sequence is performed essentially as described in Example 1 above.

EXAMPLE 3

HCV Drug Susceptibility and Resistance Test Using Resistance Test Vectors Comprising Patient-Derived Segment(s) and a Functional Indicator Gene Expressed from a Replication Defective Minigenome Indicator Gene Viral Vector—Construction HCV replication-dependent expression of an indicator gene is achieved by constructing an artificial HCV subgenomic viral vector, or "minigenome", consisting of the HCV 5' UTR and, if required, an amino-terminal portion of the C open reading frame (required as part of the IRES), an IG, for example luciferase, and the HCV 3' UTR (see FIG. 19). Luciferase is produced bearing an N-terminal extension derived from the C open reading frame; alternatively, the ATG at the beginning of the C open reading frame is mutated so that translation begins at the ATG of luciferase. The 5' UTR plus the N-terminus of C and 3' UTR contain all cis-acting signals required for translation, replication, and packaging of the RNA. The luciferase minigenome is co-transfected, either as DNA or RNA (see Example 1, FIGS. 3B-3D), with a full-length helper HCV genomic construct; replication and packaging into progeny viruses of the minigenome RNA is dependent on the HCV replication machinery, including the NS3/4A protease and NS5B RDRP, produced from the helper HCV genomic RNA, as well as of the cis-acting regulatory elements of the minigenome.

Indicator gene viral vectors comprising a functional indicator gene expressed from a replication defective minigenome and a helper HCV genomic construct are constructed as follows. The minigenome contains the following elements in a 5' to 3' orientation: a promoter sequence, the HCV 5' UTR, the first 24 or 369 nucleotides of the C open reading frame, the luciferase open reading frame, the HCV 3' UTR, and a transcription terminator. The helper HCV genomic construct contains a promoter, the complete HCV cDNA, and a terminator.

In one embodiment, the IGVV contains a eukaryotic promoter at the 5' end of the HCV sequences for the production of RNA in transfected cells, and a transcription terminator at the 3' end. Examples of transcription promoters include, but are not limited to, the CMV intermediate-early promoter, or the SV40 promoter; examples of transcription terminators include, but are not limited to, the transcription terminator/polyadenylation signals found in SV40 or the human β-globin gene (see FIG. 17B). In a second embodiment, the promoter is a promoter for bacteriophage RNA polymerases such as T7, T3, or SP6, and the terminator is a sequence signalling termination of transcription that is recognized by the polymerase, or a self-cleaving ribozyme. The IGVV is transfected as DNA into cells expressing the RNA polymerase in the cytoplasm. Such expression is achieved by several methods including cotransfection with a polymerase expression vector, infection with a recombinant vaccinia virus expressing the polymerase, or by previously establishing a cell line permanently expressing the polymerase (see FIG. 17C). The IGVV additionally contains a poly-A or poly-U sequence immediately following the HCV 3' terminus, so that the transcribed RNA contains a poly-A or poly-U tail at the 3' end. In a third embodiment, the IGVV with a bacteriophage RNA polymerase promoter at the 5' end and a terminator sequence at the 3' end is transcribed in vitro and the nucleic acid representing the IGVV is transfected as RNA. The terminator may be a specific sequence recognized by the bacteriophage RNA polymerase as a termination site or a self-cleaving ribozyme. Alternatively, the terminator is a restriction endonuclease site allowing for linearization of the DNA template prior to transcription (see FIG. 17D). In this case the vector also contains a poly-A or poly-U sequence at the 3' end.

Resistance Test Vectors—Construction

Resistance test vectors comprising a functional indicator gene expressed from a replication defective minigenome and a helper HCV genomic construct are constructed from the helper HCV genomic construct and patient-derived HCV sequences as described in Example 1. The helper HCV genomic construct is modified to include PSAS for the insertion of NS3/4A or NS5B-containing PDS (described in Example 1, see FIG. 17A). In the case of a drug which targets the function of the IRES, the PSAS are introduced into the minigenome construct as well.

Drug Susceptibility and Resistance Tests

Drug resistance and susceptibility tests using an IGVV system that comprises a functional indicator gene expressed from a minigenome and a helper HCV genomic construct are carried out with resistance test vectors prepared as described above (either as DNA or RNA) by transfection, using either a one cell or two cell assay. Transfection of host cells with the resistance test vectors (the luciferase minigenome plus the helper HCV genomic construct containing the PDS) produces HCV viral particles containing an encapsidated luciferase gene RNA and/or an encapsidated HCV genomic RNA. Drug resistance and susceptibility tests are then performed as described in Example 1.

Drug Screening

Drug screening using an IGVV system that comprises a functional indicator gene expressed from a minigenome and a helper HCV genomic construct is performed essentially as described in Example 1 above.

EXAMPLE 4

HCV Drug Susceptibility and Resistance Test Using Resistance Test Vectors Comprising Patient-Derived Segment(s) and a Nonfunctional Indicator Gene Expressed from Antisense Replication Defective Minigenomes Indicator Gene Viral Vector—Construction Indicator gene viral vectors comprising a non-functional indicator gene expressed from a replication defective minigenome and a helper HCV genomic construct are constructed as follows. The minigenome contains the following elements in a 5' to 3' orientation: a promoter sequence, the HCV 3' UTR (in antisense orientation), the luciferase open reading frame (antisense), the first 24 or 369 nucleotides of the C open reading frame (antisense), the HCV 5' UTR (antisense), and a transcription terminator. The helper HCV genomic construct contains a promoter, the complete HCV cDNA (in sense orientation), and a terminator.

In this example, the minigenome is introduced into the cells as negative stranded RNA, i.e. as a replicative intermediate RNA copy of the minigenome described above (see FIG. 20). Expression in the transfected cells is dependent on the activity of NS5B, production of which is dependent in turn on the action of NS3/4A and of the cis-acting regulatory elements such as the IRES. Thus the indicator gene is non-functional until acted upon by the viral replication machinery.

In one embodiment, the IGVV contains a eukaryotic promoter at the 5' end of the HCV sequences for the production of RNA in transfected cells, and a transcription terminator at the 3' end. Examples of transcription promoters include, but are not limited to, the CMV intermediate-early promoter, or the SV40 promoter; examples of transcription terminators include, but are not limited to, the transcription terminator/polyadenylation signals found in SV40 or the human β-globin gene (see FIG. 17B). In a second embodiment, the promoter is a promoter for bacteriophage RNA polymerases such as T7, T3, or SP6, and the terminator is a sequence signalling termination of transcription that is recognized by the polymerase, or a self-cleaving ribozyme. The IGVV is transfected as DNA into cells expressing the RNA polymerase in the cytoplasm. Such expression is achieved by several methods including cotransfection with a polymerase expression vector, infection with a recombinant vaccinia virus expressing the polymerase, or by previously establishing a cell line permanently expressing the polymerase (see FIG. 17C). The IGVV additionally contains a poly-A or poly-U sequence immediately following the HCV 3' terminus, so that the transcribed RNA contains a poly-A or poly-U tail at the 3' end. In a third embodiment, the IGVV with a bacteriophage RNA polymerase promoter at the 5' end and a terminator sequence at the 3' end is transcribed in vitro and the nucleic acid representing the IGVV is transfected as RNA. The terminator may be a specific sequence recognized by the bacteriophage RNA polymerase as a termination site or a self-cleaving ribozyme. Alternatively, the terminator is a restriction endonuclease site allowing for linearization of the DNA template prior to transcription (see FIG. 17D). In this case the vector also contains a poly-A or poly-U sequence at the 3' end.

Resistance Test Vectors—Construction

Resistance test vectors comprising a non-functional indicator gene expressed from a replication defective minigenome and a helper HCV genomic construct are constructed from the helper HCV genomic construct and patient-derived HCV sequences as described in Example 1. The helper HCV genomic construct is modified to include PSAS for the insertion of NS3/4A or NS5B-containing PDS (described in Example 1, see FIG. 17A). In the case of a drug which targets the function of the IRES, the PSAS are introduced into the minigenome construct as well.

Drug Susceptibility and Resistance Tests

Drug resistance and susceptibility tests using resistance test vectors comprising a non-functional indicator gene expressed from a minigenome and a helper HCV genomic construct are carried out with resistance test vectors prepared as described above (either as DNA or RNA) by transfection, using either a one cell or two cell assay. Transfection of host cells with the resistance test vectors (the luciferase minigenome plus the helper HCV genomic construct containing the PDS) produces HCV viral particles containing an encapsidated luciferase gene RNA and/or an encapsidated HCV genomic RNA. Drug resistance and susceptibility tests are then performed as described in Example 1.

Drug Screening

Drug screening using resistance test vectors comprising a non-functional indicator gene expressed from a minigenome and a helper HCV genomic construct is performed essentially as described in Example 1 above.

EXAMPLE 5

HCV Drug Susceptibility and Resistance Test Using Resistance Test Vectors Comprising Patient-Derived Segment(s) and a Functional Indicator Gene Expressed as a Replication Defective Genome Indicator Gene Viral Vector—Construction Indicator gene viral vectors comprising a functional indicator gene expressed from a replication defective genome and a packaging vector construct are constructed as follows. The IGVV contains the following elements in a 5' to 3' orientation: a promoter sequence, the HCV 5' UTR, the first 24 or 369 nucleotides of the C open reading frame, the indicator gene open reading frame, the NS2 through NS5B portion of the HCV genome (nucleotides 2768-9373 of the H strain of HCV), the HCV 3' UTR, and a transcription terminator. The packaging vector contains a promoter, the C, E1 and E2 open reading frames of HCV (nucleotides 342-2578 of the H strain of HCV), and a terminator. In the case where the indicator gene is luciferase or another cytoplasmic protein, certain modifications will be made to ensure proper processing of the IG-NS2 junction by the host signal peptidase in the endoplasmic reticulum. In the case of a secreted indicator gene, for example secreted alkaline phosphatase, no such modifications may be required.

Infectious recombinant virions are produced from cells transfected with two vectors: an IGVV containing an IG and the viral non-structural proteins, and a second vector, the packaging vector, containing the viral structural proteins (C/E1/E2; see FIG. 21). To generate infectious particles, the IGVV DNA (or its corresponding RNA, see Example 1, FIGS. 3B-3D) is co-transfected with the packaging vector. Alternatively, particles are pseudotyped with envelope glycoprotein genes from related flaviviruses such as BVDV or classical swine fever virus (CSFV). The pseudotyped viruses are used to establish of a cell culture system for single-cycle infection assays. Viruses produced in this manner can then be used to infect target cells, and luciferase expression subsequently measured. This approach has the added advantage of minimizing the amount of manipulations performed with replication competent infectious agents.

In one embodiment, the IGVV contains a eukaryotic promoter at the 5' end of the HCV sequences for the production of RNA in transfected cells, and a transcription terminator at the 3' end. Examples of transcription promoters include, but are not limited to, the CMV intermediate-early promoter, or the SV40 promoter; examples of transcription terminators include, but are not limited to, the transcription terminator/polyadenylation signals found in SV40 or the human β-globin gene (see FIG. 17B). In a second embodiment, the promoter is a promoter for bacteriophage RNA polymerases such as T7, T3, or SP6, and the terminator is a sequence signalling termination of transcription that is recognized by the polymerase, or a self-cleaving ribozyme. The IGVV is transfected as DNA into cells expressing the RNA polymerase in the cytoplasm. Such expression is achieved by several methods including cotransfection with a polymerase expression vector, infection with a recombinant vaccinia virus expressing the polymerase, or by previously establishing a cell line permanently expressing the polymerase (see FIG. 17C). The IGVV additionally contains a poly-A or poly-U sequence immediately following the HCV 3' terminus, so that the transcribed RNA contains a poly-A or poly-U tail at the 3' end. In a third embodiment, the IGVV with a bacteriophage RNA polymerase promoter at the 5' end and a terminator sequence at the 3' end is transcribed in vitro and the nucleic acid representing the IGVV is transfected as RNA. The terminator may be a specific sequence recognized by the bacteriophage RNA polymerase as a termination site or a self-cleaving ribozyme. Alternatively, the terminator is a restriction endonuclease site allowing for linearization of the DNA template prior to transcription (see FIG. 17D). In this case the vector also contains a poly-A or poly-U sequence at the 3' end.

Resistance Test Vectors—Construction

Resistance test vectors comprising a functional indicator gene expressed from a replication defective genome and a packaging vector construct are constructed from IGVVs described above and patient-derived HCV sequences as described in Example 1. The IGVV is modified to include PSAS for the insertion of NS3/4A, NS5B, or IRES containing PDS (described in Example 1, see FIG. 17A).

Drug Susceptibility and Resistance Tests

Drug resistance and susceptibility tests are carried out with a resistance test vector prepared as described above (either as DNA or RNA) by transfection, using either a one cell or two cell assay. Transfection of host cells with a resistance test vector produces HCV viral particles containing an encapsidated indicator gene RNA. Drug resistance and susceptibility tests are performed as described in Example 1.

Drug Screening

Drug screening using an IGVV comprising a functional indicator gene expressed from a replication defective genome and a packaging vector construct is performed essentially as described in Example 1 above.

EXAMPLE 6

HCV Protease Inhibitor Susceptibility and Resistance Test Using Resistance Test Vectors Comprising Patient-Derived Segment(s) and a Functional Indicator Gene in an NS3/4a BVDV Chimeric Viral Vector Indicator Gene Viral Vector—Construction A chimeric IGVV containing a functional indicator gene and the relevant portion(s) of HCV (for example, the NS3/4A protease domain) were designed with a backbone of a related virus which replicates well in culture. An example of such a virus is BVDV. A complete cDNA for the genome of BVDV has been assembled and shown to generate infectious RNA by in vitro transcription (Vassilev et al. 1997, J. Virol. 71:471-478). The BVDV polyprotein is processed in a manner very similar to that of HCV, using both host (signal peptidase) and viral encoded proteases. The chimeric IGVV based on a BVDV backbone contains the NS3 protease domain or entire NS3/4A open reading frame of HCV which replaces the corresponding region of BVDV (FIG. 22). By mutating the cleavage sites normally recognized by BVDV NS3 protease to those recognized by HCV NS3/4A, replication of BVDV chimeric RNA and expression of the IG will be dependent on HCV NS3/4A activity.

Chimeric indicator gene viral vectors containing a functional indicator gene in an NS3/4A BVDV chimeric viral vector are constructed as follows. The IGVV contains the following elements in a 5' to 3' orientation: a promoter sequence, the BVDV 5' UTR, the C through NS2 regions of BVDV (NADL strain), the NS3/4A region of HCV, the HCV NS4A/4B cleavage site, the BVDV NS4B open reading frame, the HCV NS4B/5A cleavage site, the BVDV NS5A open reading frame, the HCV NS5A/5B cleavage site, the BVDV NS5B open reading frame, the luciferase open reading frame, the BVDV 3' UTR and a transcription terminator. In a second embodiment, the IGVV contains the luciferase open reading frame preceeded by an IRES in a similar configuration to that described in Example 2. In a third embodiment, the luciferase gene is expressed from a minigenome similar to that described in Examples 3 or 4.

In one embodiment, the IGVV contains a eukaryotic promoter at the 5' end of the HCV sequences for the production of RNA in transfected cells, and a transcription terminator at the 3' end. Examples of transcription promoters include, but are not limited to, the CMV intermediate-early promoter, or the SV40 promoter; examples of transcription terminators include, but are not limited to, the transcription terminator/polyadenylation signals found in SV40 or the human β-globin gene (see FIG. 17B). In a second embodiment, the promoter is a promoter for bacteriophage RNA polymerases such as T7, T3, or SP6, and the terminator is a sequence signalling termination of transcription that is recognized by the polymerase, or a self-cleaving ribozyme. The IGVV is transfected as DNA into cells expressing the RNA polymerase in the cytoplasm. Such expression is achieved by several methods including cotransfection with a polymerase expression vector, infection with a recombinant vaccinia virus expressing the polymerase, or by previously establishing a cell line permanently expressing the polymerase (see FIG. 17C). The IGVV additionally contains a poly-A or poly-U sequence immediately following the HCV 3' terminus, so that the transcribed RNA contains a poly-A or poly-U tail at the 3' end. In a third embodiment, the IGVV with a bacteriophage RNA polymerase promoter at the 5' end and a terminator sequence at the 3' end is transcribed in vitro and the nucleic acid representing the IGVV is transfected as RNA. The terminator may be a specific sequence recognized by the bacteriophage RNA polymerase as a termination site or a self-cleaving ribozyme. Alternatively, the terminator is a restriction endonuclease site allowing for linearization of the DNA template prior to transcription (see FIG. 17D). In this case the vector also contains poly-A or poly-U sequence at the 3' end.

Resistance Test Vectors—Construction

Resistance test vectors containing a functional indicator gene in an NS3/4A BVDV chimeric viral vector are constructed from IGVVs described above and patient-derived HCV NS3/4A sequences as described in Example 1. The IGVV is modified to include PSAS for the insertion of NS3/4A-containing PDS (described in Example 1, see FIG. 17A).

Drug Susceptibility and Resistance Tests

Drug resistance and susceptibility tests are carried out with a resistance test vector prepared as described above (either as DNA or RNA) by transfection, using either a one cell or two cell assay. Transfection of host cells with a resistance test vector produces HCV viral particles containing an encapsidated indicator gene RNA. Drug resistance and susceptibility tests are performed as described in Example 1.

Drug Screening

Drug screening using an IGVV containing a functional indicator gene expressed from an internal ribosomal initiation sequence is performed essentially as described in Example 1 above.

EXAMPLE 7

HCV Drug Susceptibility and Resistance Test Using Resistance Test Vectors Comprising Patient-Derived Segment(s) and a Functional Indicator Gene in an NS5B BVDV Chimeric Viral Vector Indicator Gene Viral Vector—Construction A chimeric IGVV containing the BVDV structural and non-structural proteins, with the exception of NS5B which is derived from HCV, is designed with a backbone of BVDV. In addition, the BVDV 5' and 3' UTRs are replaced with the corresponding regions from HCV, to ensure recognition by the cognate polymerase (FIG. 23).

Indicator gene viral vectors containing a functional indicator gene in an NS5B BVDV chimeric viral vector are constructed as follows. The IGVV contains the following elements in a 5' to 3' orientation: a promoter sequence, the HCV 5' UTR, sequences from the N-terminus of the HCV C open reading frame required for IRES function, the Npro through NS5A regions of BVDV (NADL strain), the NS5B region of HCV, the luciferase open reading frame, the HCV 3' UTR, and a transcription terminator. In a second embodiment, the IGVV contains the luciferase open reading frame preceeded by an IRES in a similar configuration to that described in Example 2. In a third embodiment, the luciferase gene is expressed from a minigenome similar to that described in Examples 3 or 4.

In one embodiment, the IGVV contains a eukaryotic promoter at the 5' end of the HCV sequences for the production of RNA in transfected cells, and a transcription terminator at the 3' end. Examples of transcription promoters include, but are not limited to, the CMV intermediate-early promoter, or the SV40 promoter; examples of transcription terminators include, but are not limited to, the transcription terminator/polyadenylation signals found in SV40 or the human β-globin gene (see FIG. 17B). In a second embodiment, the promoter is a promoter for bacteriophage RNA polymerases such as T7, T3, or SP6, and the terminator is a sequence signalling termination of transcription that is recognized by the polymerase, or a self-cleaving ribozyme. The IGVV is transfected as DNA into cells expressing the RNA polymerase in the cytoplasm. Such expression is achieved by several methods including cotransfection with a polymerase expression vector, infection with a recombinant vaccinia virus expressing the polymerase, or by previously establishing a cell line permanently expressing the polymerase (see FIG. 17C). The IGVV additionally contains a poly-A or poly-U sequence immediately following the HCV 3' terminus, so that the transcribed RNA contains a poly-A or poly-U tail at the 3' end. In a third embodiment, the IGVV with a bacteriophage RNA polymerase promoter at the 5' end and a terminator sequence at the 3' end is transcribed in vitro and the nucleic acid representing the IGVV is transfected as RNA. The terminator may be a specific sequence recognized by the bacteriophage RNA polymerase as a termination site or a self-cleaving ribozyme. Alternatively, the terminator is a restriction endonuclease site allowing for linearization of the DNA template prior to transcription (see FIG. 17D). In this case the vector also contains a poly-A or poly-U sequence at the 3' end.

Resistance Test Vectors—Construction

Resistance test vectors containing a functional indicator gene in an NS5B BVDV chimeric viral vector are constructed from IGVVs described above and patient-derived HCV NS5B sequences as described in Example 1. The IGVV is modified to include PSAS for the insertion of NS5B-containing PDS (described in Example 1, see FIG. 17A).

Drug Susceptibility and Resistance Tests

Drug resistance and susceptibility tests are carried out with a resistance test vector prepared as described above (either as DNA or RNA) by transfection, using either a one cell or two cell assay. Transfection of host cells with a resistance test vector produces HCV viral particles containing an encapsidated indicator gene RNA. Drug resistance and susceptibility tests are performed as described in Example 1.

Drug Screening

Drug screening using an IGVV containing a functional indicator gene expressed from an internal ribosomal initiation sequence is performed essentially as described in Example 1 above.

EXAMPLE 8

HCV Drug Susceptibility and Resistance Test Using Resistance Test Vector Systems Comprising Patient-Derived Segment(s), a Transcriptional Transactivator, and a Functional Indicator Gene Indicator Gene Viral Vector—Construction An indicator gene viral vector system was designed involving HCV-dependent expression and release of a transcriptional transactivator which activates the expression of an indicator gene. The indicator gene, for example luciferase, is introduced as an expression vector into the host cells by transient or stable transfection. The gene encoding the transactivator protein, for example that of HIV-1, tat, is fused to the HCV polyprotein via a NS3/4A cleavage site linker, in a manner similar to that described for the fusion of luciferase described in Example 1 (i.e. at the C-terminus or elsewhere). Upon expression of the polyprotein, and dependent on the activity of the NS3/4A protease, tat is cleaved from the polyprotein activates the transcription of a reporter gene such as luciferase which is under the control of the HIV-1 long terminal repeat (LTR).

Indicator gene viral vector systems containing a functional indicator gene comprising patient-derived segment(s), a transcriptional transactivator, and a functional indicator gene are constructed as follows. The viral vector contains the following elements in a 5' to 3' orientation: a promoter, the HCV 5' UTR, the open reading frame for the 3010 amino acid HCV polyprotein, containing within it the open reading frame for tat, located variously as described in Example 1, the 3' UTR, and a transcription terminator. The indicator gene construct contains the HIV-1 LTR, the luciferase open reading frame, and a transcription terminator. The indicator gene construct may be co-transfected with the viral vector, or, preferably, is present as a stable integrated DNA segment in the host cell DNA.

In one embodiment, the viral vector contains a eukaryotic promoter at the 5' end of the HCV sequences for the production of RNA in transfected cells, and a transcription terminator at the 3' end. Examples of transcription promoters include, but are not limited to, the CMV intermediate-early promoter, or the SV40 promoter; examples of transcription terminators include, but are not limited to, the transcription terminator/polyadenylation signals found in SV40 or the human β-globin gene (see FIG. 17B). In a second embodiment, the promoter is a promoter for bacteriophage RNA polymerases such as T7, T3, or SP6, and the terminator is a sequence signalling termination of transcription that is recognized by the polymerase, or a self-cleaving ribozyme. The viral vector is transfected as DNA into cells expressing the RNA polymerase in the cytoplasm. Such expression may be achieved by several methods including cotransfection with a polymerase expression vector, infection with a recombinant vaccinia virus expressing the polymerase, or by previously establishing a cell line permanently expressing the polymerase (see FIG. 17C). The viral vector additionally contains a poly-A or poly-U sequence immediately following the HCV 3' terminus, so that the transcribed RNA contains a poly-A or poly-U tail at the 3' end. In a third embodiment, the viral vector with a bacteriophage RNA polymerase promoter at the 5' end and a terminator sequence at the 3' end is transcribed in vitro and the nucleic acid representing the viral vector is transfected as RNA. The terminator may be a specific sequence recognized by the bacteriophage RNA polymerase as a termination site or a self-cleaving ribozyme. Alternatively, the terminator is a restriction endonuclease site allowing for linearization of the DNA template prior to transcription (see FIG. 17D). In this case the vector also contains a poly-A or poly-U sequence at the 3' end.

Resistance Test Vectors—Construction

Resistance test vectors containing a functional indicator gene comprising patient-derived segment(s), a transcriptional transactivator, and a functional indicator gene are constructed from viral vectors described above and patient-derived HCV sequences as described in Example 1. The viral vector is modified to include PSAS for the insertion of PDS containing the relevant portion of the HCV genome (described in Example 1, see FIG. 17A).

Drug Susceptibility and Resistance Tests

Drug resistance and susceptibility tests are carried out with a resistance test vector prepared as described above (either as DNA or RNA) by transfection into host cells which contain the indicator construct. Drug resistance and susceptibility tests are performed as described in Example 1.

Drug Screening

Drug screening using indicator gene viral vector systems containing a functional indicator gene comprising patient-derived segment(s), a transcriptional transactivator, and a functional indicator gene is performed essentially as described in Example 1 above.

EXAMPLE 9

Figure 26A:
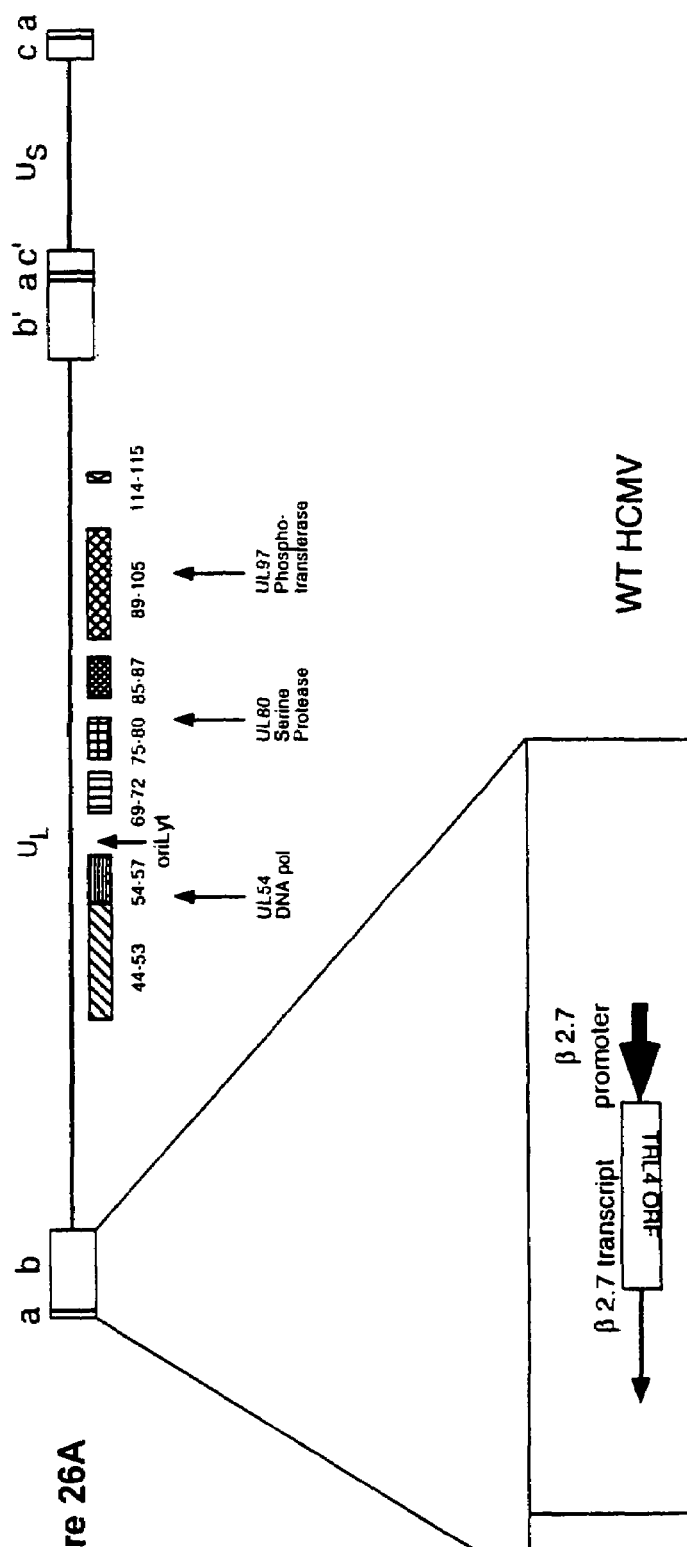
Figure 26B:
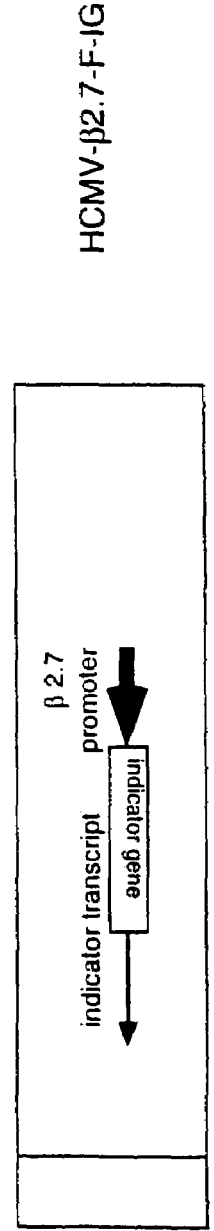
Figure 27:
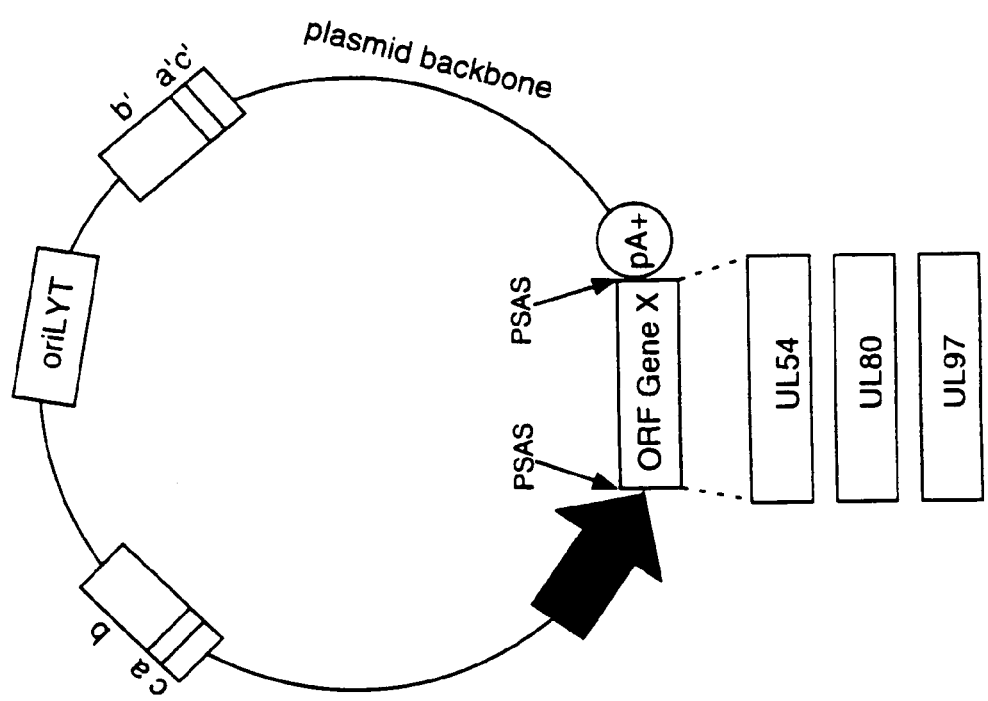

Cytomegalovirus Drug Susceptibility and Resistance Test Using Resistance Test Vectors Comprising Patient-Derived Segment(s) and a Functional Indicator Gene Embedded in a Defective Helper Virus Indicator Gene Viral Vector—Construction Indicator gene viral vectors comprising a functional indicator gene inserted into an ORF of HCMV under control of an endogenous viral promoter which in the wild type virus controls the expression of an RNA, for example, the $\beta_{2.7}$ transcript located in the $TR_L$ or "b" repeat (FIG. 26) were designed. The indicator gene viral vector (HCMV-$\beta_{2.7}$ F-IG/Δ gene X) is further modified and is defective for replication by deleting a segment of the genome containing the viral gene(s) which are the target(s) of the anti-viral drug(s). A viral gene which is the target of an anti-viral drug is refered to herein as gene X. The gene X product is provided on an amplicon plasmid (pA-CMV-VS-gene X) which contains patient sequence acceptor sites (PSAS) and the cis-acting functions required for trans-complementation of the indicator gene viral vector (specifically, these include an HCMV origin of replication and HCMV "a" sequences that direct HCMV genome cleavage and packaging) (FIG. 13). The PSAS are designed to accept the PDS into a cassette containing the regulatory signals appropriate to the individual viral gene/drug target and are derived from the context of the viral gene/drug target in the wild type HCMV. The defective indicator gene viral vector and the amplicon/gene X plasmid constitute a resistance test vector system. The defective indicator gene viral vector is propagated as a viral stock in a packaging host cell/target host cell system in which a functional copy of the viral gene X is provided in trans. Viral stocks from such a packaging host cell/target host cell line are prepared and used to infect cells and/or DNA from these viral stocks is isolated and used to transfect packaging host cell/target host cells as part of a resistance test vector system in conjunction with introduction of the amplicon/gene X plasmid by transfection into a cell type permissive for HCMV infection. Transcomplementation of the deleted gene by the amplicon/gene X plasmid results in a self-perpetuating virus population that results in increased expression of the reporter gene that is dependent on the activity of the viral gene encoded by the patient derived segment that has been introduced into the amplicon/gene X plasmid.

In another embodiment, the amplicon/gene X plasmid (pA-CMV-CS-gene X) contains PSAS that accept the PDS in such a way as to express the patient-derived gene X sequences under control of a heterologous promoter and polyadenylation signals. In one embodiment of this example, an expression cassette containing the CMV IE enhancer promoter region, PSAS, and the SV40 polyadenylation (pA) signal would be included on the amplicon/gene X plasmid (pA-CMV-CS-gene X) in addition to the cis-acting functions required for trans-complementation of the indicator gene viral vector (specifically, these include an HCMV origin of replication and HCMV "a" sequences that direct HCMV genome cleavage and packaging).

In another embodiment the helper viral vector can be supplied as a series of overlapping cosmids that upon transfection into the cell undergo recombination and result in expression of the full array of helper functions. This modification can be used to supply the helper virus sequences in all further examples in the same manner.

In various embodiments of this invention the viral gene/drug target (gene X) can be 1) the HCMV DNA polymerase (UL54), 2) the phosphotransferase (UL97), 3) the viral serine protease (UL80), 4) any viral gene that encodes a real or potential target for a drug susceptibility test or a drug screening test.

Plasmids described for the CMV resistance test vectors are named using the following conventions: lower case p indicates that the construction is a plasmid DNA molecule capable of replication in a laboratory strain of E. coli, "A" indicates that the plasmid is an amplicon and thus carries the cis-acting functions required for propagation by a helper virus, specifically these amplicon plasmids contain a viral origin of replication and "a" sequences that direct the genome maturation, cleavage and packaging and make the genomes competent for inversion, CMV indicates that the amplicon sequences are specific for the HCMV (alternatively HSV-1 could indicate the homologous signals from HSV-1 were present on the amplicon), V indicates that the regulatory regions controlling expression of the viral gene/drug target are derived from the HCMV genome and are the regulatory regions used for expression of the viral gene/drug target in the context of the whole virus, C indicates that the regulatory regions used to control expression of the viral gene/drug target are heterologous and in this example comprise the CMV IE promoter/enhancer and the SV40 polyadenylation signal, S indicates that the construct is a subgenomic construct, gene X identifies the viral gene(s) that is the target(s) of the anti-viral drug(s) and in the examples given here could be UL54, UL80 or UL97 to indicate the DNA polymerase, serine protease, or phosphotransferase, respectively. Helper viruses or indicator gene helper viral vectors are named as follows: HCMV indicates a strain of HCMV, $\beta_{2.7}$ F-IG indicates a functional indicator gene inserted into the $\beta_{2.7}$ ORF in the proper reading frame and under control of the $\beta_{2.7}$ regulatory regions, $\Delta$gene X indicates that the viral gene/drug target has been deleted from the virus and in the examples given here could be $\Delta$UL54, $\Delta$UL80 or $\Delta$UL97 to indicate deletion of the DNA polymerase, serine protease, or phosphotransferase, respectively.

Resistance Test Vectors—Construction

Resistance test vectors are prepared by 1) modifying the amplicon/gene X plasmid (pA-CMV-VS-gene X or pA-CMV-CS-gene X) by introducing unique sites, called patient sequence acceptor sites (PSAS) in the gene X coding region, 2) amplifying patient-derived segments (PDS) corresponding to the CMV drug target (gene X) by the amplification of viral DNA present in the blood or tissues of infected patients, and 3) inserting the amplified segments precisely into the amplicon/gene X plasmid at the PSAS. A further embodiment comprises isolation of viral RNA from tissues and using reverse transcription to convert the RNA into DNA copies prior to amplification of the PDS.

Drug Susceptibility and Resistance Tests

Drug susceptibility and resistance tests are carried out with a two part resistance test vector system comprising an amplicon/gene X plasmid (pA-CMV-VS-gene X or pA-CMV-CS-gene X) and corresponding indicator gene viral vector such as HCMV-$\beta_{2.7}$ F-IG/$\Delta$ gene X. In one embodiment the amplicon/gene X plasmid is transfected into packaging host cells/target host cells and the cells are then infected with the defective indicator gene viral vector. In another embodiment the amplicon/gene X plasmid and the defective indicator gene viral vector DNA are cotransfected into the packaging host cells/target host cells simultaneously. Packaging host cells/target host cells can be any cells that are permissive for wild type HCMV infection. Transcomplementation of the deleted gene by the amplicon/gene X plasmid results in a self-perpetuating virus population that results in increased expression of the reporter gene that is dependent on the activity of the viral gene/drug target encoded by the patient derived segment that has been introduced into the amplicon/gene X plasmid. Some reporter gene expression will be observed due to the basal level of expression from the defective indicator gene viral vector, however, the replication and thus amplification of the genome of the defective indicator gene viral vector due to the transcomplementation by the amplicon/gene X plasmid will result in a significant increase in the expression of the reporter gene in the target cells. Anti-viral drugs that inhibit HCMV replication through inhibition of the viral gene/drug target will limit the propagation and expansion of the defective indicator gene viral vector, which in turn can be measured as a decrease in the expression of the reporter gene product.

Drug Screening

Drug screening is carried out using a resistance test vector system composed of an amplicon/gene X plasmid (pA-CMV-VS-gene X or pA-CMV-CS-gene X) and an indicator gene viral vector such as HCMV-$\beta_{2.7}$ F-IG/$\Delta$ gene X. The PDS may be derived from the genome of a laboratory strain of HCMV or from a patient-derived sample and may be of a wild-type sequence or may contain sequences which render the viral gene/drug target resistant to known anti-viral drugs.

Drug screening is performed as follows: an amplicon/gene X plasmid (pA-CMV-VS-gene X or pA-CMV-CS-gene X) and an indicator gene viral vector such as HCMV-$\beta_{2.7}$F-IG/$\Delta$ gene X are introduced into cells in the absence or presence of potential anti-viral compounds. After maintaining the cultures for an appropriate period of time to allow spread of the defective indicator gene viral vector through the culture, the level of amplicon expression of the reporter gene is measured and the degree of inhibition in the presence of drug is calculated.

EXAMPLE 10

Cytomegalovirus Drug Susceptibility and Resistance Test Using Resistance Test Vectors Comprising Patient-Derived Segment(s) and a Functional Indicator Gene Under Control of a Viral Promoter Indicator Gene Viral Vector—Construction A target host cell line is constructed that expresses a functional indicator gene under control of a HCMV viral promoter that is dependent on viral replication for activity. A defective helper viral vector (HCMV/Δ gene X) is constructed such that it is defective for replication by virtue of the fact that a segment of the genome containing the viral gene/drug target (gene X) has been deleted from the virus. The viral gene/drug target (gene X) is provided on an amplicon plasmid (pA-CMV-VS-gene X) which contains patient sequence acceptor sites (PSAS) and the cis-acting functions required for trans-complementation of the indicator gene viral vector (specifically, these include an HCMV origin of replication and HCMV "a" sequences that direct HCMV genome cleavage and packaging). The PSAS in pA-CMV-VS-gene X are designed to accept the PDS into a cassette containing the regulatory signals appropriate to the individual viral gene/drug target and are derived from the context of the viral gene/drug target in the wild type HCMV. The defective packaging/helper viral vector (HCMV/Δ gene X) and the amplicon/gene X plasmid (pA-CMV-VS-gene X) and the indicator cell line constitute a resistance test vector system. The defective packaging/helper viral vector can be propagated as a viral stock only in a packaging host cell/target host cell system in which the deleted viral gene/drug target is provided in trans. Viral stocks from such a packaging host cell/target host cell line can be prepared and used to infect packaging host cell/target host cells or DNA from these viral stocks can be isolated and used to transfect packaging host cells/target host cells as part of a resistance test vector system in conjunction with introduction of the amplicon/gene X plasmid by transfection into a cell type permissive for HCMV infection. Transcomplementation of the deleted gene by the amplicon/gene X plasmid results in a self-perpetuating virus population that results in increased expression of the reporter gene that is dependent on the activity of the viral gene/drug target encoded by the patient derived segment that has been introduced into the amplicon/gene X plasmid.

In another embodiment, the amplicon/gene X plasmid (pA-CMV-CS-gene X) comprises PSAS that accept the PDS in such a way as to express the patient-derived viral gene drug target (gene X) under control of a heterologous promoter and polyadenylation signals. In one embodiment of this example, an expression cassette comprising the CMV IE enhancer promoter region, PSAS, and the SV40 polyadenylation (pA) signal would be included on the amplicon/gene X plasmid (pA-CMV-CS-gene X) in addition to the cis-acting functions required for trans-complementation of the indicator gene viral vector (specifically, these include an HCMV origin of replication and HCMV "a" sequences that direct HCMV genome cleavage and packaging).

In various embodiments of this invention the viral gene/drug target can be 1) the HCMV DNA polymerase (UL54), 2) the phosphotransferase (UL97), 3) the viral serine protease (UL80), 4) any viral gene that encodes a real or potential target for a drug susceptibility test or a drug screening test.

Resistance Test Vectors—Construction

Resistance test vectors are prepared by 1) modifying the amplicon/gene X plasmid (pA-CMV-VS-gene X or pA-CMV-CS-gene X) by introducing unique sites, called patient sequence acceptor sites (PSAS) in the viral gene/drug target (gene X) coding region, 2) amplifying patient-derived segments (PDS) corresponding to the CMV drug target (gene X) from viral DNA present in the blood or tissues of infected patients, and 3) inserting the amplified segments precisely into the amplicon/gene X plasmid at the PSAS. A further embodiment comprises isolation of viral RNA from tissues and using reverse transcription to convert the RNA into DNA copies prior to amplification of the PDS.

Drug Susceptibility and Resistance Tests

Drug susceptibility and resistance tests are carried out with the resistance test vector system comprising an amplicon/gene X plasmid (pA-CMV-VS-geneX or pA-CMV-CS-gene X), a defective viral vector such as HCMV/Δ gene X, and a target cell line that contains an indicator gene under the control of an HCMV promoter that is dependent on viral replication for activity. In one embodiment the amplicon/gene X plasmid is transfected into the packaging host cells/target host cells and the cells are then infected with the defective helper viral vector. In another embodiment the amplicon/gene X plasmid and the defective helper viral vector DNA are cotransfected into the packaging host cells/target host cells simultaneously. Transcomplementation of the deleted gene by the amplicon/gene X plasmid results in a self-perpetuating virus population that results in increased expression of the reporter gene that is dependent on the activity of the viral gene/drug target encoded by the patient derived/segment that has been introduced into the amplicon/gene X plasmid. Anti-viral drugs that inhibit HCMV replication through inhibition of the viral gene/drug target limit the propagation and expansion of the defective helper viral vector, which in turn is measured as a decrease in the expression of the reporter gene product.

Drug Screening

Drug screening is carried out using a resistance test vector system comprising an amplicon/gene X plasmid (pA-CMV-VS-gene X or pA-CMV-CS-gene X) and a helper viral vector such as HCMV/Δ gene X. The PDS may be derived from the genome of a laboratory strain of HCMV or from a patient-derived sample and may be of a wild-type sequence or may contain sequences which render the viral gene/drug target resistant to known anti-viral drugs.

Drug screening is performed as follows: an amplicon/gene X plasmid (pA-CMV-VS-gene X or pA-CMV-CS-gene X) and a helper viral vector such as HCMV/Δ gene X are introduced into the indicator cells in the absence or presence of potential anti-viral compounds. After maintaining the cultures for an appropriate period of time to allow spread of the defective helper viral vector through the culture, the level of expression of the reporter gene is measured and the degree of inhibition in the presence of drug is calculated.

EXAMPLE 11

Figure 25A:
Figure 25B:
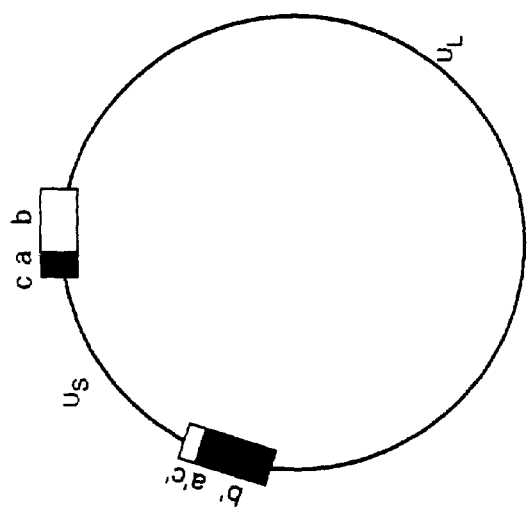
Figure 25C:
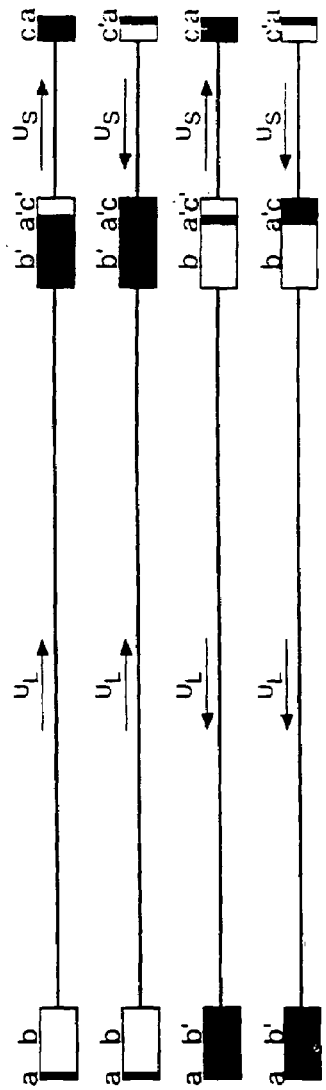
Figure 28:
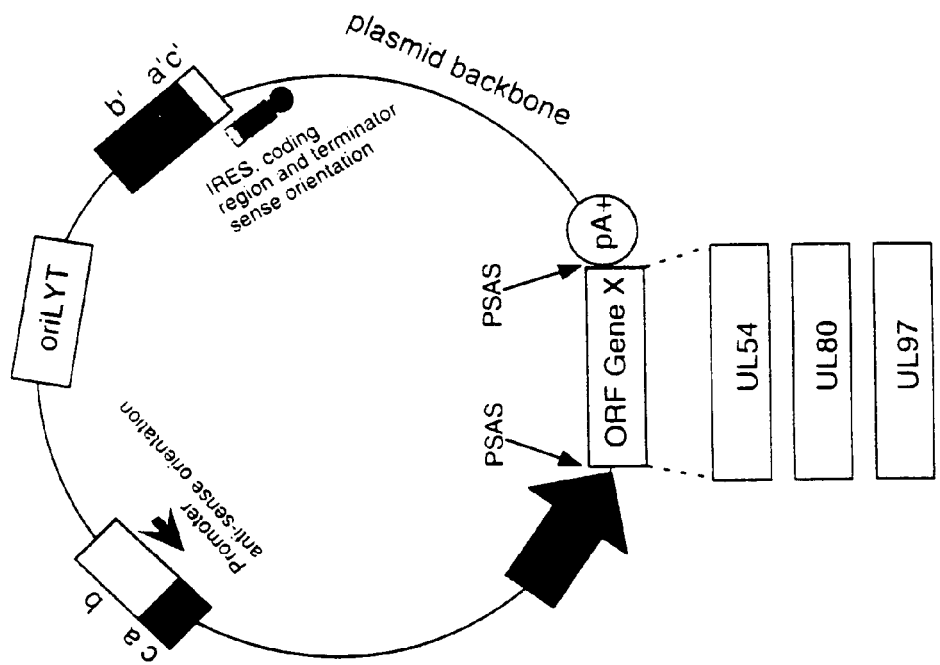
Figure 29:
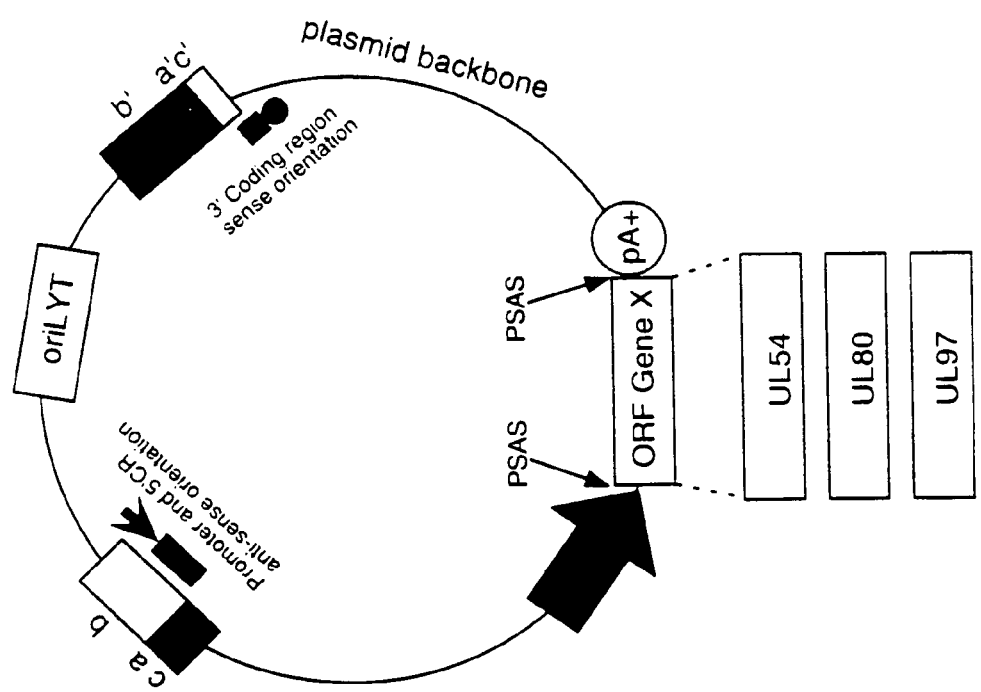
Figure 30A:
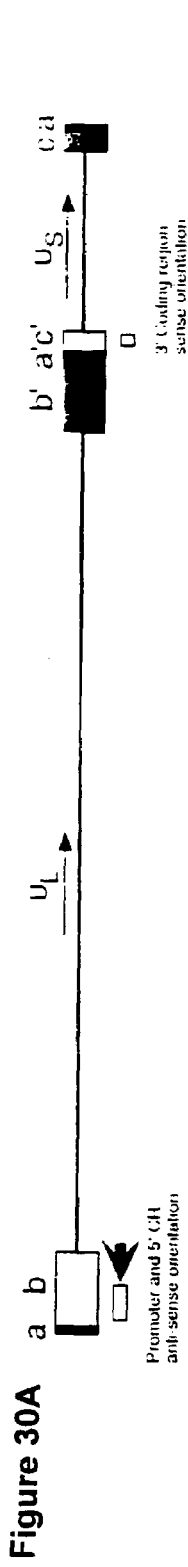
Figure 30B:
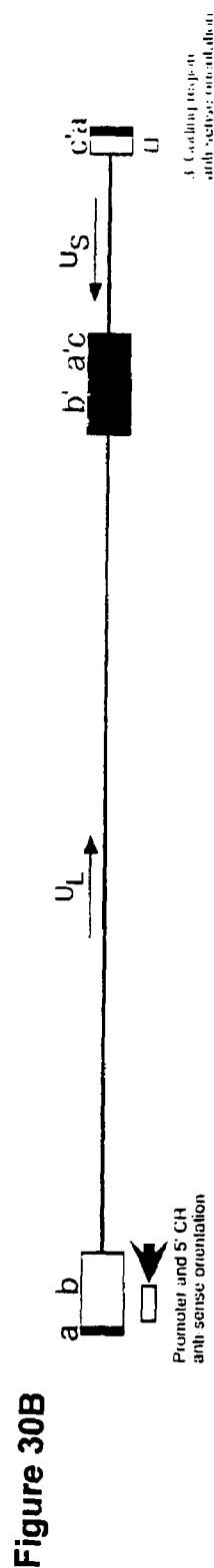
Figure 30C:
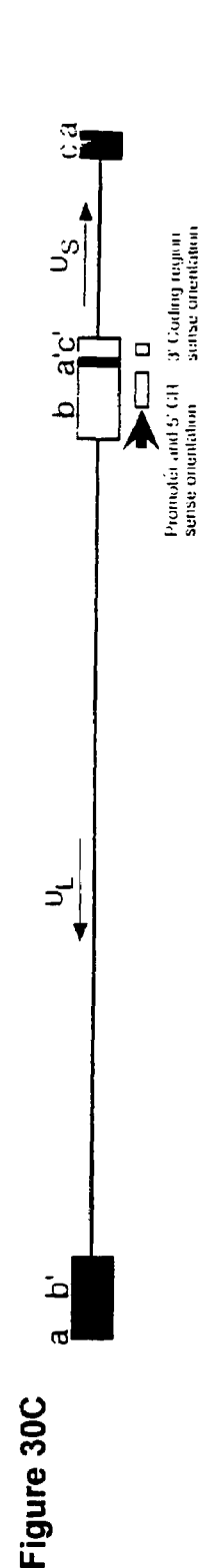
Figure 30D:
Figure 31:
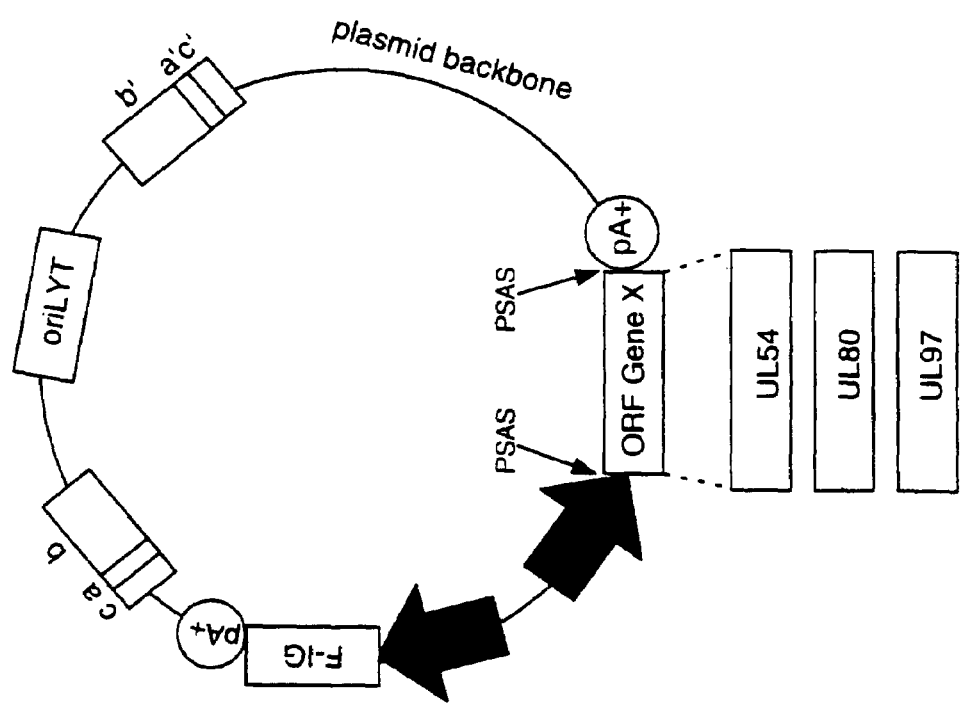

Cytomegalovirus Drug Susceptibility and Resistance Test Using Resistance Test Vectors Comprising Patient-Derived Segment(s) and a Non-Functional Indicator gene with a permuted promoter Indicator Gene Viral Vector—Construction Indicator gene viral vectors comprising a non-functional indicator gene with a permuted promoter are designed using a HCMV amplicon plasmid containing a viral gene which is the target of an anti-viral drug(s) (gene X). The indicator gene viral vector (pA-CMV-VS-gene X-(NF-IG) PP) comprising a non-functional indicator gene with a permuted promoter, all of the cis-acting regulatory elements that are required for HCMV replication (i.e. "a" sequences and the HCMV origin of replication), and a viral gene/drug target expression cassette with PSAS. The PSAS are designed to accept the PDS into a cassette comprising the regulatory signals appropriate to the individual viral gene/drug target and are derived from the context of the viral gene/drug target in the wild type HCMV. The non-functional indicator gene cassette is assembled such that the promoter region is positioned either in the wrong orientation, i.e. anti-sense, with respect to the indicator gene ORF or in the wrong position, i.e. downstream, of the indicator gene ORF (FIG. 28). The promoter and indicator gene ORF are separated and positioned within the regions of the genome that undergo inversion with respect to each other during replication of the genome (FIG. 25). This inversion, when it occurs, brings the two parts of the permuted promoter indicator gene cassette into the proper orientation to allow expression of the indicator gene product. A defective helper viral vector (HCMV/Δ gene X) is defective for replication since a segment of the genome containing the viral gene/drug target (gene X) is deleted from the virus. The indicator gene viral vector and the defective helper/packaging viral vector constitute a resistance test vector system. The defective helper viral vector (HCMV/Δ gene X) can be propagated only in a cell system in which the deleted viral gene/drug target is provided in trans. Viral stocks packaging host cell/target host cell line can be prepared and used to infect packaging host cells/target host cells or DNA from these viral stocks can be isolated and used to transfect packaging host cells/target host cells as part of a resistance test vector system in conjunction with introduction of the indicator gene viral vector by transfection into a target cell permissive for HCMV infection. Trans-complementation of the deleted gene by the indicator gene viral vector results in a self-perpetuating virus population. During replication of the indicator gene viral vector concatamers of the indicator gene viral vector are formed and inversions occur as part of the normal replication cycle of HCMV (See FIG. 25) and result in a rearrangement of the 2 segments of the permuted promoter cassette such that they now are in the proper orientation to direct transcription of an RNA that will allow expression of the reporter gene.

In another embodiment, the indicator gene viral vector contains PSAS that accept the PDS in such a way as to express the patient-derived gene X sequences under control of a heterologous promoter and polyadenylation signals. In one embodiment of this example, an expression cassette containing the CMV IE enhancer promoter region, PSASs, and the SV40 polyadenylation (pA) signal would be included on the indicator gene viral vector (pA-CMV-CS-gene X-(NF-IG) PP) in addition to the cis-acting functions required for trans-complementation of the indicator gene viral vector (specifically, these comprise an HCMV origin of replication and HCMV "a" sequences that direct HCMV genome cleavage and packaging) and the permuted promoter cassette segments.

In various embodiments of this invention the viral gene/drug target can be 1) the HCMV DNA polymerase (UL54), 2) the phosphotransferase (UL97), 3) the viral serine protease (UL80), 4) any viral gene that encodes a real or potential target for a drug susceptibility test or a drug screening test.

Resistance Test Vectors—Construction

Resistance test vectors are prepared by 1) modifying the indicator gene viral vector (pA-CMV-VS-gene X-(NF-IG) PP or pA-CMV-CS-gene X-(NF-IG) PP) by introducing unique restriction sites, called patient sequence acceptor sites (PSAS) in the viral gene/drug target (gene X) coding region, 2) amplifying patient-derived segments (PDS) corresponding to the CMV drug target (gene X) from viral DNA present in the blood or tissues of infected patients, and 3) inserting the amplified segments precisely into the amplicon/gene X plasmid at the PSAS. A further embodiment comprises isolation of viral RNA from tissues and using reverse transcription to convert the RNA into DNA copies prior to amplification of the PDS.

Drug Susceptibility and Resistance Tests

Drug susceptibility and resistance tests are carried out with the resistance test vector system comprising an indicator gene viral vector (pA-CMV-VS-gene X-NF-IG)PP or pA-CMV-CS-gene X-(NF-IG)PP) and a defective helper viral vector such as HCMV/Δ gene X. In one embodiment the indicator gene viral vector (pA-CMV-VS-gene X-(NF-IG)PP or pA-CMV-CS-gene X-(NF-IG)PP) is transfected into appropriate cells and the cells are then infected with the defective helper viral vector (HCMV/Δ gene X). In another embodiment the indicator gene viral vector and the defective helper/packaging viral vector DNA are cotransfected into the packaging host cells/target host cells simultaneously. Transcomplementation of the deleted gene by the indicator gene viral vector results in a self-perpetuating virus population. During replication of the indicator gene viral vector concatamers of the indicator gene viral vector are formed and inversions occur as part of the normal replication cycle of HCMV and result in a rearrangement of the 2 segments of the permuted promoter cassette such that they now are in the proper orientation to direct transcription of an RNA that will allow expression of the indicator gene. Expression of the indicator gene is dependent on the activity of the viral gene/drug target encoded by the patient derived segment that has been introduced into the indicator gene viral vector. Anti-viral drugs that inhibit HCMV replication through inhibition of the viral gene/drug target limits the replication of the indicator gene viral vector, which in turn limits the number of genomes in which inversion can occur and can be measured as a decrease in the expression of the reporter gene product.

Drug Screening

Drug screening is carried out using a resistance test vector system comprising an indicator gene viral vector (pA-CMV-VS-gene X-(NF-IG)PP or pA-CMV-CS-gene X-(NF-IG)PP) and a defective packaging/helper viral vector such as HCMV/Δ gene X. The PDS may be derived from the genome of a laboratory strain of HCMV or from a patient-derived sample and may be of a wild-type sequence or may contain sequences which render the viral gene/drug target resistant to known anti-viral drugs.

Drug screening is performed as follows: an indicator gene viral vector (pA-CMV-VS-gene X-(NF-IG)PP or pA-CMV-CS-gene X-(NF-IG)PP) and a defective helper viral vector such as HCMV/Δ gene X are introduced into cells in the absence or presence of potential anti-viral compounds. After maintaining the cultures for an appropriate period of time to allow replication of the indicator gene viral vector, the level of expression of the reporter gene is measured and the degree of inhibition in the presence of drug is calculated.

EXAMPLE 12

Figure 11E:
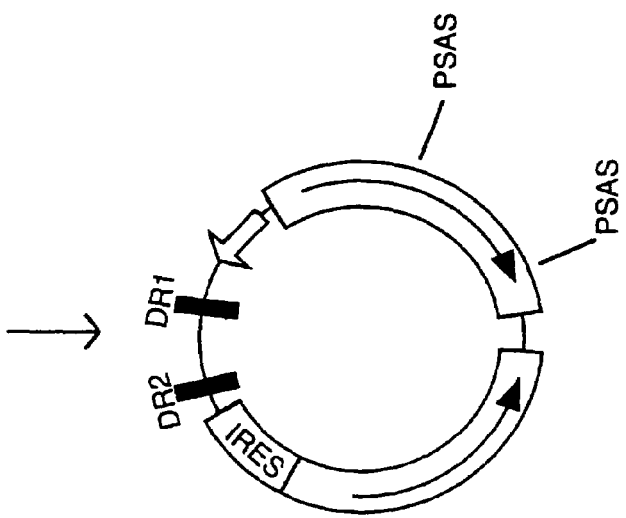

Cytomegalovirus Drug Susceptibility and Resistance Test Using Resistance Test Vectors Comprising Patient-Derived Segment(s) and a Non-Functional Indicator Gene with a Permuted Coding Region Indicator Gene Viral Vector—Construction Indicator gene viral vectors comprising a non-functional indicator gene with a permuted coding region are designed using a HCMV amplicon plasmid containing a viral gene which is the target of an anti-viral drug(s) (gene X). The indicator gene viral vector (pA-CMV-VS-gene X-(NF-IG) PCR) comprises a non-functional indicator gene with a permuted coding region, all of the cis-acting regulatory elements that are required for HCMV replication (i.e. "a" sequences and the HCMV origin of replication), and a viral gene/drug target (gene X) expression cassette with PSAS. The PSAS are designed to accept the PDS into a cassette containing the regulatory signals appropriate to the individual viral gene/drug target and are derived from the context of the viral gene/drug target in the wild type HCMV. The non-functional indicator gene cassette is assembled such that the promoter region and 5' portion of the coding region are positioned either in the wrong orientation, i.e. anti-sense, with respect to the remaining 3' portion of the coding region or in the wrong position, i.e. downstream, of the remaining 3' portion of the coding region (FIG. 15). The promoter and 5' portion of the coding region are separated from the 3' portion of the coding region and positioned within the regions of the genome that undergo inversion with respect to each other during replication of the genome (FIG. 11). This inversion, when it occurs, brings the two parts of the permuted coding region indicator gene cassette into the proper orientation to allow expression of the indicator gene product (FIG. 16). A defective helper viral vector (HCMV/Δ gene X) is defective for replication by virtue of the fact that a segment of the genome containing the viral gene/drug target (gene X) is deleted from the virus. The indicator gene viral vector and the defective helper/packaging viral vector constitute a resistance test vector system. The defective helper/packaging viral vector (HCMV/Δ gene X) is propagated only in a packaging host cell/target host cell system in which the deleted viral gene is provided in trans. Viral stocks from such a packaging host cell/target host cell line can be prepared and used to infect cells or DNA from these viral stocks can be isolated and used to transfect packaging host cells/target host cells as part of a resistance test vector system in conjunction with introduction of the indicator gene viral vector by transfection into a cell type permissive for HCMV infection. Trans-complementation of the deleted gene by the indicator gene viral vector results in a self-perpetuating virus population. During replication of the indicator gene viral vector concatamers of the indicator gene viral vector are formed and inversions occur as part of the normal replication cycle of HCMV and result in a rearrangement of the 2 segments of the permuted coding region cassette such that they now are in the proper orientation to direct transcription of an RNA that will allow expression of the reporter gene (FIG. 16).

In another embodiment, the indicator gene viral vector comprises PSAS that accept the PDS in such a way as to express the patient-derived viral gene sequences (gene X) under control of a heterologous promoter and polyadenylation signals. In one embodiment, an expression cassette comprising the CMV IE enhancer promoter region, PSASs, and the SV40 polyadenylation (pA) signal is included on the indicator gene viral vector (pA-CMV-CS-gene X-(NF-IG) PCR) in addition to the cis-acting functions required for trans-complementation of the indicator gene viral vector (specifically, these include an HCMV origin of replication and HCMV "a" sequences that direct HCMV genome cleavage and packaging) and the permuted coding region cassette segments.

In various embodiments of this invention the viral gene/drug target can be 1) the HCMV DNA polymerase (UL54), 2) the phosphotransferase (UL97), 3) the viral serine protease (UL80), 4) any viral gene that encodes a real or potential target for a drug susceptibility test or a drug screening test.

Resistance Test Vectors—Construction

Resistance test vectors are prepared by 1) modifying the indicator gene viral vector (pA-CMV-VS-gene X-(NF-IG) PCR or pA-CMV-CS-gene X-(NF-IG)PCR) by introducing unique restriction sites, called patient sequence acceptor sites (PSAS) in the viral gene/drug target (gene X) coding region, 2) amplifying patient-derived segments (PDS) corresponding to the CMV drug target (gene X) from viral DNA present in the blood or tissues of infected patients, and 3) inserting the amplified segments precisely into the amplicon/gene X plasmid at the PSAS. A further embodiment comprises isolation of viral RNA from tissues and using reverse transcription to convert the RNA into DNA copies prior to amplification of the PDS.

Drug Susceptibility and Resistance Tests

Drug susceptibility and resistance tests are carried out with the resistance test vector system comprising an indicator gene viral vector (pA-CMV-VS-gene X-(NF-IG)PCR or pA-CMV-CS-gene X-(NF-IG)PCR) and a defective helper viral vector such as HCMV/Δ gene X. In one embodiment the indicator gene viral vector (pA-CMV-VS-gene X-(NF-IG)PCR or pA-CMV-CS-gene X-(NF-IG)PCR) is transfected into appropriate target host cells and the cells are then infected with the defective helper viral vector (HCMV/Δ gene X). In another embodiment the indicator gene viral vector and the defective helper viral vector DNA are co-transfected into the cells simultaneously. Transcomplementation of the deleted gene by the indicator gene viral vector results in a self-perpetuating virus population. During replication of the indicate gene viral vector concatamers of the indicator gene viral vector are formed and inversions occur as part of the normal replication cycle of HCMV and result in a rearrangement of the 2 segments of the permuted coding region cassette such that they now are in the proper orientation to direct transcription of an RNA that will allow expression of the reporter gene (FIG. 16). Expression of the reporter gene is dependent on the activity of the viral gene/drug target encoded by the patient derived segment that has been introduced into the indicator gene viral vector. Anti-viral drugs that inhibit HCMV replication through inhibition of the viral gene/drug target limits the replication of the indicator gene viral vector, which in turn limits the number of genomes in which inversion can occur and can be measured as a decrease in the expression of the reporter gene product.

Drug Screening

Drug screening is carried out using a resistance test vector system comprising an indicator gene viral vector (pA-CMV-VS-gene X-(NF-IG)PCR or pA-CMV-CS-gene X-(NF-IG) PCR) and a defective helper viral vector such as HCMV/Δ gene X. The PDS may be derived from the genome of a laboratory strain of HCMV or from a patient-derived sample and may be of a wild-type sequence or may contain sequences which render the viral gene/drug target resistant to known anti-viral drugs.

Drug screening is performed as follows: an indicator gene viral vector (pA-CMV-VS-gene X-(NF-IG)PCR or pA-CMV-CS-gene X-(NF-IG)PCR) and a defective helper viral vector such as HCMV/Δ gene X are introduced into cells in the absence or presence of potential anti-viral compounds. After maintaining the cultures for an appropriate period of time to allow replication of the indicator gene viral vector, the level of expression of the reporter gene is measured and the degree of inhibition in the presence of drug is calculated.

EXAMPLE 13

Cytomegalovirus Drug Susceptibility and Resistance Test Using Resistance Test Vectors Comprising Patient-Derived Segment(s) and a Functional Indicator Gene Indicator Gene Viral Vector—Construction Indicator gene viral vectors containing a functional indicator gene under control of an endogenous viral promoter are based on an HCMV amplicon plasmid containing a viral gene which is the target of an anti-viral drug(s) (gene X). The indicator gene viral vector (pA-CMV-VS-gene X-F-IG) comprises a functional indicator gene under the control of a viral promoter dependent on viral replication, all of the cis-acting regulatory elements that are required for HCMV replication (i.e. "a" sequences and the HCMV origin of replication), and a viral gene/drug target (gene X) expression cassette with PSAS (FIG. 17). The PSAS are designed to accept the PDS into a cassette comprising the regulatory signals appropriate to the individual viral gene and are derived from the context of the viral gene/drug target (gene X) in the wild type HCMV. A defective helper viral vector (HCMV/Δ gene X) is defective for replication by virtue of the fact that a segment of the genome containing the viral gene/drug target has been deleted from the virus. The indicator gene viral vector and the defective helper viral vector constitute a resistance test vector system. The defective helper viral vector (HCMV/Δ gene X) can be propagated only in a packaging host cell/target host cell system in which the deleted viral gene is provided in trans. Viral stocks from such a cell line are prepared and used to infect packaging host cells/target host cells or DNA from these viral stocks are isolated and used to transfect packaging host cells/target host cells as part of a resistance test vector system in conjunction with introduction of the indicator gene viral vector by transfection into a cell type permissive for HCMV infection. Trans-complementation of the deleted gene by the indicator gene viral vector results in a self-perpetuating virus population. Replication of the indicator gene viral vector depends on the transcomplementation between the indicator gene viral vector pA-CMV-VS-gene X-F-IG and the defective helper viral vector HCMV/Δ gene X.

In another embodiment, the indicator gene viral vector comprises PSAS that accept the PDS in such a way as to express the patient-derived viral gene/drug target (gene X) under control of a heterologous promoter and polyadenylation signals. In one embodiment, an expression cassette comprising the CMV IE enhancer promoter region, PSAS, and the SV40 polyadenylation (pA) signal is included on the indicator gene viral vector (pA-CMV-CS-gene X-F-IG) in addition to the cis-acting functions required for trans-complementation of the indicator gene viral vector (specifically, these include an HCMV origin of replication and HCMV "a" sequences that direct HCMV genome cleavage and packaging) and the permuted coding region cassette segments.

In various embodiments of this invention the viral gene/drug target can be 1) the HCMV DNA polymerase (UL54), 2) the phosphotransferase (UL97), 3) the viral serine protease (UL80), 4) any viral gene that encodes a real or potential target for a drug susceptibility test or a drug screening test.

Resistance Test Vectors—Construction

Resistance test vectors are prepared by 1) modifying the indicator gene viral vector (pA-CMV-VS-gene X-F-IG or pA-CMV-CS-gene X-F-IG) by introducing unique restriction sites, called patient sequence acceptor sites (PSAS) in the viral gene/drug target (gene X) coding region, 2) amplifying patient-derived segments (PDS) corresponding to the CMV drug target (gene X) from viral DNA present in the blood or tissues of infected patients, and 3) inserting the amplified segments precisely into the amplicon/gene X plasmid at the PSAS. A further embodiment comprises isolation of viral RNA from tissues and using reverse transcription to convert the RNA into DNA copies prior to amplification of the PDS.

Drug Susceptibility and Resistance Tests

Drug susceptibility and resistance tests are carried out with the resistance test vector system comprising an indicator gene viral vector (pA-CMV-VS-gene X-F-IG or pA-CMV-CS-gene X-F-IG) and a defective helper viral vector such as HCMV/Δ gene X. In one embodiment the indicator gene viral vector (pA-CMV-VS-gene X-F-IG or pA-CMV-CS-gene X-F-IG) is transfected into appropriate packaging host cells/target host cells and the cells are then superinfected with the defective helper viral vector (HCMV/Δ gene X). In another embodiment the indicator gene viral vector and the defective helper viral vector DNA are cotransfected into the packaging host cells/target host cells simultaneously. Transcomplementation of the deleted gene by the indicator gene viral vector results in a self-perpetuating virus population that results in increased expression of the reporter gene that is directly dependent on the activity of the viral gene/drug target encoded by the patient derived segment that has been introduced into the indicator gene viral vector. Anti-viral drugs that inhibit HCMV replication through inhibition of the viral gene/drug target will limit the propagation and expansion of the defective helper viral vector, which in turn can be measured as a decrease in the expression of the reporter gene product.

Drug Screening

Drug screening is carried out using a resistance test vector system comprising an indicator gene viral vector (pA-CMV-VS-gene X-F-IG or pA-CMV-CS-gene X-F-IG) and a defective helper viral vector such as HCMV/Δ gene X. The PDS may be derived from the genome of a laboratory strain of HCMV or from a patient-derived sample and may be of a wild-type sequence or may contain sequences which render the viral gene/drug target resistant to known anti-viral drugs. Drug screening is performed as follows: an indicator gene viral vector (pA-CMV-VS-gene X-F-IG or pA-CMV-CS-gene X-F-IG) and a defective helper viral vector such as HCMV/Δ gene X are introduced into cells in the absence or presence of potential anti-viral compounds. After maintaining the cultures for an appropriate period of time to allow replication of the indicator gene viral vector, the level of expression of the reporter gene is measured and the degree of inhibition in the presence of drug is calculated.

What is claimed is:

1. A method for determining the susceptibility of a human immunodeficiency virus ("HIV") to a compound, said method comprising:
   (a) contacting a cell with a viral particle in the presence of said compound, wherein the viral particle comprises a HIV viral segment and an indicator gene, wherein expression of said indicator gene is dependent upon the HIV viral segment, and wherein said viral particle does not comprise all viral genes necessary to produce an infectious viral particle,
   (b) detecting the expression of said indicator gene, and
   (c) comparing the expression detected in step (b) and a control expression of said indicator gene, thereby determining the susceptibility of said HIV to said compound.

2. The method of claim 1, wherein said control expression of said indicator gene is determined from a standard curve generated by performing the method of claim 1 with a standard laboratory HIV viral segment.

3. The method of claim 1, wherein said control expression is determined by performing the method of claim 1 with said viral segment in a control cell, wherein said control cell is not contacted with said compound.

4. A method for determining the susceptibility of said HIV to two or more compounds, comprising performing the method of claim 1 with said two or more compounds, thereby determining the susceptibility of said HIV to said two or more compounds.

5. The method of claim 1, wherein said HIV viral segment comprises DNA encoding vif, vpr, tat, rev, vpu, and nef.

6. The method of claim 1, wherein said HIV viral segment encodes a protein that is a target of said compound.

7. The method of claim 1, wherein said HIV viral segment encodes two proteins that are targets of said compound.

8. The method of claim 1, wherein said HIV viral segment comprises an HIV gag-pol gene.

9. The method of claim 6, wherein said protein is HIV protease.

10. The method of claim 6, wherein said protein is HIV reverse transcriptase.

11. The method of claim 1, wherein said viral segment is a patient-derived segment.

12. The method of claim 1, wherein said indicator gene is a luciferase gene.

13. The method of claim 1, wherein said indicator gene is an *E. coli* lacZ gene.

14. The method of claim 1, wherein said cell is a human cell.

15. The method of claim 14, wherein said cell is a human embryonic kidney cell, a human T cell, a 293 cell, a Jurkat cell, a H9 cell, or a CEM cell.

16. The method of claim 14, wherein said cell is a 293 cell.

17. A method for determining susceptibility of an HIV present in a patient to an antiviral compound, comprising:
   (a) contacting a cell with said compound, wherein said cell comprises a patient-derived from said patient and an indicator gene, wherein expression of said indicator gene is dependent upon the patient-derived segment, and wherein said cell does not comprise all viral genes necessary to produce an infectious viral particle,
   (b) detecting the expression of said indicator gene, and
   (c) comparing the expression detected in step (b) and a control expression of said indicator gene, thereby determining the susceptibility of said HIV to said compound.

18. The method of claim 17, wherein said control expression of said indicator gene is determined from a standard curve generated by performing the method of claim 17 with a standard laboratory HIV viral segment, and wherein a decrease in the susceptibility of said HIV to said antiviral compound relative to said standard curve indicates that said HIV is resistant to said antiviral compound.

19. The method of claim 17, wherein said control expression is determined by performing the method of claim 17 with said patient-derived segment in a control cell, wherein said control cell is not contacted with said compound.

20. A method for determining the progression or development of resistance of an HIV present in a patient to an antiviral compound, comprising:
   (a) determining the susceptibility of said HIV to said antiviral compound according to the method of claim 17, wherein said patient-derived segment is obtained from said patient at a first time;
   (b) determining the susceptibility of said HIV to said antiviral compound according to the method of claim 17, wherein the patient-derived segment is obtained from said patient at a later second time; and
   (c) comparing the susceptibility of said HIV to said antiviral compound determined in steps (a) and (b), wherein a decrease in the susceptibility in (b) as compared to that in (a) determines development or progression of resistance to said antiviral compound in said HIV infecting said patient.

21. A method for determining the biological effectiveness of a candidate anti-HIV compound, comprising:
   (a) contacting a cell with a viral particle in the presence of said candidate anti-HIV compound, wherein the viral particle comprises an HIV viral segment and an indicator gene, the expression of said indicator gene is dependent upon said HIV viral segment, and said viral particle does not comprise all viral genes necessary to produce an infectious viral particle,
   (b) detecting expression of the indicator gene, and
   (c) comparing the expression detected in step (b) and a control expression of said indicator gene, thereby determining the biological effectiveness of said candidate anti-HIV compound.

22. The method of claim 21, wherein said control expression of said indicator gene is determined by performing the method of claim 21 in the absence of said candidate anti-HIV compound.

23. The method of claim 21, wherein said control activity of said indicator gene is a standard curve of expression of said indicator gene determined by performing the method of claim 21 at varying concentrations of said candidate anti-HIV compound.

* * * * *

SEQUENCE LISTING

<160> NUMBER OF SEQ ID NOS: 105

<210> SEQ ID NO 1
<211> LENGTH: 42
<212> TYPE: DNA
<213> ORGANISM: HUMAN

<400> SEQUENCE: 1
agtgaattag cccttccacc cgggtcgagc ttggcgtaat ca					42

<210> SEQ ID NO 2
<211> LENGTH: 42
<212> TYPE: DNA
<213> ORGANISM: HUMAN

<400> SEQUENCE: 2
ctgttgggaa gggcgatctc tagatgctag agattttcca ca					42

<210> SEQ ID NO 3
<211> LENGTH: 44
<212> TYPE: DNA
<213> ORGANISM: HUMAN

<400> SEQUENCE: 3
ctcctcctcc aagtctgagc ggccgccttt agcatctgat gcac					44

<210> SEQ ID NO 4
<211> LENGTH: 44
<212> TYPE: DNA
<213> ORGANISM: HUMAN

<400> SEQUENCE: 4
ctcctcctcc aagtctgagc ggccgccata tggtgtttta ctaa					44

<210> SEQ ID NO 5
<211> LENGTH: 36
<212> TYPE: DNA
<213> ORGANISM: HUMAN

<400> SEQUENCE: 5
ggtctaacca gagagacccg gttcactaaa cgagct					36

<210> SEQ ID NO 6
<211> LENGTH: 32
<212> TYPE: DNA
<213> ORGANISM: HUMAN

<400> SEQUENCE: 6
gaattcgcgg ccgcaattcc gcccctctcc ct					32

<210> SEQ ID NO 7
<211> LENGTH: 32
<212> TYPE: DNA
<213> ORGANISM: HUMAN

<400> SEQUENCE: 7
gttaacgcgg ccgcgatata gttcctcctt tc					32

<210> SEQ ID NO 8
<211> LENGTH: 32
<212> TYPE: DNA
<213> ORGANISM: HUMAN

<400> SEQUENCE: 8
gaattctcgc gaccatggaa gacgccaaaa ac                                32

<210> SEQ ID NO 9
<211> LENGTH: 36
<212> TYPE: DNA
<213> ORGANISM: HUMAN

<400> SEQUENCE: 9
gttaacagat ctctcgagtt acaatttgga ctttcc                            36

<210> SEQ ID NO 10
<211> LENGTH: 56
<212> TYPE: DNA
<213> ORGANISM: HUMAN

<400> SEQUENCE: 10
agacgggcac acactactta atacgactca ctatagggtg aagcactcaa ggcaag      56

<210> SEQ ID NO 11
<211> LENGTH: 42
<212> TYPE: DNA
<213> ORGANISM: HUMAN

<400> SEQUENCE: 11
aagagtgacc tgagggaagt taacggatac agttccttgt ct                     42

<210> SEQ ID NO 12
<211> LENGTH: 42
<212> TYPE: DNA
<213> ORGANISM: HUMAN

<400> SEQUENCE: 12
tccagcactg actaatttgt cgacttgttc atttcctcca at                     42

<210> SEQ ID NO 13
<211> LENGTH: 42
<212> TYPE: DNA
<213> ORGANISM: HUMAN

<400> SEQUENCE: 13
taacgcctat tctgctatgc cgacacccaa ttctgaaaat gg                     42

<210> SEQ ID NO 14
<211> LENGTH: 42
<212> TYPE: DNA
<213> ORGANISM: HUMAN

<400> SEQUENCE: 14
aaggatacag ttccttgtcg atcggctcct gcttctgagg gg                     42

<210> SEQ ID NO 15
<211> LENGTH: 42
<212> TYPE: DNA
<213> ORGANISM: HUMAN

<400> SEQUENCE: 15
ctaaaaatag tactttccgg atcccagcac tgactaattt at                     42

<210> SEQ ID NO 16
<211> LENGTH: 42
<212> TYPE: DNA

```
<213> ORGANISM: HUMAN

<400> SEQUENCE: 16
ttagctcctt cggtcctcca atcgttgtca gaagtaagtt gg          42

<210> SEQ ID NO 17
<211> LENGTH: 42
<212> TYPE: DNA
<213> ORGANISM: HUMAN

<400> SEQUENCE: 17
gtcccagata agtgccaagg attcgttcac taatcgaatg ga          42

<210> SEQ ID NO 18
<211> LENGTH: 33
<212> TYPE: DNA
<213> ORGANISM: HUMAN

<400> SEQUENCE: 18
gaattcgtta acttccctca gatcactctt tgg                    33

<210> SEQ ID NO 19
<211> LENGTH: 30
<212> TYPE: DNA
<213> ORGANISM: HUMAN

<400> SEQUENCE: 19
gttaacgtcg acttgttcat ttcctccaat                        30

<210> SEQ ID NO 20
<211> LENGTH: 55
<212> TYPE: DNA
<213> ORGANISM: HUMAN

<400> SEQUENCE: 20
gaattccgat cgacaaggaa ctgtatcctt aacttccct cagatcactc tttgg    55

<210> SEQ ID NO 21
<211> LENGTH: 52
<212> TYPE: DNA
<213> ORGANISM: HUMAN

<400> SEQUENCE: 21
gttaacggat cccagcactg actaatttat ctacttgttc atttcctcca at      52

<210> SEQ ID NO 22
<211> LENGTH: 33
<212> TYPE: DNA
<213> ORGANISM: HUMAN

<400> SEQUENCE: 22
gaattcgtta acttccctca ratcmctctt tgg                    33

<210> SEQ ID NO 23
<211> LENGTH: 30
<212> TYPE: DNA
<213> ORGANISM: HUMAN

<400> SEQUENCE: 23
gttaacgtcg acttkytcat ttcctccwat                        30

<210> SEQ ID NO 24
<211> LENGTH: 55
```

```
<212> TYPE: DNA
<213> ORGANISM: HUMAN

<400> SEQUENCE: 24
gaattccgat cgacaaggaa ctgtatcctt taacttccct caratcmctc tttgg          55

<210> SEQ ID NO 25
<211> LENGTH: 52
<212> TYPE: DNA
<213> ORGANISM: HUMAN

<400> SEQUENCE: 25
gttaacggat cccagcactg actaatttat ctacttkytc atttcctccw at             52

<210> SEQ ID NO 26
<211> LENGTH: 36
<212> TYPE: DNA
<213> ORGANISM: HUMAN

<400> SEQUENCE: 26
atctcttacc tgtcctatct aacaggccag gattaa                               36

<210> SEQ ID NO 27
<211> LENGTH: 35
<212> TYPE: DNA
<213> ORGANISM: HUMAN

<400> SEQUENCE: 27
gaattctcgc gaccaccatg gcgcgttcaa cgctc                                35

<210> SEQ ID NO 28
<211> LENGTH: 30
<212> TYPE: DNA
<213> ORGANISM: HUMAN

<400> SEQUENCE: 28
gttaacagat cttcatggct cgtactctat                                      30

<210> SEQ ID NO 29
<211> LENGTH: 72
<212> TYPE: DNA
<213> ORGANISM: HUMAN

<400> SEQUENCE: 29
gaattcgcgc gcaagcggcc gcaacccggg aaaagcttaa gcatgcaacc cgggaagaat     60
tcaatcgcga aa                                                         72

<210> SEQ ID NO 30
<211> LENGTH: 72
<212> TYPE: DNA
<213> ORGANISM: HUMAN

<400> SEQUENCE: 30
gttaacgcgc gcttctcgag ttgcggccgc ttgctagctt agatctttgg gccctttcgc     60
gattgaattc tt                                                         72

<210> SEQ ID NO 31
<211> LENGTH: 30
<212> TYPE: DNA
<213> ORGANISM: HUMAN

<400> SEQUENCE: 31
```

```
gaattcaagc ttggccattg catacgttgt                                30
```

<210> SEQ ID NO 32
<211> LENGTH: 24
<212> TYPE: DNA
<213> ORGANISM: HUMAN

<400> SEQUENCE: 32

```
gttaacgcat gcataagaag ccaa                                      24
```

<210> SEQ ID NO 33
<211> LENGTH: 30
<212> TYPE: DNA
<213> ORGANISM: HUMAN

<400> SEQUENCE: 33

```
gaattcgcat gctcccctgc tccgacccgg                                30
```

<210> SEQ ID NO 34
<211> LENGTH: 30
<212> TYPE: DNA
<213> ORGANISM: HUMAN

<400> SEQUENCE: 34

```
gttaacgaat tctcctgcgg ggagaagcag                                30
```

<210> SEQ ID NO 35
<211> LENGTH: 30
<212> TYPE: DNA
<213> ORGANISM: HUMAN

<400> SEQUENCE: 35

```
gaattcagat ctgccatacc acatttgtag                                30
```

<210> SEQ ID NO 36
<211> LENGTH: 30
<212> TYPE: DNA
<213> ORGANISM: HUMAN

<400> SEQUENCE: 36

```
gttaacgcta gctccagaca tgataagata                                30
```

<210> SEQ ID NO 37
<211> LENGTH: 30
<212> TYPE: DNA
<213> ORGANISM: HUMAN

<400> SEQUENCE: 37

```
gaattcgcta gcatcccgcc cctaactccg                                30
```

<210> SEQ ID NO 38
<211> LENGTH: 30
<212> TYPE: DNA
<213> ORGANISM: HUMAN

<400> SEQUENCE: 38

```
gttaacgtcg acgcaaaagc ctaggcctcc                                30
```

<210> SEQ ID NO 39
<211> LENGTH: 24
<212> TYPE: DNA
<213> ORGANISM: HUMAN

<400> SEQUENCE: 39

```
gaattctcgc gaacagttgg ccct                                           24

<210> SEQ ID NO 40
<211> LENGTH: 30
<212> TYPE: DNA
<213> ORGANISM: HUMAN

<400> SEQUENCE: 40
gttaacagat ctttacgcga acgcgaagtc                                     30

<210> SEQ ID NO 41
<211> LENGTH: 66
<212> TYPE: DNA
<213> ORGANISM: HUMAN

<400> SEQUENCE: 41
gttaacgaat tcttgcaaaa agctttgcaa gatggataaa gttttagaa actccagtag     60 gactcc                                                               66

<210> SEQ ID NO 42
<211> LENGTH: 63
<212> TYPE: DNA
<213> ORGANISM: HUMAN

<400> SEQUENCE: 42
gaattctcgc gatctagacg ttctaccttt ctcttctttt ttggaggagt cctactggag    60
ttt                                                                  63

<210> SEQ ID NO 43
<211> LENGTH: 35
<212> TYPE: DNA
<213> ORGANISM: HUMAN

<400> SEQUENCE: 43
gttaacgaat tcccaccatg attgaacaag atgga                               35

<210> SEQ ID NO 44
<211> LENGTH: 30
<212> TYPE: DNA
<213> ORGANISM: HUMAN

<400> SEQUENCE: 44
gaattcagat cttcagaaga actcgtcaag                                     30

<210> SEQ ID NO 45
<211> LENGTH: 39
<212> TYPE: DNA
<213> ORGANISM: HUMAN

<400> SEQUENCE: 45
ccccgtgcca agagtgacta cgtaagtacc gcctataga                           39

<210> SEQ ID NO 46
<211> LENGTH: 39
<212> TYPE: DNA
<213> ORGANISM: HUMAN

<400> SEQUENCE: 46
ctctgcttct ccccgcagct ggagaattca atcgcgaaa                           39

<210> SEQ ID NO 47
```

-continued

<211> LENGTH: 35
<212> TYPE: DNA
<213> ORGANISM: HUMAN

<400> SEQUENCE: 47
gttaacgaat tcccaccatg aacacgatta acatc                                    35

<210> SEQ ID NO 48
<211> LENGTH: 51
<212> TYPE: DNA
<213> ORGANISM: HUMAN

<400> SEQUENCE: 48
caggatccag acgtctggcg gccgccggtg aagcttggcc cattgcatac g                  51

<210> SEQ ID NO 49
<211> LENGTH: 50
<212> TYPE: DNA
<213> ORGANISM: HUMAN

<400> SEQUENCE: 49
ccaggctcag atctggtcta accagagaga cccggttcac taaacgagct                    50

<210> SEQ ID NO 50
<211> LENGTH: 20
<212> TYPE: DNA
<213> ORGANISM: HUMAN

<400> SEQUENCE: 50
cccatctctc tccttctagc                                                     20

<210> SEQ ID NO 51
<211> LENGTH: 23
<212> TYPE: DNA
<213> ORGANISM: HUMAN

<400> SEQUENCE: 51
agcttcaccg gcggccgcga cgt                                                 23

<210> SEQ ID NO 52
<211> LENGTH: 15
<212> TYPE: DNA
<213> ORGANISM: HUMAN

<400> SEQUENCE: 52
cgcggccgcc ggtga                                                          15

<210> SEQ ID NO 53
<211> LENGTH: 59
<212> TYPE: DNA
<213> ORGANISM: HUMAN

<400> SEQUENCE: 53
aattgtccct catatcgcct cctccaggtc tgaagatctc gtctccccgg ggagacgca          59

<210> SEQ ID NO 54
<211> LENGTH: 47
<212> TYPE: DNA
<213> ORGANISM: HUMAN

<400> SEQUENCE: 54
agaatgagaa gagctgagcc agcagcagat ggggtgggag cagtatc                       47

<210> SEQ ID NO 55
<211> LENGTH: 57
<212> TYPE: DNA
<213> ORGANISM: HUMAN

<400> SEQUENCE: 55
tatgcgtctc cccggggaga cgagatcttc agacctggag gaggcgatat gagggac    57

<210> SEQ ID NO 56
<211> LENGTH: 47
<212> TYPE: DNA
<213> ORGANISM: HUMAN

<400> SEQUENCE: 56
tcgagatact gctcccaccc catctgctgc tggctcagct cttctca    47

<210> SEQ ID NO 57
<211> LENGTH: 70
<212> TYPE: DNA
<213> ORGANISM: HUMAN

<400> SEQUENCE: 57
agcttgcctt gagtgcttca atctagagcc ataccacatt tgtagaggtt ttacttgctt    60
taaaaaacct    70

<210> SEQ ID NO 58
<211> LENGTH: 46
<212> TYPE: DNA
<213> ORGANISM: HUMAN

<400> SEQUENCE: 58
aacctctaca aatgtggtat ggctctagat tgaagcactc aaggca    46

<210> SEQ ID NO 59
<211> LENGTH: 68
<212> TYPE: DNA
<213> ORGANISM: HUMAN

<400> SEQUENCE: 59
cccacacctc cccctgaacc tgaaacataa aatgaatgca attgttgtta ttaacttgtt    60
tattgcag    68

<210> SEQ ID NO 60
<211> LENGTH: 68
<212> TYPE: DNA
<213> ORGANISM: HUMAN

<400> SEQUENCE: 60
acaacaattg cattcatttt atgtttcagg ttcaggggga ggtgtgggag gttttttaaa    60
gcaagtaa    68

<210> SEQ ID NO 61
<211> LENGTH: 68
<212> TYPE: DNA
<213> ORGANISM: HUMAN

<400> SEQUENCE: 61
cttataatgg ttacaaataa agcaatagca tcacaaattt cacaaataaa gcatttttt    60 cactgcat    68

<210> SEQ ID NO 62

```
<211> LENGTH: 68
<212> TYPE: DNA
<213> ORGANISM: HUMAN

<400> SEQUENCE: 62
tatttgtgaa atttgtgatg ctattgcttt atttgtaacc attataagct gcaataaaca    60
agttaata                                                              68

<210> SEQ ID NO 63
<211> LENGTH: 68
<212> TYPE: DNA
<213> ORGANISM: HUMAN

<400> SEQUENCE: 63
tatttgtgaa atttgtgatg ctattgcttt atttgtaacc attataagct gcaataaaca    60
agttaata                                                              68

<210> SEQ ID NO 64
<211> LENGTH: 68
<212> TYPE: DNA
<213> ORGANISM: HUMAN

<400> SEQUENCE: 64
ccagacatga taagatacat tgatgagttt ggacaaacca caactagaat gcagtgaaaa    60
aaatgctt                                                              68

<210> SEQ ID NO 65
<211> LENGTH: 79
<212> TYPE: DNA
<213> ORGANISM: HUMAN

<400> SEQUENCE: 65
ccctaactcc gcccagttcc gcccattctc cgccccatgg ctgactaatt ttttttattt    60
atgcagaggc cgaggccgc                                                  79

<210> SEQ ID NO 66
<211> LENGTH: 68
<212> TYPE: DNA
<213> ORGANISM: HUMAN

<400> SEQUENCE: 66
ttagtcagcc atgggcgga gaatgggcgg aactgggcgg agttaggggc gggatggcgc     60
gccggtgt                                                              68

<210> SEQ ID NO 67
<211> LENGTH: 79
<212> TYPE: DNA
<213> ORGANISM: HUMAN

<400> SEQUENCE: 67
ctcggcctct gagctattcc agaagtagtg aggaggcttt tttggaggcc taggcttttg    60
cggcgcgcca cctgcatta                                                  79

<210> SEQ ID NO 68
<211> LENGTH: 68
<212> TYPE: DNA
<213> ORGANISM: HUMAN

<400> SEQUENCE: 68
gcctcctcac tacttctgga atagctcaga ggccgaggcg gcctcggcct ctgcataaat    60
``` aaaaaaaa                                                                   68

<210> SEQ ID NO 69
<211> LENGTH: 46
<212> TYPE: DNA
<213> ORGANISM: HUMAN

<400> SEQUENCE: 69
tcattaatgc aggtggcgcg ccgcaaaagc ctaggcctcc aaaaaa                          46

<210> SEQ ID NO 70
<211> LENGTH: 67
<212> TYPE: DNA
<213> ORGANISM: HUMAN

<400> SEQUENCE: 70
ctagaggggg aggctaactg aaacacggaa ggagacaata ccggaaggaa cccgcgctat          60
gacggca                                                                    67

<210> SEQ ID NO 71
<211> LENGTH: 66
<212> TYPE: DNA
<213> ORGANISM: HUMAN

<400> SEQUENCE: 71
ataaaaagac agaataaaac ccacgggtgt tgggtcgttt gttcataaac ccgggcttcg          60
gtccca                                                                     66

<210> SEQ ID NO 72
<211> LENGTH: 43
<212> TYPE: DNA
<213> ORGANISM: HUMAN

<400> SEQUENCE: 72
cttccggtat tgtctccttc cgtgtttcag ttagcctccc cct                            43

<210> SEQ ID NO 73
<211> LENGTH: 44
<212> TYPE: DNA
<213> ORGANISM: HUMAN

<400> SEQUENCE: 73
gtgggtttta ttctgtcttt ttattgccgt catagcgcgg gttc                           44

<210> SEQ ID NO 74
<211> LENGTH: 46
<212> TYPE: DNA
<213> ORGANISM: HUMAN

<400> SEQUENCE: 74
ccggtgggac cgaagcccgg gtttatgaac aaacgaccca acaccc                         46

<210> SEQ ID NO 75
<211> LENGTH: 40
<212> TYPE: DNA
<213> ORGANISM: HUMAN

<400> SEQUENCE: 75
aacggcggcg ggaagttctc ctgcgtcatc gtcgggaaga                                40

<210> SEQ ID NO 76

```
<211> LENGTH: 42
<212> TYPE: DNA
<213> ORGANISM: HUMAN

<400> SEQUENCE: 76
catgttgcag ggcccctagg aaaaagggct gttggaaatg tg                        42

<210> SEQ ID NO 77
<211> LENGTH: 34
<212> TYPE: DNA
<213> ORGANISM: HUMAN

<400> SEQUENCE: 77
cactccatgt accggttctt ttagaatytc yctg                                 34

<210> SEQ ID NO 78
<211> LENGTH: 66
<212> TYPE: DNA
<213> ORGANISM: HUMAN

<400> SEQUENCE: 78
cgtttagtga accgtcagat cgcctggaga cgccatccac gctgttttga cctccataga    60
agacac                                                               66

<210> SEQ ID NO 79
<211> LENGTH: 50
<212> TYPE: DNA
<213> ORGANISM: HUMAN

<400> SEQUENCE: 79
aacagcgtgg atggcgtctc caggcgatct gacggttcac taaacgagct                50

<210> SEQ ID NO 80
<211> LENGTH: 69
<212> TYPE: DNA
<213> ORGANISM: HUMAN

<400> SEQUENCE: 80
cgggaccgat ccagcctccg cggccgggaa cggtgcattg aacgcggat tccccgtgcc     60 aagagttac                                                            69

<210> SEQ ID NO 81
<211> LENGTH: 69
<212> TYPE: DNA
<213> ORGANISM: HUMAN

<400> SEQUENCE: 81
tccgcgttcc aatgcaccgt tcccggccgc ggaggctgga tcggtcccgg tgtcttctat    60
ggaggtcaa                                                            69

<210> SEQ ID NO 82
<211> LENGTH: 66
<212> TYPE: DNA
<213> ORGANISM: HUMAN

<400> SEQUENCE: 82
gtaagtaccg cctatagagt ctataggccc accccttgg cttcttatgc atgctcccct     60
gctccg                                                               66

<210> SEQ ID NO 83
<211> LENGTH: 66
```

```
<212> TYPE: DNA
<213> ORGANISM: HUMAN

<400> SEQUENCE: 83
aagaagccaa gggggtgggc ctatagactc tataggcggt acttacgtaa ctcttggcac    60
ggggaa                                                               66

<210> SEQ ID NO 84
<211> LENGTH: 59
<212> TYPE: DNA
<213> ORGANISM: HUMAN

<400> SEQUENCE: 84
atccgggctc tcgcccgccc ggacccacag gccaccctca accgtcctgg ccccggacc    59

<210> SEQ ID NO 85
<211> LENGTH: 60
<212> TYPE: DNA
<213> ORGANISM: HUMAN

<400> SEQUENCE: 85
gagggtggcc tgtgggtccg ggcgggcgag gagcccggat cggagcaggg gagcatgcat    60

<210> SEQ ID NO 86
<211> LENGTH: 44
<212> TYPE: DNA
<213> ORGANISM: HUMAN

<400> SEQUENCE: 86
caaaccccac ccctcactct gcttctcccc gcagctgaga tctg                     44

<210> SEQ ID NO 87
<211> LENGTH: 68
<212> TYPE: DNA
<213> ORGANISM: HUMAN

<400> SEQUENCE: 87
ctagcagatc tcagctgcgg ggagaagcag actgaggggt ggggtttggg tccggggcca    60
ggacggtt                                                             68

<210> SEQ ID NO 88
<211> LENGTH: 78
<212> TYPE: DNA
<213> ORGANISM: HUMAN

<400> SEQUENCE: 88
cgggaccgat ccagcctccg cggccgggaa cggtgcattg aacgcggat tccccgtgcc     60 aagagttacc tgagatct                                                  78

<210> SEQ ID NO 89
<211> LENGTH: 34
<212> TYPE: DNA
<213> ORGANISM: HUMAN

<400> SEQUENCE: 89
ctagcagatc tcaggtaact cttggcacgg ggaa                                34

<210> SEQ ID NO 90
<211> LENGTH: 19
<212> TYPE: DNA
<213> ORGANISM: HUMAN
```

```
<400> SEQUENCE: 90
catggtggta gatctcaca                                                    19

<210> SEQ ID NO 91
<211> LENGTH: 19
<212> TYPE: DNA
<213> ORGANISM: HUMAN

<400> SEQUENCE: 91
agcttgtgag atctaccac                                                    19

<210> SEQ ID NO 92
<211> LENGTH: 14
<212> TYPE: DNA
<213> ORGANISM: HUMAN

<400> SEQUENCE: 92
agatctcaca caca                                                         14

<210> SEQ ID NO 93
<211> LENGTH: 21
<212> TYPE: DNA
<213> ORGANISM: HUMAN

<400> SEQUENCE: 93
agcttgtgtg tgagatctcc t                                                 21

<210> SEQ ID NO 94
<211> LENGTH: 67
<212> TYPE: DNA
<213> ORGANISM: HUMAN

<400> SEQUENCE: 94
ctagaggggg aggctaactg aaacacggaa ggagacaata ccggaaggaa cccgcgctat       60
gacggca                                                                 67

<210> SEQ ID NO 95
<211> LENGTH: 66
<212> TYPE: DNA
<213> ORGANISM: HUMAN

<400> SEQUENCE: 95
ataaaaagac agaataaaac ccacgggtgt tgggtcgttt gttcataaac ccgggcttcg       60
gtccca                                                                  66

<210> SEQ ID NO 96
<211> LENGTH: 43
<212> TYPE: DNA
<213> ORGANISM: HUMAN

<400> SEQUENCE: 96
cttccggtat tgtctccttc cgtgtttcag ttagcctccc cct                         43

<210> SEQ ID NO 97
<211> LENGTH: 44
<212> TYPE: DNA
<213> ORGANISM: HUMAN

<400> SEQUENCE: 97
gtgggtttta ttctgtcttt ttattgccgt catagcgcgg gttc                        44
```

```
<210> SEQ ID NO 98
<211> LENGTH: 46
<212> TYPE: DNA
<213> ORGANISM: HUMAN

<400> SEQUENCE: 98
ccggtgggac cgaagcccgg gtttatgaac aaacgaccca acaccc                    46

<210> SEQ ID NO 99
<211> LENGTH: 103
<212> TYPE: DNA
<213> ORGANISM: HUMAN

<400> SEQUENCE: 99
gaggccccaa ggggttatgc tatctagagg taccacgcgt gaattctcga ggctagcaga     60
tctccatggt attatcgtgt ttttcaaagg aaaaccacgt ccc                      103

<210> SEQ ID NO 100
<211> LENGTH: 69
<212> TYPE: DNA
<213> ORGANISM: HUMAN

<400> SEQUENCE: 100
gcataacccc ttggggcctc taaacgggtc ttgaggggtt ttttgctcac cggcgcgcca     60
cctgcatta                                                             69

<210> SEQ ID NO 101
<211> LENGTH: 87
<212> TYPE: DNA
<213> ORGANISM: HUMAN

<400> SEQUENCE: 101
cacggggacg tggttttcct ttgaaaaaca cgataatacc atggagatct gctagcctcg     60
agaattcacg cgtggtacct ctagata                                         87

<210> SEQ ID NO 102
<211> LENGTH: 53
<212> TYPE: DNA
<213> ORGANISM: HUMAN

<400> SEQUENCE: 102
tcattaatgc aggtggcgcg ccggtgagca aaaaacccct caagacccgt tta            53

<210> SEQ ID NO 103
<211> LENGTH: 49
<212> TYPE: DNA
<213> ORGANISM: HUMAN

<400> SEQUENCE: 103
aattacaccg gcgtcgccct atagtgagtc gtattagcgg ccgcgacgt                 49

<210> SEQ ID NO 104
<211> LENGTH: 41
<212> TYPE: DNA
<213> ORGANISM: HUMAN

<400> SEQUENCE: 104
cgcggccgct aatacgactc actatagggc gacgccggtg t                         41

<210> SEQ ID NO 105
<211> LENGTH: 56
<212> TYPE: DNA
```

```
<213> ORGANISM: HUMAN

<400> SEQUENCE: 105
gtctgttgtg tgactctgcc ctatagtgag tcgtattacc cttttagtca gtgtgg          56
```